(12) United States Patent
Kondo et al.

(10) Patent No.: US 9,476,059 B2
(45) Date of Patent: Oct. 25, 2016

(54) GENE CAPABLE OF IMPARTING ENVIRONMENTAL STRESS RESISTANCE TO PLANTS AND METHOD FOR UTILIZING THE SAME

(75) Inventors: Satoshi Kondo, Miyoshi (JP); Chikara Ohto, Miyoshi (JP); Norihiro Mitsukawa, Toyota (JP); Kenichi Ogawa, Kyoto (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 506 days.

(21) Appl. No.: 13/504,834

(22) PCT Filed: Oct. 22, 2010

(86) PCT No.: PCT/JP2010/006254
§ 371 (c)(1),
(2), (4) Date: Apr. 27, 2012

(87) PCT Pub. No.: WO2011/052169
PCT Pub. Date: May 5, 2011

(65) Prior Publication Data
US 2012/0216314 A1 Aug. 23, 2012

(30) Foreign Application Priority Data
Oct. 30, 2009 (JP) .................... 2009-250524

(51) Int. Cl.
| A01H 5/00 | (2006.01) |
| A01H 1/00 | (2006.01) |
| C12N 15/82 | (2006.01) |
| C07K 14/415 | (2006.01) |
| C12N 9/12 | (2006.01) |
| C12N 15/00 | (2006.01) |

(52) U.S. Cl.
CPC ......... C12N 15/8273 (2013.01); C07K 14/415 (2013.01); C12N 9/1205 (2013.01); C12N 15/8271 (2013.01)

(58) Field of Classification Search
None
See application file for complete search history.

(56) References Cited

U.S. PATENT DOCUMENTS

| 6,818,756 | B2 | 11/2004 | Sano et al. | |
|---|---|---|---|---|
| 7,176,351 | B2 | 2/2007 | Kisaka et al. | |
| 7,790,956 | B2 | 9/2010 | Dudits et al. | |
| 2005/0114925 | A1 | 5/2005 | Kisaka et al. | |
| 2006/0183137 | A1 | 8/2006 | Harper et al. | |
| 2006/0225154 | A1 | 10/2006 | Kasukabe et al. | |
| 2007/0039067 | A1 | 2/2007 | Feldmann et al. | |
| 2007/0256194 | A1* | 11/2007 | Allefs ................ | C12N 15/8282 800/279 |
| 2008/0040972 | A1 | 2/2008 | Chalivendra et al. | |
| 2008/0057093 | A1* | 3/2008 | Wan et al. .................... | 424/405 |
| 2008/0113342 | A1 | 5/2008 | Cao et al. | |
| 2008/0227639 | A1 | 9/2008 | Wu et al. | |
| 2008/0254989 | A1 | 10/2008 | Cherian | |
| 2009/0019602 | A1* | 1/2009 | Sheen et al. .................. | 800/279 |
| 2009/0126046 | A1* | 5/2009 | Valerie .......................... | 800/290 |
| 2009/0138991 | A1* | 5/2009 | Reuzeau ........................ | 800/278 |
| 2011/0225677 | A1 | 9/2011 | Kondo et al. | |
| 2011/0239330 | A1 | 9/2011 | Kondo et al. | |
| 2012/0159666 | A1 | 6/2012 | Yonekura et al. | |
| 2012/0216314 | A1 | 8/2012 | Kondo et al. | |

FOREIGN PATENT DOCUMENTS

| CN | 101182353 A | 5/2008 |
|---|---|---|
| CN | 102165063 | 8/2011 |
| JP | 8-266179 A | 10/1996 |
| JP | 9503389 | 4/1997 |
| JP | 2000515020 | 11/2000 |
| JP | 2001505410 | 4/2001 |
| JP | 2001-252084 A | 9/2001 |
| JP | 2001519659 | 10/2001 |
| JP | 200552114 | 3/2005 |
| JP | 2005130770 | 5/2005 |
| JP | 2007-530063 A | 11/2007 |
| WO | 9509911 | 4/1995 |
| WO | 9803631 | 1/1998 |
| WO | 9810082 | 3/1998 |
| WO | 9842851 | 10/1998 |
| WO | 9859039 | 12/1998 |
| WO | 2004/104162 A2 | 12/2004 |
| WO | 2005094562 | 10/2005 |
| WO | 2006005771 | 1/2006 |
| WO | 2006/069017 A2 | 6/2006 |
| WO | 2006131547 | 12/2006 |
| WO | 2007/020638 A2 | 2/2007 |
| WO | 2008/061153 A2 | 5/2008 |
| WO | 2008061153 | 5/2008 |
| WO | 2008062049 | 5/2008 |

(Continued)

OTHER PUBLICATIONS

UniPro Database, Direct submission, Acc. No. 049325, Jun. 1, 1998.*

(Continued)

*Primary Examiner* — Phuong Bui
(74) *Attorney, Agent, or Firm* — Sughrue Mion, PLLC

(57) ABSTRACT

According to the present invention, environmental stress resistance is imparted to a plant or the environmental stress resistance of a plant is improved. At least one gene selected from the group consisting of an LRR-RLP gene selected from a 1st group (including At2g33080), an LRR-RLK gene selected from a 2nd group (including At1g69990), and an LRR-RLK gene selected from a 3rd group (including At5g39390) is introduced into a plant, or an expression control region of an endogenous gene is altered in a plant.

3 Claims, 5 Drawing Sheets

(56) References Cited

FOREIGN PATENT DOCUMENTS

| WO | 2008/116829 A1 | 10/2008 |
|---|---|---|
| WO | 2009/060418 A2 | 5/2009 |
| WO | 2009060418 A2 | 5/2009 |

OTHER PUBLICATIONS

Final Office Action issued in U.S. Appl. No. 13/128,373, dated Nov. 7, 2013.
Tuteja, "Mechanisms of High Salinity Tolerance in Plants", Meth. Enzymol., 428:419-38 (2007) [Abstract, Figures and Legends only].
Peart et al., "Ubiquitin ligase-associated protein SGT1 is required for host and nonhost disease resistance in plants", PNAS, 99(16):10865-10869 (2002).
Kennel et al., "Principles and practices of nucleic acid hybridization", Progress in Nucleic Acid Research and Molecular Biology, 11:259-301 (1971).
Maniatis et al., Molecular Cloning, Cold Spring Harbor Laboratory, pp. 324-389 (1982).
Weigel et al., "Activation tagging in Arabidopsis", Plant Physiology, 122:1003-1013 (2000).
Leister, "Tandem and segmental gene duplication and recombination in the evolution of plant disease resistance genes", Trends in Genetics, 20(3):116-122 (2004).
Sweat et al., "Characterization of natural and induced variation in the LOV1 gene, a CC-NBS-LRR gene conferring victorin sensitivity and diseases susceptibility in Arabidopsis", MPMI, 21(1):7-19 (2008).
GenBank Accession No. NM_001084273.1 (Published Apr. 20, 2007).
Theologis et al., GenBank Accession No. NM_001084273.2 (Published May 28, 2011).
Cooley et al., "Members of the Arabidopis HRT/RPP8 Family of Resistance Genes Confer Resistance to Both Viral and Oomycete Pathogens", The Plant Cell, 12:663-676 (2000).
Chini et al., "Drought Tolerance Established by Enhanced Expression of the CC-NBS-LRR Gene, ADR1, Requires Salicylic Acid, EDS1 and ABI1", The Plant Journal, 38:810-822 (2004).
Meyers et al., "Genome-Wide Analysis of NBS-LRR-Encording Genes in Arabidopsis", The Plant Cell, 15:809-834 (2003).
Lorang et al., "Plant disease Susceptibility Conferred by a "Resistance" Gene", Proc. Natl. Acad. Sci., USA, 104:14861-14866 (2007).
Jaglo-Ottosen et al., "Arabidopsis CBF1 Overexpression Induces COR Genes and Enhances Freezing tolerance", Science, 280:104-106 (1998).
Kasuga,et al., Improving Plant Drought, Salt, and Freezing Tolerance by Gene Transfer of a Single Stress-Inducible Transcription Factor, Nature Biotechnology, 17:287-291 (1999).
Liu et al., "Two Transcription Factors, DREB1 and DREB2, with an EREBP/AP2 DNA Binding Domain Separate Two Cellular Signal Transduction Pathways in Drought-and Low-Temperature-Responsive Gene Expression, Respectively, in Arabidopsis", The Planet Cell, 10:1391-1406 (1998).
Chisholm et al, "Host-Micobe Interactions: Shaping the Evolution of the Plant Immune Response", Cell, 24:803-814 (2006).
Kadota et al., "Protein, Nucleic Acid and Enzyme (PNE)", 52(6)718-723 (2007).
Belkhadir et al., "Plant Disease Resistance Protein Signaling: NBS-LRR Proteins and Their Partners", Current Opinion in Plant Biology, 7:391-399 (2004).
Notice of Allowance, dated Apr. 21, 2014, issued by the United States Patent and Trademark Office, in counterpart U.S. Appl. No. 13/120,901.
Restriction Requirement for U.S. Appl. No. 13/120,901 dated Sep. 26, 2012.
Non-Final Office Action for U.S. Appl. No. 13/120,901 dated Feb. 15, 2013.
Final Office Action for U.S. Appl. No. 13/120,901 dated Jul. 30, 2013.
Non-Final Office Action for U.S. Appl. No. 13/128,373 dated Apr. 26, 2013.
Wang et al., "A Genome-Wide functional investigation into the roles of receptor-like proteins in Arabidopsis", Plant Physiology, 147:503-517 (2008).
Singh et al., "The GLK1 'Regulon' encodes disease defense related proteins and confers resistance to Fusarium graminearum in Arabidopsis", Cereal Res. Commun., 36(Suppl. B):261-265 (2008).
Rizhsky et al., "When Defense Pathways Collide: The response of Arabidopsis to a combination of drought and heat stress", Plant Physiology, 134:1683-1696 (2004).
Shiu et al., "Expansion of the receptor-like kinase/pelle gene family and receptor-like Proteins in Arabidopsis", Plant Physiology, 132:530-543 (2003).
Magome et al., "The DDF1 Transcriptional Activator Upregulates Expression of a Gibberellin-Deactivating Gene, GA2ox7, under high-salinity stress in Arabidopsis", The Plant Journal, 56:613-626 (2008).
Kobe et al., "The leucine-rich repeat as a protein recognition motif", National Diet Library, Apr. 3, 2011.
Swarbreck et al., "Receptor like Protein 33 [Arabidopsis thaliana]", GenBank Accession No. AEE74273.1 (2000), PLN Date: Apr. 12, 2013.
Wahl et al., "Molecular Hybridization of Immobilized Nucleic Acids: Theoretical Concepts and Practical Considerations", Molecular Hybridization of Nucleic Acids, Methods in Enzymology, 152:399-407 (1987).
GenBank Accession No. AEM36350, At1g58602, pp. 1-2, published Oct. 11, 2011.
Kennel et al., "Principles and practices of nucleic acid hybridization. Progress in Nucleic Acid Research and Molecular Biology.", 11:259-301 (1971).
Maniatis et al., "Molecular Cloning", A Laboratory Manual, Cold Spring Harbor Laboratory, Table of Contents and pp. 324-343 and 387-389 (1982).
Leister et al., "Tandem and segmental gene duplication and recombination in the evolution of plant disease resistance genes", Trends in Genetics, 20(3):116-122 (2004).
Sweat et al., "Characterization of natural and induced variation in the LOV1 gene, a CC-NBS-LRR gene conferring victorin sensitivity and disease susceptibility in Arabidopisis", MPMI, 21(1):7-19 (2008).
GenBank Accession No. NM_001084273.1, published Apr. 20, 2007.
Theologis et al., GenBank Accession No. NM_001084273.2, published May 28, 2011.
Meyer et al., "A leucine-rich repeat protein of carrot that exhibits antifreeze activity", FEBS Letters, 447:171-178 (1999).
Osakabe et al., "Functional analysis of a leucine-rich repeat receptor like kinase, RPK1, involved in ABA signal transduction of Arabidopsis", CD p. 4T17-10 (4P-1263) (May 7, 2008).
Arabidopsis thaliana AtRLP28 (Receptor Like Protein 28); protein binding (AtRLP28) mRNA, complete CDS, NCBI Reference Sequence: NM_128868.1, http://www.ncbi.nlm.nih.gov/nuccore/18403183?sat=14&satkey=6644359, online Aug. 21, 2009, retrieved Apr. 26, 2013.
Lin et al., "Putative Leucine-Rich Repeat Disease Resistance Protein", XP002615233, Jun. 1, 1998, Database Accession No. 049327.
Lin eta l., "Putative Leucine-Rich Repeat Disease Resistance Protein", XP002615234, Jun. 1, 1998, Database Accession No. 049325.
Lin et al., "Putatie Leucine-Rich Repeat Disease Resistance Protein", XP002615235, Jun. 1, 1998, Database Accession No. 049328.
Yanwei Cheng et al., "New Changes in the Plasma-Membrane-Associated Proteome of Rice Roots Under Salt Stress", Proteomics Journal, Jun. 2009, pp. 3100-3114, vol. 9, No. 11.
Suk Whan Hong et al., "Identification of a Receptor-Like Protein Kinase Gene Rapidly Induced by Abscisic Acid, Dehydration, High Salt, and Cold Treatments in Arabidopsis Thaliana", Plant Physiology, 1997, pp. 1203-1212, vol. 113, No. 4.

(56) References Cited

OTHER PUBLICATIONS

Laura De Lorenzo et al., "A Novel Leucine-Rich Repeat Receptor Kinase Regulates the Response of Medicago Truncatula Roots to Salt Stress", Plan Cell, Feb. 2009, pp. 668-680, vol. 21, No. 2.

Yuriko Osakabe et al., "Leucine-Rich Repeat Receptor-Like KinaseI is a Key Membrane-Bound Regulator of Abscisic Acid Early Signaling in Arabidopsis" Plant Cell, 2005, pp. 1105-1119, vol. 17.

Takashi Tamura et al., "Osmotic Stress Tolerance of Transgenic Tobacco Expressing a Gene Encoding a Membrane-Located Receptor-Like Protein from Tobacco Plants", Plant Physiology, Feb. 2003, pp. 454-462, vol. 131.

International Search Report for Entry of PCT/JP2010/006254 dated Mar. 9, 2011.

Rounsley et al., *Arabidopis thaliana*—putative leucine-rich repeat disease resistance protein, GenBank Accession No. AAC04912.1, PLN Mar. 11, 2002.

Notice of Allowance dated Jan. 13, 2014, issued in corresponding U.S. Appl. No. 13/120,901.

GenBank Accession No. Q8W3KO. Probable disease resistance protein At1g58602. Database entry created Apr. 11, 2003.

M. Kasuga et al., "A Combination of the *Arabidopsis* DREB1A Gene and Stress-Inducible rd29A Promoter Improved Drought- and Low-Temperature Stress Tolerance in Tobacco by Gene Transfer", Plant Cell Physiol. vol. 45, No. 3, 2004, pp. 346-350.

Communication dated Oct. 24, 2014, issued by the United States Patent and Trademark Office in counterpart U.S. Appl. No. 13/128,373.

Lin, X. et al., "Putative Disease Resistance Protein [Arabidopsis Thaliana]," GenBank AAF26131.1, Oct. 8, 1999, 2 pages total, accessible at http://www.ncbi.nlm.nih.gov/protein/AAF26131.1.

Communication from the United States Patent and Trademark Office issued Nov. 20, 2015 in U.S. Appl. No. 13/128,373.

Zhang, Hong-Xia, et al., "Engineering Salt-Tolerant Brassica Plants: Characterization of Yield and Seed Oil Quality in Transgenic Plants with Increased Vacuolar Sodium Accumulation," PNAS, vol. 98, No. 22, Oct. 23, 2001, pp. 12832-12836.

Sahi, Chandan, et al., "Salt Stress Response in Rice: Genetics, Molecular Biology, and Comparative Genomics," Funct. Integr. Genomics, vol. 6, 2006, pp. 263-284.

Abdin, MZ, et al., "Abiotic Stress Related Genes and their Role in Conferring Resistance in Plants," Indian Journal of Biotechnology, vol. 1, Jul. 2002, pp. 225-244.

Communication dated Aug. 6, 2015, issued by the U.S. Patent and Trademark Office in U.S. Appl. No. 13/128,373.

Office Action, dated Apr. 23, 2015, issued by the United States Patent and Trademark Office in U.S. Appl. No. 13/128,373.

* cited by examiner

Transformed plants
(LRR-RLK gene-transformed
Arabidopsis thaliana)

Wild-type plants (Arabidopsis
thaliana) shown in the frame

Salt resistance test for LRR-RLK gene (At1g69990)-transformed Arabidopsis
thaliana Transformed plants
(LRR-RLK gene-transformed
 Arabidopsis thaliana)

Wild-type plants (Arabidopsis
thaliana) shown in the frame

Salt resistance test for LRR-RLK gene (At5g39390)-transformed Arabidopsis thaliana Transformed plants
(LRR gene-transformed
Arabidopsis thaliana)

Wild-type plants (Arabidopsis
thaliana) shown in the frame

Salt resistance test for LRR gene (At3g05650)-transformed Arabidopsis thaliana

Transformed plants
(LRR gene-transformed
Arabidopsis thaliana)

Wild-type plants (Arabidopsis thaliana) shown in the frame

Salt resistance test for LRR gene (At2g33080)-transformed Arabidopsis thaliana

Transformed plants
(LRR-RLK gene-transformed
*Arabidopsis thaliana*)

Wild-type plants (*Arabidopsis thaliana*) shown in the frame

Salt resistance test for LRR-RLK gene (At1g71830)-transformed *Arabidopsis thaliana*

SEQUENCE LISTING

<160> NUMBER OF SEQ ID NOS: 66

<210> SEQ ID NO 1
<211> LENGTH: 2223
<212> TYPE: DNA
<213> ORGANISM: Arabidopsis thaliana
<220> FEATURE:
<221> NAME/KEY: CDS
<222> LOCATION: (1)..(2223)

<400> SEQUENCE: 1

-continued

| | | |
|---|---|---|
| atg tca gga tca cat ctg cgt ttg cgt ttt ctc tcg cta cta tta ctc<br>Met Ser Gly Ser His Leu Arg Leu Arg Phe Leu Ser Leu Leu Leu Leu<br>1                      5                              10                    15 | 48 | |
| tgt tgt gtc tcc tct tcg act tca agc tta ttc act ttc agt tat ccc<br>Cys Cys Val Ser Ser Ser Thr Ser Ser Leu Phe Thr Phe Ser Tyr Pro<br>                    20                          25                        30 | 96 | |
| gtt ctt gat ctt gtt gct tgt cgt tcc cat cag att caa gcc ttt aca<br>Val Leu Asp Leu Val Ala Cys Arg Ser His Gln Ile Gln Ala Phe Thr<br>                35                        40                        45 | 144 | |
| cag ttc aag aac gag ttt gat acc cat cgt tgc aac cat agt gac cac<br>Gln Phe Lys Asn Glu Phe Asp Thr His Arg Cys Asn His Ser Asp His<br>        50                        55                        60 | 192 | |
| tct aat gga gtc tgg tgc gat aac tcg acg ggt gtg gtc acg aag cta<br>Ser Asn Gly Val Trp Cys Asp Asn Ser Thr Gly Val Val Thr Lys Leu<br>65                      70                        75                        80 | 240 | |
| caa ctc aac gct tgt ctc agt gga act ctg aat ccc aac agt agc cta<br>Gln Leu Asn Ala Cys Leu Ser Gly Thr Leu Asn Pro Asn Ser Ser Leu<br>                85                        90                        95 | 288 | |
| ttc tgg ttt cat cag ctc cgt ttc ctt aat ctc tct cac aac aac ttc<br>Phe Trp Phe His Gln Leu Arg Phe Leu Asn Leu Ser His Asn Asn Phe<br>                  100                       105                    110 | 336 | |
| acc tcc act tca ttc cct tcc gag ttt ggt aat ctc aac aaa gta gag<br>Thr Ser Thr Ser Phe Pro Ser Glu Phe Gly Asn Leu Asn Lys Val Glu<br>              115                       120                    125 | 384 | |
| gtt ttg gat ctt tcc ttt aat agc ttc act ggc caa gtt cct tcc tca<br>Val Leu Asp Leu Ser Phe Asn Ser Phe Thr Gly Gln Val Pro Ser Ser<br>130                       135                       140 | 432 | |
| ttt agt aac cta agt cag cta acc gag ttg cac ctt tcc aat aac cag<br>Phe Ser Asn Leu Ser Gln Leu Thr Glu Leu His Leu Ser Asn Asn Gln<br>145                       150                       155                    160 | 480 | |
| ctc act ggt ggt ttc cca cag gta caa aat cta act aac ctc tcc cat<br>Leu Thr Gly Gly Phe Pro Gln Val Gln Asn Leu Thr Asn Leu Ser His<br>                  165                       170                    175 | 528 | |
| cta gac ttt gaa aat aat aaa ttc tct gga acc gtc cct tct tct ctc<br>Leu Asp Phe Glu Asn Asn Lys Phe Ser Gly Thr Val Pro Ser Ser Leu<br>              180                       185                    190 | 576 | |
| ctc atg atg ccc ttt tta tca tat ctt aat tta tat gga aac cat ttc<br>Leu Met Met Pro Phe Leu Ser Tyr Leu Asn Leu Tyr Gly Asn His Phe<br>            195                       200                    205 | 624 | |
| acc ggt tcc att gaa gtt tct acc tca tcg aag ctc gag atc ctt tac<br>Thr Gly Ser Ile Glu Val Ser Thr Ser Ser Lys Leu Glu Ile Leu Tyr<br>210                       215                       220 | 672 | |
| ctt ggg ctt aaa cct ttt gaa gga caa atc cta gag cct atc tca aag<br>Leu Gly Leu Lys Pro Phe Glu Gly Gln Ile Leu Glu Pro Ile Ser Lys<br>225                       230                       235                    240 | 720 | |
| ctc ata aac cta aag cgt ctt gaa ctt tct ttt cta aac ata agc tac<br>Leu Ile Asn Leu Lys Arg Leu Glu Leu Ser Phe Leu Asn Ile Ser Tyr<br>                  245                       250                    255 | 768 | |
| cca ctc gac tta aac ctc ttc tcc tct ctc aaa tct tta aca tac ctc<br>Pro Leu Asp Leu Asn Leu Phe Ser Ser Leu Lys Ser Leu Thr Tyr Leu<br>              260                       265                    270 | 816 | |
| gat ctt tcc ggt aac agt ata tct ccg aga agt tta agg tca gat tta<br>Asp Leu Ser Gly Asn Ser Ile Ser Pro Arg Ser Leu Arg Ser Asp Leu<br>            275                       280                    285 | 864 | |
| tac atc cca cta acc ctt gag aag ttg cta ttg gag caa tgc ggc atc<br>Tyr Ile Pro Leu Thr Leu Glu Lys Leu Leu Leu Glu Gln Cys Gly Ile<br>        290                       295                    300 | 912 | |
| ata gag ttt cca aac atc tta aag acc ctt cag aag ttg gag tat ata<br>Ile Glu Phe Pro Asn Ile Leu Lys Thr Leu Gln Lys Leu Glu Tyr Ile<br>305                       310                       315                    320 | 960 | |

```
gac atg tcc aac aat aga atc aat ggt aaa atc cct gag tgg tta tgg    1008
Asp Met Ser Asn Asn Arg Ile Asn Gly Lys Ile Pro Glu Trp Leu Trp
            325                 330                 335 aga ctt cct cgc cta aga tca atg agt ctt gca aat aat tct ttc aac    1056
Arg Leu Pro Arg Leu Arg Ser Met Ser Leu Ala Asn Asn Ser Phe Asn
        340                 345                 350 ggt ttc gaa ggt tca aca gat gtt tta gta aat tca tca atg gag ata    1104
Gly Phe Glu Gly Ser Thr Asp Val Leu Val Asn Ser Ser Met Glu Ile
            355                 360                 365 tta ttt atg cat tca aac aat att caa ggg gca ctt cct aat cta cca    1152
Leu Phe Met His Ser Asn Asn Ile Gln Gly Ala Leu Pro Asn Leu Pro
        370                 375                 380 ctc tct atc aaa gcc ttc tct gcg ggt tat aat aat ttc tca gga gag    1200
Leu Ser Ile Lys Ala Phe Ser Ala Gly Tyr Asn Asn Phe Ser Gly Glu
385                 390                 395                 400 ata cct ctt tca atc tgc aac aga agc tct ctt gct gct ctt tct cta    1248
Ile Pro Leu Ser Ile Cys Asn Arg Ser Ser Leu Ala Ala Leu Ser Leu
                405                 410                 415 cct tac aac aat ttc acc ggt aaa att cct caa tgt ctg agt aat ttg    1296
Pro Tyr Asn Asn Phe Thr Gly Lys Ile Pro Gln Cys Leu Ser Asn Leu
            420                 425                 430 acg ttt gtg cat ctt cga aag aac aat ttg gaa gga agt att cct gac    1344
Thr Phe Val His Leu Arg Lys Asn Asn Leu Glu Gly Ser Ile Pro Asp
        435                 440                 445 aca tta tgt gcc ggg gac tct ctt cag aca ctc gac att ggc ttc aat    1392
Thr Leu Cys Ala Gly Asp Ser Leu Gln Thr Leu Asp Ile Gly Phe Asn
450                 455                 460 cta ata tct ggg acg ctt cca aga tct ctc cta aac tgc tcg tct cta    1440
Leu Ile Ser Gly Thr Leu Pro Arg Ser Leu Leu Asn Cys Ser Ser Leu
465                 470                 475                 480 gag ttt ctt agc gtt gac aac aac aga atc aaa gac aca ttt ccc ttc    1488
Glu Phe Leu Ser Val Asp Asn Asn Arg Ile Lys Asp Thr Phe Pro Phe
                485                 490                 495 tgg ctc aag gct tta cca aat ttg caa gtc ctt atc cta agt tca aac    1536
Trp Leu Lys Ala Leu Pro Asn Leu Gln Val Leu Ile Leu Ser Ser Asn
            500                 505                 510 aaa ttg tat ggt cct ata gct cct cct cat caa agt cct ctc gcg ttt    1584
Lys Leu Tyr Gly Pro Ile Ala Pro Pro His Gln Ser Pro Leu Ala Phe
        515                 520                 525 cct gag ttg cgg ata ttt gag ata gct gat aat atg ttt act gga acc    1632
Pro Glu Leu Arg Ile Phe Glu Ile Ala Asp Asn Met Phe Thr Gly Thr
    530                 535                 540 ttg tca cca aga tac ttt gtg aac tgg aaa aca tca tca ctc acg gtg    1680
Leu Ser Pro Arg Tyr Phe Val Asn Trp Lys Thr Ser Ser Leu Thr Val
545                 550                 555                 560 aat gaa gat gga gat tta tat atg gta tac aag aat aat gca ttc ggt    1728
Asn Glu Asp Gly Asp Leu Tyr Met Val Tyr Lys Asn Asn Ala Phe Gly
                565                 570                 575 ata gat tcg tat gtg tat agg gat act ata gat atg aaa tac aaa ggg    1776
Ile Asp Ser Tyr Val Tyr Arg Asp Thr Ile Asp Met Lys Tyr Lys Gly
            580                 585                 590 tta tcc atg gag caa cag atg gtc ctc aac tcc tac agt gcc att gat    1824
Leu Ser Met Glu Gln Gln Met Val Leu Asn Ser Tyr Ser Ala Ile Asp
        595                 600                 605 ttt tct ggg aat aga tta gaa gga cag att cct aaa tct att ggt ctc    1872
Phe Ser Gly Asn Arg Leu Glu Gly Gln Ile Pro Lys Ser Ile Gly Leu
    610                 615                 620 ttg aag gaa ctc att gca ctc aat tta tca aac aac gca ttt aca tgc    1920
Leu Lys Glu Leu Ile Ala Leu Asn Leu Ser Asn Asn Ala Phe Thr Cys
```

```
cat att cct ctg tct ttg gcc aat gct act gag ctc gag tca tta gac    1968
His Ile Pro Leu Ser Leu Ala Asn Ala Thr Glu Leu Glu Ser Leu Asp
            645                 650                 655 ctg tca aga aac caa ctc tct ggg act att cct aat gga ctc aag acc    2016
Leu Ser Arg Asn Gln Leu Ser Gly Thr Ile Pro Asn Gly Leu Lys Thr
        660                 665                 670 ctc tcg ttt ttg gca tac ata aat gta tct cac aat aaa ctc aag ggt    2064
Leu Ser Phe Leu Ala Tyr Ile Asn Val Ser His Asn Lys Leu Lys Gly
    675                 680                 685 gaa aac cac aag gaa cac aga tta ttg ggc aac ata aat cct cct ttg    2112
Glu Asn His Lys Glu His Arg Leu Leu Gly Asn Ile Asn Pro Pro Leu
690                 695                 700 aag gga atg cag ggc ttt gtg gtc ttc ctt tgg agg aaa ctt gct ctg    2160
Lys Gly Met Gln Gly Phe Val Val Phe Leu Trp Arg Lys Leu Ala Leu
705                 710                 715                 720 gaa aga atg cgc cgc caa cac aac aac cta agg aag aag acg aag aac    2208
Glu Arg Met Arg Arg Gln His Asn Asn Leu Arg Lys Lys Thr Lys Asn
                725                 730                 735 agg agc aag tgc tga                                                2223
Arg Ser Lys Cys
            740

<210> SEQ ID NO 2
<211> LENGTH: 740
<212> TYPE: PRT
<213> ORGANISM: Arabidopsis thaliana

<400> SEQUENCE: 2

Met Ser Gly Ser His Leu Arg Leu Arg Phe Leu Ser Leu Leu Leu Leu
1               5                   10                  15

Cys Cys Val Ser Ser Thr Ser Ser Leu Phe Thr Phe Ser Tyr Pro
            20                  25                  30

Val Leu Asp Leu Val Ala Cys Arg Ser His Gln Ile Gln Ala Phe Thr
        35                  40                  45

Gln Phe Lys Asn Glu Phe Asp Thr His Arg Cys Asn His Ser Asp His
    50                  55                  60

Ser Asn Gly Val Trp Cys Asp Asn Ser Thr Gly Val Val Thr Lys Leu
65                  70                  75                  80

Gln Leu Asn Ala Cys Leu Ser Gly Thr Leu Asn Pro Asn Ser Ser Leu
                85                  90                  95

Phe Trp Phe His Gln Leu Arg Phe Leu Asn Leu Ser His Asn Asn Phe
            100                 105                 110

Thr Ser Thr Ser Phe Pro Ser Glu Phe Gly Asn Leu Asn Lys Val Glu
        115                 120                 125

Val Leu Asp Leu Ser Phe Asn Ser Phe Thr Gly Gln Val Pro Ser Ser
    130                 135                 140

Phe Ser Asn Leu Ser Gln Leu Thr Glu Leu His Leu Ser Asn Asn Gln
145                 150                 155                 160

Leu Thr Gly Gly Phe Pro Gln Val Gln Asn Leu Thr Asn Leu Ser His
                165                 170                 175

Leu Asp Phe Glu Asn Asn Lys Phe Ser Gly Thr Val Pro Ser Ser Leu
            180                 185                 190

Leu Met Met Pro Phe Leu Ser Tyr Leu Asn Leu Tyr Gly Asn His Phe
        195                 200                 205

Thr Gly Ser Ile Glu Val Ser Ser Ser Lys Leu Glu Ile Leu Tyr
    210                 215                 220
```

```
Leu Gly Leu Lys Pro Phe Glu Gly Gln Ile Leu Glu Pro Ile Ser Lys
225                 230                 235                 240

Leu Ile Asn Leu Lys Arg Leu Glu Leu Ser Phe Leu Asn Ile Ser Tyr
                245                 250                 255

Pro Leu Asp Leu Asn Leu Phe Ser Ser Leu Lys Ser Leu Thr Tyr Leu
            260                 265                 270

Asp Leu Ser Gly Asn Ser Ile Ser Pro Arg Ser Leu Arg Ser Asp Leu
        275                 280                 285

Tyr Ile Pro Leu Thr Leu Glu Lys Leu Leu Leu Glu Gln Cys Gly Ile
    290                 295                 300

Ile Glu Phe Pro Asn Ile Leu Lys Thr Leu Gln Lys Leu Glu Tyr Ile
305                 310                 315                 320

Asp Met Ser Asn Asn Arg Ile Asn Gly Lys Ile Pro Glu Trp Leu Trp
                325                 330                 335

Arg Leu Pro Arg Leu Arg Ser Met Ser Leu Ala Asn Asn Ser Phe Asn
            340                 345                 350

Gly Phe Glu Gly Ser Thr Asp Val Leu Val Asn Ser Ser Met Glu Ile
        355                 360                 365

Leu Phe Met His Ser Asn Asn Ile Gln Gly Ala Leu Pro Asn Leu Pro
    370                 375                 380

Leu Ser Ile Lys Ala Phe Ser Ala Gly Tyr Asn Asn Phe Ser Gly Glu
385                 390                 395                 400

Ile Pro Leu Ser Ile Cys Asn Arg Ser Ser Leu Ala Ala Leu Ser Leu
                405                 410                 415

Pro Tyr Asn Asn Phe Thr Gly Lys Ile Pro Gln Cys Leu Ser Asn Leu
            420                 425                 430

Thr Phe Val His Leu Arg Lys Asn Asn Leu Glu Gly Ser Ile Pro Asp
        435                 440                 445

Thr Leu Cys Ala Gly Asp Ser Leu Gln Thr Leu Asp Ile Gly Phe Asn
    450                 455                 460

Leu Ile Ser Gly Thr Leu Pro Arg Ser Leu Leu Asn Cys Ser Ser Leu
465                 470                 475                 480

Glu Phe Leu Ser Val Asp Asn Asn Arg Ile Lys Asp Thr Phe Pro Phe
                485                 490                 495

Trp Leu Lys Ala Leu Pro Asn Leu Gln Val Leu Ile Leu Ser Ser Asn
            500                 505                 510

Lys Leu Tyr Gly Pro Ile Ala Pro His Gln Ser Pro Leu Ala Phe
        515                 520                 525

Pro Glu Leu Arg Ile Phe Glu Ile Ala Asp Asn Met Phe Thr Gly Thr
    530                 535                 540

Leu Ser Pro Arg Tyr Phe Val Asn Trp Lys Thr Ser Ser Leu Thr Val
545                 550                 555                 560

Asn Glu Asp Gly Asp Leu Tyr Met Val Tyr Lys Asn Asn Ala Phe Gly
                565                 570                 575

Ile Asp Ser Tyr Val Tyr Arg Asp Thr Ile Asp Met Lys Tyr Lys Gly
            580                 585                 590

Leu Ser Met Glu Gln Gln Met Val Leu Asn Ser Tyr Ser Ala Ile Asp
        595                 600                 605

Phe Ser Gly Asn Arg Leu Glu Gly Gln Ile Pro Lys Ser Ile Gly Leu
    610                 615                 620

Leu Lys Glu Leu Ile Ala Leu Asn Leu Ser Asn Asn Ala Phe Thr Cys
625                 630                 635                 640
```

```
His Ile Pro Leu Ser Leu Ala Asn Ala Thr Glu Leu Glu Ser Leu Asp
                645                 650                 655

Leu Ser Arg Asn Gln Leu Ser Gly Thr Ile Pro Asn Gly Leu Lys Thr
        660                 665                 670

Leu Ser Phe Leu Ala Tyr Ile Asn Val Ser His Asn Lys Leu Lys Gly
    675                 680                 685

Glu Asn His Lys Glu His Arg Leu Leu Gly Asn Ile Asn Pro Pro Leu
690                 695                 700

Lys Gly Met Gln Gly Phe Val Val Phe Leu Trp Arg Lys Leu Ala Leu
705                 710                 715                 720

Glu Arg Met Arg Arg Gln His Asn Asn Leu Arg Lys Lys Thr Lys Asn
                725                 730                 735

Arg Ser Lys Cys
            740

<210> SEQ ID NO 3
<211> LENGTH: 1776
<212> TYPE: DNA
<213> ORGANISM: Arabidopsis thaliana
<220> FEATURE:
<221> NAME/KEY: CDS
<222> LOCATION: (1)..(1776)

<400> SEQUENCE: 3 atg aaa acg atc tca atc ttc ttc gtc atc atc tta atg tca tct tct      48
Met Lys Thr Ile Ser Ile Phe Phe Val Ile Ile Leu Met Ser Ser Ser
1               5                   10                  15 cac gca gaa gac gat gta ctc tgt ctc aaa ggc ttt aaa tca tca ctc      96
His Ala Glu Asp Asp Val Leu Cys Leu Lys Gly Phe Lys Ser Ser Leu
            20                  25                  30 aaa gat cct tca aat caa ctc aac aca tgg tct ttc cct aat tca tca     144
Lys Asp Pro Ser Asn Gln Leu Asn Thr Trp Ser Phe Pro Asn Ser Ser
        35                  40                  45 tcg tcg att tgc aaa ctc acc gga gtt tct tgc tgg aac gct aaa gag     192
Ser Ser Ile Cys Lys Leu Thr Gly Val Ser Cys Trp Asn Ala Lys Glu
    50                  55                  60 aat cga att ctc tct ctt cag ctt caa tca atg caa ctc tct ggt caa     240
Asn Arg Ile Leu Ser Leu Gln Leu Gln Ser Met Gln Leu Ser Gly Gln
65                  70                  75                  80 atc cct gaa tct ctt aaa cta tgt cgg agt tta caa tct tta gat ctt     288
Ile Pro Glu Ser Leu Lys Leu Cys Arg Ser Leu Gln Ser Leu Asp Leu
                85                  90                  95 tcc ttt aat gat ttc tcc ggt ttg att cct tca caa ata tgt tct tgg     336
Ser Phe Asn Asp Phe Ser Gly Leu Ile Pro Ser Gln Ile Cys Ser Trp
            100                 105                 110 ctt cct tat ctt gtt act tta gat ctt tcc ggt aac aaa ctc tcc ggt     384
Leu Pro Tyr Leu Val Thr Leu Asp Leu Ser Gly Asn Lys Leu Ser Gly
        115                 120                 125 tcg ata ccg tct cag atc gtt gac tgt aaa ttc tta aac agc tta gct     432
Ser Ile Pro Ser Gln Ile Val Asp Cys Lys Phe Leu Asn Ser Leu Ala
    130                 135                 140 cta aac cag aac aag tta acc ggt tcg att ccg tct gaa tta acc cgg     480
Leu Asn Gln Asn Lys Leu Thr Gly Ser Ile Pro Ser Glu Leu Thr Arg
145                 150                 155                 160 tta aac cgt ctc caa cga ctt tct cta gct gat aac gat ctc tct ggt     528
Leu Asn Arg Leu Gln Arg Leu Ser Leu Ala Asp Asn Asp Leu Ser Gly
                165                 170                 175 tcg att ccc tcc gag cta tct cat tac gga gaa gat ggt ttt cgc ggt     576
Ser Ile Pro Ser Glu Leu Ser His Tyr Gly Glu Asp Gly Phe Arg Gly
            180                 185                 190
```

```
aat ggc gga ctt tgt ggt aag ccg tta tcc aac tgc ggt tcg ttt aac        624
Asn Gly Gly Leu Cys Gly Lys Pro Leu Ser Asn Cys Gly Ser Phe Asn
            195                 200                 205 ggt aaa aac tta acg atc att gta act gct ggc gtt att gga gct gtt        672
Gly Lys Asn Leu Thr Ile Ile Val Thr Ala Gly Val Ile Gly Ala Val
    210                 215                 220 ggt tca ttg tgt gtt gga ttt ggg atg ttt tgg tgg ttc ttt att aga        720
Gly Ser Leu Cys Val Gly Phe Gly Met Phe Trp Trp Phe Phe Ile Arg
225                 230                 235                 240 gat agg agg aag atg aat aac tac ggt tat ggc gcc gga aaa tgt aag        768
Asp Arg Arg Lys Met Asn Asn Tyr Gly Tyr Gly Ala Gly Lys Cys Lys
                245                 250                 255 gat gat agt gat tgg att ggt ttg ttg aga tca cat aag ctt gtg caa        816
Asp Asp Ser Asp Trp Ile Gly Leu Leu Arg Ser His Lys Leu Val Gln
            260                 265                 270 gtt act ctg ttt cag aaa cct att gtg aag atc aaa ttg gtt gat ttg        864
Val Thr Leu Phe Gln Lys Pro Ile Val Lys Ile Lys Leu Val Asp Leu
        275                 280                 285 att gaa gct acg aac ggt ttt gat tcc ggg aat atc gtt gtt tcg tcg        912
Ile Glu Ala Thr Asn Gly Phe Asp Ser Gly Asn Ile Val Val Ser Ser
    290                 295                 300 aga agt ggt gtc tcg tac aaa gct gat ttg cct gat ggg tct aca ttg        960
Arg Ser Gly Val Ser Tyr Lys Ala Asp Leu Pro Asp Gly Ser Thr Leu
305                 310                 315                 320 gag gtt aag agg ctt agt agt tgt tgt gag ctt agt gag aaa cag ttt       1008
Glu Val Lys Arg Leu Ser Ser Cys Cys Glu Leu Ser Glu Lys Gln Phe
                325                 330                 335 agg tct gag att aac aag tta ggt cag atc agg cat ccg aat ttg gtt       1056
Arg Ser Glu Ile Asn Lys Leu Gly Gln Ile Arg His Pro Asn Leu Val
            340                 345                 350 ccg ctt ctc ggg ttt tgc gtt gtg gaa gac gag ata ttg ttg gtg tat       1104
Pro Leu Leu Gly Phe Cys Val Val Glu Asp Glu Ile Leu Leu Val Tyr
        355                 360                 365 aag cat atg gct aat ggg acg ttg tat tct cag ctg cag caa tgg gat       1152
Lys His Met Ala Asn Gly Thr Leu Tyr Ser Gln Leu Gln Gln Trp Asp
    370                 375                 380 att gat tgg cca act cgg gtt aga gtc gct gtt gga gcg gct aga ggg       1200
Ile Asp Trp Pro Thr Arg Val Arg Val Ala Val Gly Ala Ala Arg Gly
385                 390                 395                 400 cta gct tgg ttg cac cat gga tgt caa ccg ttg tat atg cat caa tat       1248
Leu Ala Trp Leu His His Gly Cys Gln Pro Leu Tyr Met His Gln Tyr
                405                 410                 415 atc agc tca aat gtg att ctt ctt gac gaa gat ttc gat gct cgt gtt       1296
Ile Ser Ser Asn Val Ile Leu Leu Asp Glu Asp Phe Asp Ala Arg Val
            420                 425                 430 att gat tac ggt ttg ggg aag tta gtg agt tct caa gac tct aaa gat       1344
Ile Asp Tyr Gly Leu Gly Lys Leu Val Ser Ser Gln Asp Ser Lys Asp
        435                 440                 445 agc tcg ttt agt aac ggc aag ttt ggt tac gtt gcg cct gag tat tcg       1392
Ser Ser Phe Ser Asn Gly Lys Phe Gly Tyr Val Ala Pro Glu Tyr Ser
    450                 455                 460 agc act atg gtt gcg tct ttg agt gga gat gtg tat ggg ttt ggg att       1440
Ser Thr Met Val Ala Ser Leu Ser Gly Asp Val Tyr Gly Phe Gly Ile
465                 470                 475                 480 gtg ctt ctt gag att gtt aca gga caa aag cct gtt ttg att aac aac       1488
Val Leu Leu Glu Ile Val Thr Gly Gln Lys Pro Val Leu Ile Asn Asn
                485                 490                 495 ggt gaa gaa ggg ttt aag gag agt tta gtg gag tgg gtg agt aag cat       1536
Gly Glu Glu Gly Phe Lys Glu Ser Leu Val Glu Trp Val Ser Lys His
```

```
                    500             505             510
ttg agt aat ggt aga agc aaa gat gct att gat aga agg att ttt ggt    1584
Leu Ser Asn Gly Arg Ser Lys Asp Ala Ile Asp Arg Arg Ile Phe Gly
        515                 520                 525 aaa gga tat gat gat gag ata atg caa gtt ttg aga att gcg tgt agt    1632
Lys Gly Tyr Asp Asp Glu Ile Met Gln Val Leu Arg Ile Ala Cys Ser
530                 535                 540 tgc gtt gta tcg agg cct aaa gaa aga ccg ttg atg atc caa gtt tat    1680
Cys Val Val Ser Arg Pro Lys Glu Arg Pro Leu Met Ile Gln Val Tyr
545                 550                 555                 560 gaa tct ttg aag aat ttg gga gat caa cat ggt ttc ttc tct gag tat    1728
Glu Ser Leu Lys Asn Leu Gly Asp Gln His Gly Phe Phe Ser Glu Tyr
            565                 570                 575 agc gat gag ttt cca ctc atc ttt aac aaa caa gaa cac tta aaa tga    1776
Ser Asp Glu Phe Pro Leu Ile Phe Asn Lys Gln Glu His Leu Lys
        580                 585                 590
```

<210> SEQ ID NO 4
<211> LENGTH: 591
<212> TYPE: PRT
<213> ORGANISM: Arabidopsis thaliana

<400> SEQUENCE: 4

```
Met Lys Thr Ile Ser Ile Phe Phe Val Ile Ile Leu Met Ser Ser Ser
1               5                   10                  15

His Ala Glu Asp Asp Val Leu Cys Leu Lys Gly Phe Lys Ser Ser Leu
            20                  25                  30

Lys Asp Pro Ser Asn Gln Leu Asn Thr Trp Ser Phe Pro Asn Ser Ser
        35                  40                  45

Ser Ser Ile Cys Lys Leu Thr Gly Val Ser Cys Trp Asn Ala Lys Glu
    50                  55                  60

Asn Arg Ile Leu Ser Leu Gln Leu Gln Ser Met Gln Leu Ser Gly Gln
65                  70                  75                  80

Ile Pro Glu Ser Leu Lys Leu Cys Arg Ser Leu Gln Ser Leu Asp Leu
                85                  90                  95

Ser Phe Asn Asp Phe Ser Gly Leu Ile Pro Ser Gln Ile Cys Ser Trp
            100                 105                 110

Leu Pro Tyr Leu Val Thr Leu Asp Leu Ser Gly Asn Lys Leu Ser Gly
        115                 120                 125

Ser Ile Pro Ser Gln Ile Val Asp Cys Lys Phe Leu Asn Ser Leu Ala
    130                 135                 140

Leu Asn Gln Asn Lys Leu Thr Gly Ser Ile Pro Ser Glu Leu Thr Arg
145                 150                 155                 160

Leu Asn Arg Leu Gln Arg Leu Ser Leu Ala Asp Asn Asp Leu Ser Gly
                165                 170                 175

Ser Ile Pro Ser Glu Leu Ser His Tyr Gly Glu Asp Gly Phe Arg Gly
            180                 185                 190

Asn Gly Gly Leu Cys Gly Lys Pro Leu Ser Asn Cys Gly Ser Phe Asn
        195                 200                 205

Gly Lys Asn Leu Thr Ile Ile Val Thr Ala Gly Val Ile Gly Ala Val
    210                 215                 220

Gly Ser Leu Cys Val Gly Phe Gly Met Phe Trp Trp Phe Phe Ile Arg
225                 230                 235                 240

Asp Arg Arg Lys Met Asn Asn Tyr Gly Tyr Gly Ala Gly Lys Cys Lys
                245                 250                 255

Asp Asp Ser Asp Trp Ile Gly Leu Leu Arg Ser His Lys Leu Val Gln
```

```
              260                 265                 270
Val Thr Leu Phe Gln Lys Pro Ile Val Lys Ile Lys Leu Val Asp Leu
        275                 280                 285

Ile Glu Ala Thr Asn Gly Phe Asp Ser Gly Asn Ile Val Val Ser Ser
        290                 295                 300

Arg Ser Gly Val Ser Tyr Lys Ala Asp Leu Pro Asp Gly Ser Thr Leu
305                 310                 315                 320

Glu Val Lys Arg Leu Ser Ser Cys Cys Glu Leu Ser Glu Lys Gln Phe
                325                 330                 335

Arg Ser Glu Ile Asn Lys Leu Gly Gln Ile Arg His Pro Asn Leu Val
                340                 345                 350

Pro Leu Leu Gly Phe Cys Val Glu Asp Glu Ile Leu Leu Val Tyr
        355                 360                 365

Lys His Met Ala Asn Gly Thr Leu Tyr Ser Gln Leu Gln Gln Trp Asp
        370                 375                 380

Ile Asp Trp Pro Thr Arg Val Arg Val Ala Val Gly Ala Ala Arg Gly
385                 390                 395                 400

Leu Ala Trp Leu His His Gly Cys Gln Pro Leu Tyr Met His Gln Tyr
                405                 410                 415

Ile Ser Ser Asn Val Ile Leu Leu Asp Glu Asp Phe Asp Ala Arg Val
                420                 425                 430

Ile Asp Tyr Gly Leu Gly Lys Leu Val Ser Ser Gln Asp Ser Lys Asp
        435                 440                 445

Ser Ser Phe Ser Asn Gly Lys Phe Gly Tyr Val Ala Pro Glu Tyr Ser
        450                 455                 460

Ser Thr Met Val Ala Ser Leu Ser Gly Asp Val Tyr Gly Phe Gly Ile
465                 470                 475                 480

Val Leu Leu Glu Ile Val Thr Gly Gln Lys Pro Val Leu Ile Asn Asn
                485                 490                 495

Gly Glu Glu Gly Phe Lys Glu Ser Leu Val Glu Trp Val Ser Lys His
            500                 505                 510

Leu Ser Asn Gly Arg Ser Lys Asp Ala Ile Asp Arg Arg Ile Phe Gly
        515                 520                 525

Lys Gly Tyr Asp Asp Glu Ile Met Gln Val Leu Arg Ile Ala Cys Ser
        530                 535                 540

Cys Val Val Ser Arg Pro Lys Glu Arg Pro Leu Met Ile Gln Val Tyr
545                 550                 555                 560

Glu Ser Leu Lys Asn Leu Gly Asp Gln His Gly Phe Phe Ser Glu Tyr
                565                 570                 575

Ser Asp Glu Phe Pro Leu Ile Phe Asn Lys Gln Glu His Leu Lys
            580                 585                 590

<210> SEQ ID NO 5
<211> LENGTH: 1509
<212> TYPE: DNA
<213> ORGANISM: Arabidopsis thaliana
<220> FEATURE:
<221> NAME/KEY: CDS
<222> LOCATION: (1)..(1509)

<400> SEQUENCE: 5 atg aag atc tct ctt ttt ttt gct ttc aat gct ctc atg tta ctt caa    48
Met Lys Ile Ser Leu Phe Phe Ala Phe Asn Ala Leu Met Leu Leu Gln
1               5                   10                  15 gtt tgc atc tta gtt ttt gct caa gct agg ttt tca aat gag act gat    96
Val Cys Ile Leu Val Phe Ala Gln Ala Arg Phe Ser Asn Glu Thr Asp
```

```
            20                  25                  30
atg caa gct ttg ctt gag ttc aag tct caa gtt act gaa aac aag aga    144
Met Gln Ala Leu Leu Glu Phe Lys Ser Gln Val Thr Glu Asn Lys Arg
        35                  40                  45 gag gtc tta gct tca tgg aat cac tcc ttt cca ctt tgc cat tgg att    192
Glu Val Leu Ala Ser Trp Asn His Ser Phe Pro Leu Cys His Trp Ile
50                  55                  60 ggg att aca tgt ggt cgg aaa caa gaa aga gtt aca agt cta gac ctt    240
Gly Ile Thr Cys Gly Arg Lys Gln Glu Arg Val Thr Ser Leu Asp Leu
65                  70                  75                  80 gga gga ttc aaa ttg tcc ggt tcg atc tca cct tct att ggt aat ctc    288
Gly Gly Phe Lys Leu Ser Gly Ser Ile Ser Pro Ser Ile Gly Asn Leu
                85                  90                  95 tca ttt ctc aga tca ctt aat ctt ggt gac aac tct ttt caa agt aat    336
Ser Phe Leu Arg Ser Leu Asn Leu Gly Asp Asn Ser Phe Gln Ser Asn
            100                 105                 110 atc cct caa gag ttc gaa gga agc gta cca acg aaa gga gtt ttt caa    384
Ile Pro Gln Glu Phe Glu Gly Ser Val Pro Thr Lys Gly Val Phe Gln
        115                 120                 125 aac ggt aca aca gtt tct gtc ttt gga aat gaa aat cta tgt gga ggc    432
Asn Gly Thr Thr Val Ser Val Phe Gly Asn Glu Asn Leu Cys Gly Gly
130                 135                 140 gtc ata gaa atg caa cta aag cca tgc att gaa tca cca agg cag aaa    480
Val Ile Glu Met Gln Leu Lys Pro Cys Ile Glu Ser Pro Arg Gln Lys
145                 150                 155                 160 aag cct ttc tca ctt gga gag aaa gtt gcc gtt ggt gta ggt gta gct    528
Lys Pro Phe Ser Leu Gly Glu Lys Val Ala Val Gly Val Gly Val Ala
                165                 170                 175 ttg ctt ttt tta ttc ata att gtg gct tct ttg tct tgg ttc aag aag    576
Leu Leu Phe Leu Phe Ile Ile Val Ala Ser Leu Ser Trp Phe Lys Lys
            180                 185                 190 aag aac gat aag ata agt tat gaa gag ctt tat aat gca aca agt ggc    624
Lys Asn Asp Lys Ile Ser Tyr Glu Glu Leu Tyr Asn Ala Thr Ser Gly
        195                 200                 205 ttc tct tca agc aat cta att ggt tca ggc aac ttc agt gat gtg ttt    672
Phe Ser Ser Ser Asn Leu Ile Gly Ser Gly Asn Phe Ser Asp Val Phe
210                 215                 220 aaa gga ttg ctt ggc ctc gag gaa aaa ctc gtc gcg gtt aaa gtt ttg    720
Lys Gly Leu Leu Gly Leu Glu Glu Lys Leu Val Ala Val Lys Val Leu
225                 230                 235                 240 aac ctc ctg aaa cat gga gca aca aaa agc ttt ata gcg gaa tgt gaa    768
Asn Leu Leu Lys His Gly Ala Thr Lys Ser Phe Ile Ala Glu Cys Glu
                245                 250                 255 tct ttc aaa ggt att agg cac cgt aac ctt gcg aaa ctg ata aca gtt    816
Ser Phe Lys Gly Ile Arg His Arg Asn Leu Ala Lys Leu Ile Thr Val
            260                 265                 270 tgc tca agc ctt gat tcc caa gga aat gat ttc aga gct tta gtc tat    864
Cys Ser Ser Leu Asp Ser Gln Gly Asn Asp Phe Arg Ala Leu Val Tyr
        275                 280                 285 gag ttc atg cca aaa gga agt cta gat atg tgg cta cag cca gaa gat    912
Glu Phe Met Pro Lys Gly Ser Leu Asp Met Trp Leu Gln Pro Glu Asp
290                 295                 300 ttg gaa agt gca aac aat cac tca agg tct tta aca ttt gca gag aaa    960
Leu Glu Ser Ala Asn Asn His Ser Arg Ser Leu Thr Phe Ala Glu Lys
305                 310                 315                 320 gtc aac ata gca ata gat gtg gct tct gct ttg gag tat ctg cat gtt    1008
Val Asn Ile Ala Ile Asp Val Ala Ser Ala Leu Glu Tyr Leu His Val
                325                 330                 335 tat tgt cat gac cct gtc gct cat tgt gat att aag cca agc aac gtt    1056
```

```
Tyr Cys His Asp Pro Val Ala His Cys Asp Ile Lys Pro Ser Asn Val
            340                 345                 350 ctt cta gac gat gat ttg acg gct cat gtt agt gac ttt ggt ttg gct      1104
Leu Leu Asp Asp Asp Leu Thr Ala His Val Ser Asp Phe Gly Leu Ala
            355                 360                 365 cgg ctc ctt tat aat ttc gat gag aaa acc ttt cta aac cag ttc agt      1152
Arg Leu Leu Tyr Asn Phe Asp Glu Lys Thr Phe Leu Asn Gln Phe Ser
370                 375                 380 tct gcc ggt gtg aga ggt acc att ggc tat gcc gca cca gaa tat gga      1200
Ser Ala Gly Val Arg Gly Thr Ile Gly Tyr Ala Ala Pro Glu Tyr Gly
385                 390                 395                 400 atg gga agc aaa cca tca ata caa gga gat gtt tac agc ttt gga gtt      1248
Met Gly Ser Lys Pro Ser Ile Gln Gly Asp Val Tyr Ser Phe Gly Val
                405                 410                 415 tta ctt ttg gag atg ttc act ggg aaa aaa ccg aca gac aat tca ttt      1296
Leu Leu Leu Glu Met Phe Thr Gly Lys Lys Pro Thr Asp Asn Ser Phe
            420                 425                 430 ggt ggc ggt tat aac ctc cac ggc tac aca aag tcg gta ttg tcg tgt      1344
Gly Gly Gly Tyr Asn Leu His Gly Tyr Thr Lys Ser Val Leu Ser Cys
            435                 440                 445 tcc acg agc aga gga ggc aga acc atg gtt gat gag tgg ttg aga cta      1392
Ser Thr Ser Arg Gly Gly Arg Thr Met Val Asp Glu Trp Leu Arg Leu
450                 455                 460 gtt ttg gaa gtg gga ata aag tgt tct gaa gaa tat cca cgg gat agg      1440
Val Leu Glu Val Gly Ile Lys Cys Ser Glu Glu Tyr Pro Arg Asp Arg
465                 470                 475                 480 atg gga atg gct gaa gcg gta cga gaa tta gtc tca atc aaa tct aag      1488
Met Gly Met Ala Glu Ala Val Arg Glu Leu Val Ser Ile Lys Ser Lys
                485                 490                 495 ttc ttt act tcc tct cga tga                                          1509
Phe Phe Thr Ser Ser Arg
            500

<210> SEQ ID NO 6
<211> LENGTH: 502
<212> TYPE: PRT
<213> ORGANISM: Arabidopsis thaliana

<400> SEQUENCE: 6

Met Lys Ile Ser Leu Phe Phe Ala Phe Asn Ala Leu Met Leu Leu Gln
1               5                   10                  15

Val Cys Ile Leu Val Phe Ala Gln Ala Arg Phe Ser Asn Glu Thr Asp
            20                  25                  30

Met Gln Ala Leu Leu Glu Phe Lys Ser Gln Val Thr Glu Asn Lys Arg
        35                  40                  45

Glu Val Leu Ala Ser Trp Asn His Ser Phe Pro Leu Cys His Trp Ile
    50                  55                  60

Gly Ile Thr Cys Gly Arg Lys Gln Glu Arg Val Thr Ser Leu Asp Leu
65                  70                  75                  80

Gly Gly Phe Lys Leu Ser Gly Ser Ile Ser Pro Ser Ile Gly Asn Leu
                85                  90                  95

Ser Phe Leu Arg Ser Leu Asn Leu Gly Asp Asn Ser Phe Gln Ser Asn
            100                 105                 110

Ile Pro Gln Glu Phe Glu Gly Ser Val Pro Thr Lys Gly Val Phe Gln
        115                 120                 125

Asn Gly Thr Thr Val Ser Val Phe Gly Asn Glu Asn Leu Cys Gly Gly
    130                 135                 140

Val Ile Glu Met Gln Leu Lys Pro Cys Ile Glu Ser Pro Arg Gln Lys
```

```
                145                 150                 155                 160
Lys Pro Phe Ser Leu Gly Glu Lys Val Ala Val Gly Val Ala
            165                 170                 175

Leu Leu Phe Leu Phe Ile Ile Val Ala Ser Leu Ser Trp Phe Lys Lys
            180                 185                 190

Lys Asn Asp Lys Ile Ser Tyr Glu Glu Leu Tyr Asn Ala Thr Ser Gly
            195                 200                 205

Phe Ser Ser Ser Asn Leu Ile Gly Ser Gly Asn Phe Ser Asp Val Phe
210                 215                 220

Lys Gly Leu Leu Gly Leu Glu Glu Lys Leu Val Ala Val Lys Val Leu
225                 230                 235                 240

Asn Leu Leu Lys His Gly Ala Thr Lys Ser Phe Ile Ala Glu Cys Glu
            245                 250                 255

Ser Phe Lys Gly Ile Arg His Arg Asn Leu Ala Lys Leu Ile Thr Val
            260                 265                 270

Cys Ser Ser Leu Asp Ser Gln Gly Asn Asp Phe Arg Ala Leu Val Tyr
            275                 280                 285

Glu Phe Met Pro Lys Gly Ser Leu Asp Met Trp Leu Gln Pro Glu Asp
290                 295                 300

Leu Glu Ser Ala Asn Asn His Ser Arg Ser Leu Thr Phe Ala Glu Lys
305                 310                 315                 320

Val Asn Ile Ala Ile Asp Val Ala Ser Ala Leu Glu Tyr Leu His Val
            325                 330                 335

Tyr Cys His Asp Pro Val Ala His Cys Asp Ile Lys Pro Ser Asn Val
            340                 345                 350

Leu Leu Asp Asp Asp Leu Thr Ala His Val Ser Asp Phe Gly Leu Ala
            355                 360                 365

Arg Leu Leu Tyr Asn Phe Asp Glu Lys Thr Phe Leu Asn Gln Phe Ser
            370                 375                 380

Ser Ala Gly Val Arg Gly Thr Ile Gly Tyr Ala Ala Pro Glu Tyr Gly
385                 390                 395                 400

Met Gly Ser Lys Pro Ser Ile Gln Gly Asp Val Tyr Ser Phe Gly Val
            405                 410                 415

Leu Leu Leu Glu Met Phe Thr Gly Lys Lys Pro Thr Asp Asn Ser Phe
            420                 425                 430

Gly Gly Gly Tyr Asn Leu His Gly Tyr Thr Lys Ser Val Leu Ser Cys
            435                 440                 445

Ser Thr Ser Arg Gly Gly Arg Thr Met Val Asp Glu Trp Leu Arg Leu
450                 455                 460

Val Leu Glu Val Gly Ile Lys Cys Ser Glu Glu Tyr Pro Arg Asp Arg
465                 470                 475                 480

Met Gly Met Ala Glu Ala Val Arg Glu Leu Val Ser Ile Lys Ser Lys
            485                 490                 495

Phe Phe Thr Ser Ser Arg
            500

<210> SEQ ID NO 7
<211> LENGTH: 3579
<212> TYPE: DNA
<213> ORGANISM: Oryza sativa
<220> FEATURE:
<221> NAME/KEY: CDS
<222> LOCATION: (1)..(3579)

<400> SEQUENCE: 7
```

```
-continued atg gct ttc ata gtt tgg gca cta cta ctc ttc ctt tta cat ctt ccc         48
Met Ala Phe Ile Val Trp Ala Leu Leu Leu Phe Leu Leu His Leu Pro
1               5                   10                  15 aca ata gcg acc gga tcc agt gcc cac ttt ggc ggt aac aac act gtt         96
Thr Ile Ala Thr Gly Ser Ser Ala His Phe Gly Gly Asn Asn Thr Val
            20                  25                  30 agg tgc cat cca aac cag gct gca gcg ctc ctc cag cta aag caa tct        144
Arg Cys His Pro Asn Gln Ala Ala Ala Leu Leu Gln Leu Lys Gln Ser
        35                  40                  45 ttc ttc tgg gtt aat tct ccg gtc atc ctt ccg aca tgg caa gat gga        192
Phe Phe Trp Val Asn Ser Pro Val Ile Leu Pro Thr Trp Gln Asp Gly
    50                  55                  60 acc gat tgt tgt acc tgg gag gga gtt ggc tgc gat gct tct tct cat        240
Thr Asp Cys Cys Thr Trp Glu Gly Val Gly Cys Asp Ala Ser Ser His
65              70                  75                  80 ctt gtc acg gta ctt gat ctc agt ggg cgg ggc atg tac agt gat agt        288
Leu Val Thr Val Leu Asp Leu Ser Gly Arg Gly Met Tyr Ser Asp Ser
            85                  90                  95 ttt gaa cct gca ctc ttc agt ctc aca tcc cta caa cgc cta gac ctt        336
Phe Glu Pro Ala Leu Phe Ser Leu Thr Ser Leu Gln Arg Leu Asp Leu
        100                 105                 110 agc atg aat tcc ttg ggt acc agc agt acc acc aaa gat gct gaa ttc        384
Ser Met Asn Ser Leu Gly Thr Ser Ser Thr Thr Lys Asp Ala Glu Phe
    115                 120                 125 gat agg ctc act tcg ctc acc cac ctc aac ctc tcc aat tcg ggc ttg        432
Asp Arg Leu Thr Ser Leu Thr His Leu Asn Leu Ser Asn Ser Gly Leu
130                 135                 140 gat ggt cag ata cct atg ggc atc aac aaa ctc att aac ctt gtg tcc        480
Asp Gly Gln Ile Pro Met Gly Ile Asn Lys Leu Ile Asn Leu Val Ser
145                 150                 155                 160 ttg gac ctt tcc aag cgc tat gtt aac gat aac agt gat atc tct ttt        528
Leu Asp Leu Ser Lys Arg Tyr Val Asn Asp Asn Ser Asp Ile Ser Phe
            165                 170                 175 aat gag agt gat gat gag att atc ttt aca ggt gac agt tat aat cat        576
Asn Glu Ser Asp Asp Glu Ile Ile Phe Thr Gly Asp Ser Tyr Asn His
        180                 185                 190 ctg cag gaa tcc agg tta atg tcc cta gta gaa aac cta agc aat ttg        624
Leu Gln Glu Ser Arg Leu Met Ser Leu Val Glu Asn Leu Ser Asn Leu
    195                 200                 205 aaa gag ctc tac ctc gac cat gtg gat atg tct aca aat gta gat gac        672
Lys Glu Leu Tyr Leu Asp His Val Asp Met Ser Thr Asn Val Asp Asp
210                 215                 220 tgg tgc aaa acc ctt gct caa tca gtt cct cgt ctt cag gta ctt agt        720
Trp Cys Lys Thr Leu Ala Gln Ser Val Pro Arg Leu Gln Val Leu Ser
225                 230                 235                 240 tta gat ggt tgc tct ctc aac act cct att cat cac tcc ctt ttg agg        768
Leu Asp Gly Cys Ser Leu Asn Thr Pro Ile His His Ser Leu Leu Arg
            245                 250                 255 ctc cat tct ctc aca gtg ata aat ctt cag tcc aac cct ggt ata gct        816
Leu His Ser Leu Thr Val Ile Asn Leu Gln Ser Asn Pro Gly Ile Ala
        260                 265                 270 gtc aat cta ttt cca gat ttc ttc atg ggt ttc gcc aat tta act gtg        864
Val Asn Leu Phe Pro Asp Phe Phe Met Gly Phe Ala Asn Leu Thr Val
    275                 280                 285 ctc cga ctt tct cat aat aat ctc gaa ggg tgg ttt cct gac aaa ttc        912
Leu Arg Leu Ser His Asn Asn Leu Glu Gly Trp Phe Pro Asp Lys Phe
290                 295                 300 ttc caa ctg aaa aat cta aga atc ctc gat ttg tcc ttt aat atg aat        960
Phe Gln Leu Lys Asn Leu Arg Ile Leu Asp Leu Ser Phe Asn Met Asn
305                 310                 315                 320
```

```
ctg tta ggg cat ttg cca aaa gtt cca acc tct ttg gag aca ttg aga    1008
Leu Leu Gly His Leu Pro Lys Val Pro Thr Ser Leu Glu Thr Leu Arg
                325             330                 335 cta gag ggg acc aac ttt tcc tat gct aaa cga att tct tct agc aat    1056
Leu Glu Gly Thr Asn Phe Ser Tyr Ala Lys Arg Ile Ser Ser Ser Asn
            340                 345                 350 ttc aat atg ctg aag gag ttg ggt ctt gaa ggg aaa tta att tct aag    1104
Phe Asn Met Leu Lys Glu Leu Gly Leu Glu Gly Lys Leu Ile Ser Lys
        355                 360                 365 gat ttt ctc acg tcg ttt ggt ttg atc tgg tct tta tgc cat cta gaa    1152
Asp Phe Leu Thr Ser Phe Gly Leu Ile Trp Ser Leu Cys His Leu Glu
    370                 375                 380 ctc ctt aat tcg gaa ttg tta gga gat tca gga tcc aat ttg ttg tca    1200
Leu Leu Asn Ser Glu Leu Leu Gly Asp Ser Gly Ser Asn Leu Leu Ser
385                 390                 395                 400 tgg ata ggg gcc cac aag aac ttg aca tgc ttg ata cta tct gag ttt    1248
Trp Ile Gly Ala His Lys Asn Leu Thr Cys Leu Ile Leu Ser Glu Phe
                405                 410                 415 gac ttc tct agc aca aag cct tca tcc att agt aac ttc aag aat ttg    1296
Asp Phe Ser Ser Thr Lys Pro Ser Ser Ile Ser Asn Phe Lys Asn Leu
            420                 425                 430 aga agc ttg tgg ttg ttt ggc tgt aac ctc act agg cca ata atg tct    1344
Arg Ser Leu Trp Leu Phe Gly Cys Asn Leu Thr Arg Pro Ile Met Ser
        435                 440                 445 gca att ggt gat ctc gtg gac ttg caa agc ttg gat atg tca aac tgc    1392
Ala Ile Gly Asp Leu Val Asp Leu Gln Ser Leu Asp Met Ser Asn Cys
    450                 455                 460 aat aca tac agt tca atg cca tct tca ata ggc aat ctc aca aat tta    1440
Asn Thr Tyr Ser Ser Met Pro Ser Ser Ile Gly Asn Leu Thr Asn Leu
465                 470                 475                 480 aaa agc ttg tat atc aac agc cct ggg ttt tta ggg cca atg ccg gct    1488
Lys Ser Leu Tyr Ile Asn Ser Pro Gly Phe Leu Gly Pro Met Pro Ala
                485                 490                 495 gca att ggc aac ctc aaa agc ttg aag agc atg gta ttc tca aat tgt    1536
Ala Ile Gly Asn Leu Lys Ser Leu Lys Ser Met Val Phe Ser Asn Cys
            500                 505                 510 gaa ttt act ggg cca atg cca tcc aca att ggc aat ctc act aag ttg    1584
Glu Phe Thr Gly Pro Met Pro Ser Thr Ile Gly Asn Leu Thr Lys Leu
        515                 520                 525 cag acc ttg gaa att gca gct tgt cgg ttt tct gga cca ata cct tat    1632
Gln Thr Leu Glu Ile Ala Ala Cys Arg Phe Ser Gly Pro Ile Pro Tyr
    530                 535                 540 tca att gga caa ctt aag gaa ttg agg gcg tta ttt att gaa ggg tgc    1680
Ser Ile Gly Gln Leu Lys Glu Leu Arg Ala Leu Phe Ile Glu Gly Cys
545                 550                 555                 560 aat atg tct ggt aga ata cca aat tca att gtc aac atg agc aaa ctg    1728
Asn Met Ser Gly Arg Ile Pro Asn Ser Ile Val Asn Met Ser Lys Leu
                565                 570                 575 ata tat ttg ggg ctt cca gca aat tat ctg agc ggc aaa att cca gca    1776
Ile Tyr Leu Gly Leu Pro Ala Asn Tyr Leu Ser Gly Lys Ile Pro Ala
            580                 585                 590 cgg ctt ttc act ctt cca gca cta ctc ttc ttg gat ctt ttt ggt aat    1824
Arg Leu Phe Thr Leu Pro Ala Leu Leu Phe Leu Asp Leu Phe Gly Asn
        595                 600                 605 cat ttt tct ggt cct ata caa gag ttt gat gct gtg cct tca tat ctg    1872
His Phe Ser Gly Pro Ile Gln Glu Phe Asp Ala Val Pro Ser Tyr Leu
    610                 615                 620 atg agt ttg cag ttg acc agc aac gaa ttg aca gga gag ttt ccc aag    1920
Met Ser Leu Gln Leu Thr Ser Asn Glu Leu Thr Gly Glu Phe Pro Lys
```

| | | | | |
|---|---|---|---|---|
| | 625 | 630 | 635 | 640 |
| tca ttc ttt gaa ctc act agt tta att gct cta gaa atc gac ttg aac<br>Ser Phe Phe Glu Leu Thr Ser Leu Ile Ala Leu Glu Ile Asp Leu Asn<br>645 650 655 | | | | 1968 |
| aac ttg gca ggc tct gtg gat ctt tca tct ttt aaa agg tta aaa aag<br>Asn Leu Ala Gly Ser Val Asp Leu Ser Ser Phe Lys Arg Leu Lys Lys<br>660 665 670 | | | | 2016 |
| ctc cgt gat ttg aat ctt tca cac aat aac ttg tct gtc att atg gat<br>Leu Arg Asp Leu Asn Leu Ser His Asn Asn Leu Ser Val Ile Met Asp<br>675 680 685 | | | | 2064 |
| gac gaa ggc gat aac tct tca tct acg tat ctc tct gaa ctt aaa gag<br>Asp Glu Gly Asp Asn Ser Ser Ser Thr Tyr Leu Ser Glu Leu Lys Glu<br>690 695 700 | | | | 2112 |
| cta gga ctt gca tgt tgc aat ata act aaa ttt cca agt att ttg act<br>Leu Gly Leu Ala Cys Cys Asn Ile Thr Lys Phe Pro Ser Ile Leu Thr<br>705 710 715 720 | | | | 2160 |
| cgt ctg agt gac atg tct tat ttg gac ctt tct tgc aat aaa atc agt<br>Arg Leu Ser Asp Met Ser Tyr Leu Asp Leu Ser Cys Asn Lys Ile Ser<br>725 730 735 | | | | 2208 |
| ggg aac ata cca aag tgg ata tgg gag aaa tgg agc agt agc gtc gtg<br>Gly Asn Ile Pro Lys Trp Ile Trp Glu Lys Trp Ser Ser Ser Val Val<br>740 745 750 | | | | 2256 |
| cat tta aat ctc tcc cac aac atg ctc acc agt atg gaa gtt gct tca<br>His Leu Asn Leu Ser His Asn Met Leu Thr Ser Met Glu Val Ala Ser<br>755 760 765 | | | | 2304 |
| tat ctt ctc cct ttt aat agg cac ttt gaa act ttg gat ctt agt tcc<br>Tyr Leu Leu Pro Phe Asn Arg His Phe Glu Thr Leu Asp Leu Ser Ser<br>770 775 780 | | | | 2352 |
| aat atg ctt caa gga cag att cct ata cca aac tta tca gct gaa ttc<br>Asn Met Leu Gln Gly Gln Ile Pro Ile Pro Asn Leu Ser Ala Glu Phe<br>785 790 795 800 | | | | 2400 |
| ttg gat tat tca cat aat gca ttc tct tct att ctg cca aac ttc act<br>Leu Asp Tyr Ser His Asn Ala Phe Ser Ser Ile Leu Pro Asn Phe Thr<br>805 810 815 | | | | 2448 |
| tta tat ctt agt aaa acc tgg tat ctc agc atg tcc aag aat aat ata<br>Leu Tyr Leu Ser Lys Thr Trp Tyr Leu Ser Met Ser Lys Asn Asn Ile<br>820 825 830 | | | | 2496 |
| agt gga aat ata cca cat tct att tgc aat tca agc ctg ctg gta ctt<br>Ser Gly Asn Ile Pro His Ser Ile Cys Asn Ser Ser Leu Leu Val Leu<br>835 840 845 | | | | 2544 |
| aac ctg gcg cat aac aac ttt agt ggg cca ttt ccg tcc tgc cta atg<br>Asn Leu Ala His Asn Asn Phe Ser Gly Pro Phe Pro Ser Cys Leu Met<br>850 855 860 | | | | 2592 |
| gaa caa acg tac ttc aga aac ata tta aat ttg agg gga aat cac ttt<br>Glu Gln Thr Tyr Phe Arg Asn Ile Leu Asn Leu Arg Gly Asn His Phe<br>865 870 875 880 | | | | 2640 |
| gaa ggg atg tta cct acc aat gtt aca aga tgt gct ttc cag aca ata<br>Glu Gly Met Leu Pro Thr Asn Val Thr Arg Cys Ala Phe Gln Thr Ile<br>885 890 895 | | | | 2688 |
| gat tta aat ggg aat aag att gaa ggt cgg ctt cca agg gca cta ggt<br>Asp Leu Asn Gly Asn Lys Ile Glu Gly Arg Leu Pro Arg Ala Leu Gly<br>900 905 910 | | | | 2736 |
| aac tgc aca tat ttg gaa gtc ctt gac ttg gga aat aat aaa att gcc<br>Asn Cys Thr Tyr Leu Glu Val Leu Asp Leu Gly Asn Asn Lys Ile Ala<br>915 920 925 | | | | 2784 |
| gac act ttt cca tct tgg cta gga agt ctt tcc aat ctt cgt gtc ctt<br>Asp Thr Phe Pro Ser Trp Leu Gly Ser Leu Ser Asn Leu Arg Val Leu<br>930 935 940 | | | | 2832 |
| gtc ttg aga tca aac cgg ttg tac ggt tct ata ggt tat acg ttt gag | | | | 2880 |

```
Val Leu Arg Ser Asn Arg Leu Tyr Gly Ser Ile Gly Tyr Thr Phe Glu
945                 950                 955                 960 gac aaa tct gga gat cac ttc cca aac ttg caa atc att gat ttg gcc    2928
Asp Lys Ser Gly Asp His Phe Pro Asn Leu Gln Ile Ile Asp Leu Ala
                965                 970                 975 tca aac aac ttc act ggc agt ttg cat ccg caa tgg ttt gaa aag ttt    2976
Ser Asn Asn Phe Thr Gly Ser Leu His Pro Gln Trp Phe Glu Lys Phe
            980                 985                 990 ata tct atg aag aag tac aat aat aca gga gaa act atc agc cat cgt    3024
Ile Ser Met Lys Lys Tyr Asn Asn Thr Gly Glu Thr Ile Ser His Arg
        995                 1000                1005 cat agc ata tca gat gga ttt tac caa gat act gtc aca atc tca        3069
His Ser Ile Ser Asp Gly Phe Tyr Gln Asp Thr Val Thr Ile Ser
    1010                1015                1020 tgc aaa ggg ttc tct atg act ttt gaa agg atc tta act acc ttg        3114
Cys Lys Gly Phe Ser Met Thr Phe Glu Arg Ile Leu Thr Thr Leu
    1025                1030                1035 aca gca atc gac tta tct gat aat gca ttg gaa gga agc att cct        3159
Thr Ala Ile Asp Leu Ser Asp Asn Ala Leu Glu Gly Ser Ile Pro
    1040                1045                1050 gag tcg gtc gga aaa ctt gtt tca cta cat gtg cta aac ctg tca        3204
Glu Ser Val Gly Lys Leu Val Ser Leu His Val Leu Asn Leu Ser
    1055                1060                1065 cat aat gcc ttc agt gga aga att cca ccc cag att ggc ggc ata        3249
His Asn Ala Phe Ser Gly Arg Ile Pro Pro Gln Ile Gly Gly Ile
    1070                1075                1080 act gct ctg gag tca ctg gac ctg tct tcg aat tgg att tca ggg        3294
Thr Ala Leu Glu Ser Leu Asp Leu Ser Ser Asn Trp Ile Ser Gly
    1085                1090                1095 gag att cct caa gag ctt act aac ctg aca ttt cta acc gtc ttg        3339
Glu Ile Pro Gln Glu Leu Thr Asn Leu Thr Phe Leu Thr Val Leu
    1100                1105                1110 aac ctg agc aat aac caa ttg gag gga aag ata cca gag tca cgt        3384
Asn Leu Ser Asn Asn Gln Leu Glu Gly Lys Ile Pro Glu Ser Arg
    1115                1120                1125 caa ttt gca aca ttt gaa aac agt tca tat gaa ggc aac gca gga        3429
Gln Phe Ala Thr Phe Glu Asn Ser Ser Tyr Glu Gly Asn Ala Gly
    1130                1135                1140 ctt tgt gga gac cca ttg cct aaa tgt gcc agt tgg agt cct cca        3474
Leu Cys Gly Asp Pro Leu Pro Lys Cys Ala Ser Trp Ser Pro Pro
    1145                1150                1155 agt gct gaa cca cat gta gag agc tcc tct gag cat gtc gat att        3519
Ser Ala Glu Pro His Val Glu Ser Ser Ser Glu His Val Asp Ile
    1160                1165                1170 gtg atg ttt ctc ttt gtt ggc gtg ggc ttt gga gtt gga ttt gca        3564
Val Met Phe Leu Phe Val Gly Val Gly Phe Gly Val Gly Phe Ala
    1175                1180                1185 gta gct gtc cag tga                                                3579
Val Ala Val Gln
    1190

<210> SEQ ID NO 8
<211> LENGTH: 1192
<212> TYPE: PRT
<213> ORGANISM: Oryza sativa

<400> SEQUENCE: 8

Met Ala Phe Ile Val Trp Ala Leu Leu Leu Phe Leu Leu His Leu Pro
1               5                   10                  15

Thr Ile Ala Thr Gly Ser Ser Ala His Phe Gly Gly Asn Asn Thr Val
```

```
            20                  25                  30
Arg Cys His Pro Asn Gln Ala Ala Leu Leu Gln Leu Lys Gln Ser
        35                  40                  45
Phe Phe Trp Val Asn Ser Pro Val Ile Leu Pro Thr Trp Gln Asp Gly
    50                  55                  60
Thr Asp Cys Cys Thr Trp Glu Gly Val Gly Cys Asp Ala Ser Ser His
65                  70                  75                  80
Leu Val Thr Val Leu Asp Leu Ser Gly Arg Gly Met Tyr Ser Asp Ser
                85                  90                  95
Phe Glu Pro Ala Leu Phe Ser Leu Thr Ser Leu Gln Arg Leu Asp Leu
                100                 105                 110
Ser Met Asn Ser Leu Gly Thr Ser Ser Thr Thr Lys Asp Ala Glu Phe
            115                 120                 125
Asp Arg Leu Thr Ser Leu Thr His Leu Asn Leu Ser Asn Ser Gly Leu
        130                 135                 140
Asp Gly Gln Ile Pro Met Gly Ile Asn Lys Leu Ile Asn Leu Val Ser
145                 150                 155                 160
Leu Asp Leu Ser Lys Arg Tyr Val Asn Asp Asn Ser Asp Ile Ser Phe
                165                 170                 175
Asn Glu Ser Asp Asp Glu Ile Ile Phe Thr Gly Asp Ser Tyr Asn His
                180                 185                 190
Leu Gln Glu Ser Arg Leu Met Ser Leu Val Glu Asn Leu Ser Asn Leu
            195                 200                 205
Lys Glu Leu Tyr Leu Asp His Val Asp Met Ser Thr Asn Val Asp Asp
        210                 215                 220
Trp Cys Lys Thr Leu Ala Gln Ser Val Pro Arg Leu Gln Val Leu Ser
225                 230                 235                 240
Leu Asp Gly Cys Ser Leu Asn Thr Pro Ile His Ser Leu Leu Arg
                245                 250                 255
Leu His Ser Leu Thr Val Ile Asn Leu Gln Ser Asn Pro Gly Ile Ala
            260                 265                 270
Val Asn Leu Phe Pro Asp Phe Phe Met Gly Phe Ala Asn Leu Thr Val
        275                 280                 285
Leu Arg Leu Ser His Asn Asn Leu Glu Gly Trp Phe Pro Asp Lys Phe
    290                 295                 300
Phe Gln Leu Lys Asn Leu Arg Ile Leu Asp Leu Ser Phe Asn Met Asn
305                 310                 315                 320
Leu Leu Gly His Leu Pro Lys Val Pro Thr Ser Leu Glu Thr Leu Arg
                325                 330                 335
Leu Glu Gly Thr Asn Phe Ser Tyr Ala Lys Arg Ile Ser Ser Ser Asn
            340                 345                 350
Phe Asn Met Leu Lys Glu Leu Gly Leu Glu Gly Lys Leu Ile Ser Lys
        355                 360                 365
Asp Phe Leu Thr Ser Phe Gly Leu Ile Trp Ser Leu Cys His Leu Glu
    370                 375                 380
Leu Leu Asn Ser Glu Leu Leu Gly Asp Ser Gly Ser Asn Leu Leu Ser
385                 390                 395                 400
Trp Ile Gly Ala His Lys Asn Leu Thr Cys Leu Ile Leu Ser Glu Phe
                405                 410                 415
Asp Phe Ser Ser Thr Lys Pro Ser Ser Ile Ser Asn Phe Lys Asn Leu
            420                 425                 430
Arg Ser Leu Trp Leu Phe Gly Cys Asn Leu Thr Arg Pro Ile Met Ser
        435                 440                 445
```

-continued

Ala Ile Gly Asp Leu Val Asp Leu Gln Ser Leu Asp Met Ser Asn Cys
            450                 455                 460

Asn Thr Tyr Ser Ser Met Pro Ser Ser Ile Gly Asn Leu Thr Asn Leu
465                 470                 475                 480

Lys Ser Leu Tyr Ile Asn Ser Pro Gly Phe Leu Gly Pro Met Pro Ala
                485                 490                 495

Ala Ile Gly Asn Leu Lys Ser Leu Lys Ser Met Val Phe Ser Asn Cys
            500                 505                 510

Glu Phe Thr Gly Pro Met Pro Ser Thr Ile Gly Asn Leu Thr Lys Leu
            515                 520                 525

Gln Thr Leu Glu Ile Ala Ala Cys Arg Phe Ser Gly Pro Ile Pro Tyr
            530                 535                 540

Ser Ile Gly Gln Leu Lys Glu Leu Arg Ala Leu Phe Ile Glu Gly Cys
545                 550                 555                 560

Asn Met Ser Gly Arg Ile Pro Asn Ser Ile Val Asn Met Ser Lys Leu
                565                 570                 575

Ile Tyr Leu Gly Leu Pro Ala Asn Tyr Leu Ser Gly Lys Ile Pro Ala
            580                 585                 590

Arg Leu Phe Thr Leu Pro Ala Leu Leu Phe Leu Asp Leu Phe Gly Asn
            595                 600                 605

His Phe Ser Gly Pro Ile Gln Glu Phe Asp Ala Val Pro Ser Tyr Leu
        610                 615                 620

Met Ser Leu Gln Leu Thr Ser Asn Glu Leu Thr Gly Glu Phe Pro Lys
625                 630                 635                 640

Ser Phe Phe Glu Leu Thr Ser Leu Ile Ala Leu Glu Ile Asp Leu Asn
                645                 650                 655

Asn Leu Ala Gly Ser Val Asp Leu Ser Ser Phe Lys Arg Leu Lys Lys
            660                 665                 670

Leu Arg Asp Leu Asn Leu Ser His Asn Asn Leu Ser Val Ile Met Asp
            675                 680                 685

Asp Glu Gly Asp Asn Ser Ser Ser Thr Tyr Leu Ser Glu Leu Lys Glu
        690                 695                 700

Leu Gly Leu Ala Cys Cys Asn Ile Thr Lys Phe Pro Ser Ile Leu Thr
705                 710                 715                 720

Arg Leu Ser Asp Met Ser Tyr Leu Asp Leu Ser Cys Asn Lys Ile Ser
                725                 730                 735

Gly Asn Ile Pro Lys Trp Ile Trp Glu Lys Trp Ser Ser Val Val
            740                 745                 750

His Leu Asn Leu Ser His Asn Met Leu Thr Ser Met Glu Val Ala Ser
            755                 760                 765

Tyr Leu Leu Pro Phe Asn Arg His Phe Glu Thr Leu Asp Leu Ser Ser
770                 775                 780

Asn Met Leu Gln Gly Gln Ile Pro Ile Pro Asn Leu Ser Ala Glu Phe
785                 790                 795                 800

Leu Asp Tyr Ser His Asn Ala Phe Ser Ser Ile Leu Pro Asn Phe Thr
                805                 810                 815

Leu Tyr Leu Ser Lys Thr Trp Tyr Leu Ser Met Ser Lys Asn Asn Ile
                820                 825                 830

Ser Gly Asn Ile Pro His Ser Ile Cys Asn Ser Ser Leu Leu Val Leu
            835                 840                 845

Asn Leu Ala His Asn Asn Phe Ser Gly Pro Phe Pro Ser Cys Leu Met
            850                 855                 860

```
Glu Gln Thr Tyr Phe Arg Asn Ile Leu Asn Leu Arg Gly Asn His Phe
865                 870                 875                 880

Glu Gly Met Leu Pro Thr Asn Val Thr Arg Cys Ala Phe Gln Thr Ile
            885                 890                 895

Asp Leu Asn Gly Asn Lys Ile Glu Gly Arg Leu Pro Arg Ala Leu Gly
        900                 905                 910

Asn Cys Thr Tyr Leu Glu Val Leu Asp Leu Gly Asn Asn Lys Ile Ala
            915                 920                 925

Asp Thr Phe Pro Ser Trp Leu Gly Ser Leu Ser Asn Leu Arg Val Leu
    930                 935                 940

Val Leu Arg Ser Asn Arg Leu Tyr Gly Ser Ile Gly Tyr Thr Phe Glu
945                 950                 955                 960

Asp Lys Ser Gly Asp His Phe Pro Asn Leu Gln Ile Ile Asp Leu Ala
                965                 970                 975

Ser Asn Asn Phe Thr Gly Ser Leu His Pro Gln Trp Phe Glu Lys Phe
            980                 985                 990

Ile Ser Met Lys Lys Tyr Asn Asn Thr Gly Glu Thr Ile Ser His Arg
        995                 1000                1005

His Ser Ile Ser Asp Gly Phe Tyr Gln Asp Thr Val Thr Ile Ser
    1010                1015                1020

Cys Lys Gly Phe Ser Met Thr Phe Glu Arg Ile Leu Thr Thr Leu
    1025                1030                1035

Thr Ala Ile Asp Leu Ser Asp Asn Ala Leu Glu Gly Ser Ile Pro
    1040                1045                1050

Glu Ser Val Gly Lys Leu Val Ser Leu His Val Leu Asn Leu Ser
    1055                1060                1065

His Asn Ala Phe Ser Gly Arg Ile Pro Pro Gln Ile Gly Gly Ile
    1070                1075                1080

Thr Ala Leu Glu Ser Leu Asp Leu Ser Ser Asn Trp Ile Ser Gly
    1085                1090                1095

Glu Ile Pro Gln Glu Leu Thr Asn Leu Thr Phe Leu Thr Val Leu
    1100                1105                1110

Asn Leu Ser Asn Asn Gln Leu Glu Gly Lys Ile Pro Glu Ser Arg
    1115                1120                1125

Gln Phe Ala Thr Phe Glu Asn Ser Ser Tyr Glu Gly Asn Ala Gly
    1130                1135                1140

Leu Cys Gly Asp Pro Leu Pro Lys Cys Ala Ser Trp Ser Pro Pro
    1145                1150                1155

Ser Ala Glu Pro His Val Glu Ser Ser Ser Glu His Val Asp Ile
    1160                1165                1170

Val Met Phe Leu Phe Val Gly Val Gly Phe Gly Val Gly Phe Ala
    1175                1180                1185

Val Ala Val Gln
    1190

<210> SEQ ID NO 9
<211> LENGTH: 2175
<212> TYPE: DNA
<213> ORGANISM: Brassica oleracea
<220> FEATURE:
<221> NAME/KEY: CDS
<222> LOCATION: (1)..(2175)

<400> SEQUENCE: 9 atg tct gaa tct cgt gtg cgt ttg cat ttt ctc ttg tta atc ttg ctc        48
Met Ser Glu Ser Arg Val Arg Leu His Phe Leu Leu Leu Ile Leu Leu
```

|   |   |   |   |   |   |   |   |   |   |   |   |   |   |   |   |   |
|---|---|---|---|---|---|---|---|---|---|---|---|---|---|---|---|---|
| 1 |   |   |   | 5 |   |   |   |   | 10 |   |   |   |   | 15 |   |   |

```
tgt ttt gtc tcc cct tca agc ttc ttc gat tta aac atg gac tat agt        96
Cys Phe Val Ser Pro Ser Ser Phe Phe Asp Leu Asn Met Asp Tyr Ser
                 20                  25                  30 agc tat gtt gct tgt cct ccc cct cag att caa gct ctc act gag ttc       144
Ser Tyr Val Ala Cys Pro Pro Pro Gln Ile Gln Ala Leu Thr Glu Phe
                 35                  40                  45 atg aac gag ttt gat agc agc cac tgc aac ctc agt gat ccc ttt aat       192
Met Asn Glu Phe Asp Ser Ser His Cys Asn Leu Ser Asp Pro Phe Asn
 50                  55                  60 gga gtc tgg tgc gat aac tcg acc agt gcg gtc aca aag cta cga ctc       240
Gly Val Trp Cys Asp Asn Ser Thr Ser Ala Val Thr Lys Leu Arg Leu
 65                  70                  75                  80 agg gcc tgt ctc agt gga act cta aag ccc aac agt agc cta ttc agg       288
Arg Ala Cys Leu Ser Gly Thr Leu Lys Pro Asn Ser Ser Leu Phe Arg
                 85                  90                  95 tta cat cat ctt cgt tac ctt gac ctc aat caa aac aac ttc atc tca       336
Leu His His Leu Arg Tyr Leu Asp Leu Asn Gln Asn Asn Phe Ile Ser
                100                 105                 110 tct tca ctt cct tct gaa ttt ggc aat ctc aac agg tta gag gtc tta       384
Ser Ser Leu Pro Ser Glu Phe Gly Asn Leu Asn Arg Leu Glu Val Leu
                115                 120                 125 tct ctt tac aat aat ggc ttc gta ggc caa gtt cct tcc tca ttt aat       432
Ser Leu Tyr Asn Asn Gly Phe Val Gly Gln Val Pro Ser Ser Phe Asn
130                 135                 140 aac cta agc ctt ctt tcc gtt tta gac ctt tcc caa aat gag ctc acc       480
Asn Leu Ser Leu Leu Ser Val Leu Asp Leu Ser Gln Asn Glu Leu Thr
145                 150                 155                 160 ggt agt ttc cca ctt gta agg aat cta aca aag ctc tcg tat tta ggc       528
Gly Ser Phe Pro Leu Val Arg Asn Leu Thr Lys Leu Ser Tyr Leu Gly
                165                 170                 175 ctt tct tat aat cat ttc tct gga act ctg aat ccc aac agt act agc       576
Leu Ser Tyr Asn His Phe Ser Gly Thr Leu Asn Pro Asn Ser Thr Ser
                180                 185                 190 ctg ttt gag ttg cac cac ctc cgt tac ctt tat cta agt tac aac aac       624
Leu Phe Glu Leu His His Leu Arg Tyr Leu Tyr Leu Ser Tyr Asn Asn
                195                 200                 205 ttc agt tca tca ctc cct tct gaa ttt gga aat ctc aac aga cta gag       672
Phe Ser Ser Ser Leu Pro Ser Glu Phe Gly Asn Leu Asn Arg Leu Glu
210                 215                 220 gtc ttg tct ctt tcc tcc aat gac ttt ttc ggg caa gtt cct ccc aca       720
Val Leu Ser Leu Ser Ser Asn Asp Phe Phe Gly Gln Val Pro Pro Thr
225                 230                 235                 240 att agt aac cta acc tcg tta acc gaa ttg tac ctt gaa cac aac cag       768
Ile Ser Asn Leu Thr Ser Leu Thr Glu Leu Tyr Leu Glu His Asn Gln
                245                 250                 255 ctc act ggt agt ttc cca ctt gta caa aat ctt acc atg ctc tca ttt       816
Leu Thr Gly Ser Phe Pro Leu Val Gln Asn Leu Thr Met Leu Ser Phe
                260                 265                 270 cta tat atc aat gag aat cac ttc tct gga acc att cca tct tct ctc       864
Leu Tyr Ile Asn Glu Asn His Phe Ser Gly Thr Ile Pro Ser Ser Leu
                275                 280                 285 ttc acc atg cct ttc tta tca att ctc gat ctg aga gaa aac gat ctc       912
Phe Thr Met Pro Phe Leu Ser Ile Leu Asp Leu Arg Glu Asn Asp Leu
290                 295                 300 acc ggt tct att gaa ttt cct aac tcc tct acc cca tct agg ctc gag       960
Thr Gly Ser Ile Glu Phe Pro Asn Ser Ser Thr Pro Ser Arg Leu Glu
305                 310                 315                 320 aaa ata tct ctt aag act ctt ctc ttt atc tcg aag ttc cta act ccc      1008
```

-continued

| | | |
|---|---|---|
| Lys Ile Ser Leu Lys Thr Leu Leu Phe Ile Ser Lys Phe Leu Thr Pro<br>325                         330                        335 | | |

```
tca tac atc cca tca aac atg gca atg ttg ttc tta aag cac tgt ggc       1056
Ser Tyr Ile Pro Ser Asn Met Ala Met Leu Phe Leu Lys His Cys Gly
        340                 345                 350 ctc aaa gag ttc cca aac ata ttc aag acc ctt aaa aaa atg gag gct       1104
Leu Lys Glu Phe Pro Asn Ile Phe Lys Thr Leu Lys Lys Met Glu Ala
            355                 360                 365 ata gac gta tcc aac aat aga atc tac ggg aaa atc cct gag tgg tta       1152
Ile Asp Val Ser Asn Asn Arg Ile Tyr Gly Lys Ile Pro Glu Trp Leu
370                 375                 380 tgg agc ctt cct ctt ctt cat tta gtg aat att tta aat aat tct ttt       1200
Trp Ser Leu Pro Leu Leu His Leu Val Asn Ile Leu Asn Asn Ser Phe
385                 390                 395                 400 gac ggt ttc gaa gga tca acg gaa gtt tta gta aat tca tcg gtt tgg       1248
Asp Gly Phe Glu Gly Ser Thr Glu Val Leu Val Asn Ser Ser Val Trp
                405                 410                 415 cta tta ctt ttg gag aat cac aac ttt gaa cct gca ctt cct agt cta       1296
Leu Leu Leu Leu Glu Asn His Asn Phe Glu Pro Ala Leu Pro Ser Leu
            420                 425                 430 cca cac tct atc aac gcc ttc tcc gcg ggt cat aac aat ttc act gga       1344
Pro His Ser Ile Asn Ala Phe Ser Ala Gly His Asn Asn Phe Thr Gly
        435                 440                 445 gag ata cct ctt tca atc tgc acc aga acc tca ctt aag gtc ctt gat       1392
Glu Ile Pro Leu Ser Ile Cys Thr Arg Thr Ser Leu Lys Val Leu Asp
450                 455                 460 cta aac gtc aac aac ctc att ggt ccg gtt tct caa tgt ttc tgt aat       1440
Leu Asn Val Asn Asn Leu Ile Gly Pro Val Ser Gln Cys Phe Cys Asn
465                 470                 475                 480 gtc acg ttt gta aat ctc cgg aaa aac aat ttg gaa gga act att cct       1488
Val Thr Phe Val Asn Leu Arg Lys Asn Asn Leu Glu Gly Thr Ile Pro
                485                 490                 495 gag act ttc att gtc ggt tcc tcg ata agg aca ctt gat gtt gga tac       1536
Glu Thr Phe Ile Val Gly Ser Ser Ile Arg Thr Leu Asp Val Gly Tyr
            500                 505                 510 aat tct gta atc gga aac ttt cca agg tct ctt ttg aac tgc tca tct       1584
Asn Ser Val Ile Gly Asn Phe Pro Arg Ser Leu Leu Asn Cys Ser Ser
        515                 520                 525 cta gag ttt cta aga tct gac aac aat cca atc aaa gac aca ttt cct       1632
Leu Glu Phe Leu Arg Ser Asp Asn Asn Pro Ile Lys Asp Thr Phe Pro
530                 535                 540 ttc tgg ctc aag gct tta cca aag tta caa gtc ctt acc cta agt tca       1680
Phe Trp Leu Lys Ala Leu Pro Lys Leu Gln Val Leu Thr Leu Ser Ser
545                 550                 555                 560 aac aag ttt tat ggt cct ata tct cct cct cat caa ggt cct ctt cgg       1728
Asn Lys Phe Tyr Gly Pro Ile Ser Pro Pro His Gln Gly Pro Leu Arg
                565                 570                 575 ttt ctc cag ctg aga ata ctt gag ata tct gat aat aag ttt act gga       1776
Phe Leu Gln Leu Arg Ile Leu Glu Ile Ser Asp Asn Lys Phe Thr Gly
            580                 585                 590 agc ttg ttc tca aga tac ttt gag aat tgg aaa gca ttc tct ccc atg       1824
Ser Leu Phe Ser Arg Tyr Phe Glu Asn Trp Lys Ala Phe Ser Pro Met
        595                 600                 605 atg aat gaa tat gtg ggt tta tat gtg gtt tat tcc aag aat cct tat       1872
Met Asn Glu Tyr Val Gly Leu Tyr Val Val Tyr Ser Lys Asn Pro Tyr
610                 615                 620 ggt gta gtt gtc tat acc ttt ttg gat atc ata gat ttg aaa tac aaa       1920
Gly Val Val Val Tyr Thr Phe Leu Asp Ile Ile Asp Leu Lys Tyr Lys
625                 630                 635                 640
```

```
ggt cta aac atg gag caa gtt ccg gtt ctc act tcc tat cct ccc att    1968
Gly Leu Asn Met Glu Gln Val Pro Val Leu Thr Ser Tyr Pro Pro Ile
                645                 650                 655 gat ttt tct aga aat cta ctt gaa gga aat att cct gaa tcc att gga    2016
Asp Phe Ser Arg Asn Leu Leu Glu Gly Asn Ile Pro Glu Ser Ile Gly
            660                 665                 670 ctt tta aag gca ttg att gca cta aac tta ttc aac aat cct ttt atc    2064
Leu Leu Lys Ala Leu Ile Ala Leu Asn Leu Phe Asn Asn Pro Phe Ile
        675                 680                 685 cgc cat att cct tcc tct ttg gca aat ctt aag gag ctc tcc tca cta    2112
Arg His Ile Pro Ser Ser Leu Ala Asn Leu Lys Glu Leu Ser Ser Leu
    690                 695                 700 gac atg tct agg aac caa ctc ttc cgg act att cct aat gga cct aag    2160
Asp Met Ser Arg Asn Gln Leu Phe Arg Thr Ile Pro Asn Gly Pro Lys
705                 710                 715                 720 caa ctc tat ctt tag                                                2175
Gln Leu Tyr Leu
```

<210> SEQ ID NO 10
<211> LENGTH: 724
<212> TYPE: PRT
<213> ORGANISM: Brassica oleracea

<400> SEQUENCE: 10

```
Met Ser Glu Ser Arg Val Arg Leu His Phe Leu Leu Leu Ile Leu Leu
1               5                   10                  15

Cys Phe Val Ser Pro Ser Ser Phe Phe Asp Leu Asn Met Asp Tyr Ser
                20                  25                  30

Ser Tyr Val Ala Cys Pro Pro Gln Ile Gln Ala Leu Thr Glu Phe
            35                  40                  45

Met Asn Glu Phe Asp Ser His Cys Asn Leu Ser Asp Pro Phe Asn
    50                  55                  60

Gly Val Trp Cys Asp Asn Ser Thr Ser Ala Val Thr Lys Leu Arg Leu
65                  70                  75                  80

Arg Ala Cys Leu Ser Gly Thr Leu Lys Pro Asn Ser Ser Leu Phe Arg
                85                  90                  95

Leu His His Leu Arg Tyr Leu Asp Leu Asn Gln Asn Asn Phe Ile Ser
            100                 105                 110

Ser Ser Leu Pro Ser Glu Phe Gly Asn Leu Asn Arg Leu Glu Val Leu
        115                 120                 125

Ser Leu Tyr Asn Asn Gly Phe Val Gly Gln Val Pro Ser Ser Phe Asn
    130                 135                 140

Asn Leu Ser Leu Leu Ser Val Leu Asp Leu Ser Gln Asn Glu Leu Thr
145                 150                 155                 160

Gly Ser Phe Pro Leu Val Arg Asn Leu Thr Lys Leu Ser Tyr Leu Gly
                165                 170                 175

Leu Ser Tyr Asn His Phe Ser Gly Thr Leu Asn Pro Asn Ser Thr Ser
            180                 185                 190

Leu Phe Glu Leu His His Leu Arg Tyr Leu Tyr Leu Ser Tyr Asn Asn
        195                 200                 205

Phe Ser Ser Ser Leu Pro Ser Glu Phe Gly Asn Leu Asn Arg Leu Glu
    210                 215                 220

Val Leu Ser Leu Ser Ser Asn Asp Phe Phe Gly Gln Val Pro Pro Thr
225                 230                 235                 240

Ile Ser Asn Leu Thr Ser Leu Thr Glu Leu Tyr Leu Glu His Asn Gln
                245                 250                 255
```

```
Leu Thr Gly Ser Phe Pro Leu Val Gln Asn Leu Thr Met Leu Ser Phe
            260                 265                 270

Leu Tyr Ile Asn Glu Asn His Phe Ser Gly Thr Ile Pro Ser Ser Leu
        275                 280                 285

Phe Thr Met Pro Phe Leu Ser Ile Leu Asp Leu Arg Glu Asn Asp Leu
    290                 295                 300

Thr Gly Ser Ile Glu Phe Pro Asn Ser Ser Thr Pro Ser Arg Leu Glu
305                 310                 315                 320

Lys Ile Ser Leu Lys Thr Leu Leu Phe Ile Ser Lys Phe Leu Thr Pro
                325                 330                 335

Ser Tyr Ile Pro Ser Asn Met Ala Met Leu Phe Leu Lys His Cys Gly
            340                 345                 350

Leu Lys Glu Phe Pro Asn Ile Phe Lys Thr Leu Lys Lys Met Glu Ala
        355                 360                 365

Ile Asp Val Ser Asn Asn Arg Ile Tyr Gly Lys Ile Pro Glu Trp Leu
370                 375                 380

Trp Ser Leu Pro Leu Leu His Leu Val Asn Ile Leu Asn Asn Ser Phe
385                 390                 395                 400

Asp Gly Phe Glu Gly Ser Thr Glu Val Leu Val Asn Ser Ser Val Trp
                405                 410                 415

Leu Leu Leu Leu Glu Asn His Asn Phe Glu Pro Ala Leu Pro Ser Leu
            420                 425                 430

Pro His Ser Ile Asn Ala Phe Ser Ala Gly His Asn Asn Phe Thr Gly
        435                 440                 445

Glu Ile Pro Leu Ser Ile Cys Thr Arg Thr Ser Leu Lys Val Leu Asp
450                 455                 460

Leu Asn Val Asn Asn Leu Ile Gly Pro Val Ser Gln Cys Phe Cys Asn
465                 470                 475                 480

Val Thr Phe Val Asn Leu Arg Lys Asn Asn Leu Glu Gly Thr Ile Pro
                485                 490                 495

Glu Thr Phe Ile Val Gly Ser Ser Ile Arg Thr Leu Asp Val Gly Tyr
            500                 505                 510

Asn Ser Val Ile Gly Asn Phe Pro Arg Ser Leu Leu Asn Cys Ser Ser
        515                 520                 525

Leu Glu Phe Leu Arg Ser Asp Asn Asn Pro Ile Lys Asp Thr Phe Pro
530                 535                 540

Phe Trp Leu Lys Ala Leu Pro Lys Leu Gln Val Leu Thr Leu Ser Ser
545                 550                 555                 560

Asn Lys Phe Tyr Gly Pro Ile Ser Pro Pro His Gln Gly Pro Leu Arg
                565                 570                 575

Phe Leu Gln Leu Arg Ile Leu Glu Ile Ser Asp Asn Lys Phe Thr Gly
            580                 585                 590

Ser Leu Phe Ser Arg Tyr Phe Glu Asn Trp Lys Ala Phe Ser Pro Met
        595                 600                 605

Met Asn Glu Tyr Val Gly Leu Tyr Val Val Tyr Ser Lys Asn Pro Tyr
610                 615                 620

Gly Val Val Val Tyr Thr Phe Leu Asp Ile Ile Asp Leu Lys Tyr Lys
625                 630                 635                 640

Gly Leu Asn Met Glu Gln Val Pro Val Leu Thr Ser Tyr Pro Pro Ile
                645                 650                 655

Asp Phe Ser Arg Asn Leu Leu Glu Gly Asn Ile Pro Glu Ser Ile Gly
            660                 665                 670

Leu Leu Lys Ala Leu Ile Ala Leu Asn Leu Phe Asn Asn Pro Phe Ile
```

-continued

```
                675                 680                 685
Arg His Ile Pro Ser Ser Leu Ala Asn Leu Lys Glu Leu Ser Ser Leu
            690                 695                 700

Asp Met Ser Arg Asn Gln Leu Phe Arg Thr Ile Pro Asn Gly Pro Lys
705                 710                 715                 720

Gln Leu Tyr Leu

<210> SEQ ID NO 11
<211> LENGTH: 1869
<212> TYPE: DNA
<213> ORGANISM: Oryza sativa
<220> FEATURE:
<221> NAME/KEY: CDS
<222> LOCATION: (1)..(1869)

<400> SEQUENCE: 11 atg cct ccc tcg ccg cct ccc ctc ctc ctc ctc ctc gcg gtc ctc ctc      48
Met Pro Pro Ser Pro Pro Pro Leu Leu Leu Leu Leu Ala Val Leu Leu
1               5                  10                  15 gca gcc gcg ccg gcg gcg gcg cag tcg gcg acg ccc cgg gag gac gac      96
Ala Ala Ala Pro Ala Ala Ala Gln Ser Ala Thr Pro Arg Glu Asp Asp
                20                  25                  30 gtg cgg tgc ctc aag gag gtg aag gcc gag ctc cgg gac ccg gac ggg     144
Val Arg Cys Leu Lys Glu Val Lys Ala Glu Leu Arg Asp Pro Asp Gly
        35                  40                  45 cgc ctc tcg gcg tgg agc ttc ggc aac acc tcg gcg gga gcc ctg tgc     192
Arg Leu Ser Ala Trp Ser Phe Gly Asn Thr Ser Ala Gly Ala Leu Cys
    50                  55                  60 ctg ctg tcg ggg gtg tcg tgc tgg aac ccg cag gag tcg cgc atc atc     240
Leu Leu Ser Gly Val Ser Cys Trp Asn Pro Gln Glu Ser Arg Ile Ile
65                  70                  75                  80 ggc ctc tcg ctc tcc ggg ttc ggc ctc cag ggc ggg atc ccc tcc gcg     288
Gly Leu Ser Leu Ser Gly Phe Gly Leu Gln Gly Gly Ile Pro Ser Ala
                85                  90                  95 ctg cag ttc tgc agc gcc gcc acc acg ctc gac ctc tcc aac aac gcg     336
Leu Gln Phe Cys Ser Ala Ala Thr Thr Leu Asp Leu Ser Asn Asn Ala
                100                 105                 110 ctg gtg ggg gtt atc ccg ccc gcg ctc tgc gac tgg atc ccg ttc gtc     384
Leu Val Gly Val Ile Pro Pro Ala Leu Cys Asp Trp Ile Pro Phe Val
        115                 120                 125 gtc aac ctc gac ctc tcc ggg aac cag ctc tcc ggc cag ctc ccc agc     432
Val Asn Leu Asp Leu Ser Gly Asn Gln Leu Ser Gly Gln Leu Pro Ser
    130                 135                 140 gag ctc gcc aac tgc cgc ttc ctc aac tcg ctc aag ctc tcc ggc aac     480
Glu Leu Ala Asn Cys Arg Phe Leu Asn Ser Leu Lys Leu Ser Gly Asn
145                 150                 155                 160 tcc ttc tcc ggc cag atc ccc gac tcc ctc ggc cgc ctc gac cgc ctc     528
Ser Phe Ser Gly Gln Ile Pro Asp Ser Leu Gly Arg Leu Asp Arg Leu
                165                 170                 175 aag tcg ctc gac ctc tcc gac aac agg ctc gac ggc cag atc ccg ccc     576
Lys Ser Leu Asp Leu Ser Asp Asn Arg Leu Asp Gly Gln Ile Pro Pro
                180                 185                 190 cag ctc gcc acg ttc ggg aag gac tcc ttc gcc ggt aac aag ggc ctg     624
Gln Leu Ala Thr Phe Gly Lys Asp Ser Phe Ala Gly Asn Lys Gly Leu
        195                 200                 205 tgc ggc cgc ccc gtg tcc tcg cga tgc ggc cgc gcg ctg agc ggc gcg     672
Cys Gly Arg Pro Val Ser Ser Arg Cys Gly Arg Ala Leu Ser Gly Ala
    210                 215                 220 ggc ctc ggc atc gtc atc gcc gcg ggg gtg ttc gga gcc gcc gcg tcg     720
Gly Leu Gly Ile Val Ile Ala Ala Gly Val Phe Gly Ala Ala Ala Ser
```

| | | | | | | | | | | | | | | | |
|---|---|---|---|---|---|---|---|---|---|---|---|---|---|---|---|
| | 225 | | | | 230 | | | | 235 | | | | 240 | | |
| ctg | ctc | ctc | gcc | ttc | ttc | ttc | tgg | cgt | tgc | acc | ggg | aag | agc | aag | ggc | 768 |
| Leu | Leu | Leu | Ala | Phe | Phe | Phe | Trp | Arg | Cys | Thr | Gly | Lys | Ser | Lys | Gly |
| | | | | 245 | | | | 250 | | | | 255 | | | |
| ggt | cgc | cgc | cgc | cgc | cgc | gga | ggg | agc | gag | tcc | ggc | ggc | ggc | tcc | gcg | 816 |
| Gly | Arg | Arg | Arg | Arg | Arg | Gly | Gly | Ser | Glu | Ser | Gly | Gly | Gly | Ser | Ala |
| | | | 260 | | | | | 265 | | | | | 270 | | |
| gag | gac | ggg | agc | tgg | tgg | gcg | gag | cgg | ctg | cgg | gcg | gcg | cac | aac | cgg | 864 |
| Glu | Asp | Gly | Ser | Trp | Trp | Ala | Glu | Arg | Leu | Arg | Ala | Ala | His | Asn | Arg |
| | | | | 275 | | | | | 280 | | | | | 285 | |
| ctg | gcg | ccc | gtc | tcg | ctg | ttc | cag | aag | ccg | atc | gtc | aag | gtc | aag | ctc | 912 |
| Leu | Ala | Pro | Val | Ser | Leu | Phe | Gln | Lys | Pro | Ile | Val | Lys | Val | Lys | Leu |
| | 290 | | | | | 295 | | | | | 300 | | | | |
| gcc | gac | ctg | atg | gcg | gcc | acc | cag | gac | ttc | agc | acg | agc | cac | atc | gtg | 960 |
| Ala | Asp | Leu | Met | Ala | Ala | Thr | Gln | Asp | Phe | Ser | Thr | Ser | His | Ile | Val |
| 305 | | | | | 310 | | | | | 315 | | | | | 320 |
| gtg | gcc | ggg | agc | tcg | cgg | gcg | ggg | acg | gcg | tac | cga | gcc | gtg | ctg | cgc | 1008 |
| Val | Ala | Gly | Ser | Ser | Arg | Ala | Gly | Thr | Ala | Tyr | Arg | Ala | Val | Leu | Arg |
| | | | | 325 | | | | | 330 | | | | | 335 | |
| gac | ggc | tcc | gct | ctg | acg | gtg | aag | cgg | ctc | cac | tcg | tgc | ccg | ttg | tcg | 1056 |
| Asp | Gly | Ser | Ala | Leu | Thr | Val | Lys | Arg | Leu | His | Ser | Cys | Pro | Leu | Ser |
| | | | 340 | | | | | 345 | | | | | 350 | | |
| gag | aag | gcg | ttc | cgg | gca | gag | atg | gga | cgg | gtt | ggg | cag | ctg | cgg | cac | 1104 |
| Glu | Lys | Ala | Phe | Arg | Ala | Glu | Met | Gly | Arg | Val | Gly | Gln | Leu | Arg | His |
| | | | | 355 | | | | | 360 | | | | | 365 | |
| cct | aac | atc | gtg | ccg | ctg | ctg | ggg | ttc | tgt | gtc | gtt | gag | gat | gag | cgg | 1152 |
| Pro | Asn | Ile | Val | Pro | Leu | Leu | Gly | Phe | Cys | Val | Val | Glu | Asp | Glu | Arg |
| | 370 | | | | | 375 | | | | | 380 | | | | |
| ctg | ctt | gtg | tac | aag | cat | atg | gag | agt | gga | gct | ctt | tct | tcg | gtg | atg | 1200 |
| Leu | Leu | Val | Tyr | Lys | His | Met | Glu | Ser | Gly | Ala | Leu | Ser | Ser | Val | Met |
| 385 | | | | | 390 | | | | | 395 | | | | | 400 |
| aag | gag | cca | ggg | gag | gca | ccg | ctg | gat | tgg | gcg | aca | cgg | ctt | cgg | att | 1248 |
| Lys | Glu | Pro | Gly | Glu | Ala | Pro | Leu | Asp | Trp | Ala | Thr | Arg | Leu | Arg | Ile |
| | | | | 405 | | | | | 410 | | | | | 415 | |
| gct | gtc | ggg | gcg | gca | cgc | ggt | ctt | gct | tgg | ctg | cac | cat | ggg | ttc | caa | 1296 |
| Ala | Val | Gly | Ala | Ala | Arg | Gly | Leu | Ala | Trp | Leu | His | His | Gly | Phe | Gln |
| | | | 420 | | | | | 425 | | | | | 430 | | |
| gtt | ccg | caa | att | cac | cag | aat | ttg | agc | tca | agt | gca | gtg | ctt | ctg | gat | 1344 |
| Val | Pro | Gln | Ile | His | Gln | Asn | Leu | Ser | Ser | Ser | Ala | Val | Leu | Leu | Asp |
| | | | | 435 | | | | | 440 | | | | | 445 | |
| gag | gac | tat | gaa | gct | cgg | ttc | aca | gat | gtt | ggg | ctt | aca | agg | ctg | gtc | 1392 |
| Glu | Asp | Tyr | Glu | Ala | Arg | Phe | Thr | Asp | Val | Gly | Leu | Thr | Arg | Leu | Val |
| | 450 | | | | | 455 | | | | | 460 | | | | |
| cga | atg | gca | cca | ggc | gag | ggt | gga | gat | aca | agc | ccc | ttc | ctg | aat | ggg | 1440 |
| Arg | Met | Ala | Pro | Gly | Glu | Gly | Gly | Asp | Thr | Ser | Pro | Phe | Leu | Asn | Gly |
| 465 | | | | | 470 | | | | | 475 | | | | | 480 |
| gac | ttc | ggg | gag | tat | ggg | tat | gtc | gcc | cca | gag | tgt | gct | agc | aat | cca | 1488 |
| Asp | Phe | Gly | Glu | Tyr | Gly | Tyr | Val | Ala | Pro | Glu | Cys | Ala | Ser | Asn | Pro |
| | | | | 485 | | | | | 490 | | | | | 495 | |
| gtt | gct | acc | atg | aag | ggt | gat | gtg | tat | gca | ttt | ggt | gtg | ata | ctg | ctc | 1536 |
| Val | Ala | Thr | Met | Lys | Gly | Asp | Val | Tyr | Ala | Phe | Gly | Val | Ile | Leu | Leu |
| | | | 500 | | | | | 505 | | | | | 510 | | |
| gag | ctc | gtg | agt | ggg | cag | gag | gct | gcc | act | gta | acg | ggt | gat | gcg | gca | 1584 |
| Glu | Leu | Val | Ser | Gly | Gln | Glu | Ala | Ala | Thr | Val | Thr | Gly | Asp | Ala | Ala |
| | | | | 515 | | | | | 520 | | | | | 525 | |
| ggt | gaa | gga | ttc | aag | ggg | aca | ttg | gtg | gat | tgg | gta | aat | cag | ctt | aag | 1632 |
| Gly | Glu | Gly | Phe | Lys | Gly | Thr | Leu | Val | Asp | Trp | Val | Asn | Gln | Leu | Lys |
| | 530 | | | | | 535 | | | | | 540 | | | | |
| gcc | tcc | ggc | cgg | atc | ggt | gat | gct | gtt | cat | aaa | tca | ttg | cgt | ggg | aat | 1680 |

```
Ala Ser Gly Arg Ile Gly Asp Ala Val His Lys Ser Leu Arg Gly Asn
545                 550                 555                 560 ggc cat gat tca gag att gat gag ttt gtg aag ata gct ttt gcg tgt    1728
Gly His Asp Ser Glu Ile Asp Glu Phe Val Lys Ile Ala Phe Ala Cys
                565                 570                 575 atc atg gtt cac ccg agg gag agg ttc tca atg tac cgg gtt tac cac    1776
Ile Met Val His Pro Arg Glu Arg Phe Ser Met Tyr Arg Val Tyr His
            580                 585                 590 tct ctg aag agc att gga cag ggt cgt gat gtc tca gag caa ttt gat    1824
Ser Leu Lys Ser Ile Gly Gln Gly Arg Asp Val Ser Glu Gln Phe Asp
        595                 600                 605 gag ttc ccg ctg gcc tat aac aag gat gaa tca gat acc atg taa        1869
Glu Phe Pro Leu Ala Tyr Asn Lys Asp Glu Ser Asp Thr Met
    610                 615                 620

<210> SEQ ID NO 12
<211> LENGTH: 622
<212> TYPE: PRT
<213> ORGANISM: Oryza sativa

<400> SEQUENCE: 12

Met Pro Pro Ser Pro Pro Leu Leu Leu Leu Ala Val Leu Leu
1               5                   10                  15

Ala Ala Ala Pro Ala Ala Gln Ser Ala Thr Pro Arg Glu Asp Asp
                20                  25                  30

Val Arg Cys Leu Lys Glu Val Lys Ala Glu Leu Arg Asp Pro Asp Gly
                35                  40                  45

Arg Leu Ser Ala Trp Ser Phe Gly Asn Thr Ser Ala Gly Ala Leu Cys
    50                  55                  60

Leu Leu Ser Gly Val Ser Cys Trp Asn Pro Gln Glu Ser Arg Ile Ile
65                  70                  75                  80

Gly Leu Ser Leu Ser Gly Phe Gly Leu Gln Gly Gly Ile Pro Ser Ala
                85                  90                  95

Leu Gln Phe Cys Ser Ala Ala Thr Thr Leu Asp Leu Ser Asn Asn Ala
                100                 105                 110

Leu Val Gly Val Ile Pro Pro Ala Leu Cys Asp Trp Ile Pro Phe Val
            115                 120                 125

Val Asn Leu Asp Leu Ser Gly Asn Gln Leu Ser Gly Gln Leu Pro Ser
        130                 135                 140

Glu Leu Ala Asn Cys Arg Phe Leu Asn Ser Leu Lys Leu Ser Gly Asn
145                 150                 155                 160

Ser Phe Ser Gly Gln Ile Pro Asp Ser Leu Gly Arg Leu Asp Arg Leu
                165                 170                 175

Lys Ser Leu Asp Leu Ser Asp Asn Arg Leu Asp Gly Gln Ile Pro Pro
            180                 185                 190

Gln Leu Ala Thr Phe Gly Lys Asp Ser Phe Ala Gly Asn Lys Gly Leu
        195                 200                 205

Cys Gly Arg Pro Val Ser Ser Arg Cys Gly Arg Ala Leu Ser Gly Ala
    210                 215                 220

Gly Leu Gly Ile Val Ile Ala Ala Gly Val Phe Gly Ala Ala Ser
225                 230                 235                 240

Leu Leu Leu Ala Phe Phe Phe Trp Arg Cys Thr Gly Lys Ser Lys Gly
                245                 250                 255

Gly Arg Arg Arg Arg Gly Gly Ser Glu Ser Gly Gly Ser Ala
            260                 265                 270

Glu Asp Gly Ser Trp Trp Ala Glu Arg Leu Arg Ala Ala His Asn Arg
```

```
            275                 280                 285
Leu Ala Pro Val Ser Leu Phe Gln Lys Pro Ile Val Lys Val Lys Leu
290                 295                 300

Ala Asp Leu Met Ala Ala Thr Gln Asp Phe Ser Thr Ser His Ile Val
305                 310                 315                 320

Val Ala Gly Ser Ser Arg Ala Gly Thr Ala Tyr Arg Ala Val Leu Arg
                325                 330                 335

Asp Gly Ser Ala Leu Thr Val Lys Arg Leu His Ser Cys Pro Leu Ser
            340                 345                 350

Glu Lys Ala Phe Arg Ala Glu Met Gly Arg Val Gly Gln Leu Arg His
        355                 360                 365

Pro Asn Ile Val Pro Leu Leu Gly Phe Cys Val Val Glu Asp Glu Arg
    370                 375                 380

Leu Leu Val Tyr Lys His Met Glu Ser Gly Ala Leu Ser Ser Val Met
385                 390                 395                 400

Lys Glu Pro Gly Glu Ala Pro Leu Asp Trp Ala Thr Arg Leu Arg Ile
                405                 410                 415

Ala Val Gly Ala Ala Arg Gly Leu Ala Trp Leu His His Gly Phe Gln
            420                 425                 430

Val Pro Gln Ile His Gln Asn Leu Ser Ser Ser Ala Val Leu Leu Asp
        435                 440                 445

Glu Asp Tyr Glu Ala Arg Phe Thr Asp Val Gly Leu Thr Arg Leu Val
    450                 455                 460

Arg Met Ala Pro Gly Glu Gly Asp Thr Ser Pro Phe Leu Asn Gly
465                 470                 475                 480

Asp Phe Gly Glu Tyr Gly Tyr Val Ala Pro Glu Cys Ala Ser Asn Pro
                485                 490                 495

Val Ala Thr Met Lys Gly Asp Val Tyr Ala Phe Gly Val Ile Leu Leu
            500                 505                 510

Glu Leu Val Ser Gly Gln Glu Ala Ala Thr Val Thr Gly Asp Ala Ala
        515                 520                 525

Gly Glu Gly Phe Lys Gly Thr Leu Val Asp Trp Val Asn Gln Leu Lys
    530                 535                 540

Ala Ser Gly Arg Ile Gly Asp Ala Val His Lys Ser Leu Arg Gly Asn
545                 550                 555                 560

Gly His Asp Ser Glu Ile Asp Glu Phe Val Lys Ile Ala Phe Ala Cys
                565                 570                 575

Ile Met Val His Pro Arg Glu Arg Phe Ser Met Tyr Arg Val Tyr His
            580                 585                 590

Ser Leu Lys Ser Ile Gly Gln Gly Arg Asp Val Ser Glu Gln Phe Asp
        595                 600                 605

Glu Phe Pro Leu Ala Tyr Asn Lys Asp Glu Ser Asp Thr Met
    610                 615                 620

<210> SEQ ID NO 13
<211> LENGTH: 1842
<212> TYPE: DNA
<213> ORGANISM: Picea sitchensis
<220> FEATURE:
<221> NAME/KEY: CDS
<222> LOCATION: (1)..(1842)

<400> SEQUENCE: 13 atg aga aaa ttc ggg tgt ttg agc ctt ctt ggg gtc atg cta ttg att     48
Met Arg Lys Phe Gly Cys Leu Ser Leu Leu Gly Val Met Leu Leu Ile
1               5                   10                  15
```

| | | |
|---|---|---|
| ctt caa ctg aca tgc cct gtt tcc tcc cag ccc agt gtt gca gaa aat<br>Leu Gln Leu Thr Cys Pro Val Ser Ser Gln Pro Ser Val Ala Glu Asn<br>20              25              30 | 96 | |
| gat ata cag tgt ctt caa agt aca aag aat cat ttg aaa gac cct caa<br>Asp Ile Gln Cys Leu Gln Ser Thr Lys Asn His Leu Lys Asp Pro Gln<br>35              40              45 | 144 | |
| gat aac ctc tac acc tgg aac ttt gat aac agt acg aag ggg ttt att<br>Asp Asn Leu Tyr Thr Trp Asn Phe Asp Asn Ser Thr Lys Gly Phe Ile<br>50              55              60 | 192 | |
| tgc aat ttt ctg gga att act tgt tgg cac aac gat gat aac aaa gtg<br>Cys Asn Phe Leu Gly Ile Thr Cys Trp His Asn Asp Asp Asn Lys Val<br>65              70              75              80 | 240 | |
| ctg tca att tcg ctt caa gag atg ggc ctt caa ggt gag ttt cca cct<br>Leu Ser Ile Ser Leu Gln Glu Met Gly Leu Gln Gly Glu Phe Pro Pro<br>85              90              95 | 288 | |
| gga gta aag tac tgt ggg agt atg acg agc ttg act ctc tcc caa aat<br>Gly Val Lys Tyr Cys Gly Ser Met Thr Ser Leu Thr Leu Ser Gln Asn<br>100             105             110 | 336 | |
| agt ctt acg ggg acc att ccc aag gag ctc tgc caa tgg ctt cct tat<br>Ser Leu Thr Gly Thr Ile Pro Lys Glu Leu Cys Gln Trp Leu Pro Tyr<br>115             120             125 | 384 | |
| ctg gta acc att gat ctc tcc cag aac gag ttt acg gga tct att cct<br>Leu Val Thr Ile Asp Leu Ser Gln Asn Glu Phe Thr Gly Ser Ile Pro<br>130             135             140 | 432 | |
| gcc gag ctt cat aat tgc aca tat ctc aat atc ctc cgc ctg aat ggc<br>Ala Glu Leu His Asn Cys Thr Tyr Leu Asn Ile Leu Arg Leu Asn Gly<br>145             150             155             160 | 480 | |
| aat caa ctt aca ggg gaa att ccg tgg caa ttg tca cgg ctc gat cga<br>Asn Gln Leu Thr Gly Glu Ile Pro Trp Gln Leu Ser Arg Leu Asp Arg<br>165             170             175 | 528 | |
| ctc acg gaa ttg aat gtt gca aac aac aag ctt act gga tat ata cct<br>Leu Thr Glu Leu Asn Val Ala Asn Asn Lys Leu Thr Gly Tyr Ile Pro<br>180             185             190 | 576 | |
| tca tta gaa cac aac atg agt gcc tct tat ttt cag aat aac cct ggg<br>Ser Leu Glu His Asn Met Ser Ala Ser Tyr Phe Gln Asn Asn Pro Gly<br>195             200             205 | 624 | |
| cta tgt ggg aaa ccc ctt tca aat aca tgc gtc ggg aag gga aag tcc<br>Leu Cys Gly Lys Pro Leu Ser Asn Thr Cys Val Gly Lys Gly Lys Ser<br>210             215             220 | 672 | |
| tca ata ggt gtt gct att ggg gca gct gtt gca ggc gta ttg att gtg<br>Ser Ile Gly Val Ala Ile Gly Ala Ala Val Ala Gly Val Leu Ile Val<br>225             230             235             240 | 720 | |
| tca ttg ctc ggt ttt gca ttt tgg tgg tgg ttt atc aga ata agc ccg<br>Ser Leu Leu Gly Phe Ala Phe Trp Trp Trp Phe Ile Arg Ile Ser Pro<br>245             250             255 | 768 | |
| aag aaa ttg gct gaa atg aag gac gag aac aag tgg gca aaa cgg att<br>Lys Lys Leu Ala Glu Met Lys Asp Glu Asn Lys Trp Ala Lys Arg Ile<br>260             265             270 | 816 | |
| agg gct ccg aag tct atc caa gtg tcc atg ttt gag aag ccc att aac<br>Arg Ala Pro Lys Ser Ile Gln Val Ser Met Phe Glu Lys Pro Ile Asn<br>275             280             285 | 864 | |
| aaa atc aag ctc tct gat cta atg gct gcc aca aac gat ttc agc cct<br>Lys Ile Lys Leu Ser Asp Leu Met Ala Ala Thr Asn Asp Phe Ser Pro<br>290             295             300 | 912 | |
| gaa aac atc ata ggg tca ggc agg aca ggc act gtt tat aga gcg aca<br>Glu Asn Ile Ile Gly Ser Gly Arg Thr Gly Thr Val Tyr Arg Ala Thr<br>305             310             315             320 | 960 | |
| ctg act gac gga tct gtt atg gcg ata aaa agg ctt cga gac tct gcc<br>Leu Thr Asp Gly Ser Val Met Ala Ile Lys Arg Leu Arg Asp Ser Ala | 1008 | |

```
                        325                 330                 335
caa tct gaa aag cag ttt aag gct gaa atg aat acg tta gcc cgc ttg      1056
Gln Ser Glu Lys Gln Phe Lys Ala Glu Met Asn Thr Leu Ala Arg Leu
        340                 345                 350 agg cac cgg aat ctt gtt cct ctt ctg ggt tac tgc att gcc gga caa      1104
Arg His Arg Asn Leu Val Pro Leu Leu Gly Tyr Cys Ile Ala Gly Gln
            355                 360                 365 gag aag ctt tta gtg tac aaa cac atg gct aat gga agc ttg tgg gac      1152
Glu Lys Leu Leu Val Tyr Lys His Met Ala Asn Gly Ser Leu Trp Asp
370                 375                 380 tgc ctg caa agc aag gag aat cca gcg aat aat ttg gat tgg acc gca      1200
Cys Leu Gln Ser Lys Glu Asn Pro Ala Asn Asn Leu Asp Trp Thr Ala
385                 390                 395                 400 agg ctc aaa att gga att ggc gga gct aga gga atg gca tgg ctt cat      1248
Arg Leu Lys Ile Gly Ile Gly Gly Ala Arg Gly Met Ala Trp Leu His
            405                 410                 415 cac agt tgc aac cct cgt gtc ata cac cgt aat ata agt tca aac agt      1296
His Ser Cys Asn Pro Arg Val Ile His Arg Asn Ile Ser Ser Asn Ser
                420                 425                 430 att ctt ctt gat gat gaa tat gag cct aga ata aca gat ttt gga ttg      1344
Ile Leu Leu Asp Asp Glu Tyr Glu Pro Arg Ile Thr Asp Phe Gly Leu
                435                 440                 445 gca agg ttg atg aat cca gta gat act cat ctt agc act ttc ata aat      1392
Ala Arg Leu Met Asn Pro Val Asp Thr His Leu Ser Thr Phe Ile Asn
450                 455                 460 ggt gat ttt gga gat ttg ggc tat gta gca ccc gaa tac atg cgc acc      1440
Gly Asp Phe Gly Asp Leu Gly Tyr Val Ala Pro Glu Tyr Met Arg Thr
465                 470                 475                 480 ttg gtg gct act ttg aaa gga gat gtg tac agc ttt gga gtg gtt ctt      1488
Leu Val Ala Thr Leu Lys Gly Asp Val Tyr Ser Phe Gly Val Val Leu
            485                 490                 495 cta gaa tta gtt aca gga cag aag cct atc aat gtt gaa aat gga gag      1536
Leu Glu Leu Val Thr Gly Gln Lys Pro Ile Asn Val Glu Asn Gly Glu
                500                 505                 510 gat ggc ttc aag ggt aat tta gta gat tgg att act aaa ctt tca aat      1584
Asp Gly Phe Lys Gly Asn Leu Val Asp Trp Ile Thr Lys Leu Ser Asn
                515                 520                 525 gat ggc cgc atc agc gaa gct atc gac aaa tct ttg ata ggc agg gga      1632
Asp Gly Arg Ile Ser Glu Ala Ile Asp Lys Ser Leu Ile Gly Arg Gly
530                 535                 540 caa gaa gat gag ctc ctg caa ttt atg agg gtt gca tgt gcg tgt gtg      1680
Gln Glu Asp Glu Leu Leu Gln Phe Met Arg Val Ala Cys Ala Cys Val
545                 550                 555                 560 ttg tct ggg gcc aag gaa agg cct tca atg tat gag gtc tat cat ttg      1728
Leu Ser Gly Ala Lys Glu Arg Pro Ser Met Tyr Glu Val Tyr His Leu
            565                 570                 575 cta aga gca att ggt gag aag tac aac ttc tca gac ggg aat gat gag      1776
Leu Arg Ala Ile Gly Glu Lys Tyr Asn Phe Ser Asp Gly Asn Asp Glu
                580                 585                 590 att cca ttg aca tca gga aca gct gac aat gac cgt tca agt gag ctt      1824
Ile Pro Leu Thr Ser Gly Thr Ala Asp Asn Asp Arg Ser Ser Glu Leu
                595                 600                 605 ata gtg gca ttt gaa taa                                              1842
Ile Val Ala Phe Glu
            610

<210> SEQ ID NO 14
<211> LENGTH: 613
<212> TYPE: PRT
<213> ORGANISM: Picea sitchensis
```

<400> SEQUENCE: 14

```
Met Arg Lys Phe Gly Cys Leu Ser Leu Leu Gly Val Met Leu Leu Ile
1               5                   10                  15

Leu Gln Leu Thr Cys Pro Val Ser Ser Gln Pro Ser Val Ala Glu Asn
            20                  25                  30

Asp Ile Gln Cys Leu Gln Ser Thr Lys Asn His Leu Lys Asp Pro Gln
        35                  40                  45

Asp Asn Leu Tyr Thr Trp Asn Phe Asp Asn Ser Thr Lys Gly Phe Ile
    50                  55                  60

Cys Asn Phe Leu Gly Ile Thr Cys Trp His Asn Asp Asp Asn Lys Val
65                  70                  75                  80

Leu Ser Ile Ser Leu Gln Glu Met Gly Leu Gln Gly Glu Phe Pro Pro
                85                  90                  95

Gly Val Lys Tyr Cys Gly Ser Met Thr Ser Leu Thr Leu Ser Gln Asn
            100                 105                 110

Ser Leu Thr Gly Thr Ile Pro Lys Glu Leu Cys Gln Trp Leu Pro Tyr
        115                 120                 125

Leu Val Thr Ile Asp Leu Ser Gln Asn Glu Phe Thr Gly Ser Ile Pro
    130                 135                 140

Ala Glu Leu His Asn Cys Thr Tyr Leu Asn Ile Leu Arg Leu Asn Gly
145                 150                 155                 160

Asn Gln Leu Thr Gly Glu Ile Pro Trp Gln Leu Ser Arg Leu Asp Arg
                165                 170                 175

Leu Thr Glu Leu Asn Val Ala Asn Asn Lys Leu Thr Gly Tyr Ile Pro
            180                 185                 190

Ser Leu Glu His Asn Met Ser Ala Ser Tyr Phe Gln Asn Asn Pro Gly
        195                 200                 205

Leu Cys Gly Lys Pro Leu Ser Asn Thr Cys Val Gly Lys Gly Lys Ser
    210                 215                 220

Ser Ile Gly Val Ala Ile Gly Ala Ala Val Ala Gly Val Leu Ile Val
225                 230                 235                 240

Ser Leu Leu Gly Phe Ala Phe Trp Trp Phe Ile Arg Ile Ser Pro
                245                 250                 255

Lys Lys Leu Ala Glu Met Lys Asp Glu Asn Lys Trp Ala Lys Arg Ile
            260                 265                 270

Arg Ala Pro Lys Ser Ile Gln Val Ser Met Phe Glu Lys Pro Ile Asn
        275                 280                 285

Lys Ile Lys Leu Ser Asp Leu Met Ala Ala Thr Asn Asp Phe Ser Pro
    290                 295                 300

Glu Asn Ile Ile Gly Ser Gly Arg Thr Gly Thr Val Tyr Arg Ala Thr
305                 310                 315                 320

Leu Thr Asp Gly Ser Val Met Ala Ile Lys Arg Leu Arg Asp Ser Ala
                325                 330                 335

Gln Ser Glu Lys Gln Phe Lys Ala Glu Met Asn Thr Leu Ala Arg Leu
            340                 345                 350

Arg His Arg Asn Leu Val Pro Leu Leu Gly Tyr Cys Ile Ala Gly Gln
        355                 360                 365

Glu Lys Leu Leu Val Tyr Lys His Met Ala Asn Gly Ser Leu Trp Asp
    370                 375                 380

Cys Leu Gln Ser Lys Glu Asn Pro Ala Asn Asn Leu Asp Trp Thr Ala
385                 390                 395                 400

Arg Leu Lys Ile Gly Ile Gly Gly Ala Arg Gly Met Ala Trp Leu His
```

His Ser Cys Asn Pro Arg Val Ile His Arg Asn Ile Ser Ser Asn Ser
                420                 425                 430

Ile Leu Leu Asp Asp Glu Tyr Glu Pro Arg Ile Thr Asp Phe Gly Leu
            435                 440                 445

Ala Arg Leu Met Asn Pro Val Asp Thr His Leu Ser Thr Phe Ile Asn
450                 455                 460

Gly Asp Phe Gly Asp Leu Gly Tyr Val Ala Pro Glu Tyr Met Arg Thr
465                 470                 475                 480

Leu Val Ala Thr Leu Lys Gly Asp Val Tyr Ser Phe Gly Val Val Leu
            485                 490                 495

Leu Glu Leu Val Thr Gly Gln Lys Pro Ile Asn Val Glu Asn Gly Glu
            500                 505                 510

Asp Gly Phe Lys Gly Asn Leu Val Asp Trp Ile Thr Lys Leu Ser Asn
            515                 520                 525

Asp Gly Arg Ile Ser Glu Ala Ile Asp Lys Ser Leu Ile Gly Arg Gly
        530                 535                 540

Gln Glu Asp Glu Leu Leu Gln Phe Met Arg Val Ala Cys Ala Cys Val
545                 550                 555                 560

Leu Ser Gly Ala Lys Glu Arg Pro Ser Met Tyr Glu Val Tyr His Leu
            565                 570                 575

Leu Arg Ala Ile Gly Lys Tyr Asn Phe Ser Asp Gly Asn Asp Glu
            580                 585                 590

Ile Pro Leu Thr Ser Gly Thr Ala Asp Asn Asp Arg Ser Ser Glu Leu
            595                 600                 605

Ile Val Ala Phe Glu
            610

<210> SEQ ID NO 15
<211> LENGTH: 613
<212> TYPE: PRT
<213> ORGANISM: Vitis vinifera

<400> SEQUENCE: 15

Met Lys Leu Ser Glu Asp Leu Arg Gly His Ile Gln Gly Cys Ser Leu
1               5                   10                  15

Val Leu Leu Thr Ile Val Ile Leu Cys Cys Val Ala Leu Phe Ser Ala
            20                  25                  30

Ala Val Ala Glu Asp Val Lys Cys Leu Arg Gly Val Lys Glu Ser
        35                  40                  45

Leu Ser Asp Pro Gln Gly Lys Leu Ser Ser Trp Ser Phe Ser Asn Ile
    50                  55                  60

Ser Val Gly Ser Leu Cys Lys Phe Val Gly Val Ala Cys Trp Asn Asp
65                  70                  75                  80

Arg Glu Asn Arg Ile Phe Gly Leu Glu Leu Pro Asp Met Lys Leu Ser
                85                  90                  95

Gly Glu Ile Pro Lys Pro Leu Glu Tyr Cys Gln Ser Met Gln Thr Leu
            100                 105                 110

Asp Leu Ser Gly Asn Arg Leu Tyr Gly Asn Ile Pro Ser Gln Ile Cys
        115                 120                 125

Thr Trp Leu Pro Tyr Leu Val Thr Leu Asp Leu Ser Asn Asn Asp Leu
    130                 135                 140

Ser Gly Thr Ile Pro Pro Asp Leu Ala Asn Cys Ser Phe Leu Asn Ser
145                 150                 155                 160

```
Leu Leu Leu Ala Asp Asn Gln Leu Ser Gly Ile Ile Pro Ser Gln Leu
            165                 170                 175
Ser Ser Leu Gly Arg Leu Lys Lys Phe Ser Val Ala Asn Asn Arg Leu
        180                 185                 190
Thr Gly Thr Ile Pro Ser Ala Phe Gly Lys Phe Asp Lys Ala Gly Phe
    195                 200                 205
Asp Gly Asn Ser Gly Leu Cys Gly Arg Pro Leu Gly Ser Lys Cys Gly
210                 215                 220
Gly Leu Asn Lys Lys Ser Leu Ala Ile Ile Ala Ala Gly Val Phe
225                 230                 235                 240
Gly Ala Ala Ser Leu Leu Gly Phe Gly Leu Trp Trp Trp Phe
            245                 250                 255
Phe Ala Arg Leu Arg Gly Gln Arg Lys Arg Arg Tyr Gly Ile Gly Arg
        260                 265                 270
Asp Asp His Ser Ser Trp Thr Glu Arg Leu Arg Ala His Lys Leu Val
    275                 280                 285
Gln Val Thr Leu Phe Gln Lys Pro Ile Val Lys Val Lys Leu Ala Asp
290                 295                 300
Leu Met Ala Ala Thr Asn Asn Phe His Pro Glu Asn Ile Ile Asn Ser
305                 310                 315                 320
Thr Arg Thr Gly Thr Ser Tyr Lys Ala Ile Leu Pro Asp Gly Ser Ala
            325                 330                 335
Leu Ala Ile Lys Arg Leu Asn Thr Cys Asn Leu Gly Glu Lys Gln Phe
        340                 345                 350
Arg Ser Glu Met Asn Arg Leu Gly Gln Phe Arg His Pro Asn Leu Ala
    355                 360                 365
Pro Leu Leu Gly Phe Cys Ala Val Glu Glu Glu Lys Leu Leu Val Tyr
370                 375                 380
Lys Tyr Met Ser Asn Gly Thr Leu Tyr Ser Leu Leu His Gly Asn Gly
385                 390                 395                 400
Thr Pro Met Asp Trp Ala Thr Arg Phe Arg Ile Gly Leu Gly Ala Ala
            405                 410                 415
Arg Gly Leu Ala Trp Leu His His Gly Cys Gln Pro Pro Leu Leu His
        420                 425                 430
Glu Asn Ile Ser Ser Asn Val Ile Leu Ile Asp Asp Phe Asp Ala
    435                 440                 445
Arg Ile Val Asp Phe Gly Leu Ala Arg Leu Met Ala Thr Ser Asp Ser
    450                 455                 460
Asn Gly Ser Ser Phe Val Asn Gly Gly Leu Gly Glu Phe Gly Tyr Val
465                 470                 475                 480
Ala Pro Glu Tyr Ser Ser Thr Met Val Ala Ser Leu Lys Gly Asp Val
            485                 490                 495
Tyr Gly Phe Gly Val Val Leu Glu Leu Val Thr Gly Gln Lys Pro
        500                 505                 510
Leu Glu Val Thr Asn Ala Glu Glu Gly Phe Lys Gly Asn Leu Val Glu
    515                 520                 525
Trp Val Asn Gln Leu Cys Gly Ser Gly Arg Asn Lys Asp Val Ile Asp
530                 535                 540
Glu Ala Leu Cys Gly Lys Gly His Asp Glu Glu Ile Leu Gln Phe Leu
545                 550                 555                 560
Lys Ile Ala Cys Asn Cys Leu Gly Pro Arg Pro Lys Asp Arg Leu Ser
            565                 570                 575
Met Tyr Gln Ala Phe Glu Ser Leu Lys Ser Met Gly Asp His His Gly
```

|  |  |  | 580 |  |  |  | 585 |  |  |  | 590 |  |  |
|--|--|--|--|--|--|--|--|--|--|--|--|--|--|
| Phe | Ser | Glu | His | Tyr | Asp | Glu | Phe | Pro | Leu | Ile | Phe | Gly | Lys | Gln | Asp |
|  |  |  | 595 |  |  |  | 600 |  |  |  | 605 |  |  |

His Asp Asn Gln Ala
    610

```
<210> SEQ ID NO 16
<211> LENGTH: 2889
<212> TYPE: DNA
<213> ORGANISM: Oryza sativa
<220> FEATURE:
<221> NAME/KEY: CDS
<222> LOCATION: (1)..(2889)

<400> SEQUENCE: 16
```

| atg | aac | acc | ctc | acc | gga | agc | atc | cca | tca | gag | att | gga | aac | ctt | gca | 48 |
|--|--|--|--|--|--|--|--|--|--|--|--|--|--|--|--|--|
| Met | Asn | Thr | Leu | Thr | Gly | Ser | Ile | Pro | Ser | Glu | Ile | Gly | Asn | Leu | Ala |  |
| 1 |  |  |  | 5 |  |  |  |  | 10 |  |  |  |  | 15 |  |  |

| aac | ctc | atg | act | ctg | aac | ctg | caa | ttc | agc | aac | ctc | act | ggg | gga | atc | 96 |
|--|--|--|--|--|--|--|--|--|--|--|--|--|--|--|--|--|
| Asn | Leu | Met | Thr | Leu | Asn | Leu | Gln | Phe | Ser | Asn | Leu | Thr | Gly | Gly | Ile |  |
|  |  | 20 |  |  |  |  | 25 |  |  |  |  | 30 |  |  |  |  |

| cca | gag | gag | ata | ggt | gat | ctt | gct | ggc | ctt | gtt | gga | cta | ggt | ctt | ggt | 144 |
|--|--|--|--|--|--|--|--|--|--|--|--|--|--|--|--|--|
| Pro | Glu | Glu | Ile | Gly | Asp | Leu | Ala | Gly | Leu | Val | Gly | Leu | Gly | Leu | Gly |  |
|  | 35 |  |  |  |  | 40 |  |  |  |  | 45 |  |  |  |  |  |

| tct | aat | cag | ctg | gca | ggc | tcc | att | cct | gcc | tca | ctt | gga | aac | ctt | tca | 192 |
|--|--|--|--|--|--|--|--|--|--|--|--|--|--|--|--|--|
| Ser | Asn | Gln | Leu | Ala | Gly | Ser | Ile | Pro | Ala | Ser | Leu | Gly | Asn | Leu | Ser |  |
| 50 |  |  |  |  | 55 |  |  |  |  | 60 |  |  |  |  |  |  |

| gca | ctc | aag | tac | ctt | agc | atc | cct | tct | gca | aag | ttg | aca | ggg | agc | ata | 240 |
|--|--|--|--|--|--|--|--|--|--|--|--|--|--|--|--|--|
| Ala | Leu | Lys | Tyr | Leu | Ser | Ile | Pro | Ser | Ala | Lys | Leu | Thr | Gly | Ser | Ile |  |
| 65 |  |  |  | 70 |  |  |  |  | 75 |  |  |  |  | 80 |  |  |

| cca | tcg | ctg | caa | aac | ctt | tca | tca | ctt | ctt | gtc | ctt | gaa | ttg | gga | gag | 288 |
|--|--|--|--|--|--|--|--|--|--|--|--|--|--|--|--|--|
| Pro | Ser | Leu | Gln | Asn | Leu | Ser | Ser | Leu | Leu | Val | Leu | Glu | Leu | Gly | Glu |  |
|  |  |  |  | 85 |  |  |  |  | 90 |  |  |  |  | 95 |  |  |

| aac | aat | ctc | gaa | gga | act | gtg | cct | gca | tgg | ttg | ggg | aac | ctc | tca | tct | 336 |
|--|--|--|--|--|--|--|--|--|--|--|--|--|--|--|--|--|
| Asn | Asn | Leu | Glu | Gly | Thr | Val | Pro | Ala | Trp | Leu | Gly | Asn | Leu | Ser | Ser |  |
|  |  |  | 100 |  |  |  |  | 105 |  |  |  |  | 110 |  |  |  |

| cta | gtg | ttt | gtt | agt | ctc | cag | caa | aat | cgg | ctc | tca | gga | cac | atc | cct | 384 |
|--|--|--|--|--|--|--|--|--|--|--|--|--|--|--|--|--|
| Leu | Val | Phe | Val | Ser | Leu | Gln | Gln | Asn | Arg | Leu | Ser | Gly | His | Ile | Pro |  |
|  |  | 115 |  |  |  |  | 120 |  |  |  |  | 125 |  |  |  |  |

| gaa | tca | tta | ggt | aga | ctt | cag | atg | ctt | act | agc | ctt | gat | ctt | tca | caa | 432 |
|--|--|--|--|--|--|--|--|--|--|--|--|--|--|--|--|--|
| Glu | Ser | Leu | Gly | Arg | Leu | Gln | Met | Leu | Thr | Ser | Leu | Asp | Leu | Ser | Gln |  |
| 130 |  |  |  |  | 135 |  |  |  |  | 140 |  |  |  |  |  |  |

| aat | aat | ctt | att | tca | ggc | tcc | ata | cca | gat | tct | ctt | gga | aac | ctt | ggt | 480 |
|--|--|--|--|--|--|--|--|--|--|--|--|--|--|--|--|--|
| Asn | Asn | Leu | Ile | Ser | Gly | Ser | Ile | Pro | Asp | Ser | Leu | Gly | Asn | Leu | Gly |  |
| 145 |  |  |  |  | 150 |  |  |  |  | 155 |  |  |  |  | 160 |  |

| gcc | ttg | agt | agc | ctt | cgt | ctg | gat | tat | aat | aaa | cta | gaa | ggt | tcg | ttt | 528 |
|--|--|--|--|--|--|--|--|--|--|--|--|--|--|--|--|--|
| Ala | Leu | Ser | Ser | Leu | Arg | Leu | Asp | Tyr | Asn | Lys | Leu | Glu | Gly | Ser | Phe |  |
|  |  |  |  | 165 |  |  |  |  | 170 |  |  |  |  | 175 |  |  |

| cct | cct | tca | ctg | ctc | aac | ctt | tcc | tcc | ctt | gat | gat | ctt | ggt | tta | caa | 576 |
|--|--|--|--|--|--|--|--|--|--|--|--|--|--|--|--|--|
| Pro | Pro | Ser | Leu | Leu | Asn | Leu | Ser | Ser | Leu | Asp | Asp | Leu | Gly | Leu | Gln |  |
|  |  |  | 180 |  |  |  |  | 185 |  |  |  |  | 190 |  |  |  |

| agc | aat | cgc | ctc | agc | ggg | gct | ctt | cca | cct | gat | att | ggc | aat | aag | ctt | 624 |
|--|--|--|--|--|--|--|--|--|--|--|--|--|--|--|--|--|
| Ser | Asn | Arg | Leu | Ser | Gly | Ala | Leu | Pro | Pro | Asp | Ile | Gly | Asn | Lys | Leu |  |
|  | 195 |  |  |  |  | 200 |  |  |  |  | 205 |  |  |  |  |  |

| ccg | aat | cta | caa | agg | ttt | gtt | gta | gac | atc | aat | caa | ttt | cat | gga | aca | 672 |
|--|--|--|--|--|--|--|--|--|--|--|--|--|--|--|--|--|
| Pro | Asn | Leu | Gln | Arg | Phe | Val | Val | Asp | Ile | Asn | Gln | Phe | His | Gly | Thr |  |
| 210 |  |  |  |  | 215 |  |  |  |  | 220 |  |  |  |  |  |  |

| atc | cca | cca | tcc | ttg | tgt | aat | gcc | acc | atg | ctt | caa | gtt | ctg | caa | aca | 720 |
|--|--|--|--|--|--|--|--|--|--|--|--|--|--|--|--|--|
| Ile | Pro | Pro | Ser | Leu | Cys | Asn | Ala | Thr | Met | Leu | Gln | Val | Leu | Gln | Thr |  |
| 225 |  |  |  |  | 230 |  |  |  |  | 235 |  |  |  |  | 240 |  |

```
gta tac aac ttt ttg tca gga aga att cct cag tgt ctt gga att caa     768
Val Tyr Asn Phe Leu Ser Gly Arg Ile Pro Gln Cys Leu Gly Ile Gln
                245                 250                 255 cag aag agc tta tca gtt gtg gcc ctt tca aaa aat cag ctt gaa gca     816
Gln Lys Ser Leu Ser Val Val Ala Leu Ser Lys Asn Gln Leu Glu Ala
                260                 265                 270 aca aat gat gct gat tgg gtt ttc tta tcc agc ttg gcg aat tgc agc     864
Thr Asn Asp Ala Asp Trp Val Phe Leu Ser Ser Leu Ala Asn Cys Ser
            275                 280                 285 aat ttg aat gca tta gat ttg ggt tac aac aag ctt caa ggt gag cta     912
Asn Leu Asn Ala Leu Asp Leu Gly Tyr Asn Lys Leu Gln Gly Glu Leu
        290                 295                 300 ccg agt tca att ggg aat ctt tct tcg cat ttg agc tat ctt atc ata     960
Pro Ser Ser Ile Gly Asn Leu Ser Ser His Leu Ser Tyr Leu Ile Ile
305                 310                 315                 320 gcg aac aac aat ata gaa gga aaa ata cct gaa gga ata ggg aac ttg    1008
Ala Asn Asn Asn Ile Glu Gly Lys Ile Pro Glu Gly Ile Gly Asn Leu
                325                 330                 335 atc aac tta aaa ttg ctc tat atg gat att aac cgt tta gag gga att    1056
Ile Asn Leu Lys Leu Leu Tyr Met Asp Ile Asn Arg Leu Glu Gly Ile
                340                 345                 350 att cca gct tct ctt ggc aaa ctc aag atg ctg aat aaa tta tct ata    1104
Ile Pro Ala Ser Leu Gly Lys Leu Lys Met Leu Asn Lys Leu Ser Ile
            355                 360                 365 cca tat aat aac ctg tct gga tcc att cca cca act ctt ggc aat ctt    1152
Pro Tyr Asn Asn Leu Ser Gly Ser Ile Pro Pro Thr Leu Gly Asn Leu
        370                 375                 380 aca gga cta aat cta cta caa ctc caa gga aat gca ctc aat ggg tcc    1200
Thr Gly Leu Asn Leu Leu Gln Leu Gln Gly Asn Ala Leu Asn Gly Ser
385                 390                 395                 400 att cct tcc aat ctt agc agt tgt cct cta gaa cta ttg gat ctt tca    1248
Ile Pro Ser Asn Leu Ser Ser Cys Pro Leu Glu Leu Leu Asp Leu Ser
                405                 410                 415 tat aac agc ctc act ggc ttg ata cct aaa caa ctt ttt ctc att tct    1296
Tyr Asn Ser Leu Thr Gly Leu Ile Pro Lys Gln Leu Phe Leu Ile Ser
                420                 425                 430 act ttg tcc agt aac atg ttt ttg gga cat aat ttt tta tcg ggg gct    1344
Thr Leu Ser Ser Asn Met Phe Leu Gly His Asn Phe Leu Ser Gly Ala
            435                 440                 445 tta cca gct gaa atg ggt aat cta aaa aat ctt gga gag ttt gat ttt    1392
Leu Pro Ala Glu Met Gly Asn Leu Lys Asn Leu Gly Glu Phe Asp Phe
        450                 455                 460 tct tca aac aac att tct gga gag att cct aca tct att ggt gaa tgt    1440
Ser Ser Asn Asn Ile Ser Gly Glu Ile Pro Thr Ser Ile Gly Glu Cys
465                 470                 475                 480 aag agc ttg cag cag ctc aat ata tct gga aat tcc ctc caa ggg ata    1488
Lys Ser Leu Gln Gln Leu Asn Ile Ser Gly Asn Ser Leu Gln Gly Ile
                485                 490                 495 att cca tcg tcg ctt ggg caa cta aag ggc ctc ctg gtg ctt gac ctt    1536
Ile Pro Ser Ser Leu Gly Gln Leu Lys Gly Leu Leu Val Leu Asp Leu
                500                 505                 510 tct gac aat aat tta tct gga ggc atc cct gca ttt ctt ggg ggc atg    1584
Ser Asp Asn Asn Leu Ser Gly Gly Ile Pro Ala Phe Leu Gly Gly Met
            515                 520                 525 aga ggt cta tct att ttg aac ctc tca tac aac aaa ttt gaa ggt gaa    1632
Arg Gly Leu Ser Ile Leu Asn Leu Ser Tyr Asn Lys Phe Glu Gly Glu
        530                 535                 540 gtt ccc aga gat ggc gtt ttt cta aat gca aca gct acc ttc ctc gct    1680
Val Pro Arg Asp Gly Val Phe Leu Asn Ala Thr Ala Thr Phe Leu Ala
545                 550                 555                 560
```

```
gga aat gat gac ctg tgt ggc ggt atc cca gag atg aaa ttg cca ccc    1728
Gly Asn Asp Asp Leu Cys Gly Gly Ile Pro Glu Met Lys Leu Pro Pro
            565                 570                 575 tgc ttc aac caa acc acc aag aag gca tcc agg aaa ctt atc atc ata    1776
Cys Phe Asn Gln Thr Thr Lys Lys Ala Ser Arg Lys Leu Ile Ile Ile
        580                 585                 590 atc tcc ata tgc aga ata atg cca tta atc aca tta ata ttt atg ctg    1824
Ile Ser Ile Cys Arg Ile Met Pro Leu Ile Thr Leu Ile Phe Met Leu
    595                 600                 605 ttt gca ttc tac tat agg aac aag aag gca aaa cca aac cca caa ata    1872
Phe Ala Phe Tyr Tyr Arg Asn Lys Lys Ala Lys Pro Asn Pro Gln Ile
610                 615                 620 tca ctc att agt gag caa tat acg agg gtt tct tat gct gaa tta gtc    1920
Ser Leu Ile Ser Glu Gln Tyr Thr Arg Val Ser Tyr Ala Glu Leu Val
625                 630                 635                 640 aat gca aca aat ggt ttt gcc tct gat aac ctc ata gga gca gga agc    1968
Asn Ala Thr Asn Gly Phe Ala Ser Asp Asn Leu Ile Gly Ala Gly Ser
            645                 650                 655 ttt ggc tcg gtc tat aag gga aga atg aca aac aat gac caa caa gta    2016
Phe Gly Ser Val Tyr Lys Gly Arg Met Thr Asn Asn Asp Gln Gln Val
        660                 665                 670 gtt gct gtg aag gtg ctc aac ctc aca caa cgt ggt gca tct caa agt    2064
Val Ala Val Lys Val Leu Asn Leu Thr Gln Arg Gly Ala Ser Gln Ser
    675                 680                 685 ttc atg gca gaa tgt gag aca ctg aga tgt gtt cga cac cgg aac ctt    2112
Phe Met Ala Glu Cys Glu Thr Leu Arg Cys Val Arg His Arg Asn Leu
690                 695                 700 gtg aag ata ttg act gta tgc tcg agt att gat ttt cag ggc aat gag    2160
Val Lys Ile Leu Thr Val Cys Ser Ser Ile Asp Phe Gln Gly Asn Glu
705                 710                 715                 720 ttc aag gcc att gta tat gag tac cta cca aat gga aat tta gac caa    2208
Phe Lys Ala Ile Val Tyr Glu Tyr Leu Pro Asn Gly Asn Leu Asp Gln
            725                 730                 735 tgg cta cac cct aat atc atg gga caa agt gaa cac aag gca tta gat    2256
Trp Leu His Pro Asn Ile Met Gly Gln Ser Glu His Lys Ala Leu Asp
        740                 745                 750 ctc act gca aga cta cgc att gca atc gat gtg gca tct tca ctt gaa    2304
Leu Thr Ala Arg Leu Arg Ile Ala Ile Asp Val Ala Ser Ser Leu Glu
    755                 760                 765 tat ctt cac caa tat aag cca tcg cca atc att cac tgt gat ctt aag    2352
Tyr Leu His Gln Tyr Lys Pro Ser Pro Ile Ile His Cys Asp Leu Lys
770                 775                 780 cca agc aat gtt ctc ctc gac agt gac atg gtt gct cat gtt agc gat    2400
Pro Ser Asn Val Leu Leu Asp Ser Asp Met Val Ala His Val Ser Asp
785                 790                 795                 800 ttc ggg ctt gca agg ttt ctg cat cag gag tcg gag aaa tca agt ggt    2448
Phe Gly Leu Ala Arg Phe Leu His Gln Glu Ser Glu Lys Ser Ser Gly
            805                 810                 815 tgg gca tca atg aga gga aca gtc ggt tat gct gca cca gag tat gga    2496
Trp Ala Ser Met Arg Gly Thr Val Gly Tyr Ala Ala Pro Glu Tyr Gly
        820                 825                 830 att ggc aat gaa gtc tca att caa ggt gat gtc tat agc tat ggc ata    2544
Ile Gly Asn Glu Val Ser Ile Gln Gly Asp Val Tyr Ser Tyr Gly Ile
    835                 840                 845 ctg ttg cta gag atg ttc acc aga aaa aga ccc aca gac gat gaa ttc    2592
Leu Leu Leu Glu Met Phe Thr Arg Lys Arg Pro Thr Asp Asp Glu Phe
850                 855                 860 ggg gaa gcg gtt ggg ctt cgc aag tat gtc caa atg gca ttg cca gac    2640
Gly Glu Ala Val Gly Leu Arg Lys Tyr Val Gln Met Ala Leu Pro Asp
```

```
                865                 870                 875                 880
aat gcg gct aat gtt ctg gat caa cag tta cta cca gag aca gaa gat        2688
Asn Ala Ala Asn Val Leu Asp Gln Gln Leu Leu Pro Glu Thr Glu Asp
                    885                 890                 895 ggc gga gca atc aag tca aac tct tac aac ggc aag gat cta aga att        2736
Gly Gly Ala Ile Lys Ser Asn Ser Tyr Asn Gly Lys Asp Leu Arg Ile
            900                 905                 910 act tgt gtc act tcg gtt atg cgc att gga atc tcc tgc tca gag gag        2784
Thr Cys Val Thr Ser Val Met Arg Ile Gly Ile Ser Cys Ser Glu Glu
        915                 920                 925 gca cca acg gac cgc gtg caa atc gga gac gct ctg aag gag ttg caa        2832
Ala Pro Thr Asp Arg Val Gln Ile Gly Asp Ala Leu Lys Glu Leu Gln
    930                 935                 940 gca ata aga gac aag ttt gag aaa cat gtg tcc aat gaa gga aca tca        2880
Ala Ile Arg Asp Lys Phe Glu Lys His Val Ser Asn Glu Gly Thr Ser
945                 950                 955                 960 agc caa tga                                                            2889
Ser Gln <210> SEQ ID NO 17
<211> LENGTH: 962
<212> TYPE: PRT
<213> ORGANISM: Oryza sativa

<400> SEQUENCE: 17

Met Asn Thr Leu Thr Gly Ser Ile Pro Ser Glu Ile Gly Asn Leu Ala
1               5                   10                  15

Asn Leu Met Thr Leu Asn Leu Gln Phe Ser Asn Leu Thr Gly Gly Ile
                20                  25                  30

Pro Glu Glu Ile Gly Asp Leu Ala Gly Leu Val Gly Leu Gly Leu Gly
            35                  40                  45

Ser Asn Gln Leu Ala Gly Ser Ile Pro Ala Ser Leu Gly Asn Leu Ser
        50                  55                  60

Ala Leu Lys Tyr Leu Ser Ile Pro Ser Ala Lys Leu Thr Gly Ser Ile
65                  70                  75                  80

Pro Ser Leu Gln Asn Leu Ser Ser Leu Val Leu Glu Leu Gly Glu
                85                  90                  95

Asn Asn Leu Glu Gly Thr Val Pro Ala Trp Leu Gly Asn Leu Ser Ser
                100                 105                 110

Leu Val Phe Val Ser Leu Gln Gln Asn Arg Leu Ser Gly His Ile Pro
            115                 120                 125

Glu Ser Leu Gly Arg Leu Gln Met Leu Thr Ser Leu Asp Leu Ser Gln
        130                 135                 140

Asn Asn Leu Ile Ser Gly Ser Ile Pro Asp Ser Leu Gly Asn Leu Gly
145                 150                 155                 160

Ala Leu Ser Ser Leu Arg Leu Asp Tyr Asn Lys Leu Glu Gly Ser Phe
                165                 170                 175

Pro Pro Ser Leu Leu Asn Leu Ser Leu Asp Asp Leu Gly Leu Gln
            180                 185                 190

Ser Asn Arg Leu Ser Gly Ala Leu Pro Pro Asp Ile Gly Asn Lys Leu
        195                 200                 205

Pro Asn Leu Gln Arg Phe Val Val Asp Ile Asn Gln Phe His Gly Thr
    210                 215                 220

Ile Pro Pro Ser Leu Cys Asn Ala Thr Met Leu Gln Val Leu Gln Thr
225                 230                 235                 240

Val Tyr Asn Phe Leu Ser Gly Arg Ile Pro Gln Cys Leu Gly Ile Gln
```

```
                    245                 250                 255
Gln Lys Ser Leu Ser Val Val Ala Leu Ser Lys Asn Gln Leu Glu Ala
            260                 265                 270

Thr Asn Asp Ala Asp Trp Val Phe Leu Ser Ser Leu Ala Asn Cys Ser
        275                 280                 285

Asn Leu Asn Ala Leu Asp Leu Gly Tyr Asn Lys Leu Gln Gly Glu Leu
    290                 295                 300

Pro Ser Ser Ile Gly Asn Leu Ser Ser His Leu Ser Tyr Leu Ile Ile
305                 310                 315                 320

Ala Asn Asn Asn Ile Glu Gly Lys Ile Pro Glu Gly Ile Gly Asn Leu
                325                 330                 335

Ile Asn Leu Lys Leu Leu Tyr Met Asp Ile Asn Arg Leu Glu Gly Ile
            340                 345                 350

Ile Pro Ala Ser Leu Gly Lys Leu Lys Met Leu Asn Lys Leu Ser Ile
        355                 360                 365

Pro Tyr Asn Asn Leu Ser Gly Ser Ile Pro Thr Leu Gly Asn Leu
    370                 375                 380

Thr Gly Leu Asn Leu Leu Gln Leu Gln Gly Asn Ala Leu Asn Gly Ser
385                 390                 395                 400

Ile Pro Ser Asn Leu Ser Ser Cys Pro Leu Glu Leu Leu Asp Leu Ser
                405                 410                 415

Tyr Asn Ser Leu Thr Gly Leu Ile Pro Lys Gln Leu Phe Leu Ile Ser
            420                 425                 430

Thr Leu Ser Ser Asn Met Phe Leu Gly His Asn Phe Leu Ser Gly Ala
        435                 440                 445

Leu Pro Ala Glu Met Gly Asn Leu Lys Asn Leu Gly Glu Phe Asp Phe
    450                 455                 460

Ser Ser Asn Asn Ile Ser Gly Glu Ile Pro Thr Ser Ile Gly Glu Cys
465                 470                 475                 480

Lys Ser Leu Gln Gln Leu Asn Ile Ser Gly Asn Ser Leu Gln Gly Ile
                485                 490                 495

Ile Pro Ser Ser Leu Gly Gln Leu Lys Gly Leu Leu Val Leu Asp Leu
            500                 505                 510

Ser Asp Asn Asn Leu Ser Gly Gly Ile Pro Ala Phe Leu Gly Gly Met
        515                 520                 525

Arg Gly Leu Ser Ile Leu Asn Leu Ser Tyr Asn Lys Phe Glu Gly Glu
    530                 535                 540

Val Pro Arg Asp Gly Val Phe Leu Asn Ala Thr Ala Thr Phe Leu Ala
545                 550                 555                 560

Gly Asn Asp Asp Leu Cys Gly Gly Ile Pro Glu Met Lys Leu Pro Pro
                565                 570                 575

Cys Phe Asn Gln Thr Thr Lys Lys Ala Ser Arg Lys Leu Ile Ile Ile
            580                 585                 590

Ile Ser Ile Cys Arg Ile Met Pro Leu Ile Thr Leu Ile Phe Met Leu
        595                 600                 605

Phe Ala Phe Tyr Tyr Arg Asn Lys Lys Ala Lys Pro Asn Pro Gln Ile
    610                 615                 620

Ser Leu Ile Ser Glu Gln Tyr Thr Arg Val Ser Tyr Ala Glu Leu Val
625                 630                 635                 640

Asn Ala Thr Asn Gly Phe Ala Ser Asp Asn Leu Ile Gly Ala Gly Ser
                645                 650                 655

Phe Gly Ser Val Tyr Lys Gly Arg Met Thr Asn Asn Asp Gln Gln Val
            660                 665                 670
```

```
Val Ala Val Lys Val Leu Asn Leu Thr Gln Arg Gly Ala Ser Gln Ser
            675                 680                 685

Phe Met Ala Glu Cys Glu Thr Leu Arg Cys Val Arg His Arg Asn Leu
            690                 695                 700

Val Lys Ile Leu Thr Val Cys Ser Ser Ile Asp Phe Gln Gly Asn Glu
705                 710                 715                 720

Phe Lys Ala Ile Val Tyr Glu Tyr Leu Pro Asn Gly Asn Leu Asp Gln
            725                 730                 735

Trp Leu His Pro Asn Ile Met Gly Gln Ser Glu His Lys Ala Leu Asp
            740                 745                 750

Leu Thr Ala Arg Leu Arg Ile Ala Ile Asp Val Ala Ser Ser Leu Glu
            755                 760                 765

Tyr Leu His Gln Tyr Lys Pro Ser Pro Ile Ile His Cys Asp Leu Lys
            770                 775                 780

Pro Ser Asn Val Leu Leu Asp Ser Asp Met Val Ala His Val Ser Asp
785                 790                 795                 800

Phe Gly Leu Ala Arg Phe Leu His Gln Glu Ser Glu Lys Ser Ser Gly
            805                 810                 815

Trp Ala Ser Met Arg Gly Thr Val Gly Tyr Ala Ala Pro Glu Tyr Gly
            820                 825                 830

Ile Gly Asn Glu Val Ser Ile Gln Gly Asp Val Tyr Ser Tyr Gly Ile
            835                 840                 845

Leu Leu Leu Glu Met Phe Thr Arg Lys Arg Pro Thr Asp Asp Glu Phe
850                 855                 860

Gly Glu Ala Val Gly Leu Arg Lys Tyr Val Gln Met Ala Leu Pro Asp
865                 870                 875                 880

Asn Ala Ala Asn Val Leu Asp Gln Gln Leu Leu Pro Glu Thr Glu Asp
            885                 890                 895

Gly Gly Ala Ile Lys Ser Asn Ser Tyr Asn Gly Lys Asp Leu Arg Ile
            900                 905                 910

Thr Cys Val Thr Ser Val Met Arg Ile Gly Ile Ser Cys Ser Glu Glu
            915                 920                 925

Ala Pro Thr Asp Arg Val Gln Ile Gly Asp Ala Leu Lys Glu Leu Gln
            930                 935                 940

Ala Ile Arg Asp Lys Phe Glu Lys His Val Ser Asn Glu Gly Thr Ser
945                 950                 955                 960

Ser Gln

<210> SEQ ID NO 18
<211> LENGTH: 3348
<212> TYPE: DNA
<213> ORGANISM: Oryza sativa
<220> FEATURE:
<221> NAME/KEY: CDS
<222> LOCATION: (1)..(3348)

<400> SEQUENCE: 18 atg tca ttc agg tcg ctc ata agg agt gac cca acc cag gca ctc gca      48
Met Ser Phe Arg Ser Leu Ile Arg Ser Asp Pro Thr Gln Ala Leu Ala
1               5                   10                  15 tcc tgg ggc aac caa tcc atc ccg atg tgc caa tgg cgt ggt gtg gcg      96
Ser Trp Gly Asn Gln Ser Ile Pro Met Cys Gln Trp Arg Gly Val Ala
                20                  25                  30 tgt ggg ctg agt gga cgc cgc aca ggc cgt gtg gtg gcg ctg gac ctc     144
Cys Gly Leu Ser Gly Arg Arg Thr Gly Arg Val Val Ala Leu Asp Leu
            35                  40                  45
```

```
acc aag ctc aac ctt gta ggc gcc atc tca cct ttg ctc ggc aac ctc      192
Thr Lys Leu Asn Leu Val Gly Ala Ile Ser Pro Leu Leu Gly Asn Leu
 50              55                  60 aca tac ctg agg cgg ctc cat ctc cac aag aat cgc ctc cat ggc gag      240
Thr Tyr Leu Arg Arg Leu His Leu His Lys Asn Arg Leu His Gly Glu
 65              70                  75                  80 ata ccg tcg gag ctc ggc cat ctc cga gac ctg aga cac ctc aac cgc      288
Ile Pro Ser Glu Leu Gly His Leu Arg Asp Leu Arg His Leu Asn Arg
                 85                  90                  95 agc tac aac tcc atc caa ggg ccg atc cca gcg acg ctt tca acc tgc      336
Ser Tyr Asn Ser Ile Gln Gly Pro Ile Pro Ala Thr Leu Ser Thr Cys
            100                 105                 110 aga gga atg gag aac att tgg ctc tac agc aac aag ctg cag ggc caa      384
Arg Gly Met Glu Asn Ile Trp Leu Tyr Ser Asn Lys Leu Gln Gly Gln
        115                 120                 125 ata cca agt gag ttt gga tcc ctg caa aat ctt cag gca ctt gtt ctt      432
Ile Pro Ser Glu Phe Gly Ser Leu Gln Asn Leu Gln Ala Leu Val Leu
    130                 135                 140 ggg gaa aat aga ctt act gga agc atc cct tca ttc att gga agc ctc      480
Gly Glu Asn Arg Leu Thr Gly Ser Ile Pro Ser Phe Ile Gly Ser Leu
145                 150                 155                 160 gcg aat ctg aaa ttt cta atc cta gaa gaa aac aac ttt aca gga gaa      528
Ala Asn Leu Lys Phe Leu Ile Leu Glu Glu Asn Asn Phe Thr Gly Glu
                165                 170                 175 att cca tca gac ata ggc aga ctg gcc aat ctc act gtt cta gga cta      576
Ile Pro Ser Asp Ile Gly Arg Leu Ala Asn Leu Thr Val Leu Gly Leu
            180                 185                 190 ggt tct aat caa ctc tca gga cca att cct gcc tca ata gga aat ctc      624
Gly Ser Asn Gln Leu Ser Gly Pro Ile Pro Ala Ser Ile Gly Asn Leu
        195                 200                 205 tcg gca cta caa ttt ctt agt gtc ttc tct aat aac ctg gta gga agc      672
Ser Ala Leu Gln Phe Leu Ser Val Phe Ser Asn Asn Leu Val Gly Ser
    210                 215                 220 atc cca ccg atg caa cgc ttg tcc tct ctc gaa ttc ttt gaa cta ggg      720
Ile Pro Pro Met Gln Arg Leu Ser Ser Leu Glu Phe Phe Glu Leu Gly
225                 230                 235                 240 aag aac aat atc gaa gga agc atc cca act tgg ctg gga aac ctc tca      768
Lys Asn Asn Ile Glu Gly Ser Ile Pro Thr Trp Leu Gly Asn Leu Ser
                245                 250                 255 tca tta ctt act gtg aaa ctt gga ggc aat aga cta gat ggg aac atc      816
Ser Leu Leu Thr Val Lys Leu Gly Gly Asn Arg Leu Asp Gly Asn Ile
            260                 265                 270 cct gaa tca ctg ggg aaa ctg aag ttg ctt aca tct ctt gat cta tca      864
Pro Glu Ser Leu Gly Lys Leu Lys Leu Leu Thr Ser Leu Asp Leu Ser
        275                 280                 285 agt aat aat cta gtg ggc cca gta cct gat act att gga aac cta tat      912
Ser Asn Asn Leu Val Gly Pro Val Pro Asp Thr Ile Gly Asn Leu Tyr
    290                 295                 300 tcc att aag cag ttt cat gta gaa aat aat gag cta gaa ggt tct tta      960
Ser Ile Lys Gln Phe His Val Glu Asn Asn Glu Leu Glu Gly Ser Leu
305                 310                 315                 320 cct tct tca ata ttc aat ctt tcc tct ctt gaa gaa ctc aac tta caa     1008
Pro Ser Ser Ile Phe Asn Leu Ser Ser Leu Glu Glu Leu Asn Leu Gln
                325                 330                 335 acc aac aac cta aat ggg acc att cca ctt gac tta ggc aac cgc ctg     1056
Thr Asn Asn Leu Asn Gly Thr Ile Pro Leu Asp Leu Gly Asn Arg Leu
            340                 345                 350 cca aag ctc cag tta ttc cta ata tct gaa aac cag ttt cat ggc tca     1104
Pro Lys Leu Gln Leu Phe Leu Ile Ser Glu Asn Gln Phe His Gly Ser
```

```
                355              360              365
att cca ccc tcc ctg tgc aat att tct acg ctt aga tgg atc caa aca    1152
Ile Pro Pro Ser Leu Cys Asn Ile Ser Thr Leu Arg Trp Ile Gln Thr
370             375             380 gta aac aat tct ttg tca gga acc atc ccc caa tgc ata gga atc aac    1200
Val Asn Asn Ser Leu Ser Gly Thr Ile Pro Gln Cys Ile Gly Ile Asn
385             390             395             400 caa aag agc tta tat tcc gta act ttt gca gtg aat cag ttt gaa acg    1248
Gln Lys Ser Leu Tyr Ser Val Thr Phe Ala Val Asn Gln Phe Glu Thr
            405             410             415 agt aat aaa tat ggt tgg agc ttc atg tct agt tta act aac tgc agc    1296
Ser Asn Lys Tyr Gly Trp Ser Phe Met Ser Ser Leu Thr Asn Cys Ser
        420             425             430 aat ttg cga cta ctt gat gtg ggt gac aac aag ctt aca ggt gag cta    1344
Asn Leu Arg Leu Leu Asp Val Gly Asp Asn Lys Leu Thr Gly Glu Leu
        435             440             445 cca aat tca att ggc aat ctt tcc aca cgt ctt gag tat ttt gtc acc    1392
Pro Asn Ser Ile Gly Asn Leu Ser Thr Arg Leu Glu Tyr Phe Val Thr
450             455             460 aac tac aac agt atg act ggc aaa ata cct gaa ggg cta ggg aat ctg    1440
Asn Tyr Asn Ser Met Thr Gly Lys Ile Pro Glu Gly Leu Gly Asn Leu
465             470             475             480 gtc agc ttg aag ttc atc gag atg aac aat aac ttc tac gag ggc aca    1488
Val Ser Leu Lys Phe Ile Glu Met Asn Asn Asn Phe Tyr Glu Gly Thr
            485             490             495 ata cca gac tct ctt ggc aaa ctc aag aac ctg aat aga cta tat ctc    1536
Ile Pro Asp Ser Leu Gly Lys Leu Lys Asn Leu Asn Arg Leu Tyr Leu
        500             505             510 act aac aac aac ctt tca gga tcc att cca tca agt atc ggc aac ctt    1584
Thr Asn Asn Asn Leu Ser Gly Ser Ile Pro Ser Ser Ile Gly Asn Leu
        515             520             525 cgt atg cta aca tta tta tct gtt gca ggc aat gca ctt agt gga gaa    1632
Arg Met Leu Thr Leu Leu Ser Val Ala Gly Asn Ala Leu Ser Gly Glu
530             535             540 ata ccc ccc agt ctc agc aat tgc cct ttg gaa cag ttg aaa ctc tca    1680
Ile Pro Pro Ser Leu Ser Asn Cys Pro Leu Glu Gln Leu Lys Leu Ser
545             550             555             560 tac aat aat ctt act ggg ttg att cca aaa gaa ctt ttc gcc atc tct    1728
Tyr Asn Asn Leu Thr Gly Leu Ile Pro Lys Glu Leu Phe Ala Ile Ser
            565             570             575 gtc ttg tct act tct ttg att ttg gat cat aat ttt ata act ggg cct    1776
Val Leu Ser Thr Ser Leu Ile Leu Asp His Asn Phe Ile Thr Gly Pro
        580             585             590 ctg ccc tct gaa gtg ggt aat cta aca aac ctt gca tta ctt gat ttc    1824
Leu Pro Ser Glu Val Gly Asn Leu Thr Asn Leu Ala Leu Leu Asp Phe
        595             600             605 tct agc aat ttg att tct gga gag atc ccg tcc tcc att ggt gag tgc    1872
Ser Ser Asn Leu Ile Ser Gly Glu Ile Pro Ser Ser Ile Gly Glu Cys
610             615             620 cag agt cta caa tat ctc aat aca tct gga aac tta ctc caa ggg caa    1920
Gln Ser Leu Gln Tyr Leu Asn Thr Ser Gly Asn Leu Leu Gln Gly Gln
625             630             635             640 att cca cca tca cta gat caa cca aag ggc ctc ctg ttg ctt gat ctt    1968
Ile Pro Pro Ser Leu Asp Gln Pro Lys Gly Leu Leu Leu Leu Asp Leu
            645             650             655 tct cat aat aat tta tcc gga agc atc cct aag ttc ctt ggg acc atg    2016
Ser His Asn Asn Leu Ser Gly Ser Ile Pro Lys Phe Leu Gly Thr Met
        660             665             670 aca ggg ctt gct agt ttg aat ctt tca ttc aac aac ttt gag ggt gat    2064
Thr Gly Leu Ala Ser Leu Asn Leu Ser Phe Asn Asn Phe Glu Gly Asp
```

```
                Thr Gly Leu Ala Ser Leu Asn Leu Ser Phe Asn Asn Phe Glu Gly Asp
                            675                 680                 685 gtc cca aaa gat gga atc ttt agc aat gcg act cct gct tta att gag         2112
Val Pro Lys Asp Gly Ile Phe Ser Asn Ala Thr Pro Ala Leu Ile Glu
        690                 695                 700 gga aat aat ggc cta tgt aat gga atc cct caa ctg aag ttg cca ccc         2160
Gly Asn Asn Gly Leu Cys Asn Gly Ile Pro Gln Leu Lys Leu Pro Pro
705                 710                 715                 720 tgc tct cat cag aca aca aaa cac aag aag caa aca tgg aaa att gcc         2208
Cys Ser His Gln Thr Thr Lys His Lys Lys Gln Thr Trp Lys Ile Ala
                725                 730                 735 atg gca att tct ata tgc agc aca gtt cta ttt atg gca gta gta gcc         2256
Met Ala Ile Ser Ile Cys Ser Thr Val Leu Phe Met Ala Val Val Ala
            740                 745                 750 aca tct ttc gtg ttc cac aaa cgg gcc aag aag aca aat gca aac cga         2304
Thr Ser Phe Val Phe His Lys Arg Ala Lys Lys Thr Asn Ala Asn Arg
        755                 760                 765 caa aca tca ctt att aaa gag cag cat atg aga gtt tct tac act gaa         2352
Gln Thr Ser Leu Ile Lys Glu Gln His Met Arg Val Ser Tyr Thr Glu
    770                 775                 780 ttg gct gaa gca aca aaa ggt ttt act tct gag aac ctc att gga gca         2400
Leu Ala Glu Ala Thr Lys Gly Phe Thr Ser Glu Asn Leu Ile Gly Ala
785                 790                 795                 800 ggg agc ttc ggc tct gtg tac aag gga aga atg aaa atc aat gac caa         2448
Gly Ser Phe Gly Ser Val Tyr Lys Gly Arg Met Lys Ile Asn Asp Gln
                805                 810                 815 caa gta gct gtt gct gtg aaa gtg ttc aac ctc aag cag cgt ggt tca         2496
Gln Val Ala Val Ala Val Lys Val Phe Asn Leu Lys Gln Arg Gly Ser
            820                 825                 830 tct aag agt ttt gca gca gaa tgt gag act tta aga tgt gtt cga cat         2544
Ser Lys Ser Phe Ala Ala Glu Cys Glu Thr Leu Arg Cys Val Arg His
        835                 840                 845 cgg aac ctt gta aag gta ctg acc gta tgc tca agt atc gat ttt cag         2592
Arg Asn Leu Val Lys Val Leu Thr Val Cys Ser Ser Ile Asp Phe Gln
    850                 855                 860 ggc cgt gat ttc aag gcc att gta tac aag ttc cta ccg aat aga aat         2640
Gly Arg Asp Phe Lys Ala Ile Val Tyr Lys Phe Leu Pro Asn Arg Asn
865                 870                 875                 880 tta gat caa tgg cta cac caa aat atc atg gaa gat ggt gaa cac aag         2688
Leu Asp Gln Trp Leu His Gln Asn Ile Met Glu Asp Gly Glu His Lys
                885                 890                 895 gca tta gat ctc atc acg cga cta gaa atc gca att gat gtg gca tcc         2736
Ala Leu Asp Leu Ile Thr Arg Leu Glu Ile Ala Ile Asp Val Ala Ser
            900                 905                 910 tca ctt gaa tat ctt cac caa tat aag gca tcg cca atc att cac tgt         2784
Ser Leu Glu Tyr Leu His Gln Tyr Lys Ala Ser Pro Ile Ile His Cys
        915                 920                 925 gat ctt aag cca agc aat gtt ctc ctc gac gat gag atg gtt gca cat         2832
Asp Leu Lys Pro Ser Asn Val Leu Leu Asp Asp Glu Met Val Ala His
    930                 935                 940 gtt ggt gat ttt ggc ctt gca aga ttt ctt cac cag gac cca gag caa         2880
Val Gly Asp Phe Gly Leu Ala Arg Phe Leu His Gln Asp Pro Glu Gln
945                 950                 955                 960 tca agt ggt tgg gca tca atg aga ggc aca act ggt tat gct gct cca         2928
Ser Ser Gly Trp Ala Ser Met Arg Gly Thr Thr Gly Tyr Ala Ala Pro
                965                 970                 975 gag tat gga ctg ggc aac gaa gtc tca atc cat ggc gat gta tat agc         2976
Glu Tyr Gly Leu Gly Asn Glu Val Ser Ile His Gly Asp Val Tyr Ser
            980                 985                 990
```

```
tat ggt ata ttg ttg ctg gag atg ttt agc ggg aag aga cca aca gac    3024
Tyr Gly Ile Leu Leu Leu Glu Met Phe Ser Gly Lys Arg Pro Thr Asp
            995                 1000                1005 agc gaa ttt gga gaa tcc ctt ggc ctc cat aat tat gtc aat atg        3069
Ser Glu Phe Gly Glu Ser Leu Gly Leu His Asn Tyr Val Asn Met
    1010                1015                1020 gca ttg cca gac agg acg gct agt gtc ata gac ctt agc tta cta        3114
Ala Leu Pro Asp Arg Thr Ala Ser Val Ile Asp Leu Ser Leu Leu
1025                1030                1035 gaa gag aca gtg gat ggc gaa gca aag aca tca aaa tct aac cag        3159
Glu Glu Thr Val Asp Gly Glu Ala Lys Thr Ser Lys Ser Asn Gln
1040                1045                1050 aca aga gaa atg aga att gct tgc att acc tca att ctg cat gtt        3204
Thr Arg Glu Met Arg Ile Ala Cys Ile Thr Ser Ile Leu His Val
    1055                1060                1065 gga gtt tcc tgt tca gtg gag aca cca aca gat cgc atg cca atc        3249
Gly Val Ser Cys Ser Val Glu Thr Pro Thr Asp Arg Met Pro Ile
1070                1075                1080 gga gat gcc ctg aaa gag ctg cag aga ata aga gac aag ttc cac        3294
Gly Asp Ala Leu Lys Glu Leu Gln Arg Ile Arg Asp Lys Phe His
1085                1090                1095 agg gag ttg caa gga gca gga gcg aca aac cat caa gac att caa        3339
Arg Glu Leu Gln Gly Ala Gly Ala Thr Asn His Gln Asp Ile Gln
1100                1105                1110 atc tgt tga                                                         3348
Ile Cys
    1115

<210> SEQ ID NO 19
<211> LENGTH: 1115
<212> TYPE: PRT
<213> ORGANISM: Oryza sativa

<400> SEQUENCE: 19

Met Ser Phe Arg Ser Leu Ile Arg Ser Asp Pro Thr Gln Ala Leu Ala
1               5                   10                  15

Ser Trp Gly Asn Gln Ser Ile Pro Met Cys Gln Trp Arg Gly Val Ala
            20                  25                  30

Cys Gly Leu Ser Gly Arg Arg Thr Gly Arg Val Val Ala Leu Asp Leu
        35                  40                  45

Thr Lys Leu Asn Leu Val Gly Ala Ile Ser Pro Leu Leu Gly Asn Leu
    50                  55                  60

Thr Tyr Leu Arg Arg Leu His Leu His Lys Asn Arg Leu His Gly Glu
65                  70                  75                  80

Ile Pro Ser Glu Leu Gly His Leu Arg Asp Leu Arg His Leu Asn Arg
                85                  90                  95

Ser Tyr Asn Ser Ile Gln Gly Pro Ile Pro Ala Thr Leu Ser Thr Cys
            100                 105                 110

Arg Gly Met Glu Asn Ile Trp Leu Tyr Ser Asn Lys Leu Gln Gly Gln
        115                 120                 125

Ile Pro Ser Glu Phe Gly Ser Leu Gln Asn Leu Gln Ala Leu Val Leu
    130                 135                 140

Gly Glu Asn Arg Leu Thr Gly Ser Ile Pro Ser Phe Ile Gly Ser Leu
145                 150                 155                 160

Ala Asn Leu Lys Phe Leu Ile Leu Glu Glu Asn Asn Phe Thr Gly Glu
                165                 170                 175

Ile Pro Ser Asp Ile Gly Arg Leu Ala Asn Leu Thr Val Leu Gly Leu
            180                 185                 190
```

```
Gly Ser Asn Gln Leu Ser Gly Pro Ile Pro Ala Ser Ile Gly Asn Leu
        195                 200                 205

Ser Ala Leu Gln Phe Leu Ser Val Phe Ser Asn Asn Leu Val Gly Ser
        210                 215                 220

Ile Pro Pro Met Gln Arg Leu Ser Ser Leu Glu Phe Phe Glu Leu Gly
225                 230                 235                 240

Lys Asn Asn Ile Glu Gly Ser Ile Pro Thr Trp Leu Gly Asn Leu Ser
                245                 250                 255

Ser Leu Leu Thr Val Lys Leu Gly Gly Asn Arg Leu Asp Gly Asn Ile
            260                 265                 270

Pro Glu Ser Leu Gly Lys Leu Lys Leu Leu Thr Ser Leu Asp Leu Ser
        275                 280                 285

Ser Asn Asn Leu Val Gly Pro Val Pro Asp Thr Ile Gly Asn Leu Tyr
        290                 295                 300

Ser Ile Lys Gln Phe His Val Glu Asn Asn Glu Leu Glu Gly Ser Leu
305                 310                 315                 320

Pro Ser Ser Ile Phe Asn Leu Ser Ser Leu Glu Glu Leu Asn Leu Gln
                325                 330                 335

Thr Asn Asn Leu Asn Gly Thr Ile Pro Leu Asp Leu Gly Asn Arg Leu
            340                 345                 350

Pro Lys Leu Gln Leu Phe Leu Ile Ser Glu Asn Gln Phe His Gly Ser
        355                 360                 365

Ile Pro Pro Ser Leu Cys Asn Ile Ser Thr Leu Arg Trp Ile Gln Thr
        370                 375                 380

Val Asn Asn Ser Leu Ser Gly Thr Ile Pro Gln Cys Ile Gly Ile Asn
385                 390                 395                 400

Gln Lys Ser Leu Tyr Ser Val Thr Phe Ala Val Asn Gln Phe Glu Thr
                405                 410                 415

Ser Asn Lys Tyr Gly Trp Ser Phe Met Ser Ser Leu Thr Asn Cys Ser
            420                 425                 430

Asn Leu Arg Leu Leu Asp Val Gly Asp Asn Lys Leu Thr Gly Glu Leu
        435                 440                 445

Pro Asn Ser Ile Gly Asn Leu Ser Thr Arg Leu Glu Tyr Phe Val Thr
        450                 455                 460

Asn Tyr Asn Ser Met Thr Gly Lys Ile Pro Glu Gly Leu Gly Asn Leu
465                 470                 475                 480

Val Ser Leu Lys Phe Ile Glu Met Asn Asn Asn Phe Tyr Glu Gly Thr
                485                 490                 495

Ile Pro Asp Ser Leu Gly Lys Leu Lys Asn Leu Asn Arg Leu Tyr Leu
            500                 505                 510

Thr Asn Asn Asn Leu Ser Gly Ser Ile Pro Ser Ser Ile Gly Asn Leu
        515                 520                 525

Arg Met Leu Thr Leu Leu Ser Val Ala Gly Asn Ala Leu Ser Gly Glu
        530                 535                 540

Ile Pro Pro Ser Leu Ser Asn Cys Pro Leu Glu Gln Leu Lys Leu Ser
545                 550                 555                 560

Tyr Asn Asn Leu Thr Gly Leu Ile Pro Lys Glu Leu Phe Ala Ile Ser
                565                 570                 575

Val Leu Ser Thr Ser Leu Ile Leu Asp His Asn Phe Ile Thr Gly Pro
            580                 585                 590

Leu Pro Ser Glu Val Gly Asn Leu Thr Asn Leu Ala Leu Leu Asp Phe
        595                 600                 605
```

```
Ser Ser Asn Leu Ile Ser Gly Glu Ile Pro Ser Ser Ile Gly Glu Cys
610                 615                 620

Gln Ser Leu Gln Tyr Leu Asn Thr Ser Gly Asn Leu Leu Gln Gly Gln
625                 630                 635                 640

Ile Pro Pro Ser Leu Asp Gln Pro Lys Gly Leu Leu Leu Asp Leu
                    645                 650                 655

Ser His Asn Asn Leu Ser Gly Ser Ile Pro Lys Phe Leu Gly Thr Met
                660                 665                 670

Thr Gly Leu Ala Ser Leu Asn Leu Ser Phe Asn Asn Phe Glu Gly Asp
            675                 680                 685

Val Pro Lys Asp Gly Ile Phe Ser Asn Ala Thr Pro Ala Leu Ile Glu
690                 695                 700

Gly Asn Asn Gly Leu Cys Asn Gly Ile Pro Gln Leu Lys Leu Pro Pro
705                 710                 715                 720

Cys Ser His Gln Thr Thr Lys His Lys Lys Gln Thr Trp Lys Ile Ala
                725                 730                 735

Met Ala Ile Ser Ile Cys Ser Thr Val Leu Phe Met Ala Val Val Ala
            740                 745                 750

Thr Ser Phe Val Phe His Lys Arg Ala Lys Thr Asn Ala Asn Arg
        755                 760                 765

Gln Thr Ser Leu Ile Lys Glu Gln His Met Arg Val Ser Tyr Thr Glu
770                 775                 780

Leu Ala Glu Ala Thr Lys Gly Phe Thr Ser Glu Asn Leu Ile Gly Ala
785                 790                 795                 800

Gly Ser Phe Gly Ser Val Tyr Lys Gly Arg Met Lys Ile Asn Asp Gln
                805                 810                 815

Gln Val Ala Val Ala Val Lys Val Phe Asn Leu Lys Gln Arg Gly Ser
            820                 825                 830

Ser Lys Ser Phe Ala Ala Glu Cys Glu Thr Leu Arg Cys Val Arg His
        835                 840                 845

Arg Asn Leu Val Lys Val Leu Thr Val Cys Ser Ser Ile Asp Phe Gln
    850                 855                 860

Gly Arg Asp Phe Lys Ala Ile Val Tyr Lys Phe Leu Pro Asn Arg Asn
865                 870                 875                 880

Leu Asp Gln Trp Leu His Gln Asn Ile Met Glu Asp Gly Glu His Lys
                885                 890                 895

Ala Leu Asp Leu Ile Thr Arg Leu Glu Ile Ala Ile Asp Val Ala Ser
            900                 905                 910

Ser Leu Glu Tyr Leu His Gln Tyr Lys Ala Ser Pro Ile Ile His Cys
        915                 920                 925

Asp Leu Lys Pro Ser Asn Val Leu Leu Asp Asp Glu Met Val Ala His
    930                 935                 940

Val Gly Asp Phe Gly Leu Ala Arg Phe Leu His Gln Asp Pro Glu Gln
945                 950                 955                 960

Ser Ser Gly Trp Ala Ser Met Arg Gly Thr Thr Gly Tyr Ala Ala Pro
                965                 970                 975

Glu Tyr Gly Leu Gly Asn Glu Val Ser Ile His Gly Asp Val Tyr Ser
            980                 985                 990

Tyr Gly Ile Leu Leu Leu Glu Met  Phe Ser Gly Lys Arg  Pro Thr Asp
        995                 1000                1005

Ser Glu  Phe Gly Glu Ser Leu  Gly Leu His Asn Tyr  Val Asn Met
    1010                1015                1020

Ala Leu  Pro Asp Arg Thr Ala  Ser Val Ile Asp Leu  Ser Leu Leu
```

```
                    1025                1030                1035

Glu Glu Thr Val Asp Gly Glu Ala Lys Thr Ser Lys Ser Asn Gln
    1040                1045                1050

Thr Arg Glu Met Arg Ile Ala Cys Ile Thr Ser Ile Leu His Val
    1055                1060                1065

Gly Val Ser Cys Ser Val Glu Thr Pro Thr Asp Arg Met Pro Ile
    1070                1075                1080

Gly Asp Ala Leu Lys Glu Leu Gln Arg Ile Arg Asp Lys Phe His
    1085                1090                1095

Arg Glu Leu Gln Gly Ala Gly Ala Thr Asn His Gln Asp Ile Gln
    1100                1105                1110

Ile Cys
    1115

<210> SEQ ID NO 20
<211> LENGTH: 5715
<212> TYPE: DNA
<213> ORGANISM: Vitis vinifera
<220> FEATURE:
<221> NAME/KEY: CDS
<222> LOCATION: (1)..(5715)
<220> FEATURE:
<221> NAME/KEY: misc_feature
<222> LOCATION: (3)..(3)
<223> OTHER INFORMATION: The 'Xaa' at location 3 stands for Val, or Leu.
<220> FEATURE:
<221> NAME/KEY: misc_feature
<222> LOCATION: (762)..(762)
<223> OTHER INFORMATION: The 'Xaa' at location 762 stands for Ile, or
      Phe.
<220> FEATURE:
<221> NAME/KEY: misc_feature
<222> LOCATION: (1160)..(1160)
<223> OTHER INFORMATION: The 'Xaa' at location 1160 stands for Gln, or
      Leu.
<220> FEATURE:
<221> NAME/KEY: misc_feature
<222> LOCATION: (1367)..(1367)
<223> OTHER INFORMATION: The 'Xaa' at location 1367 stands for Glu, or
      Gln.
<220> FEATURE:
<221> NAME/KEY: misc_feature
<222> LOCATION: (1402)..(1402)
<223> OTHER INFORMATION: The 'Xaa' at location 1402 stands for Gly, or
      Arg.
<220> FEATURE:
<221> NAME/KEY: misc_feature
<222> LOCATION: (1418)..(1418)
<223> OTHER INFORMATION: The 'Xaa' at location 1418 stands for Gln, or
      His.
<220> FEATURE:
<221> NAME/KEY: misc_feature
<222> LOCATION: (1426)..(1426)
<223> OTHER INFORMATION: The 'Xaa' at location 1426 stands for Gly, or
      Asp.
<220> FEATURE:
<221> NAME/KEY: misc_feature
<222> LOCATION: (1444)..(1444)
<223> OTHER INFORMATION: The 'Xaa' at location 1444 stands for Leu.
<220> FEATURE:
<221> NAME/KEY: misc_feature
<222> LOCATION: (1674)..(1674)
<223> OTHER INFORMATION: The 'Xaa' at location 1674 stands for Ile, or
      Phe.
<220> FEATURE:
<221> NAME/KEY: misc_feature
<222> LOCATION: (1710)..(1710)
<223> OTHER INFORMATION: The 'Xaa' at location 1710 stands for Thr.
<220> FEATURE:
<221> NAME/KEY: misc_feature
<222> LOCATION: (1718)..(1718)
<223> OTHER INFORMATION: The 'Xaa' at location 1718 stands for Arg, or
```

-continued

His.

<400> SEQUENCE: 20

```
atg cac kta cat tgc cca ctt ctc ttc ata gtc tgt cca gtt act acc     48
Met His Xaa His Cys Pro Leu Leu Phe Ile Val Cys Pro Val Thr Thr
1               5                   10                  15 tgc ctt gcc aat tac cag cca tgc tac tct ctc ttc aag acc aat act     96
Cys Leu Ala Asn Tyr Gln Pro Cys Tyr Ser Leu Phe Lys Thr Asn Thr
                20                  25                  30 ttg att cca ttt cgc tca ttt atc ttc cat tca att ctt gta cca tac    144
Leu Ile Pro Phe Arg Ser Phe Ile Phe His Ser Ile Leu Val Pro Tyr
            35                  40                  45 acc atc atc ttc ctc cat tca cca tct cca acc act tca tcc acc att    192
Thr Ile Ile Phe Leu His Ser Pro Ser Pro Thr Thr Ser Ser Thr Ile
50                  55                  60 ttg tat ggc aac gag act gat agg ctg gcc tta cta gcc atc aaa gca    240
Leu Tyr Gly Asn Glu Thr Asp Arg Leu Ala Leu Leu Ala Ile Lys Ala
65                  70                  75                  80 cag ata acc caa gac cca ctt gga atc acc act tca tgg aac gat tct    288
Gln Ile Thr Gln Asp Pro Leu Gly Ile Thr Thr Ser Trp Asn Asp Ser
                85                  90                  95 gtc cat ttc tgc aac tgg act ggt gtc aca tgc gga cac cgt cac cag    336
Val His Phe Cys Asn Trp Thr Gly Val Thr Cys Gly His Arg His Gln
                100                 105                 110 cga gtt aac acc ttg aac ctc agc tcc ctt cac ttg gtg ggg tct cta    384
Arg Val Asn Thr Leu Asn Leu Ser Ser Leu His Leu Val Gly Ser Leu
            115                 120                 125 tct cct tct ata ggg aac ctc acc ttc ctt acc ggt ctc aac ctc gaa    432
Ser Pro Ser Ile Gly Asn Leu Thr Phe Leu Thr Gly Leu Asn Leu Glu
        130                 135                 140 ctc aac aac ttc cat ggc caa atc cca caa gaa ctt ggg cgt ctg tcc    480
Leu Asn Asn Phe His Gly Gln Ile Pro Gln Glu Leu Gly Arg Leu Ser
145                 150                 155                 160 aga ctc aga gct ctt aac ttg acc aac aac tcc ttc tcc gga gag att    528
Arg Leu Arg Ala Leu Asn Leu Thr Asn Asn Ser Phe Ser Gly Glu Ile
                165                 170                 175 cct gcc aat ctc tcc cgc tgc tct aac ctc gtt tat ttt cgt ctg ggc    576
Pro Ala Asn Leu Ser Arg Cys Ser Asn Leu Val Tyr Phe Arg Leu Gly
            180                 185                 190 ttc aac aac tta att ggg agg atc cca tct tgg ctt ggc tca tat cca    624
Phe Asn Asn Leu Ile Gly Arg Ile Pro Ser Trp Leu Gly Ser Tyr Pro
        195                 200                 205 aag gtt gtg agg atg caa ctt cac tac aac aat ctg acc ggg cca gtc    672
Lys Val Val Arg Met Gln Leu His Tyr Asn Asn Leu Thr Gly Pro Val
    210                 215                 220 cca gat tct tta ggc aac ctc act agc att aaa tct ctg tct ttt gca    720
Pro Asp Ser Leu Gly Asn Leu Thr Ser Ile Lys Ser Leu Ser Phe Ala
225                 230                 235                 240 gtc aat cac ttg gag gga agc ata cca caa gca tta ggc cag ttg cag    768
Val Asn His Leu Glu Gly Ser Ile Pro Gln Ala Leu Gly Gln Leu Gln
                245                 250                 255 act tta gag ttt atg gga ttg ggc atg aat gga ttc tct ggt atc atc    816
Thr Leu Glu Phe Met Gly Leu Gly Met Asn Gly Phe Ser Gly Ile Ile
            260                 265                 270 cct tcc tca gtt tac aat atg tca tca ttg gaa gta ttt tct ttg cca    864
Pro Ser Ser Val Tyr Asn Met Ser Ser Leu Glu Val Phe Ser Leu Pro
        275                 280                 285 tat aat aaa ctt tat ggt agt tta ccc tgg gac ctg gcc ttc act ctt    912
Tyr Asn Lys Leu Tyr Gly Ser Leu Pro Trp Asp Leu Ala Phe Thr Leu
    290                 295                 300
```

```
cct aat ctc caa gtt tta aat att ggc aat aat gac ttt act ggt ccc    960
Pro Asn Leu Gln Val Leu Asn Ile Gly Asn Asn Asp Phe Thr Gly Pro
305                 310                 315                 320 cta ccc tca tca tta tca aat gcc tct aac ctt ctt gaa ttc gat atc   1008
Leu Pro Ser Ser Leu Ser Asn Ala Ser Asn Leu Leu Glu Phe Asp Ile
                325                 330                 335 acc atg agt aac ttt act ggg aaa gtt tca atc gac ttt gga ggc atg   1056
Thr Met Ser Asn Phe Thr Gly Lys Val Ser Ile Asp Phe Gly Gly Met
            340                 345                 350 cct aat ctt tgg gga ctg ttt ctt gct tcc aac cct ctg gga aaa gga   1104
Pro Asn Leu Trp Gly Leu Phe Leu Ala Ser Asn Pro Leu Gly Lys Gly
        355                 360                 365 gag gcc gat gat ttg agt ttc ttg aac tct tta atg aaa tgc agg gct   1152
Glu Ala Asp Asp Leu Ser Phe Leu Asn Ser Leu Met Lys Cys Arg Ala
370                 375                 380 ttg aag gtg ttg gat ctc agt ggt agt caa ttt gga ggg gtg ttg ccg   1200
Leu Lys Val Leu Asp Leu Ser Gly Ser Gln Phe Gly Gly Val Leu Pro
385                 390                 395                 400 aat tct ata gcc aac ctc tca acc caa ctt atg aaa tta aaa ttg gac   1248
Asn Ser Ile Ala Asn Leu Ser Thr Gln Leu Met Lys Leu Lys Leu Asp
                405                 410                 415 aac aat cag ttg tcg gga aca att cct cca ggg att ggg aac ctg gtt   1296
Asn Asn Gln Leu Ser Gly Thr Ile Pro Pro Gly Ile Gly Asn Leu Val
            420                 425                 430 aat ctg act gac tta ata tta gca aac aat gat ttc aca ggg agc att   1344
Asn Leu Thr Asp Leu Ile Leu Ala Asn Asn Asp Phe Thr Gly Ser Ile
        435                 440                 445 cct gtc ctt att ggg aac ctt cag atg tta ggt cga ata gat ttg tct   1392
Pro Val Leu Ile Gly Asn Leu Gln Met Leu Gly Arg Ile Asp Leu Ser
450                 455                 460 aga aat cag tta tcg ggt cat att cca tcc tca cta gga aac atc aca   1440
Arg Asn Gln Leu Ser Gly His Ile Pro Ser Ser Leu Gly Asn Ile Thr
465                 470                 475                 480 cga ttg tat tcc ctt cat ctt caa aac aat cac tta agc ggg aaa att   1488
Arg Leu Tyr Ser Leu His Leu Gln Asn Asn His Leu Ser Gly Lys Ile
                485                 490                 495 cct tct agt ttt ggg aat ctt ttg tac ctg caa gag cta gac ctt tct   1536
Pro Ser Ser Phe Gly Asn Leu Leu Tyr Leu Gln Glu Leu Asp Leu Ser
            500                 505                 510 tac aac tct ctc aat ggt act ata cct gaa aag gtt atg gat ctt gtt   1584
Tyr Asn Ser Leu Asn Gly Thr Ile Pro Glu Lys Val Met Asp Leu Val
        515                 520                 525 tcc ctt acg att tcc ctt aat cta gct aga aat caa ttg act ggt ttg   1632
Ser Leu Thr Ile Ser Leu Asn Leu Ala Arg Asn Gln Leu Thr Gly Leu
530                 535                 540 cta ccg tcc gaa gtg aga aaa ctg aaa aat ctg ggg cay ttg gac gtt   1680
Leu Pro Ser Glu Val Arg Lys Leu Lys Asn Leu Gly His Leu Asp Val
545                 550                 555                 560 tct gag aat aag ttg tct ggt gaa att cct gat ggc ctt ggc agt tgt   1728
Ser Glu Asn Lys Leu Ser Gly Glu Ile Pro Asp Gly Leu Gly Ser Cys
                565                 570                 575 tta acc ttg gag cac ctt cat atg gaa ggt aac ttc ttt aaa ggt tcc   1776
Leu Thr Leu Glu His Leu His Met Glu Gly Asn Phe Phe Lys Gly Ser
            580                 585                 590 att cct cca tct ttt att tct ttg aga ggt ctc ctg gac ttg gat ctc   1824
Ile Pro Pro Ser Phe Ile Ser Leu Arg Gly Leu Leu Asp Leu Asp Leu
        595                 600                 605 tca cgc aat aac ctt tct ggc caa att cct gaa ttt ctt cag caa ctt   1872
Ser Arg Asn Asn Leu Ser Gly Gln Ile Pro Glu Phe Leu Gln Gln Leu
```

```
                    610                 615                 620
tcc ctc agc aat ttg aac ctg tct ttc aac aat ttt gaa ggc cag cta       1920
Ser Leu Ser Asn Leu Asn Leu Ser Phe Asn Asn Phe Glu Gly Gln Leu
625                 630                 635                 640 cca acc aaa ggg gtc ttc aat aat gca act tcc act tca gta gct ggg       1968
Pro Thr Lys Gly Val Phe Asn Asn Ala Thr Ser Thr Ser Val Ala Gly
                645                 650                 655 aat aat aag ctt tgt ggg ggt ata cct gaa tta cat ttg cct gca tgc       2016
Asn Asn Lys Leu Cys Gly Gly Ile Pro Glu Leu His Leu Pro Ala Cys
            660                 665                 670 cct gtc act aag cca aaa aca gga gaa tcg aag cgc gga ctc aag ttg       2064
Pro Val Thr Lys Pro Lys Thr Gly Glu Ser Lys Arg Gly Leu Lys Leu
        675                 680                 685 atg atc gga tta ctt act ggc ttt ctg gga tta gtt ttg ata atg tct       2112
Met Ile Gly Leu Leu Thr Gly Phe Leu Gly Leu Val Leu Ile Met Ser
    690                 695                 700 ctt cta gtt atc aat cgg ctg aga aga gta aag aga gag cct tct caa       2160
Leu Leu Val Ile Asn Arg Leu Arg Arg Val Lys Arg Glu Pro Ser Gln
705                 710                 715                 720 aca tct gcg tca tcc aag gat ttg atc ttg aat gtg tcc tat gat ggt       2208
Thr Ser Ala Ser Ser Lys Asp Leu Ile Leu Asn Val Ser Tyr Asp Gly
                725                 730                 735 ctt ttc aaa gca act gga gga ttt tct tct gcc aac ttg atc ggt aca       2256
Leu Phe Lys Ala Thr Gly Gly Phe Ser Ser Ala Asn Leu Ile Gly Thr
            740                 745                 750 ggt ggc ttt ggt tct gtg tac aaa gga wtt ctg ggt caa gat gag aca       2304
Gly Gly Phe Gly Ser Val Tyr Lys Gly Xaa Leu Gly Gln Asp Glu Thr
        755                 760                 765 gtg gtt gca gtt aag gta ata cag cta cat cag cgt gga gct gtt aag       2352
Val Val Ala Val Lys Val Ile Gln Leu His Gln Arg Gly Ala Val Lys
    770                 775                 780 agc ttc aag gca gag tgc gag gcc ttg aga aac att agg cat cgg aat       2400
Ser Phe Lys Ala Glu Cys Glu Ala Leu Arg Asn Ile Arg His Arg Asn
785                 790                 795                 800 ctc gtc aaa gtc tta acc act tgc tca agt gtt gat tac caa ggc aat       2448
Leu Val Lys Val Leu Thr Thr Cys Ser Ser Val Asp Tyr Gln Gly Asn
                805                 810                 815 gat ttc aaa gct cta gtc tat gag ttc atg ccc aat ggg agt ttg gaa       2496
Asp Phe Lys Ala Leu Val Tyr Glu Phe Met Pro Asn Gly Ser Leu Glu
            820                 825                 830 aat tgg ctg cac cca gtc cca aca cca gat gaa ata aat gat gtc ctt       2544
Asn Trp Leu His Pro Val Pro Thr Pro Asp Glu Ile Asn Asp Val Leu
        835                 840                 845 cgg att tta agc ctt ccc caa aga ttg aac att gcc att gat gtg gct       2592
Arg Ile Leu Ser Leu Pro Gln Arg Leu Asn Ile Ala Ile Asp Val Ala
    850                 855                 860 tcc gca ctg gat tat ctt cat cac cat tgc cat aag ccc att gtt cat       2640
Ser Ala Leu Asp Tyr Leu His His His Cys His Lys Pro Ile Val His
865                 870                 875                 880 tgt gat ttg aag cca agc aac att ctt ctt gac aat gac atg act gct       2688
Cys Asp Leu Lys Pro Ser Asn Ile Leu Leu Asp Asn Asp Met Thr Ala
                885                 890                 895 cat gtg ggt gat ttc ggg cta gcg aga ttc att cca gaa gcc gca ggt       2736
His Val Gly Asp Phe Gly Leu Ala Arg Phe Ile Pro Glu Ala Ala Gly
            900                 905                 910 aga tct cac ccc agt cag agc agc tct att gga ttg aag gga acc att       2784
Arg Ser His Pro Ser Gln Ser Ser Ser Ile Gly Leu Lys Gly Thr Ile
        915                 920                 925 ggt tat gca gca cca gag tat gga atg gga act aag gtt tca gcc ctt       2832
```

```
                    -continued

Gly Tyr Ala Ala Pro Glu Tyr Gly Met Gly Thr Lys Val Ser Ala Leu
    930             935                 940 ggt gac aca tac agc tat ggg att ctc cta ttg gag atg ttt acc ggg       2880
Gly Asp Thr Tyr Ser Tyr Gly Ile Leu Leu Leu Glu Met Phe Thr Gly
945                 950                 955                 960 aag agg cct act gag agc atg ttc agt gat caa ctg aat ctc cat aat       2928
Lys Arg Pro Thr Glu Ser Met Phe Ser Asp Gln Leu Asn Leu His Asn
                    965                 970                 975 ttt gtg aag atg gca ttg cct gaa cga ata gct gac att ata gac cca       2976
Phe Val Lys Met Ala Leu Pro Glu Arg Ile Ala Asp Ile Ile Asp Pro
                980                 985                 990 ttt ttc ctc tct agt gaa gca aaa gag gag gaa aca act gcc gca gat       3024
Phe Phe Leu Ser Ser Glu Ala Lys Glu Glu Glu Thr Thr Ala Ala Asp
            995                 1000                1005 agt tct aat ctg gca cat atg aaa aga gag aaa atg cat gag tgc           3069
Ser Ser Asn Leu Ala His Met Lys Arg Glu Lys Met His Glu Cys
    1010                1015                1020 ttg atc tca ata ctt aga att gga gtt tct tgt tca ctg gaa tct           3114
Leu Ile Ser Ile Leu Arg Ile Gly Val Ser Cys Ser Leu Glu Ser
    1025                1030                1035 ccc agr gag cga atg gcc att aca gaa gct atc aaa gaa ctg caa           3159
Pro Arg Glu Arg Met Ala Ile Thr Glu Ala Ile Lys Glu Leu Gln
    1040                1045                1050 ctt atc aga aaa att ctt ctt gga aat ggg ata act gat gcc cct           3204
Leu Ile Arg Lys Ile Leu Leu Gly Asn Gly Ile Thr Asp Ala Pro
    1055                1060                1065 ctc agg gcc atg agc tcg tgg aat gat tct ctc cac ttc tgc caa           3249
Leu Arg Ala Met Ser Ser Trp Asn Asp Ser Leu His Phe Cys Gln
    1070                1075                1080 tgg caa ggc gtg tct tgc agt ggc agg cat caa aga gtc acc gtc           3294
Trp Gln Gly Val Ser Cys Ser Gly Arg His Gln Arg Val Thr Val
    1085                1090                1095 tta aat ttg cat tca ttg ggt ctg gtg ggt tct atc cct cct cta           3339
Leu Asn Leu His Ser Leu Gly Leu Val Gly Ser Ile Pro Pro Leu
    1100                1105                1110 att gga aac ctt agt ttc ctc aga acc atc aat cta tcc aac aac           3384
Ile Gly Asn Leu Ser Phe Leu Arg Thr Ile Asn Leu Ser Asn Asn
    1115                1120                1125 agt ttt caa ggt gag gtc cct cct gta gtc agg atg cag att cta           3429
Ser Phe Gln Gly Glu Val Pro Pro Val Val Arg Met Gln Ile Leu
    1130                1135                1140 aac ttg aca aat aac tgg ttg gaa gga caa atc cca gct aac ctt           3474
Asn Leu Thr Asn Asn Trp Leu Glu Gly Gln Ile Pro Ala Asn Leu
    1145                1150                1155 tct cwa tgt tct aat atg aga atc ctt ggc ctg ggc aac aac aat           3519
Ser Xaa Cys Ser Asn Met Arg Ile Leu Gly Leu Gly Asn Asn Asn
    1160                1165                1170 ttc tgg gga gaa gtt cct tct gag ctc ggc tcc tta tcc aac atg           3564
Phe Trp Gly Glu Val Pro Ser Glu Leu Gly Ser Leu Ser Asn Met
    1175                1180                1185 ctg caa ctt ttt att gat tac aac agt ttg acg ggt acc ata gca           3609
Leu Gln Leu Phe Ile Asp Tyr Asn Ser Leu Thr Gly Thr Ile Ala
    1190                1195                1200 cct act ttt ggg aac ttg tca tct ctc aga gtt ctt gtt gca gct           3654
Pro Thr Phe Gly Asn Leu Ser Ser Leu Arg Val Leu Val Ala Ala
    1205                1210                1215 tcc aat gag ttg aac gga agt atc cca cat tca ctg ggt cgc cta           3699
Ser Asn Glu Leu Asn Gly Ser Ile Pro His Ser Leu Gly Arg Leu
    1220                1225                1230
```

-continued

| | | | | | | | | | | | |
|---|---|---|---|---|---|---|---|---|---|---|---|
| caa | agc | tta | gtg | acg | ctt | gta | ctc | tcc | acg | aat | caa | cta | tcc | ggt | 3744 |
| Gln | Ser | Leu | Val | Thr | Leu | Val | Leu | Ser | Thr | Asn | Gln | Leu | Ser | Gly | |
| | 1235 | | | | 1240 | | | | | 1245 | | | | | |

| acg | atc | cct | cca | tcg | atc | tcc | aac | ctt | aca | tct | ctt | act | caa | ttt | 3789 |
| Thr | Ile | Pro | Pro | Ser | Ile | Ser | Asn | Leu | Thr | Ser | Leu | Thr | Gln | Phe | |
| | 1250 | | | | 1255 | | | | | 1260 | | | | | |

| ggt | gtt | gca | ttt | aat | caa | ttg | aaa | gga | agt | ctt | cca | ttg | gat | tta | 3834 |
| Gly | Val | Ala | Phe | Asn | Gln | Leu | Lys | Gly | Ser | Leu | Pro | Leu | Asp | Leu | |
| | 1265 | | | | 1270 | | | | | 1275 | | | | | |

| tgg | tcc | act | ctc | tct | aag | ctt | cgg | ctc | ttt | tct | gtc | cac | caa | ttg | 3879 |
| Trp | Ser | Thr | Leu | Ser | Lys | Leu | Arg | Leu | Phe | Ser | Val | His | Gln | Leu | |
| | 1280 | | | | 1285 | | | | | 1290 | | | | | |

| aaa | ata | ttg | ttc | cta | agt | gat | aat | aat | ttt | gga | ggg | gtg | tta | ccc | 3924 |
| Lys | Ile | Leu | Phe | Leu | Ser | Asp | Asn | Asn | Phe | Gly | Gly | Val | Leu | Pro | |
| | 1295 | | | | 1300 | | | | | 1305 | | | | | |

| aat | tcc | ttg | ggc | aac | ctc | tca | acc | caa | ctc | cag | tgg | cta | tca | ttc | 3969 |
| Asn | Ser | Leu | Gly | Asn | Leu | Ser | Thr | Gln | Leu | Gln | Trp | Leu | Ser | Phe | |
| | 1310 | | | | 1315 | | | | | 1320 | | | | | |

| gca | gca | aat | caa | atc | tct | gga | aac | atc | cca | aca | ggc | att | gga | aat | 4014 |
| Ala | Ala | Asn | Gln | Ile | Ser | Gly | Asn | Ile | Pro | Thr | Gly | Ile | Gly | Asn | |
| | 1325 | | | | 1330 | | | | | 1335 | | | | | |

| ctc | gca | aac | tta | att | gca | tta | gat | atg | cac | aaa | aat | caa | ttc | aca | 4059 |
| Leu | Ala | Asn | Leu | Ile | Ala | Leu | Asp | Met | His | Lys | Asn | Gln | Phe | Thr | |
| | 1340 | | | | 1345 | | | | | 1350 | | | | | |

| gga | agt | att | cca | acc | tcc | aat | ggg | aat | ctt | cac | aag | cta | saa | gaa | 4104 |
| Gly | Ser | Ile | Pro | Thr | Ser | Asn | Gly | Asn | Leu | His | Lys | Leu | Xaa | Glu | |
| | 1355 | | | | 1360 | | | | | 1365 | | | | | |

| gtg | ggt | ttc | gat | aaa | aat | aag | ttg | tca | ggg | gta | atc | cct | tcc | tct | 4149 |
| Val | Gly | Phe | Asp | Lys | Asn | Lys | Leu | Ser | Gly | Val | Ile | Pro | Ser | Ser | |
| | 1370 | | | | 1375 | | | | | 1380 | | | | | |

| atc | gga | aac | tta | aca | ttg | ttg | aac | cag | ctc | tgg | tta | gag | gaa | aat | 4194 |
| Ile | Gly | Asn | Leu | Thr | Leu | Leu | Asn | Gln | Leu | Trp | Leu | Glu | Glu | Asn | |
| | 1385 | | | | 1390 | | | | | 1395 | | | | | |

| aat | ttt | cag | rga | agt | ata | cct | tca | act | ctt | gga | aat | tgc | cac | aat | 4239 |
| Asn | Phe | Gln | Xaa | Ser | Ile | Pro | Ser | Thr | Leu | Gly | Asn | Cys | His | Asn | |
| | 1400 | | | | 1405 | | | | | 1410 | | | | | |

| ttg | ata | ttg | ttg | cak | ctt | tat | ggc | aat | aac | cta | agt | grt | gac | ata | 4284 |
| Leu | Ile | Leu | Leu | Xaa | Leu | Tyr | Gly | Asn | Asn | Leu | Ser | Xaa | Asp | Ile | |
| | 1415 | | | | 1420 | | | | | 1425 | | | | | |

| ccc | cga | gaa | gtt | att | ggc | cta | tca | tct | tta | gcg | aaa | tcc | ctc | aac | 4329 |
| Pro | Arg | Glu | Val | Ile | Gly | Leu | Ser | Ser | Leu | Ala | Lys | Ser | Leu | Asn | |
| | 1430 | | | | 1435 | | | | | 1440 | | | | | |

| ytr | gct | cga | aat | agt | ctc | agt | ggt | tta | cta | ccc | tgg | gaa | gtg | ggt | 4374 |
| Xaa | Ala | Arg | Asn | Ser | Leu | Ser | Gly | Leu | Leu | Pro | Trp | Glu | Val | Gly | |
| | 1445 | | | | 1450 | | | | | 1455 | | | | | |

| aac | ttg | aga | aac | ctt | gtt | gaa | ttg | gac | att | tcc | caa | aac | cag | tta | 4419 |
| Asn | Leu | Arg | Asn | Leu | Val | Glu | Leu | Asp | Ile | Ser | Gln | Asn | Gln | Leu | |
| | 1460 | | | | 1465 | | | | | 1470 | | | | | |

| tct | ggt | gat | att | cct | agc | agt | ctt | ggc | agt | tgt | att | aga | ttg | gaa | 4464 |
| Ser | Gly | Asp | Ile | Pro | Ser | Ser | Leu | Gly | Ser | Cys | Ile | Arg | Leu | Glu | |
| | 1475 | | | | 1480 | | | | | 1485 | | | | | |

| cgc | ctt | tat | atg | tat | gat | aat | tcc | ttt | ggt | ggg | gac | atc | cca | cag | 4509 |
| Arg | Leu | Tyr | Met | Tyr | Asp | Asn | Ser | Phe | Gly | Gly | Asp | Ile | Pro | Gln | |
| | 1490 | | | | 1495 | | | | | 1500 | | | | | |

| tcg | ttg | aat | act | ctg | aga | ggt | ctc | gaa | gag | cta | gat | ctt | tca | cac | 4554 |
| Ser | Leu | Asn | Thr | Leu | Arg | Gly | Leu | Glu | Glu | Leu | Asp | Leu | Ser | His | |
| | 1505 | | | | 1510 | | | | | 1515 | | | | | |

| aac | aac | ctg | tcg | ggt | gaa | att | cca | aga | tac | ttg | gct | act | att | ccc | 4599 |
| Asn | Asn | Leu | Ser | Gly | Glu | Ile | Pro | Arg | Tyr | Leu | Ala | Thr | Ile | Pro | |
| | 1520 | | | | 1525 | | | | | 1530 | | | | | |

```
                                              -continued ttg agg aat ttg aac ctt tct ttg aat gat ttc gaa ggt gag ata       4644
Leu Arg Asn Leu Asn Leu Ser Leu Asn Asp Phe Glu Gly Glu Ile
    1535            1540                1545 cca gta gat gga gtt ttc aga aat gca agt gca att tca att gct       4689
Pro Val Asp Gly Val Phe Arg Asn Ala Ser Ala Ile Ser Ile Ala
    1550            1555                1560 gga aat gac agg ctt tgt ggg ggt ata cct gaa cta cag ttg cca       4734
Gly Asn Asp Arg Leu Cys Gly Gly Ile Pro Glu Leu Gln Leu Pro
    1565            1570                1575 aga tgc tct aaa gac cag aag aga aag cag aaa atg tct ctc acc       4779
Arg Cys Ser Lys Asp Gln Lys Arg Lys Gln Lys Met Ser Leu Thr
    1580            1585                1590 ctc aaa tta aca atc cct ata gga ctt tcg gga ata att ttg atg       4824
Leu Lys Leu Thr Ile Pro Ile Gly Leu Ser Gly Ile Ile Leu Met
    1595            1600                1605 tcc tgt ata atc ctt cgt cgg ctt aaa aaa gtg agc aaa ggc caa       4869
Ser Cys Ile Ile Leu Arg Arg Leu Lys Lys Val Ser Lys Gly Gln
    1610            1615                1620 ccc tcg gaa tct ctg ttg cag gac cga ttt atg aat att tct tat       4914
Pro Ser Glu Ser Leu Leu Gln Asp Arg Phe Met Asn Ile Ser Tyr
    1625            1630                1635 ggg ctg ctt gtc aaa gca aca gat gga tac tct tca gcc cat ttg       4959
Gly Leu Leu Val Lys Ala Thr Asp Gly Tyr Ser Ser Ala His Leu
    1640            1645                1650 att ggt aca aga agc tta ggc tca gta tac aag gga att ctt cat       5004
Ile Gly Thr Arg Ser Leu Gly Ser Val Tyr Lys Gly Ile Leu His
    1655            1660                1665 cca aac gaa aca gtc wtt gca gtg aag gta ttc aac ctt cag aac       5049
Pro Asn Glu Thr Val Xaa Ala Val Lys Val Phe Asn Leu Gln Asn
    1670            1675                1680 aga gga gct tcc aag agt ttc atg gcc gag tgc gaa gct ttg aga       5094
Arg Gly Ala Ser Lys Ser Phe Met Ala Glu Cys Glu Ala Leu Arg
    1685            1690                1695 aac att cgg cat cgg aat ctt gtc aag atc ata acw gct tgc tca       5139
Asn Ile Arg His Arg Asn Leu Val Lys Ile Ile Xaa Ala Cys Ser
    1700            1705                1710 agc gtt gac ttt crt ggt aac gac ttc aaa gcc cta gtt tat gaa       5184
Ser Val Asp Phe Xaa Gly Asn Asp Phe Lys Ala Leu Val Tyr Glu
    1715            1720                1725 tac atg cca aat gga agc ctc gag act tgg ttg cat cag ttt gtc       5229
Tyr Met Pro Asn Gly Ser Leu Glu Thr Trp Leu His Gln Phe Val
    1730            1735                1740 cca gaa ggg aat gca cat ggg cag agg agt cta aac ctt ctt cag       5274
Pro Glu Gly Asn Ala His Gly Gln Arg Ser Leu Asn Leu Leu Gln
    1745            1750                1755 cga tta aat ata gca att gat gtg ggt tca gcc ttg gat tat ctt       5319
Arg Leu Asn Ile Ala Ile Asp Val Gly Ser Ala Leu Asp Tyr Leu
    1760            1765                1770 cat aac caa tgc caa gat cca atc ata cat tgt gat ata aaa cca       5364
His Asn Gln Cys Gln Asp Pro Ile Ile His Cys Asp Ile Lys Pro
    1775            1780                1785 aag ttt ggc atg gga agt gat ctg tca act caa ggg gat gtg cat       5409
Lys Phe Gly Met Gly Ser Asp Leu Ser Thr Gln Gly Asp Val His
    1790            1795                1800 agc cat ggg ata ctc ttg ttg gaa atg ttc aca ggg aaa aaa cct       5454
Ser His Gly Ile Leu Leu Leu Glu Met Phe Thr Gly Lys Lys Pro
    1805            1810                1815 act gat gac atg ttc aac gat ggc ctc agc ctt cat aag ttt gtg       5499
Thr Asp Asp Met Phe Asn Asp Gly Leu Ser Leu His Lys Phe Val
```

```
                        1820                1825                1830
gac  atg  gct  ttg  cca  gga  gga  gca  acg  gag  att  gtg  gat  cat  gta       5544
Asp  Met  Ala  Leu  Pro  Gly  Gly  Ala  Thr  Glu  Ile  Val  Asp  His  Val
     1835                1840                1845 cgg  aca  ctc  ttg  gga  gga  gaa  gag  gag  gaa  gcg  gcc  agt  gtc  agc       5589
Arg  Thr  Leu  Leu  Gly  Gly  Glu  Glu  Glu  Glu  Ala  Ala  Ser  Val  Ser
     1850                1855                1860 gtt  tgt  tta  att  tct  ata  ctt  gga  ata  gga  gtt  gca  tgt  tct  aag       5634
Val  Cys  Leu  Ile  Ser  Ile  Leu  Gly  Ile  Gly  Val  Ala  Cys  Ser  Lys
     1865                1870                1875 gaa  tca  cca  aga  gaa  cga  atg  gat  att  tgt  gat  gct  gtc  ctg  gaa       5679
Glu  Ser  Pro  Arg  Glu  Arg  Met  Asp  Ile  Cys  Asp  Ala  Val  Leu  Glu
     1880                1885                1890 gta  cat  agt  att  aag  gac  atg  att  gat  gaa  act  tag                      5715
Val  His  Ser  Ile  Lys  Asp  Met  Ile  Asp  Glu  Thr
     1895                1900
```

<210> SEQ ID NO 21
<211> LENGTH: 1904
<212> TYPE: PRT
<213> ORGANISM: Vitis vinifera
<220> FEATURE:
<221> NAME/KEY: misc_feature
<222> LOCATION: (3)..(3)
<223> OTHER INFORMATION: The 'Xaa' at location 3 stands for Val, or Leu.
<220> FEATURE:
<221> NAME/KEY: misc_feature
<222> LOCATION: (762)..(762)
<223> OTHER INFORMATION: The 'Xaa' at location 762 stands for Ile, or
      Phe.
<220> FEATURE:
<221> NAME/KEY: misc_feature
<222> LOCATION: (1160)..(1160)
<223> OTHER INFORMATION: The 'Xaa' at location 1160 stands for Gln, or
      Leu.
<220> FEATURE:
<221> NAME/KEY: misc_feature
<222> LOCATION: (1367)..(1367)
<223> OTHER INFORMATION: The 'Xaa' at location 1367 stands for Glu, or
      Gln.
<220> FEATURE:
<221> NAME/KEY: misc_feature
<222> LOCATION: (1402)..(1402)
<223> OTHER INFORMATION: The 'Xaa' at location 1402 stands for Gly, or
      Arg.
<220> FEATURE:
<221> NAME/KEY: misc_feature
<222> LOCATION: (1418)..(1418)
<223> OTHER INFORMATION: The 'Xaa' at location 1418 stands for Gln, or
      His.
<220> FEATURE:
<221> NAME/KEY: misc_feature
<222> LOCATION: (1426)..(1426)
<223> OTHER INFORMATION: The 'Xaa' at location 1426 stands for Gly, or
      Asp.
<220> FEATURE:
<221> NAME/KEY: misc_feature
<222> LOCATION: (1444)..(1444)
<223> OTHER INFORMATION: The 'Xaa' at location 1444 stands for Leu.
<220> FEATURE:
<221> NAME/KEY: misc_feature
<222> LOCATION: (1674)..(1674)
<223> OTHER INFORMATION: The 'Xaa' at location 1674 stands for Ile, or
      Phe.
<220> FEATURE:
<221> NAME/KEY: misc_feature
<222> LOCATION: (1710)..(1710)
<223> OTHER INFORMATION: The 'Xaa' at location 1710 stands for Thr.
<220> FEATURE:
<221> NAME/KEY: misc_feature
<222> LOCATION: (1718)..(1718)
<223> OTHER INFORMATION: The 'Xaa' at location 1718 stands for Arg, or
      His.

<400> SEQUENCE: 21

```
Met His Xaa His Cys Pro Leu Leu Phe Ile Val Cys Pro Val Thr Thr
1               5                   10                  15

Cys Leu Ala Asn Tyr Gln Pro Cys Tyr Ser Leu Phe Lys Thr Asn Thr
            20                  25                  30

Leu Ile Pro Phe Arg Ser Phe Ile Phe His Ser Ile Leu Val Pro Tyr
        35                  40                  45

Thr Ile Ile Phe Leu His Ser Pro Ser Pro Thr Thr Ser Ser Thr Ile
    50                  55                  60

Leu Tyr Gly Asn Glu Thr Asp Arg Leu Ala Leu Leu Ala Ile Lys Ala
65                  70                  75                  80

Gln Ile Thr Gln Asp Pro Leu Gly Ile Thr Thr Ser Trp Asn Asp Ser
                85                  90                  95

Val His Phe Cys Asn Trp Thr Gly Val Thr Cys Gly His Arg His Gln
            100                 105                 110

Arg Val Asn Thr Leu Asn Leu Ser Ser Leu His Leu Val Gly Ser Leu
        115                 120                 125

Ser Pro Ser Ile Gly Asn Leu Thr Phe Leu Thr Gly Leu Asn Leu Glu
    130                 135                 140

Leu Asn Asn Phe His Gly Gln Ile Pro Gln Glu Leu Gly Arg Leu Ser
145                 150                 155                 160

Arg Leu Arg Ala Leu Asn Leu Thr Asn Asn Ser Phe Ser Gly Glu Ile
                165                 170                 175

Pro Ala Asn Leu Ser Arg Cys Ser Asn Leu Val Tyr Phe Arg Leu Gly
            180                 185                 190

Phe Asn Asn Leu Ile Gly Arg Ile Pro Ser Trp Leu Gly Ser Tyr Pro
        195                 200                 205

Lys Val Val Arg Met Gln Leu His Tyr Asn Asn Leu Thr Gly Pro Val
    210                 215                 220

Pro Asp Ser Leu Gly Asn Leu Thr Ser Ile Lys Ser Leu Ser Phe Ala
225                 230                 235                 240

Val Asn His Leu Glu Gly Ser Ile Pro Gln Ala Leu Gly Gln Leu Gln
                245                 250                 255

Thr Leu Glu Phe Met Gly Leu Gly Met Asn Gly Phe Ser Gly Ile Ile
            260                 265                 270

Pro Ser Ser Val Tyr Asn Met Ser Ser Leu Glu Val Phe Ser Leu Pro
        275                 280                 285

Tyr Asn Lys Leu Tyr Gly Ser Leu Pro Trp Asp Leu Ala Phe Thr Leu
    290                 295                 300

Pro Asn Leu Gln Val Leu Asn Ile Gly Asn Asn Asp Phe Thr Gly Pro
305                 310                 315                 320

Leu Pro Ser Ser Leu Ser Asn Ala Ser Asn Leu Leu Glu Phe Asp Ile
                325                 330                 335

Thr Met Ser Asn Phe Thr Gly Lys Val Ser Ile Asp Phe Gly Gly Met
            340                 345                 350

Pro Asn Leu Trp Gly Leu Phe Leu Ala Ser Asn Pro Leu Gly Lys Gly
        355                 360                 365

Glu Ala Asp Asp Leu Ser Phe Leu Asn Ser Leu Met Lys Cys Arg Ala
    370                 375                 380

Leu Lys Val Leu Asp Leu Ser Gly Ser Gln Phe Gly Gly Val Leu Pro
385                 390                 395                 400

Asn Ser Ile Ala Asn Leu Ser Thr Gln Leu Met Lys Leu Lys Leu Asp
```

```
            405                 410                 415
Asn Asn Gln Leu Ser Gly Thr Ile Pro Pro Gly Ile Gly Asn Leu Val
            420                 425                 430
Asn Leu Thr Asp Leu Ile Leu Ala Asn Asn Asp Phe Thr Gly Ser Ile
            435                 440                 445
Pro Val Leu Ile Gly Asn Leu Gln Met Leu Gly Arg Ile Asp Leu Ser
            450                 455                 460
Arg Asn Gln Leu Ser Gly His Ile Pro Ser Ser Leu Gly Asn Ile Thr
465                 470                 475                 480
Arg Leu Tyr Ser Leu His Leu Gln Asn Asn His Leu Ser Gly Lys Ile
            485                 490                 495
Pro Ser Ser Phe Gly Asn Leu Leu Tyr Leu Gln Glu Leu Asp Leu Ser
            500                 505                 510
Tyr Asn Ser Leu Asn Gly Thr Ile Pro Glu Lys Val Met Asp Leu Val
            515                 520                 525
Ser Leu Thr Ile Ser Leu Asn Leu Ala Arg Asn Gln Leu Thr Gly Leu
            530                 535                 540
Leu Pro Ser Glu Val Arg Lys Leu Lys Asn Leu Gly His Leu Asp Val
545                 550                 555                 560
Ser Glu Asn Lys Leu Ser Gly Glu Ile Pro Asp Gly Leu Gly Ser Cys
            565                 570                 575
Leu Thr Leu Glu His Leu His Met Glu Gly Asn Phe Phe Lys Gly Ser
            580                 585                 590
Ile Pro Pro Ser Phe Ile Ser Leu Arg Gly Leu Leu Asp Leu Asp Leu
            595                 600                 605
Ser Arg Asn Asn Leu Ser Gly Gln Ile Pro Glu Phe Leu Gln Gln Leu
            610                 615                 620
Ser Leu Ser Asn Leu Asn Leu Ser Phe Asn Asn Phe Glu Gly Gln Leu
625                 630                 635                 640
Pro Thr Lys Gly Val Phe Asn Asn Ala Thr Ser Thr Ser Val Ala Gly
            645                 650                 655
Asn Asn Lys Leu Cys Gly Gly Ile Pro Glu Leu His Leu Pro Ala Cys
            660                 665                 670
Pro Val Thr Lys Pro Lys Thr Gly Glu Ser Lys Arg Gly Leu Lys Leu
            675                 680                 685
Met Ile Gly Leu Leu Thr Gly Phe Leu Gly Leu Val Leu Ile Met Ser
            690                 695                 700
Leu Leu Val Ile Asn Arg Leu Arg Arg Val Lys Arg Glu Pro Ser Gln
705                 710                 715                 720
Thr Ser Ala Ser Ser Lys Asp Leu Ile Leu Asn Val Ser Tyr Asp Gly
            725                 730                 735
Leu Phe Lys Ala Thr Gly Gly Phe Ser Ser Ala Asn Leu Ile Gly Thr
            740                 745                 750
Gly Gly Phe Gly Ser Val Tyr Lys Gly Xaa Leu Gly Gln Asp Glu Thr
            755                 760                 765
Val Val Ala Val Lys Val Ile Gln Leu His Gln Arg Gly Ala Val Lys
            770                 775                 780
Ser Phe Lys Ala Glu Cys Glu Ala Leu Arg Asn Ile Arg His Arg Asn
785                 790                 795                 800
Leu Val Lys Val Leu Thr Thr Cys Ser Ser Val Asp Tyr Gln Gly Asn
            805                 810                 815
Asp Phe Lys Ala Leu Val Tyr Glu Phe Met Pro Asn Gly Ser Leu Glu
            820                 825                 830
```

```
Asn Trp Leu His Pro Val Pro Thr Pro Asp Glu Ile Asn Asp Val Leu
        835                 840                 845

Arg Ile Leu Ser Leu Pro Gln Arg Leu Asn Ile Ala Ile Asp Val Ala
        850                 855                 860

Ser Ala Leu Asp Tyr Leu His His Cys His Lys Pro Ile Val His
865                 870                 875                 880

Cys Asp Leu Lys Pro Ser Asn Ile Leu Leu Asp Asn Asp Met Thr Ala
                885                 890                 895

His Val Gly Asp Phe Gly Leu Ala Arg Phe Ile Pro Glu Ala Ala Gly
                900                 905                 910

Arg Ser His Pro Ser Gln Ser Ser Ile Gly Leu Lys Gly Thr Ile
        915                 920                 925

Gly Tyr Ala Ala Pro Glu Tyr Gly Met Gly Thr Lys Val Ser Ala Leu
        930                 935                 940

Gly Asp Thr Tyr Ser Tyr Gly Ile Leu Leu Leu Glu Met Phe Thr Gly
945                 950                 955                 960

Lys Arg Pro Thr Glu Ser Met Phe Ser Asp Gln Leu Asn Leu His Asn
                965                 970                 975

Phe Val Lys Met Ala Leu Pro Glu Arg Ile Ala Asp Ile Asp Pro
        980                 985                 990

Phe Phe Leu Ser Ser Glu Ala Lys Glu Glu Glu Thr Thr Ala Ala Asp
        995                 1000                1005

Ser Ser Asn Leu Ala His Met Lys Arg Glu Lys Met His Glu Cys
1010                1015                1020

Leu Ile Ser Ile Leu Arg Ile Gly Val Ser Cys Ser Leu Glu Ser
1025                1030                1035

Pro Arg Glu Arg Met Ala Ile Thr Glu Ala Ile Lys Glu Leu Gln
1040                1045                1050

Leu Ile Arg Lys Ile Leu Leu Gly Asn Gly Ile Thr Asp Ala Pro
1055                1060                1065

Leu Arg Ala Met Ser Ser Trp Asn Asp Ser Leu His Phe Cys Gln
1070                1075                1080

Trp Gln Gly Val Ser Cys Ser Gly Arg His Gln Arg Val Thr Val
1085                1090                1095

Leu Asn Leu His Ser Leu Gly Leu Val Gly Ser Ile Pro Pro Leu
1100                1105                1110

Ile Gly Asn Leu Ser Phe Leu Arg Thr Ile Asn Leu Ser Asn Asn
1115                1120                1125

Ser Phe Gln Gly Glu Val Pro Pro Val Val Arg Met Gln Ile Leu
1130                1135                1140

Asn Leu Thr Asn Asn Trp Leu Glu Gly Gln Ile Pro Ala Asn Leu
1145                1150                1155

Ser Xaa Cys Ser Asn Met Arg Ile Leu Gly Leu Gly Asn Asn Asn
1160                1165                1170

Phe Trp Gly Glu Val Pro Ser Glu Leu Gly Ser Leu Ser Asn Met
1175                1180                1185

Leu Gln Leu Phe Ile Asp Tyr Asn Ser Leu Thr Gly Thr Ile Ala
1190                1195                1200

Pro Thr Phe Gly Asn Leu Ser Ser Leu Arg Val Leu Val Ala Ala
1205                1210                1215

Ser Asn Glu Leu Asn Gly Ser Ile Pro His Ser Leu Gly Arg Leu
1220                1225                1230
```

```
Gln Ser Leu Val Thr Leu Val Leu Ser Thr Asn Gln Leu Ser Gly
    1235                1240                1245

Thr Ile Pro Pro Ser Ile Ser Asn Leu Thr Ser Leu Thr Gln Phe
    1250                1255                1260

Gly Val Ala Phe Asn Gln Leu Lys Gly Ser Leu Pro Leu Asp Leu
    1265                1270                1275

Trp Ser Thr Leu Ser Lys Leu Arg Leu Phe Ser Val His Gln Leu
    1280                1285                1290

Lys Ile Leu Phe Leu Ser Asp Asn Asn Phe Gly Gly Val Leu Pro
    1295                1300                1305

Asn Ser Leu Gly Asn Leu Ser Thr Gln Leu Gln Trp Leu Ser Phe
    1310                1315                1320

Ala Ala Asn Gln Ile Ser Gly Asn Ile Pro Thr Gly Ile Gly Asn
    1325                1330                1335

Leu Ala Asn Leu Ile Ala Leu Asp Met His Lys Asn Gln Phe Thr
    1340                1345                1350

Gly Ser Ile Pro Thr Ser Asn Gly Asn Leu His Lys Leu Xaa Glu
    1355                1360                1365

Val Gly Phe Asp Lys Asn Lys Leu Ser Gly Val Ile Pro Ser Ser
    1370                1375                1380

Ile Gly Asn Leu Thr Leu Leu Asn Gln Leu Trp Leu Glu Glu Asn
    1385                1390                1395

Asn Phe Gln Xaa Ser Ile Pro Ser Thr Leu Gly Asn Cys His Asn
    1400                1405                1410

Leu Ile Leu Leu Xaa Leu Tyr Gly Asn Asn Leu Ser Xaa Asp Ile
    1415                1420                1425

Pro Arg Glu Val Ile Gly Leu Ser Ser Leu Ala Lys Ser Leu Asn
    1430                1435                1440

Xaa Ala Arg Asn Ser Leu Ser Gly Leu Leu Pro Trp Glu Val Gly
    1445                1450                1455

Asn Leu Arg Asn Leu Val Glu Leu Asp Ile Ser Gln Asn Gln Leu
    1460                1465                1470

Ser Gly Asp Ile Pro Ser Ser Leu Gly Ser Cys Ile Arg Leu Glu
    1475                1480                1485

Arg Leu Tyr Met Tyr Asp Asn Ser Phe Gly Gly Asp Ile Pro Gln
    1490                1495                1500

Ser Leu Asn Thr Leu Arg Gly Leu Glu Glu Leu Asp Leu Ser His
    1505                1510                1515

Asn Asn Leu Ser Gly Glu Ile Pro Arg Tyr Leu Ala Thr Ile Pro
    1520                1525                1530

Leu Arg Asn Leu Asn Leu Ser Leu Asn Asp Phe Glu Gly Glu Ile
    1535                1540                1545

Pro Val Asp Gly Val Phe Arg Asn Ala Ser Ala Ile Ser Ile Ala
    1550                1555                1560

Gly Asn Asp Arg Leu Cys Gly Gly Ile Pro Glu Leu Gln Leu Pro
    1565                1570                1575

Arg Cys Ser Lys Asp Gln Lys Arg Lys Gln Lys Met Ser Leu Thr
    1580                1585                1590

Leu Lys Leu Thr Ile Pro Ile Gly Leu Ser Gly Ile Ile Leu Met
    1595                1600                1605

Ser Cys Ile Ile Leu Arg Arg Leu Lys Lys Val Ser Lys Gly Gln
    1610                1615                1620

Pro Ser Glu Ser Leu Leu Gln Asp Arg Phe Met Asn Ile Ser Tyr
```

| | | | | | | | | | | |
|---|---|---|---|---|---|---|---|---|---|---|
| | | 1625 | | | 1630 | | | 1635 | | |
| Gly | Leu | Leu | Val | Lys | Ala | Thr | Asp | Gly | Tyr | Ser | Ser | Ala | His | Leu |
| | | | 1640 | | | | 1645 | | | | 1650 | | | |
| Ile | Gly | Thr | Arg | Ser | Leu | Gly | Ser | Val | Tyr | Lys | Gly | Ile | Leu | His |
| | 1655 | | | | | 1660 | | | | | 1665 | | | |
| Pro | Asn | Glu | Thr | Val | Xaa | Ala | Val | Lys | Val | Phe | Asn | Leu | Gln | Asn |
| | | 1670 | | | | | 1675 | | | | | 1680 | | |
| Arg | Gly | Ala | Ser | Lys | Ser | Phe | Met | Ala | Glu | Cys | Glu | Ala | Leu | Arg |
| | | | 1685 | | | | | 1690 | | | | | 1695 | |
| Asn | Ile | Arg | His | Arg | Asn | Leu | Val | Lys | Ile | Ile | Xaa | Ala | Cys | Ser |
| | | | | 1700 | | | | | 1705 | | | | | 1710 |
| Ser | Val | Asp | Phe | Xaa | Gly | Asn | Asp | Phe | Lys | Ala | Leu | Val | Tyr | Glu |
| | | 1715 | | | | | 1720 | | | | | 1725 | | |
| Tyr | Met | Pro | Asn | Gly | Ser | Leu | Glu | Thr | Trp | Leu | His | Gln | Phe | Val |
| | | | 1730 | | | | | 1735 | | | | | 1740 | |
| Pro | Glu | Gly | Asn | Ala | His | Gly | Gln | Arg | Ser | Leu | Asn | Leu | Leu | Gln |
| | | | | 1745 | | | | | 1750 | | | | | 1755 |
| Arg | Leu | Asn | Ile | Ala | Ile | Asp | Val | Gly | Ser | Ala | Leu | Asp | Tyr | Leu |
| | | 1760 | | | | | 1765 | | | | | 1770 | | |
| His | Asn | Gln | Cys | Gln | Asp | Pro | Ile | Ile | His | Cys | Asp | Ile | Lys | Pro |
| | | | 1775 | | | | | 1780 | | | | | 1785 | |
| Lys | Phe | Gly | Met | Gly | Ser | Asp | Leu | Ser | Thr | Gln | Gly | Asp | Val | His |
| | | | | 1790 | | | | | 1795 | | | | | 1800 |
| Ser | His | Gly | Ile | Leu | Leu | Leu | Glu | Met | Phe | Thr | Gly | Lys | Lys | Pro |
| | | 1805 | | | | | 1810 | | | | | 1815 | | |
| Thr | Asp | Asp | Met | Phe | Asn | Asp | Gly | Leu | Ser | Leu | His | Lys | Phe | Val |
| | | | 1820 | | | | | 1825 | | | | | 1830 | |
| Asp | Met | Ala | Leu | Pro | Gly | Gly | Ala | Thr | Glu | Ile | Val | Asp | His | Val |
| | | | | 1835 | | | | | 1840 | | | | | 1845 |
| Arg | Thr | Leu | Leu | Gly | Gly | Glu | Glu | Glu | Ala | Ala | Ser | Val | Ser |
| | | 1850 | | | | | 1855 | | | | | 1860 | | |
| Val | Cys | Leu | Ile | Ser | Ile | Leu | Gly | Ile | Gly | Val | Ala | Cys | Ser | Lys |
| | | | 1865 | | | | | 1870 | | | | | 1875 | |
| Glu | Ser | Pro | Arg | Glu | Arg | Met | Asp | Ile | Cys | Asp | Ala | Val | Leu | Glu |
| | | | | 1880 | | | | | 1885 | | | | | 1890 |
| Val | His | Ser | Ile | Lys | Asp | Met | Ile | Asp | Glu | Thr | | | | |
| | | 1895 | | | | | 1900 | | | | | | | |

<210> SEQ ID NO 22
<211> LENGTH: 2661
<212> TYPE: DNA
<213> ORGANISM: Vitis vinifera
<220> FEATURE:
<221> NAME/KEY: CDS
<222> LOCATION: (1)..(2661)

<400> SEQUENCE: 22

```
atg ctg atg tta ata aaa aac aaa ctc tca gga ata ctt cca tcc tct       48
Met Leu Met Leu Ile Lys Asn Lys Leu Ser Gly Ile Leu Pro Ser Ser
1               5                   10                  15 ctt ggg aat cta gag aac cta att caa ctt gtt tta ggg aga aac tat       96
Leu Gly Asn Leu Glu Asn Leu Ile Gln Leu Val Leu Gly Arg Asn Tyr
            20                  25                  30 ttt cag ggc aaa att cct tca agt ctg ggg aaa tgc caa aat ttg ctc      144
Phe Gln Gly Lys Ile Pro Ser Ser Leu Gly Lys Cys Gln Asn Leu Leu
        35                  40                  45
```

```
ttc ttg gat ctt tct ctc aac aat ctt agt ggc acc ata ccc cct caa    192
Phe Leu Asp Leu Ser Leu Asn Asn Leu Ser Gly Thr Ile Pro Pro Gln
 50                  55                  60 gtt gtt agt tta tca tcc tta tca att tct ctt gat ata tcc gac aac    240
Val Val Ser Leu Ser Ser Leu Ser Ile Ser Leu Asp Ile Ser Asp Asn
 65                  70                  75                  80 cgt ttg act ggt gcc ctt ccc att gaa gtt ggg aat ttg aaa aat ttg    288
Arg Leu Thr Gly Ala Leu Pro Ile Glu Val Gly Asn Leu Lys Asn Leu
                 85                  90                  95 ggt gta cta gat gtt tct aat aat atg ttg tct ggt gga att ccc agc    336
Gly Val Leu Asp Val Ser Asn Asn Met Leu Ser Gly Gly Ile Pro Ser
                    100                 105                 110 agc gtt ggt agc tgc act agt ctg gaa tac ctg tcc atg aag ggc aac    384
Ser Val Gly Ser Cys Thr Ser Leu Glu Tyr Leu Ser Met Lys Gly Asn
                115                 120                 125 ttc ttc caa ggt tcc att cct tca tct ttt agt tca tta aga ggc att    432
Phe Phe Gln Gly Ser Ile Pro Ser Ser Phe Ser Ser Leu Arg Gly Ile
130                 135                 140 cgc att tta gat ctg tct cac aac aat ttg tca ggc aaa att cca gaa    480
Arg Ile Leu Asp Leu Ser His Asn Asn Leu Ser Gly Lys Ile Pro Glu
145                 150                 155                 160 ttt ctt caa gac att cac ttt cag tta gtg aat cta tct tac aat gat    528
Phe Leu Gln Asp Ile His Phe Gln Leu Val Asn Leu Ser Tyr Asn Asp
                165                 170                 175 ttt gag ggc atc tta cca aca gaa ggt gtc ttt aag aat gtg agt gca    576
Phe Glu Gly Ile Leu Pro Thr Glu Gly Val Phe Lys Asn Val Ser Ala
                180                 185                 190 act tcc atc atg gga aac agt aag ctc tgt ggg ggc att cct gaa ttt    624
Thr Ser Ile Met Gly Asn Ser Lys Leu Cys Gly Gly Ile Pro Glu Phe
            195                 200                 205 cag ctg cca aaa tgc aac ttg caa gag cct aag aaa agg gga ctg agc    672
Gln Leu Pro Lys Cys Asn Leu Gln Glu Pro Lys Lys Arg Gly Leu Ser
210                 215                 220 ctt gcc ttg aag ata ata atc gcc act gtt tct ggg ctt tta gca ata    720
Leu Ala Leu Lys Ile Ile Ile Ala Thr Val Ser Gly Leu Leu Ala Ile
225                 230                 235                 240 act tgt gtg ctg tct ttc cta atc ttt ctc tgg ttg aga aag aaa aaa    768
Thr Cys Val Leu Ser Phe Leu Ile Phe Leu Trp Leu Arg Lys Lys Lys
                245                 250                 255 gga gaa cct gct tca agc tct tca gag aaa tca ctt ctg aag gtg tcc    816
Gly Glu Pro Ala Ser Ser Ser Ser Glu Lys Ser Leu Leu Lys Val Ser
                260                 265                 270 tac cag agt ctc cta agg gca act gat ggg ttc tct tcc tcc aac ttg    864
Tyr Gln Ser Leu Leu Arg Ala Thr Asp Gly Phe Ser Ser Ser Asn Leu
            275                 280                 285 att ggt gtt ggt agc ttt ggg tct gta tat aaa gga att ctt gat cat    912
Ile Gly Val Gly Ser Phe Gly Ser Val Tyr Lys Gly Ile Leu Asp His
290                 295                 300 gat gga aca gcc att gct gtg aag gta ctt aac ctt ctg cgg aaa gga    960
Asp Gly Thr Ala Ile Ala Val Lys Val Leu Asn Leu Leu Arg Lys Gly
305                 310                 315                 320 gct tcc aag agt ttc ata gct gag tgt gag gcc ttg agg aac atc aga   1008
Ala Ser Lys Ser Phe Ile Ala Glu Cys Glu Ala Leu Arg Asn Ile Arg
                325                 330                 335 cat cgg aat ctg gtc aag gta ctc act gca tgt tca ggt gtt gat tat   1056
His Arg Asn Leu Val Lys Val Leu Thr Ala Cys Ser Gly Val Asp Tyr
                340                 345                 350 cag ggt aat gat ttc aaa gct gtt gtt tat gag ttt atg gtc aac gga   1104
Gln Gly Asn Asp Phe Lys Ala Val Val Tyr Glu Phe Met Val Asn Gly
            355                 360                 365
```

```
agc ttg gag cag tgg ctt cat cca act cct aca aca gca gaa gca tct     1152
Ser Leu Glu Gln Trp Leu His Pro Thr Pro Thr Thr Ala Glu Ala Ser
    370                 375                 380 gcg cca cca agg aag ctt aat ttt ctt caa aga cta aac att gcc att     1200
Ala Pro Pro Arg Lys Leu Asn Phe Leu Gln Arg Leu Asn Ile Ala Ile
385                 390                 395                 400 gat gtt gct tgt gca ttg gat tat ctt cat cat cag tgc cag aca cca     1248
Asp Val Ala Cys Ala Leu Asp Tyr Leu His His Gln Cys Gln Thr Pro
                405                 410                 415 ata gtc cac tgc gac ctc aag cca agc aat gtt ctt ctg gat act gaa     1296
Ile Val His Cys Asp Leu Lys Pro Ser Asn Val Leu Leu Asp Thr Glu
            420                 425                 430 atg act gga cat gta ggc gac ttt gga atc gca aaa ttc ctt cca gaa     1344
Met Thr Gly His Val Gly Asp Phe Gly Ile Ala Lys Phe Leu Pro Glu
        435                 440                 445 gca gcc acc aga gtt cct gaa att caa tca agc tcc att gga ata aga     1392
Ala Ala Thr Arg Val Pro Glu Ile Gln Ser Ser Ser Ile Gly Ile Arg
    450                 455                 460 gga acc att ggc tac gct gct cca gag tat ggt atg gga agt gag gtt     1440
Gly Thr Ile Gly Tyr Ala Ala Pro Glu Tyr Gly Met Gly Ser Glu Val
465                 470                 475                 480 tca acc agt ggt gat gta tac agc ttt ggc ata ctg ttg ttg gag atg     1488
Ser Thr Ser Gly Asp Val Tyr Ser Phe Gly Ile Leu Leu Leu Glu Met
                485                 490                 495 ttt acc ggg aag aga ccc act gag gac atg ttt aaa gac agc ctg aac     1536
Phe Thr Gly Lys Arg Pro Thr Glu Asp Met Phe Lys Asp Ser Leu Asn
            500                 505                 510 att cat aac ttt gtt aag acg gct gtg cct gaa cgg gtg gcg gag att     1584
Ile His Asn Phe Val Lys Thr Ala Val Pro Glu Arg Val Ala Glu Ile
        515                 520                 525 gca gat cca gta ctt ctt cag gaa gga gta gaa atg gac aat act acg     1632
Ala Asp Pro Val Leu Leu Gln Glu Gly Val Glu Met Asp Asn Thr Thr
    530                 535                 540 agc cag aga aga atg gca agt aag gtt ggt cgt ctg ggc cga tta gag     1680
Ser Gln Arg Arg Met Ala Ser Lys Val Gly Arg Leu Gly Arg Leu Glu
545                 550                 555                 560 aca ttg cgc ctc gac agt aat tca tta gat ggt gaa att ccc tcc aat     1728
Thr Leu Arg Leu Asp Ser Asn Ser Leu Asp Gly Glu Ile Pro Ser Asn
                565                 570                 575 ata tcc agt tgc tct aat ctc att tct cta act atc ggt ttc aac agt     1776
Ile Ser Ser Cys Ser Asn Leu Ile Ser Leu Thr Ile Gly Phe Asn Ser
            580                 585                 590 gtg gta ggg aaa ctt cct gaa gag ctt ggc tca ttg tcc atg ctc caa     1824
Val Val Gly Lys Leu Pro Glu Glu Leu Gly Ser Leu Ser Met Leu Gln
        595                 600                 605 ttt ctt gca gtt cag cga aac aat cta tca gga agt atc cct cct ttt     1872
Phe Leu Ala Val Gln Arg Asn Asn Leu Ser Gly Ser Ile Pro Pro Phe
    610                 615                 620 gga aac tta tca tct ctt ggg aag ttc tct gca acc cag aat aat ttg     1920
Gly Asn Leu Ser Ser Leu Gly Lys Phe Ser Ala Thr Gln Asn Asn Leu
625                 630                 635                 640 gtt ggg agg agt ctt ccc tca gat ata ggc aac tcc cct cct aat ctt     1968
Val Gly Arg Ser Leu Pro Ser Asp Ile Gly Asn Ser Pro Pro Asn Leu
                645                 650                 655 gaa tcc ctt ggc atc agc ctt aac cga ttc act gga acc ttt cct cta     2016
Glu Ser Leu Gly Ile Ser Leu Asn Arg Phe Thr Gly Thr Phe Pro Leu
            660                 665                 670 gca aac cta ata att aca ggt aat caa ctt aca gga aaa gtg ccg agt     2064
Ala Asn Leu Ile Ile Thr Gly Asn Gln Leu Thr Gly Lys Val Pro Ser
```

|  |  |  |  |  |  |  |  |  |  |  |  |  |  |  |  |
|---|---|---|---|---|---|---|---|---|---|---|---|---|---|---|---|
|  |  |  |  | 675 |  |  |  | 680 |  |  |  | 685 |  |  |  |
| tta | gaa | aag | ctg | aat | cag | ttc | gca | tgg | ctt | agc | agg | tcc | aca | aac | aat | 2112 |
| Leu | Glu | Lys | Leu | Asn | Gln | Phe | Ala | Trp | Leu | Ser | Arg | Ser | Thr | Asn | Asn |
|  | 690 |  |  |  | 695 |  |  |  |  | 700 |  |  |  |  |  |
| ctt | gga | agt | ggg | gaa | gct | gat | gac | tta | aac | ttt | ctc | ata | ggg | aat | tgc | 2160 |
| Leu | Gly | Ser | Gly | Glu | Ala | Asp | Asp | Leu | Asn | Phe | Leu | Ile | Gly | Asn | Cys |
| 705 |  |  |  |  | 710 |  |  |  |  | 715 |  |  |  |  | 720 |
| caa | aat | ttg | cta | gct | ttg | gat | ctt | tcc | tat | aac | aat | ctc | agt | ggt | agc | 2208 |
| Gln | Asn | Leu | Leu | Ala | Leu | Asp | Leu | Ser | Tyr | Asn | Asn | Leu | Ser | Gly | Ser |
|  |  |  |  | 725 |  |  |  |  | 730 |  |  |  |  | 735 |  |
| ata | ccc | cct | caa | gta | gtc | agt | ttc | tca | tcc | cta | tcg | atc | tat | ctt | ggt | 2256 |
| Ile | Pro | Pro | Gln | Val | Val | Ser | Phe | Ser | Ser | Leu | Ser | Ile | Tyr | Leu | Gly |
|  |  | 740 |  |  |  |  | 745 |  |  |  |  | 750 |  |  |  |
| cta | tcc | caa | aac | tac | ttg | act | ggt | cct | ctt | cca | ata | gaa | gtt | gga | aat | 2304 |
| Leu | Ser | Gln | Asn | Tyr | Leu | Thr | Gly | Pro | Leu | Pro | Ile | Glu | Val | Gly | Asn |
|  |  |  | 755 |  |  |  |  | 760 |  |  |  |  | 765 |  |  |
| ttg | aaa | aat | ctt | ggt | gaa | tta | gat | gtt | tct | gat | aat | ata | tta | tca | ggt | 2352 |
| Leu | Lys | Asn | Leu | Gly | Glu | Leu | Asp | Val | Ser | Asp | Asn | Ile | Leu | Ser | Gly |
| 770 |  |  |  |  | 775 |  |  |  |  | 780 |  |  |  |  |  |
| gaa | att | cca | agc | agt | ctt | ggc | agt | ggc | atc | aga | ctg | gag | ctc | cta | tcc | 2400 |
| Glu | Ile | Pro | Ser | Ser | Leu | Gly | Ser | Gly | Ile | Arg | Leu | Glu | Leu | Leu | Ser |
| 785 |  |  |  |  | 790 |  |  |  |  | 795 |  |  |  |  | 800 |
| atg | cag | ggc | aac | tcc | ttc | caa | ggg | tcc | att | cct | tca | tct | ttc | agg | tca | 2448 |
| Met | Gln | Gly | Asn | Ser | Phe | Gln | Gly | Ser | Ile | Pro | Ser | Ser | Phe | Arg | Ser |
|  |  |  |  | 805 |  |  |  |  | 810 |  |  |  |  | 815 |  |
| ttg | caa | ggc | cta | att | gaa | ctc | tac | ttg | gga | agt | aat | aat | ttt | gag | gga | 2496 |
| Leu | Gln | Gly | Leu | Ile | Glu | Leu | Tyr | Leu | Gly | Ser | Asn | Asn | Phe | Glu | Gly |
|  |  |  | 820 |  |  |  |  | 825 |  |  |  |  | 830 |  |  |
| agc | atc | ccc | cat | aca | tta | ggc | cag | ttg | aca | agc | tta | gtg | tct | ctt | tct | 2544 |
| Ser | Ile | Pro | His | Thr | Leu | Gly | Gln | Leu | Thr | Ser | Leu | Val | Ser | Leu | Ser |
|  |  | 835 |  |  |  |  | 840 |  |  |  |  | 845 |  |  |  |
| ctg | ggc | ata | aac | aac | ctg | tct | ggt | atc | att | cct | ccc | tcc | atc | tat | aat | 2592 |
| Leu | Gly | Ile | Asn | Asn | Leu | Ser | Gly | Ile | Ile | Pro | Pro | Ser | Ile | Tyr | Asn |
| 850 |  |  |  |  | 855 |  |  |  |  | 860 |  |  |  |  |  |
| ctc | ctt | tcc | atc | att | tcc | ttt | tgg | atg | cct | gta | aac | agc | atc | cat | ggg | 2640 |
| Leu | Leu | Ser | Ile | Ile | Ser | Phe | Trp | Met | Pro | Val | Asn | Ser | Ile | His | Gly |
| 865 |  |  |  |  | 870 |  |  |  |  | 875 |  |  |  |  | 880 |
| agt | ctt | tct | ttt | caa | ctg | tga |  |  |  |  |  |  |  |  |  | 2661 |
| Ser | Leu | Ser | Phe | Gln | Leu |  |  |  |  |  |  |  |  |  |  |
|  |  |  |  | 885 |  |  |  |  |  |  |  |  |  |  |  |

<210> SEQ ID NO 23
<211> LENGTH: 886
<212> TYPE: PRT
<213> ORGANISM: Vitis vinifera

<400> SEQUENCE: 23

Met Leu Met Leu Ile Lys Asn Lys Leu Ser Gly Ile Leu Pro Ser Ser
1               5                   10                  15

Leu Gly Asn Leu Glu Asn Leu Ile Gln Leu Val Leu Gly Arg Asn Tyr
            20                  25                  30

Phe Gln Gly Lys Ile Pro Ser Ser Leu Gly Lys Cys Gln Asn Leu Leu
        35                  40                  45

Phe Leu Asp Leu Ser Leu Asn Asn Leu Ser Gly Thr Ile Pro Pro Gln
    50                  55                  60

Val Val Ser Leu Ser Ser Leu Ser Ile Ser Leu Asp Ile Ser Asp Asn
65                  70                  75                  80

Arg Leu Thr Gly Ala Leu Pro Ile Glu Val Gly Asn Leu Lys Asn Leu
                85                  90                  95

```
Gly Val Leu Asp Val Ser Asn Met Leu Ser Gly Ile Pro Ser
                100                 105                 110

Ser Val Gly Ser Cys Thr Ser Leu Glu Tyr Leu Ser Met Lys Gly Asn
    115                 120                 125

Phe Phe Gln Gly Ser Ile Pro Ser Ser Phe Ser Leu Arg Gly Ile
130                 135                 140

Arg Ile Leu Asp Leu Ser His Asn Asn Leu Ser Gly Lys Ile Pro Glu
145                 150                 155                 160

Phe Leu Gln Asp Ile His Phe Gln Leu Val Asn Leu Ser Tyr Asn Asp
                165                 170                 175

Phe Glu Gly Ile Leu Pro Thr Glu Gly Val Phe Lys Asn Val Ser Ala
                180                 185                 190

Thr Ser Ile Met Gly Asn Ser Lys Leu Cys Gly Gly Ile Pro Glu Phe
                195                 200                 205

Gln Leu Pro Lys Cys Asn Leu Gln Glu Pro Lys Lys Arg Gly Leu Ser
    210                 215                 220

Leu Ala Leu Lys Ile Ile Ile Ala Thr Val Ser Gly Leu Leu Ala Ile
225                 230                 235                 240

Thr Cys Val Leu Ser Phe Leu Ile Phe Leu Trp Leu Arg Lys Lys Lys
                245                 250                 255

Gly Glu Pro Ala Ser Ser Ser Ser Glu Lys Ser Leu Leu Lys Val Ser
                260                 265                 270

Tyr Gln Ser Leu Leu Arg Ala Thr Asp Gly Phe Ser Ser Ser Asn Leu
    275                 280                 285

Ile Gly Val Gly Ser Phe Gly Ser Val Tyr Lys Gly Ile Leu Asp His
                290                 295                 300

Asp Gly Thr Ala Ile Ala Val Lys Val Leu Asn Leu Leu Arg Lys Gly
305                 310                 315                 320

Ala Ser Lys Ser Phe Ile Ala Glu Cys Glu Ala Leu Arg Asn Ile Arg
                325                 330                 335

His Arg Asn Leu Val Lys Val Leu Thr Ala Cys Ser Gly Val Asp Tyr
                340                 345                 350

Gln Gly Asn Asp Phe Lys Ala Val Val Tyr Glu Phe Met Val Asn Gly
    355                 360                 365

Ser Leu Glu Gln Trp Leu His Pro Thr Pro Thr Thr Ala Glu Ala Ser
370                 375                 380

Ala Pro Pro Arg Lys Leu Asn Phe Leu Gln Arg Leu Asn Ile Ala Ile
385                 390                 395                 400

Asp Val Ala Cys Ala Leu Asp Tyr Leu His His Gln Cys Gln Thr Pro
                405                 410                 415

Ile Val His Cys Asp Leu Lys Pro Ser Asn Val Leu Leu Asp Thr Glu
                420                 425                 430

Met Thr Gly His Val Gly Asp Phe Gly Ile Ala Lys Phe Leu Pro Glu
                435                 440                 445

Ala Ala Thr Arg Val Pro Glu Ile Gln Ser Ser Ile Gly Ile Arg
    450                 455                 460

Gly Thr Ile Gly Tyr Ala Ala Pro Glu Tyr Gly Met Gly Ser Glu Val
465                 470                 475                 480

Ser Thr Ser Gly Asp Val Tyr Ser Phe Gly Ile Leu Leu Glu Met
            485                 490                 495

Phe Thr Gly Lys Arg Pro Thr Glu Asp Met Phe Lys Ser Leu Asn
                500                 505                 510
```

```
Ile His Asn Phe Val Lys Thr Ala Val Pro Glu Arg Val Ala Glu Ile
            515                 520                 525

Ala Asp Pro Val Leu Leu Gln Glu Gly Val Glu Met Asp Asn Thr Thr
530                 535                 540

Ser Gln Arg Arg Met Ala Ser Lys Val Gly Arg Leu Gly Arg Leu Glu
545                 550                 555                 560

Thr Leu Arg Leu Asp Ser Asn Ser Leu Asp Gly Glu Ile Pro Ser Asn
                565                 570                 575

Ile Ser Ser Cys Ser Asn Leu Ile Ser Leu Thr Ile Gly Phe Asn Ser
            580                 585                 590

Val Val Gly Lys Leu Pro Glu Glu Leu Gly Ser Leu Ser Met Leu Gln
        595                 600                 605

Phe Leu Ala Val Gln Arg Asn Asn Leu Ser Gly Ser Ile Pro Pro Phe
    610                 615                 620

Gly Asn Leu Ser Ser Leu Gly Lys Phe Ser Ala Thr Gln Asn Asn Leu
625                 630                 635                 640

Val Gly Arg Ser Leu Pro Ser Asp Ile Gly Asn Ser Pro Pro Asn Leu
                645                 650                 655

Glu Ser Leu Gly Ile Ser Leu Asn Arg Phe Thr Gly Thr Phe Pro Leu
            660                 665                 670

Ala Asn Leu Ile Ile Thr Gly Asn Gln Leu Thr Gly Lys Val Pro Ser
        675                 680                 685

Leu Glu Lys Leu Asn Gln Phe Ala Trp Leu Ser Arg Ser Thr Asn Asn
    690                 695                 700

Leu Gly Ser Gly Glu Ala Asp Asp Leu Asn Phe Leu Ile Gly Asn Cys
705                 710                 715                 720

Gln Asn Leu Leu Ala Leu Asp Leu Ser Tyr Asn Asn Leu Ser Gly Ser
                725                 730                 735

Ile Pro Pro Gln Val Val Ser Phe Ser Ser Leu Ser Ile Tyr Leu Gly
            740                 745                 750

Leu Ser Gln Asn Tyr Leu Thr Gly Pro Leu Pro Ile Glu Val Gly Asn
        755                 760                 765

Leu Lys Asn Leu Gly Glu Leu Asp Val Ser Asp Asn Ile Leu Ser Gly
    770                 775                 780

Glu Ile Pro Ser Ser Leu Gly Ser Gly Ile Arg Leu Glu Leu Leu Ser
785                 790                 795                 800

Met Gln Gly Asn Ser Phe Gln Gly Ser Ile Pro Ser Ser Phe Arg Ser
                805                 810                 815

Leu Gln Gly Leu Ile Glu Leu Tyr Leu Gly Ser Asn Asn Phe Glu Gly
            820                 825                 830

Ser Ile Pro His Thr Leu Gly Gln Leu Thr Ser Leu Val Ser Leu Ser
        835                 840                 845

Leu Gly Ile Asn Asn Leu Ser Gly Ile Ile Pro Pro Ser Ile Tyr Asn
    850                 855                 860

Leu Leu Ser Ile Ile Ser Phe Trp Met Pro Val Asn Ser Ile His Gly
865                 870                 875                 880

Ser Leu Ser Phe Gln Leu
                885

<210> SEQ ID NO 24
<211> LENGTH: 2379
<212> TYPE: DNA
<213> ORGANISM: Arabidopsis thaliana
<220> FEATURE:
<221> NAME/KEY: CDS
```

<222> LOCATION: (1)..(2379)

<400> SEQUENCE: 24

| | | | | | | | | | | | | | | | | |
|---|---|---|---|---|---|---|---|---|---|---|---|---|---|---|---|---|
| atg | aaa | tcg | aat | ttg | gcc | gtt | ttc | ttc | ata | act | tgt | ttc | ttc | tgt | tgc | 48 |
| Met | Lys | Ser | Asn | Leu | Ala | Val | Phe | Phe | Ile | Thr | Cys | Phe | Phe | Cys | Cys | |
| 1 | | | | 5 | | | | | 10 | | | | | 15 | | |

| gtc | ttt | gtg | acc | agc | gat | tca | gtt | tac | act | cta | cca | ttt | cct | ttc | cca | 96 |
|---|---|---|---|---|---|---|---|---|---|---|---|---|---|---|---|---|
| Val | Phe | Val | Thr | Ser | Asp | Ser | Val | Tyr | Thr | Leu | Pro | Phe | Pro | Phe | Pro | |
| | | | 20 | | | | | 25 | | | | | 30 | | | |

| cgc | gat | caa | gtt | gag | att | ctg | ttg | gaa | ttg | aag | aat | gag | ttt | cca | tcc | 144 |
|---|---|---|---|---|---|---|---|---|---|---|---|---|---|---|---|---|
| Arg | Asp | Gln | Val | Glu | Ile | Leu | Leu | Glu | Leu | Lys | Asn | Glu | Phe | Pro | Ser | |
| | | | 35 | | | | | 40 | | | | | 45 | | | |

| ttc | aac | tgc | gac | ctc | act | tgg | aaa | ctc | gat | tac | ttt | ggt | cga | atg | gac | 192 |
|---|---|---|---|---|---|---|---|---|---|---|---|---|---|---|---|---|
| Phe | Asn | Cys | Asp | Leu | Thr | Trp | Lys | Leu | Asp | Tyr | Phe | Gly | Arg | Met | Asp | |
| | 50 | | | | | 55 | | | | | 60 | | | | | |

| act | aga | gca | aat | ata | agc | tcc | tgg | acc | aaa | gac | tct | gac | tcc | ttt | agt | 240 |
|---|---|---|---|---|---|---|---|---|---|---|---|---|---|---|---|---|
| Thr | Arg | Ala | Asn | Ile | Ser | Ser | Trp | Thr | Lys | Asp | Ser | Asp | Ser | Phe | Ser | |
| 65 | | | | | 70 | | | | | 75 | | | | | 80 | |

| ggg | gtt | tcc | ttt | gat | agc | gag | acc | ggt | gtg | gtg | aag | gag | ctg | tcc | ctt | 288 |
|---|---|---|---|---|---|---|---|---|---|---|---|---|---|---|---|---|
| Gly | Val | Ser | Phe | Asp | Ser | Glu | Thr | Gly | Val | Val | Lys | Glu | Leu | Ser | Leu | |
| | | | | 85 | | | | | 90 | | | | | 95 | | |

| ggt | cgt | caa | tgt | ctt | act | agt | ctc | aag | gct | aat | agt | agc | ctc | ttc | aga | 336 |
|---|---|---|---|---|---|---|---|---|---|---|---|---|---|---|---|---|
| Gly | Arg | Gln | Cys | Leu | Thr | Ser | Leu | Lys | Ala | Asn | Ser | Ser | Leu | Phe | Arg | |
| | | | 100 | | | | | 105 | | | | | 110 | | | |

| ttc | caa | cac | ctc | agg | tac | ctc | gat | ctc | tct | gaa | aat | cat | ttt | gac | tcg | 384 |
|---|---|---|---|---|---|---|---|---|---|---|---|---|---|---|---|---|
| Phe | Gln | His | Leu | Arg | Tyr | Leu | Asp | Leu | Ser | Glu | Asn | His | Phe | Asp | Ser | |
| | | 115 | | | | | 120 | | | | | 125 | | | | |

| tcc | cct | ata | ccc | tct | gga | ttt | ggt | aga | ctg | acc | tac | ttg | gaa | tcc | ttg | 432 |
|---|---|---|---|---|---|---|---|---|---|---|---|---|---|---|---|---|
| Ser | Pro | Ile | Pro | Ser | Gly | Phe | Gly | Arg | Leu | Thr | Tyr | Leu | Glu | Ser | Leu | |
| | 130 | | | | | 135 | | | | | 140 | | | | | |

| gat | ctt | agc | aaa | aat | ggg | ttt | ata | gga | gaa | gtt | cca | tcc | tca | ata | agt | 480 |
|---|---|---|---|---|---|---|---|---|---|---|---|---|---|---|---|---|
| Asp | Leu | Ser | Lys | Asn | Gly | Phe | Ile | Gly | Glu | Val | Pro | Ser | Ser | Ile | Ser | |
| 145 | | | | | 150 | | | | | 155 | | | | | 160 | |

| aac | cta | agc | cgg | tta | acc | aat | tta | gac | ctt | tca | tat | aac | aag | ctc | acc | 528 |
|---|---|---|---|---|---|---|---|---|---|---|---|---|---|---|---|---|
| Asn | Leu | Ser | Arg | Leu | Thr | Asn | Leu | Asp | Leu | Ser | Tyr | Asn | Lys | Leu | Thr | |
| | | | | 165 | | | | | 170 | | | | | 175 | | |

| ggt | ggt | att | ccc | aat | cta | cat | agt | tta | acc | ctt | ctt | gag | aat | ata | gac | 576 |
|---|---|---|---|---|---|---|---|---|---|---|---|---|---|---|---|---|
| Gly | Gly | Ile | Pro | Asn | Leu | His | Ser | Leu | Thr | Leu | Leu | Glu | Asn | Ile | Asp | |
| | | | 180 | | | | | 185 | | | | | 190 | | | |

| cta | tca | tat | aat | aag | ttt | tct | gga | gcc | att | cct | tct | tac | ctc | ttc | acc | 624 |
|---|---|---|---|---|---|---|---|---|---|---|---|---|---|---|---|---|
| Leu | Ser | Tyr | Asn | Lys | Phe | Ser | Gly | Ala | Ile | Pro | Ser | Tyr | Leu | Phe | Thr | |
| | | 195 | | | | | 200 | | | | | 205 | | | | |

| atg | cct | ttt | cta | gtt | tct | ctt | aac | cta | cgc | caa | aac | cat | ctt | agt | gac | 672 |
|---|---|---|---|---|---|---|---|---|---|---|---|---|---|---|---|---|
| Met | Pro | Phe | Leu | Val | Ser | Leu | Asn | Leu | Arg | Gln | Asn | His | Leu | Ser | Asp | |
| | 210 | | | | | 215 | | | | | 220 | | | | | |

| cct | ctt | gag | aat | ata | aat | tat | tct | gca | acc | tct | aaa | ctt | tta | att | tta | 720 |
|---|---|---|---|---|---|---|---|---|---|---|---|---|---|---|---|---|
| Pro | Leu | Glu | Asn | Ile | Asn | Tyr | Ser | Ala | Thr | Ser | Lys | Leu | Leu | Ile | Leu | |
| 225 | | | | | 230 | | | | | 235 | | | | | 240 | |

| gac | atg | gct | tat | aac | ctt | atg | agt | cat | cga | atc | cta | gaa | cct | atc | tca | 768 |
|---|---|---|---|---|---|---|---|---|---|---|---|---|---|---|---|---|
| Asp | Met | Ala | Tyr | Asn | Leu | Met | Ser | His | Arg | Ile | Leu | Glu | Pro | Ile | Ser | |
| | | | | 245 | | | | | 250 | | | | | 255 | | |

| aaa | tta | gcc | aac | ctc | ata | caa | att | gac | tta | tct | ttt | cag | aag | aca | ccc | 816 |
|---|---|---|---|---|---|---|---|---|---|---|---|---|---|---|---|---|
| Lys | Leu | Ala | Asn | Leu | Ile | Gln | Ile | Asp | Leu | Ser | Phe | Gln | Lys | Thr | Pro | |
| | | | 260 | | | | | 265 | | | | | 270 | | | |

| tac | aca | ttc | aac | ttt | gat | ttc | ttg | ctc | ttc | aag | tct | cta | gtg | cgt | ttg | 864 |
|---|---|---|---|---|---|---|---|---|---|---|---|---|---|---|---|---|
| Tyr | Thr | Phe | Asn | Phe | Asp | Phe | Leu | Leu | Phe | Lys | Ser | Leu | Val | Arg | Leu | |
| | | 275 | | | | | 280 | | | | | 285 | | | | |

| gat | ctt | tcc | gga | aat | agt | gtt | tca | gtg | gtt | ggt | acc | ggt | tca | gaa | aat | 912 |
|---|---|---|---|---|---|---|---|---|---|---|---|---|---|---|---|---|
| Asp | Leu | Ser | Gly | Asn | Ser | Val | Ser | Val | Val | Gly | Thr | Gly | Ser | Glu | Asn | |
| | 290 | | | | | 295 | | | | | 300 | | | | | |

```
ttg aca cat cta gac ttg tcg agc tgc aac atc acc gag ttc ccg atg      960
Leu Thr His Leu Asp Leu Ser Ser Cys Asn Ile Thr Glu Phe Pro Met
305             310                 315                 320 ttt att aag gac tta caa aga tta tgg tgg tta gac att tcc aat aat     1008
Phe Ile Lys Asp Leu Gln Arg Leu Trp Trp Leu Asp Ile Ser Asn Asn
            325                 330                 335 aga att aaa gga aaa gtg cct gag ttg tta tgg act ctg cct tct atg     1056
Arg Ile Lys Gly Lys Val Pro Glu Leu Leu Trp Thr Leu Pro Ser Met
                340                 345                 350 ctc cat gta aat ctc tca cgc aac tcc ttt gat tcc ttg gaa ggt acg     1104
Leu His Val Asn Leu Ser Arg Asn Ser Phe Asp Ser Leu Glu Gly Thr
            355                 360                 365 cca aaa ata atc ctc aat tcg tcg att tcg gag tta gat ttg agt tca     1152
Pro Lys Ile Ile Leu Asn Ser Ser Ile Ser Glu Leu Asp Leu Ser Ser
370                 375                 380 aat gcc ttc aaa gga tct ttt cct att att cca cct tat gtc aac atc     1200
Asn Ala Phe Lys Gly Ser Phe Pro Ile Ile Pro Pro Tyr Val Asn Ile
385             390                 395                 400 atg gct gca tca aat aac tat ttc act gga ggc ata cca ctt ata ttc     1248
Met Ala Ala Ser Asn Asn Tyr Phe Thr Gly Gly Ile Pro Leu Ile Phe
                405                 410                 415 tgc aaa aga tat cga ctc agt ctc ctt gat cta tca aac aac aac ttc     1296
Cys Lys Arg Tyr Arg Leu Ser Leu Leu Asp Leu Ser Asn Asn Asn Phe
            420                 425                 430 agt ggg aca att ccg aga tgc ttg aca aat gtg tca ctc gga cta gaa     1344
Ser Gly Thr Ile Pro Arg Cys Leu Thr Asn Val Ser Leu Gly Leu Glu
                435                 440                 445 gcg ttg aaa ctc agt aac aac agc ctc act ggg aga ctt ccg gac ata     1392
Ala Leu Lys Leu Ser Asn Asn Ser Leu Thr Gly Arg Leu Pro Asp Ile
450                 455                 460 gaa gac cgc tta gta cta ctt gac gtt ggc cac aac caa ata agt ggg     1440
Glu Asp Arg Leu Val Leu Leu Asp Val Gly His Asn Gln Ile Ser Gly
465             470                 475                 480 aag ctt cca agg tct cta gta aac tgc aca acc cta aag ttt cta aat     1488
Lys Leu Pro Arg Ser Leu Val Asn Cys Thr Thr Leu Lys Phe Leu Asn
                485                 490                 495 gtg gaa gga aac cac atc aac gac act ttc cct ttc tgg ctg aag gct     1536
Val Glu Gly Asn His Ile Asn Asp Thr Phe Pro Phe Trp Leu Lys Ala
            500                 505                 510 ttg acg cgt ctt gaa atc att gtt ctg aga tca aac aga ttc cac ggt     1584
Leu Thr Arg Leu Glu Ile Ile Val Leu Arg Ser Asn Arg Phe His Gly
            515                 520                 525 ccc att tct tct cct gag gtc tct ctt tca ttt acg gca ctg cgg ata     1632
Pro Ile Ser Ser Pro Glu Val Ser Leu Ser Phe Thr Ala Leu Arg Ile
530                 535                 540 att gat att tcc cgt aac agc ttc aac ggg agc cta ccg caa aac tac     1680
Ile Asp Ile Ser Arg Asn Ser Phe Asn Gly Ser Leu Pro Gln Asn Tyr
545             550                 555                 560 ttt gcg aat tgg agt gca cct ttg gtt aat acc cca caa gga tat cgt     1728
Phe Ala Asn Trp Ser Ala Pro Leu Val Asn Thr Pro Gln Gly Tyr Arg
                565                 570                 575 tgg cca gag tac aca gga gat gaa cac tct aaa tat gag acc ccg ctt     1776
Trp Pro Glu Tyr Thr Gly Asp Glu His Ser Lys Tyr Glu Thr Pro Leu
            580                 585                 590 tgg tct tat cct tcc att cat ttg aga ata aaa gga cga agc ata gag     1824
Trp Ser Tyr Pro Ser Ile His Leu Arg Ile Lys Gly Arg Ser Ile Glu
            595                 600                 605 ttg gga aag att cca gat aca tac acg tcg ata gat ttc tca gga aat     1872
Leu Gly Lys Ile Pro Asp Thr Tyr Thr Ser Ile Asp Phe Ser Gly Asn
```

```
                                  610                 615                 620
agt ttt gaa gga cag att cca gaa tca ata ggt gat ttg aaa tcg ttg         1920
Ser Phe Glu Gly Gln Ile Pro Glu Ser Ile Gly Asp Leu Lys Ser Leu
625                 630                 635                 640 att gtt ctg gac tta tct aac aac tct ttc act ggt cgt att cca tcg         1968
Ile Val Leu Asp Leu Ser Asn Asn Ser Phe Thr Gly Arg Ile Pro Ser
                645                 650                 655 tcg ttg gcc aaa ctt aaa caa ctc gag tca ttg gat cta tct caa aac         2016
Ser Leu Ala Lys Leu Lys Gln Leu Glu Ser Leu Asp Leu Ser Gln Asn
            660                 665                 670 cga atc tct gga aat ata cct caa gag cta aga gag ctg acg ttt ttg         2064
Arg Ile Ser Gly Asn Ile Pro Gln Glu Leu Arg Glu Leu Thr Phe Leu
        675                 680                 685 gga tat gtt aac atg tca cat aac aga ctc acc ggc caa ata cca cag         2112
Gly Tyr Val Asn Met Ser His Asn Arg Leu Thr Gly Gln Ile Pro Gln
    690                 695                 700 agt aca cag gtt gga ggg caa cct aaa tcc tcc ttt gaa ggg aat atc         2160
Ser Thr Gln Val Gly Gly Gln Pro Lys Ser Ser Phe Glu Gly Asn Ile
705                 710                 715                 720 aat ctt tgt ggt ctt cct ctt caa gag agt tgt tta agg gga aat gga         2208
Asn Leu Cys Gly Leu Pro Leu Gln Glu Ser Cys Leu Arg Gly Asn Gly
                725                 730                 735 gta cca tca aca cca cat aca caa gag caa gaa cta cca aag caa gaa         2256
Val Pro Ser Thr Pro His Thr Gln Glu Gln Glu Leu Pro Lys Gln Glu
            740                 745                 750 cat gcg ttg aac tgg aaa gca gct gcg ata ggc tat gga ccc gga gtg         2304
His Ala Leu Asn Trp Lys Ala Ala Ala Ile Gly Tyr Gly Pro Gly Val
        755                 760                 765 ttg ttt gga ctg gcg atc gga caa gcc ttt gct cga tac aaa ccg gtc         2352
Leu Phe Gly Leu Ala Ile Gly Gln Ala Phe Ala Arg Tyr Lys Pro Val
    770                 775                 780 ttg ttc tat aag ttg ttt cga ctt tga                                     2379
Leu Phe Tyr Lys Leu Phe Arg Leu
785                 790

<210> SEQ ID NO 25
<211> LENGTH: 792
<212> TYPE: PRT
<213> ORGANISM: Arabidopsis thaliana

<400> SEQUENCE: 25

Met Lys Ser Asn Leu Ala Val Phe Phe Ile Thr Cys Phe Cys Cys
1               5                   10                  15

Val Phe Val Thr Ser Asp Ser Val Tyr Thr Leu Pro Phe Pro Phe Pro
                20                  25                  30

Arg Asp Gln Val Glu Ile Leu Leu Glu Leu Lys Asn Glu Phe Pro Ser
            35                  40                  45

Phe Asn Cys Asp Leu Thr Trp Lys Leu Asp Tyr Phe Gly Arg Met Asp
        50                  55                  60

Thr Arg Ala Asn Ile Ser Ser Trp Thr Lys Asp Ser Asp Ser Phe Ser
65                  70                  75                  80

Gly Val Ser Phe Asp Ser Glu Thr Gly Val Val Lys Glu Leu Ser Leu
                85                  90                  95

Gly Arg Gln Cys Leu Thr Ser Leu Lys Ala Asn Ser Ser Leu Phe Arg
            100                 105                 110

Phe Gln His Leu Arg Tyr Leu Asp Leu Ser Glu Asn His Phe Asp Ser
        115                 120                 125

Ser Pro Ile Pro Ser Gly Phe Gly Arg Leu Thr Tyr Leu Glu Ser Leu
```

```
            130                 135                 140
Asp Leu Ser Lys Asn Gly Phe Ile Gly Glu Val Pro Ser Ser Ile Ser
145                 150                 155                 160

Asn Leu Ser Arg Leu Thr Asn Leu Asp Leu Ser Tyr Asn Lys Leu Thr
                165                 170                 175

Gly Gly Ile Pro Asn Leu His Ser Leu Thr Leu Leu Glu Asn Ile Asp
                    180                 185                 190

Leu Ser Tyr Asn Lys Phe Ser Gly Ala Ile Pro Ser Tyr Leu Phe Thr
                195                 200                 205

Met Pro Phe Leu Val Ser Leu Asn Leu Arg Gln Asn His Leu Ser Asp
        210                 215                 220

Pro Leu Glu Asn Ile Asn Tyr Ser Ala Thr Ser Lys Leu Leu Ile Leu
225                 230                 235                 240

Asp Met Ala Tyr Asn Leu Met Ser His Arg Ile Leu Glu Pro Ile Ser
                245                 250                 255

Lys Leu Ala Asn Leu Ile Gln Ile Asp Leu Ser Phe Gln Lys Thr Pro
                260                 265                 270

Tyr Thr Phe Asn Phe Asp Phe Leu Leu Phe Lys Ser Leu Val Arg Leu
            275                 280                 285

Asp Leu Ser Gly Asn Ser Val Ser Val Gly Thr Gly Ser Glu Asn
        290                 295                 300

Leu Thr His Leu Asp Leu Ser Ser Cys Asn Ile Thr Glu Phe Pro Met
305                 310                 315                 320

Phe Ile Lys Asp Leu Gln Arg Leu Trp Trp Leu Asp Ile Ser Asn Asn
                325                 330                 335

Arg Ile Lys Gly Lys Val Pro Glu Leu Leu Trp Thr Leu Pro Ser Met
                340                 345                 350

Leu His Val Asn Leu Ser Arg Asn Ser Phe Asp Ser Leu Glu Gly Thr
            355                 360                 365

Pro Lys Ile Ile Leu Asn Ser Ser Ile Ser Glu Leu Asp Leu Ser Ser
    370                 375                 380

Asn Ala Phe Lys Gly Ser Phe Pro Ile Ile Pro Pro Tyr Val Asn Ile
385                 390                 395                 400

Met Ala Ala Ser Asn Asn Tyr Phe Thr Gly Gly Ile Pro Leu Ile Phe
                405                 410                 415

Cys Lys Arg Tyr Arg Leu Ser Leu Leu Asp Leu Ser Asn Asn Asn Phe
                420                 425                 430

Ser Gly Thr Ile Pro Arg Cys Leu Thr Asn Val Ser Leu Gly Leu Glu
            435                 440                 445

Ala Leu Lys Leu Ser Asn Asn Ser Leu Thr Gly Arg Leu Pro Asp Ile
    450                 455                 460

Glu Asp Arg Leu Val Leu Leu Asp Val Gly His Asn Gln Ile Ser Gly
465                 470                 475                 480

Lys Leu Pro Arg Ser Leu Val Asn Cys Thr Thr Leu Lys Phe Leu Asn
                485                 490                 495

Val Glu Gly Asn His Ile Asn Asp Thr Phe Pro Phe Trp Leu Lys Ala
                500                 505                 510

Leu Thr Arg Leu Glu Ile Ile Val Leu Arg Ser Asn Arg Phe His Gly
            515                 520                 525

Pro Ile Ser Ser Pro Glu Val Ser Leu Ser Phe Thr Ala Leu Arg Ile
        530                 535                 540

Ile Asp Ile Ser Arg Asn Ser Phe Asn Gly Ser Leu Pro Gln Asn Tyr
545                 550                 555                 560
```

```
Phe Ala Asn Trp Ser Ala Pro Leu Val Asn Thr Pro Gln Gly Tyr Arg
                565                 570                 575

Trp Pro Glu Tyr Thr Gly Asp Glu His Ser Lys Tyr Glu Thr Pro Leu
            580                 585                 590

Trp Ser Tyr Pro Ser Ile His Leu Arg Ile Lys Gly Arg Ser Ile Glu
        595                 600                 605

Leu Gly Lys Ile Pro Asp Thr Tyr Thr Ser Ile Asp Phe Ser Gly Asn
    610                 615                 620

Ser Phe Glu Gly Gln Ile Pro Glu Ser Ile Gly Asp Leu Lys Ser Leu
625                 630                 635                 640

Ile Val Leu Asp Leu Ser Asn Asn Ser Phe Thr Gly Arg Ile Pro Ser
                645                 650                 655

Ser Leu Ala Lys Leu Lys Gln Leu Glu Ser Leu Asp Leu Ser Gln Asn
            660                 665                 670

Arg Ile Ser Gly Asn Ile Pro Gln Glu Leu Arg Glu Leu Thr Phe Leu
        675                 680                 685

Gly Tyr Val Asn Met Ser His Asn Arg Leu Thr Gly Gln Ile Pro Gln
    690                 695                 700

Ser Thr Gln Val Gly Gly Gln Pro Lys Ser Ser Phe Glu Gly Asn Ile
705                 710                 715                 720

Asn Leu Cys Gly Leu Pro Leu Gln Glu Ser Cys Leu Arg Gly Asn Gly
                725                 730                 735

Val Pro Ser Thr Pro His Thr Gln Glu Gln Glu Leu Pro Lys Gln Glu
            740                 745                 750

His Ala Leu Asn Trp Lys Ala Ala Ile Gly Tyr Gly Pro Gly Val
        755                 760                 765

Leu Phe Gly Leu Ala Ile Gly Gln Ala Phe Ala Arg Tyr Lys Pro Val
    770                 775                 780

Leu Phe Tyr Lys Leu Phe Arg Leu
785                 790

<210> SEQ ID NO 26
<211> LENGTH: 2016
<212> TYPE: DNA
<213> ORGANISM: Arabidopsis thaliana
<220> FEATURE:
<221> NAME/KEY: CDS
<222> LOCATION: (1)..(2016)

<400> SEQUENCE: 26 atg aag act atg tcc aaa tcg tct ttg cgt ttg cat ttt ctc tcg cta      48
Met Lys Thr Met Ser Lys Ser Ser Leu Arg Leu His Phe Leu Ser Leu
1               5                   10                  15 ctc tta ctt tgt tgt gtc tcc cct tca agc ttt gtc att ata aga ttc      96
Leu Leu Leu Cys Cys Val Ser Pro Ser Ser Phe Val Ile Ile Arg Phe
            20                  25                  30 att aca cat aat cat ttt gat ggt cta gta cgt tgt cat ccc cac aag     144
Ile Thr His Asn His Phe Asp Gly Leu Val Arg Cys His Pro His Lys
        35                  40                  45 ttt caa gcc ctt acg cag ttc aag aac gag ttt gat acc cgc cgt tgc     192
Phe Gln Ala Leu Thr Gln Phe Lys Asn Glu Phe Asp Thr Arg Arg Cys
    50                  55                  60 aac cac agt aac tac ttt aat gga atc tgg tgt gat aac tcc aag gtg     240
Asn His Ser Asn Tyr Phe Asn Gly Ile Trp Cys Asp Asn Ser Lys Val
65                  70                  75                  80 cgg tca caa agc tac gac tac ggg act gtc tca gtg gaa ctc tca aat     288
Arg Ser Gln Ser Tyr Asp Tyr Gly Thr Val Ser Val Glu Leu Ser Asn
```

```
                    85                  90                  95
caa aca gta gcc tct tcc agt ttc atc atc ttc gct acc ttg atc tct       336
Gln Thr Val Ala Ser Ser Ser Phe Ile Ile Phe Ala Thr Leu Ile Ser
            100                 105                 110 ctc aca aca act tca cct cct ctt ccc tcc ctt ccg agt ttg ttt ccc       384
Leu Thr Thr Thr Ser Pro Pro Leu Pro Ser Leu Pro Ser Leu Phe Pro
            115                 120                 125 act ttg cgg aat cta acc aag ctc aca gtt tta gac ctt tct cat aat       432
Thr Leu Arg Asn Leu Thr Lys Leu Thr Val Leu Asp Leu Ser His Asn
130                 135                 140 cac ttc tcc gga act ttg aag ccc aac aat agc ctc ttt gag tta cac       480
His Phe Ser Gly Thr Leu Lys Pro Asn Asn Ser Leu Phe Glu Leu His
145                 150                 155                 160 cac ctt cgt tac ctt aat ctc gag gtc aac aac ttc agt tcc tca ctc       528
His Leu Arg Tyr Leu Asn Leu Glu Val Asn Asn Phe Ser Ser Ser Leu
            165                 170                 175 cct tcc gag ttt ggc tat ctc aac aat tta cag cac tgt ggc ctc aaa       576
Pro Ser Glu Phe Gly Tyr Leu Asn Asn Leu Gln His Cys Gly Leu Lys
            180                 185                 190 gag ttc cca aac ata ttc aag acc ctt aaa aaa atg gag gct ata gac       624
Glu Phe Pro Asn Ile Phe Lys Thr Leu Lys Lys Met Glu Ala Ile Asp
            195                 200                 205 gta tcc aac aat aga atc aac ggg aaa atc cct gag tgg tta tgg agc       672
Val Ser Asn Asn Arg Ile Asn Gly Lys Ile Pro Glu Trp Leu Trp Ser
210                 215                 220 ctt cct ctt ctt cat tta gtg aat att tta aat aat tct ttt gac ggt       720
Leu Pro Leu Leu His Leu Val Asn Ile Leu Asn Asn Ser Phe Asp Gly
225                 230                 235                 240 ttc gaa gga tca acg gaa gtt tta gta aat tca tcg gtt cgg ata tta       768
Phe Glu Gly Ser Thr Glu Val Leu Val Asn Ser Ser Val Arg Ile Leu
            245                 250                 255 ctt ttg gag tca aac aac ttt gaa gga gca ctt cct agt cta cca cac       816
Leu Leu Glu Ser Asn Asn Phe Glu Gly Ala Leu Pro Ser Leu Pro His
            260                 265                 270 tct atc aac gcc ttc tcc gcg ggt cat aac aat ttc act gga gag ata       864
Ser Ile Asn Ala Phe Ser Ala Gly His Asn Asn Phe Thr Gly Glu Ile
            275                 280                 285 cct ctt tca atc tgc acc aga acc tca ctt ggt gtc ctt gat cta aac       912
Pro Leu Ser Ile Cys Thr Arg Thr Ser Leu Gly Val Leu Asp Leu Asn
290                 295                 300 tac aac aac ctc att ggt ccg gtt tct caa tgt ttg agt aat gtc acg       960
Tyr Asn Asn Leu Ile Gly Pro Val Ser Gln Cys Leu Ser Asn Val Thr
305                 310                 315                 320 ttt gta aat ctc cgg aaa aac aat ttg gaa gga act att cct gag act      1008
Phe Val Asn Leu Arg Lys Asn Asn Leu Glu Gly Thr Ile Pro Glu Thr
            325                 330                 335 ttc att gtc ggt tcc tcg ata agg aca ctt gat gtt gga tac aat cga      1056
Phe Ile Val Gly Ser Ser Ile Arg Thr Leu Asp Val Gly Tyr Asn Arg
            340                 345                 350 cta acg gga aag ctt cca agg tct ctt ttg aac tgc tca tct cta gag      1104
Leu Thr Gly Lys Leu Pro Arg Ser Leu Leu Asn Cys Ser Ser Leu Glu
            355                 360                 365 ttt cta agc gtt gac aac aac aga atc aaa gac aca ttt cct ttc tgg      1152
Phe Leu Ser Val Asp Asn Asn Arg Ile Lys Asp Thr Phe Pro Phe Trp
370                 375                 380 ctc aag gct tta cca aag tta caa gtc ctt acc cta agt tca aac aag      1200
Leu Lys Ala Leu Pro Lys Leu Gln Val Leu Thr Leu Ser Ser Asn Lys
385                 390                 395                 400 ttt tat ggt cct ata tct cct cct cat caa ggt cct ctc ggg ttt cca      1248
```

```
Phe Tyr Gly Pro Ile Ser Pro Pro His Gln Gly Pro Leu Gly Phe Pro
                405                 410                 415 gag ctg aga ata ctt gag ata tct gat aat aag ttt act gga agc ttg       1296
Glu Leu Arg Ile Leu Glu Ile Ser Asp Asn Lys Phe Thr Gly Ser Leu
                420                 425                 430 tcg tca aga tac ttt gag aat tgg aaa gca tcg tcc gcc atg atg aat       1344
Ser Ser Arg Tyr Phe Glu Asn Trp Lys Ala Ser Ser Ala Met Met Asn
                435                 440                 445 gaa tat gtg ggt tta tat atg gtt tac gag aag aat cct tat ggt gta       1392
Glu Tyr Val Gly Leu Tyr Met Val Tyr Glu Lys Asn Pro Tyr Gly Val
    450                 455                 460 gtt gtc tat acc ttt ttg gat cgt ata gat ttg aaa tac aaa ggt cta       1440
Val Val Tyr Thr Phe Leu Asp Arg Ile Asp Leu Lys Tyr Lys Gly Leu
465                 470                 475                 480 aac atg gag caa gcg agg gtt ctc act tcc tac agc gcc att gat ttt       1488
Asn Met Glu Gln Ala Arg Val Leu Thr Ser Tyr Ser Ala Ile Asp Phe
                485                 490                 495 tct aga aat cta ctt gaa gga aat att cct gaa tcc att gga ctt tta       1536
Ser Arg Asn Leu Leu Glu Gly Asn Ile Pro Glu Ser Ile Gly Leu Leu
                500                 505                 510 aag gca ttg att gca cta aac tta tcg aac aac gct ttt aca ggc cat       1584
Lys Ala Leu Ile Ala Leu Asn Leu Ser Asn Asn Ala Phe Thr Gly His
                515                 520                 525 att cct cag tct ttg gca aat ctt aag gag ctc cag tca cta gac atg       1632
Ile Pro Gln Ser Leu Ala Asn Leu Lys Glu Leu Gln Ser Leu Asp Met
530                 535                 540 tct agg aac caa ctc tca ggg act att cct aat gga ctc aag caa ctc       1680
Ser Arg Asn Gln Leu Ser Gly Thr Ile Pro Asn Gly Leu Lys Gln Leu
545                 550                 555                 560 tcg ttt ttg gct tac ata agt gtg tct cat aac caa ctc aag ggt gaa       1728
Ser Phe Leu Ala Tyr Ile Ser Val Ser His Asn Gln Leu Lys Gly Glu
                565                 570                 575 ata cca caa gga aca caa att act ggg caa ttg aaa tct tcc ttt gaa       1776
Ile Pro Gln Gly Thr Gln Ile Thr Gly Gln Leu Lys Ser Ser Phe Glu
                580                 585                 590 ggg aat gta gga ctt tgt ggt ctt cct ctc gag gaa agg tgc ttc gac       1824
Gly Asn Val Gly Leu Cys Gly Leu Pro Leu Glu Glu Arg Cys Phe Asp
                595                 600                 605 aat agt gca tct cca acg cag cac cac aag caa gac gaa gaa gaa gaa       1872
Asn Ser Ala Ser Pro Thr Gln His His Lys Gln Asp Glu Glu Glu Glu
610                 615                 620 gaa gaa caa gtg tta cac tgg aaa gcg gtg gca atg ggg tat gga cct       1920
Glu Glu Gln Val Leu His Trp Lys Ala Val Ala Met Gly Tyr Gly Pro
625                 630                 635                 640 gga ttg ttg gtt gga ttt gca att gca tat gtc att gct tca tac aag       1968
Gly Leu Leu Val Gly Phe Ala Ile Ala Tyr Val Ile Ala Ser Tyr Lys
                645                 650                 655 ccg gag tgg cta acc aag ata att ggt ccg aat aag cgc aga aac tag       2016
Pro Glu Trp Leu Thr Lys Ile Ile Gly Pro Asn Lys Arg Arg Asn
                660                 665                 670

<210> SEQ ID NO 27
<211> LENGTH: 671
<212> TYPE: PRT
<213> ORGANISM: Arabidopsis thaliana

<400> SEQUENCE: 27

Met Lys Thr Met Ser Lys Ser Ser Leu Arg Leu His Phe Leu Ser Leu
1               5                   10                  15

Leu Leu Leu Cys Cys Val Ser Pro Ser Ser Phe Val Ile Ile Arg Phe
```

```
                20                  25                  30
Ile Thr His Asn His Phe Asp Gly Leu Val Arg Cys His Pro His Lys
             35                  40                  45
Phe Gln Ala Leu Thr Gln Phe Lys Asn Glu Phe Asp Thr Arg Arg Cys
         50                  55                  60
Asn His Ser Asn Tyr Phe Asn Gly Ile Trp Cys Asp Asn Ser Lys Val
 65                  70                  75                  80
Arg Ser Gln Ser Tyr Asp Tyr Gly Thr Val Ser Val Glu Leu Ser Asn
                 85                  90                  95
Gln Thr Val Ala Ser Ser Ser Phe Ile Ile Phe Ala Thr Leu Ile Ser
                100                 105                 110
Leu Thr Thr Thr Ser Pro Pro Leu Pro Ser Leu Pro Ser Leu Phe Pro
             115                 120                 125
Thr Leu Arg Asn Leu Thr Lys Leu Thr Val Leu Asp Leu Ser His Asn
             130                 135                 140
His Phe Ser Gly Thr Leu Lys Pro Asn Asn Ser Leu Phe Glu Leu His
145                 150                 155                 160
His Leu Arg Tyr Leu Asn Leu Glu Val Asn Asn Phe Ser Ser Ser Leu
                165                 170                 175
Pro Ser Glu Phe Gly Tyr Leu Asn Asn Leu Gln His Cys Gly Leu Lys
            180                 185                 190
Glu Phe Pro Asn Ile Phe Lys Thr Leu Lys Lys Met Glu Ala Ile Asp
            195                 200                 205
Val Ser Asn Asn Arg Ile Asn Gly Lys Ile Pro Glu Trp Leu Trp Ser
            210                 215                 220
Leu Pro Leu Leu His Leu Val Asn Ile Leu Asn Asn Ser Phe Asp Gly
225                 230                 235                 240
Phe Glu Gly Ser Thr Glu Val Leu Val Asn Ser Ser Val Arg Ile Leu
                245                 250                 255
Leu Leu Glu Ser Asn Asn Phe Glu Gly Ala Leu Pro Ser Leu Pro His
            260                 265                 270
Ser Ile Asn Ala Phe Ser Ala Gly His Asn Asn Phe Thr Gly Glu Ile
            275                 280                 285
Pro Leu Ser Ile Cys Thr Arg Thr Ser Leu Gly Val Leu Asp Leu Asn
290                 295                 300
Tyr Asn Asn Leu Ile Gly Pro Val Ser Gln Cys Leu Ser Asn Val Thr
305                 310                 315                 320
Phe Val Asn Leu Arg Lys Asn Asn Leu Glu Gly Thr Ile Pro Glu Thr
            325                 330                 335
Phe Ile Val Gly Ser Ser Ile Arg Thr Leu Asp Val Gly Tyr Asn Arg
            340                 345                 350
Leu Thr Gly Lys Leu Pro Arg Ser Leu Leu Asn Cys Ser Ser Leu Glu
            355                 360                 365
Phe Leu Ser Val Asp Asn Asn Arg Ile Lys Asp Thr Phe Pro Phe Trp
            370                 375                 380
Leu Lys Ala Leu Pro Lys Leu Gln Val Leu Thr Leu Ser Ser Asn Lys
385                 390                 395                 400
Phe Tyr Gly Pro Ile Ser Pro His Gln Gly Pro Leu Gly Phe Pro
                405                 410                 415
Glu Leu Arg Ile Leu Glu Ile Ser Asp Asn Lys Phe Thr Gly Ser Leu
            420                 425                 430
Ser Ser Arg Tyr Phe Glu Asn Trp Lys Ala Ser Ser Ala Met Met Asn
            435                 440                 445
```

```
Glu Tyr Val Gly Leu Tyr Met Tyr Glu Lys Asn Pro Tyr Gly Val
    450                 455                 460

Val Val Tyr Thr Phe Leu Asp Arg Ile Asp Leu Lys Tyr Lys Gly Leu
465                 470                 475                 480

Asn Met Glu Gln Ala Arg Val Leu Thr Ser Tyr Ser Ala Ile Asp Phe
                485                 490                 495

Ser Arg Asn Leu Leu Glu Gly Asn Ile Pro Glu Ser Ile Gly Leu Leu
                500                 505                 510

Lys Ala Leu Ile Ala Leu Asn Leu Ser Asn Asn Ala Phe Thr Gly His
                515                 520                 525

Ile Pro Gln Ser Leu Ala Asn Leu Lys Glu Leu Gln Ser Leu Asp Met
    530                 535                 540

Ser Arg Asn Gln Leu Ser Gly Thr Ile Pro Asn Gly Leu Lys Gln Leu
545                 550                 555                 560

Ser Phe Leu Ala Tyr Ile Ser Val Ser His Asn Gln Leu Lys Gly Glu
                565                 570                 575

Ile Pro Gln Gly Thr Gln Ile Thr Gly Gln Leu Lys Ser Ser Phe Glu
                580                 585                 590

Gly Asn Val Gly Leu Cys Gly Leu Pro Leu Glu Glu Arg Cys Phe Asp
                595                 600                 605

Asn Ser Ala Ser Pro Thr Gln His His Lys Gln Asp Glu Glu Glu Glu
                610                 615                 620

Glu Glu Gln Val Leu His Trp Lys Ala Val Ala Met Gly Tyr Gly Pro
625                 630                 635                 640

Gly Leu Leu Val Gly Phe Ala Ile Ala Tyr Val Ile Ala Ser Tyr Lys
                645                 650                 655

Pro Glu Trp Leu Thr Lys Ile Ile Gly Pro Asn Lys Arg Arg Asn
                660                 665                 670
```

<210> SEQ ID NO 28
<211> LENGTH: 2673
<212> TYPE: DNA
<213> ORGANISM: Arabidopsis thaliana
<220> FEATURE:
<221> NAME/KEY: CDS
<222> LOCATION: (1)..(2673)

<400> SEQUENCE: 28

```
atg tca aag gcg ctt ttg cat ttg cat ttt ctt tct ctg ttt tta ctc      48
Met Ser Lys Ala Leu Leu His Leu His Phe Leu Ser Leu Phe Leu Leu
1               5                   10                  15 tgt tgt gtc tgc cat tca agt att ttt act tta aat ttt cat ttt act      96
Cys Cys Val Cys His Ser Ser Ile Phe Thr Leu Asn Phe His Phe Thr
                20                  25                  30 ggt att gtg gcc tgt cgt ccc cac cag att caa gcc ttc acg aag ttc     144
Gly Ile Val Ala Cys Arg Pro His Gln Ile Gln Ala Phe Thr Lys Phe
            35                  40                  45 acg aac gag ttt gac acc cgc ggt tgc aac aac agt gac acc ttt aat     192
Thr Asn Glu Phe Asp Thr Arg Gly Cys Asn Asn Ser Asp Thr Phe Asn
        50                  55                  60 gga gtc tgg tgc gat aac tcg acg ggt gcg gtc gca gtg cta caa cta     240
Gly Val Trp Cys Asp Asn Ser Thr Gly Ala Val Ala Val Leu Gln Leu
65                  70                  75                  80 agg aag tgt ctc agt gga act ttg aag tcc aac agt agc ctc ttc ggg     288
Arg Lys Cys Leu Ser Gly Thr Leu Lys Ser Asn Ser Ser Leu Phe Gly
                85                  90                  95 ttt cat caa ctc cgt tac gtt gat ctc caa aac aac aac tta acc tcc     336
```

```
            Phe His Gln Leu Arg Tyr Val Asp Leu Gln Asn Asn Asn Leu Thr Ser
                         100                 105                 110 tct tca ctc cct tcc ggg ttt gga aat ctc aaa aga tta gag ggc ttg      384
Ser Ser Leu Pro Ser Gly Phe Gly Asn Leu Lys Arg Leu Glu Gly Leu
            115                 120                 125 ttt ctt tcc tct aat ggc ttc ctc ggc caa gtt cct tcc tca ttc agt      432
Phe Leu Ser Ser Asn Gly Phe Leu Gly Gln Val Pro Ser Ser Phe Ser
130                 135                 140 aac cta aca atg ctt gct caa tta gac ctt tct tat aac aag ctc act      480
Asn Leu Thr Met Leu Ala Gln Leu Asp Leu Ser Tyr Asn Lys Leu Thr
145                 150                 155                 160 ggt agt ttc cca ctt gtc cgg ggt cta aga aag ctc att gtt tta gac      528
Gly Ser Phe Pro Leu Val Arg Gly Leu Arg Lys Leu Ile Val Leu Asp
                165                 170                 175 ctt tca tat aat cac ttc tcc gga act ctg aat cca aac agt agc ctc      576
Leu Ser Tyr Asn His Phe Ser Gly Thr Leu Asn Pro Asn Ser Ser Leu
                180                 185                 190 ttt gag ttg cac cag cta cgt tac ctt aat ctc gct ttt aac aac ttt      624
Phe Glu Leu His Gln Leu Arg Tyr Leu Asn Leu Ala Phe Asn Asn Phe
            195                 200                 205 agt tcc tca ctc cct tcc aaa ttt ggc aat ctc cat aga tta gag aac      672
Ser Ser Ser Leu Pro Ser Lys Phe Gly Asn Leu His Arg Leu Glu Asn
210                 215                 220 ttg att ctt tcc tct aat ggc ttt tct ggt caa gtt cct tcc aca att      720
Leu Ile Leu Ser Ser Asn Gly Phe Ser Gly Gln Val Pro Ser Thr Ile
225                 230                 235                 240 agt aac ctg acc cgg tta act aag ttg tac ctt gac caa aac aag ctc      768
Ser Asn Leu Thr Arg Leu Thr Lys Leu Tyr Leu Asp Gln Asn Lys Leu
                245                 250                 255 act agt agt ttc cca ctt gta cag aat cta acc aac ctc tac gaa tta      816
Thr Ser Ser Phe Pro Leu Val Gln Asn Leu Thr Asn Leu Tyr Glu Leu
                260                 265                 270 gac ctt tca tat aat aag ttc ttt gga gtc atc cct tct tct ctc ctc      864
Asp Leu Ser Tyr Asn Lys Phe Phe Gly Val Ile Pro Ser Ser Leu Leu
            275                 280                 285 act ctg cct ttc tta gca cat ctt gct cta cgt gaa aac aat ctt gct      912
Thr Leu Pro Phe Leu Ala His Leu Ala Leu Arg Glu Asn Asn Leu Ala
290                 295                 300 ggt tct gtt gaa gtt tca aac tcc tct acc tca tct agg ctc gaa atc      960
Gly Ser Val Glu Val Ser Asn Ser Ser Thr Ser Ser Arg Leu Glu Ile
305                 310                 315                 320 atg tat ctc ggg tct aac cat ttt gaa gga caa atc cta gag cct atc     1008
Met Tyr Leu Gly Ser Asn His Phe Glu Gly Gln Ile Leu Glu Pro Ile
                325                 330                 335 tca aag ctc atc aac ctc aag cat ctt gac ctt tct ttc cta aac aca     1056
Ser Lys Leu Ile Asn Leu Lys His Leu Asp Leu Ser Phe Leu Asn Thr
                340                 345                 350 agc tac cca ata gac tta aaa ctc ttc tcc tcc ctc aaa tct ttg cgg     1104
Ser Tyr Pro Ile Asp Leu Lys Leu Phe Ser Ser Leu Lys Ser Leu Arg
            355                 360                 365 tct ctg gat ctt tct gga aac agt ata tct tcg gcc agt tta agt tca     1152
Ser Leu Asp Leu Ser Gly Asn Ser Ile Ser Ser Ala Ser Leu Ser Ser
370                 375                 380 gat tca tac atc ccg ttg acc ctg gaa atg ttg acc ttg agg cac tgt     1200
Asp Ser Tyr Ile Pro Leu Thr Leu Glu Met Leu Thr Leu Arg His Cys
385                 390                 395                 400 gac atc aac gag ttc ccc aac atc tta aag acc ctc aag gag ttg gtg     1248
Asp Ile Asn Glu Phe Pro Asn Ile Leu Lys Thr Leu Lys Glu Leu Val
                405                 410                 415
```

| | | | | | | | | | | | | | | | | |
|---|---|---|---|---|---|---|---|---|---|---|---|---|---|---|---|---|
| tat | ata | gac | ata | tcc | aac | aac | aga | atg | aaa | ggg | aag | atc | cct | gag | tgg | 1296 |
| Tyr | Ile | Asp | Ile | Ser | Asn | Asn | Arg | Met | Lys | Gly | Lys | Ile | Pro | Glu | Trp | |
| | | | 420 | | | | 425 | | | | 430 | | | | | |
| tta | tgg | agc | cta | cct | ctt | cta | cag | tca | gta | act | ctt | gga | aat | aat | tat | 1344 |
| Leu | Trp | Ser | Leu | Pro | Leu | Leu | Gln | Ser | Val | Thr | Leu | Gly | Asn | Asn | Tyr | |
| | 435 | | | | 440 | | | | 445 | | | | | | | |
| ttc | aca | ggt | ttc | caa | ggt | tcg | gcg | gag | att | tta | gta | aat | tca | tca | gtg | 1392 |
| Phe | Thr | Gly | Phe | Gln | Gly | Ser | Ala | Glu | Ile | Leu | Val | Asn | Ser | Ser | Val | |
| | 450 | | | | 455 | | | | 460 | | | | | | | |
| ctg | cta | tta | tat | ttg | gat | tca | aac | aat | ttt | gaa | gga | gca | ctt | cct | gat | 1440 |
| Leu | Leu | Leu | Tyr | Leu | Asp | Ser | Asn | Asn | Phe | Glu | Gly | Ala | Leu | Pro | Asp | |
| 465 | | | | 470 | | | | 475 | | | | 480 | | | | |
| cta | cca | ctc | tct | atc | aaa | ggc | ttc | ggt | gtg | gct | agt | aat | agt | ttc | aca | 1488 |
| Leu | Pro | Leu | Ser | Ile | Lys | Gly | Phe | Gly | Val | Ala | Ser | Asn | Ser | Phe | Thr | |
| | | | 485 | | | | 490 | | | | 495 | | | | | |
| agt | gag | ata | cct | ctt | tca | atc | tgc | aac | cga | agc | tct | ctc | gct | gct | att | 1536 |
| Ser | Glu | Ile | Pro | Leu | Ser | Ile | Cys | Asn | Arg | Ser | Ser | Leu | Ala | Ala | Ile | |
| | | 500 | | | | 505 | | | | 510 | | | | | | |
| gat | cta | tcc | tac | aac | aac | ttc | act | ggt | ccc | att | cct | cca | tgt | ttg | cgt | 1584 |
| Asp | Leu | Ser | Tyr | Asn | Asn | Phe | Thr | Gly | Pro | Ile | Pro | Pro | Cys | Leu | Arg | |
| | | 515 | | | | 520 | | | | 525 | | | | | | |
| aat | ttg | gaa | ctt | gtg | tat | ctc | cgg | aac | aac | aac | ctg | gaa | gga | agt | atc | 1632 |
| Asn | Leu | Glu | Leu | Val | Tyr | Leu | Arg | Asn | Asn | Asn | Leu | Glu | Gly | Ser | Ile | |
| 530 | | | | 535 | | | | 540 | | | | | | | | |
| cct | gac | gcg | ctc | tgt | gat | ggt | gcc | tct | tta | cgg | aca | ctc | gat | gtt | agc | 1680 |
| Pro | Asp | Ala | Leu | Cys | Asp | Gly | Ala | Ser | Leu | Arg | Thr | Leu | Asp | Val | Ser | |
| 545 | | | | 550 | | | | 555 | | | | 560 | | | | |
| cat | aac | cga | tta | aca | ggg | aag | ctt | cca | agg | tct | ttt | gta | aac | tgc | tca | 1728 |
| His | Asn | Arg | Leu | Thr | Gly | Lys | Leu | Pro | Arg | Ser | Phe | Val | Asn | Cys | Ser | |
| | | | 565 | | | | 570 | | | | 575 | | | | | |
| tcg | cta | aag | ttt | cta | agc | gtt | ata | aac | aac | aga | att | gaa | gat | acg | ttt | 1776 |
| Ser | Leu | Lys | Phe | Leu | Ser | Val | Ile | Asn | Asn | Arg | Ile | Glu | Asp | Thr | Phe | |
| | | 580 | | | | 585 | | | | 590 | | | | | | |
| ccg | ttc | tgg | ctc | aaa | gct | tta | ccg | aat | ttg | caa | gtc | ctt | act | ctt | cgc | 1824 |
| Pro | Phe | Trp | Leu | Lys | Ala | Leu | Pro | Asn | Leu | Gln | Val | Leu | Thr | Leu | Arg | |
| | 595 | | | | 600 | | | | 605 | | | | | | | |
| tca | aac | aga | ttt | tat | ggt | cct | ata | tct | cct | ccg | cat | caa | ggt | cct | ctc | 1872 |
| Ser | Asn | Arg | Phe | Tyr | Gly | Pro | Ile | Ser | Pro | Pro | His | Gln | Gly | Pro | Leu | |
| 610 | | | | 615 | | | | 620 | | | | | | | | |
| ggg | ttt | cca | gag | ctg | cgg | ata | ttt | gaa | ata | tct | gac | aat | aag | ttt | aca | 1920 |
| Gly | Phe | Pro | Glu | Leu | Arg | Ile | Phe | Glu | Ile | Ser | Asp | Asn | Lys | Phe | Thr | |
| 625 | | | | 630 | | | | 635 | | | | 640 | | | | |
| gga | agc | ttg | cca | cca | aac | tac | ttt | gtg | aac | tgg | aaa | gca | tca | tca | cgc | 1968 |
| Gly | Ser | Leu | Pro | Pro | Asn | Tyr | Phe | Val | Asn | Trp | Lys | Ala | Ser | Ser | Arg | |
| | | | 645 | | | | 650 | | | | 655 | | | | | |
| acg | atg | aat | caa | gat | ggg | ggt | tta | tat | atg | gta | tac | gag | gag | aag | ctg | 2016 |
| Thr | Met | Asn | Gln | Asp | Gly | Gly | Leu | Tyr | Met | Val | Tyr | Glu | Glu | Lys | Leu | |
| | | 660 | | | | 665 | | | | 670 | | | | | | |
| ttc | gac | gaa | ggc | ggc | tat | ggt | tat | aca | gat | gct | tta | gat | ttg | caa | tac | 2064 |
| Phe | Asp | Glu | Gly | Gly | Tyr | Gly | Tyr | Thr | Asp | Ala | Leu | Asp | Leu | Gln | Tyr | |
| | | 675 | | | | 680 | | | | 685 | | | | | | |
| aaa | ggt | cta | cac | atg | gag | caa | gct | aag | gcc | ctc | act | tcc | tac | gcc | gcc | 2112 |
| Lys | Gly | Leu | His | Met | Glu | Gln | Ala | Lys | Ala | Leu | Thr | Ser | Tyr | Ala | Ala | |
| | 690 | | | | 695 | | | | 700 | | | | | | | |
| att | gat | ttt | tct | gga | aat | aga | ctc | gaa | gga | cag | att | cct | gaa | tct | att | 2160 |
| Ile | Asp | Phe | Ser | Gly | Asn | Arg | Leu | Glu | Gly | Gln | Ile | Pro | Glu | Ser | Ile | |
| 705 | | | | 710 | | | | 715 | | | | 720 | | | | |
| ggt | ctc | ttg | aag | gca | ctg | att | gca | gtc | aat | ata | tca | aac | aac | gcc | ttc | 2208 |
| Gly | Leu | Leu | Lys | Ala | Leu | Ile | Ala | Val | Asn | Ile | Ser | Asn | Asn | Ala | Phe | |
| | | | 725 | | | | 730 | | | | 735 | | | | | |

```
aca ggc cat att ccc ctg tct atg gcc aat ctt gag aat ctc gag tca    2256
Thr Gly His Ile Pro Leu Ser Met Ala Asn Leu Glu Asn Leu Glu Ser
        740                 745                 750 cta gac atg tca aga aac caa ctc tcg ggg act att cct aat gga cta    2304
Leu Asp Met Ser Arg Asn Gln Leu Ser Gly Thr Ile Pro Asn Gly Leu
        755                 760                 765 ggg agc att tcg ttt ttg gcg tac atc aac gtg tct cac aac caa ctc    2352
Gly Ser Ile Ser Phe Leu Ala Tyr Ile Asn Val Ser His Asn Gln Leu
770                 775                 780 acg ggt gaa ata cca caa gga aca cag att act ggg caa tct aaa tct    2400
Thr Gly Glu Ile Pro Gln Gly Thr Gln Ile Thr Gly Gln Ser Lys Ser
785                 790                 795                 800 tcc ttc gaa ggg aat gca ggg ctt tgt ggt ctt cct ctc aag gaa agt    2448
Ser Phe Glu Gly Asn Ala Gly Leu Cys Gly Leu Pro Leu Lys Glu Ser
                805                 810                 815 tgc ttc ggc act ggt gca cct ccg atg tat cac caa aag caa gaa gac    2496
Cys Phe Gly Thr Gly Ala Pro Pro Met Tyr His Gln Lys Gln Glu Asp
                820                 825                 830 aaa gaa gaa gaa gaa gaa gaa gaa gaa gaa gaa gaa gtg ttg aac        2544
Lys Glu Glu Glu Glu Glu Glu Glu Glu Glu Glu Glu Val Leu Asn
            835                 840                 845 ggg aga gca gtg gca ata ggg tat gga tct gga tta ttg ctt gga ttg    2592
Gly Arg Ala Val Ala Ile Gly Tyr Gly Ser Gly Leu Leu Leu Gly Leu
850                 855                 860 gca ata gca caa gtt att gct tca tac aaa ccg gag tgg ctt gtc aag    2640
Ala Ile Ala Gln Val Ile Ala Ser Tyr Lys Pro Glu Trp Leu Val Lys
865                 870                 875                 880 ata att ggt ctg aat aaa cgc aga aag cgt tag                        2673
Ile Ile Gly Leu Asn Lys Arg Arg Lys Arg
                885                 890

<210> SEQ ID NO 29
<211> LENGTH: 890
<212> TYPE: PRT
<213> ORGANISM: Arabidopsis thaliana

<400> SEQUENCE: 29

Met Ser Lys Ala Leu Leu His Leu His Phe Leu Ser Leu Phe Leu Leu
1               5                   10                  15

Cys Cys Val Cys His Ser Ser Ile Phe Thr Leu Asn Phe His Phe Thr
            20                  25                  30

Gly Ile Val Ala Cys Arg Pro His Gln Ile Gln Ala Phe Thr Lys Phe
        35                  40                  45

Thr Asn Glu Phe Asp Thr Arg Gly Cys Asn Asn Ser Asp Thr Phe Asn
    50                  55                  60

Gly Val Trp Cys Asp Asn Ser Thr Gly Ala Val Ala Val Leu Gln Leu
65                  70                  75                  80

Arg Lys Cys Leu Ser Gly Thr Leu Lys Ser Asn Ser Ser Leu Phe Gly
                85                  90                  95

Phe His Gln Leu Arg Tyr Val Asp Leu Gln Asn Asn Asn Leu Thr Ser
            100                 105                 110

Ser Ser Leu Pro Ser Gly Phe Gly Asn Leu Lys Arg Leu Glu Gly Leu
        115                 120                 125

Phe Leu Ser Ser Asn Gly Phe Leu Gly Gln Val Pro Ser Ser Phe Ser
    130                 135                 140

Asn Leu Thr Met Leu Ala Gln Leu Asp Leu Ser Tyr Asn Lys Leu Thr
145                 150                 155                 160
```

```
Gly Ser Phe Pro Leu Val Arg Gly Leu Arg Lys Leu Ile Val Leu Asp
                165                 170                 175
Leu Ser Tyr Asn His Phe Ser Gly Thr Leu Asn Pro Asn Ser Ser Leu
            180                 185                 190
Phe Glu Leu His Gln Leu Arg Tyr Leu Asn Leu Ala Phe Asn Asn Phe
        195                 200                 205
Ser Ser Ser Leu Pro Ser Lys Phe Gly Asn Leu His Arg Leu Glu Asn
    210                 215                 220
Leu Ile Leu Ser Ser Asn Gly Phe Ser Gly Gln Val Pro Ser Thr Ile
225                 230                 235                 240
Ser Asn Leu Thr Arg Leu Thr Lys Leu Tyr Leu Asp Gln Asn Lys Leu
                245                 250                 255
Thr Ser Ser Phe Pro Leu Val Gln Asn Leu Thr Asn Leu Tyr Glu Leu
            260                 265                 270
Asp Leu Ser Tyr Asn Lys Phe Phe Gly Val Ile Pro Ser Ser Leu Leu
        275                 280                 285
Thr Leu Pro Phe Leu Ala His Leu Ala Leu Arg Glu Asn Asn Leu Ala
    290                 295                 300
Gly Ser Val Glu Val Ser Asn Ser Ser Thr Ser Ser Arg Leu Glu Ile
305                 310                 315                 320
Met Tyr Leu Gly Ser Asn His Phe Glu Gly Gln Ile Leu Glu Pro Ile
                325                 330                 335
Ser Lys Leu Ile Asn Leu Lys His Leu Asp Leu Ser Phe Leu Asn Thr
            340                 345                 350
Ser Tyr Pro Ile Asp Leu Lys Leu Phe Ser Ser Leu Lys Ser Leu Arg
        355                 360                 365
Ser Leu Asp Leu Ser Gly Asn Ser Ile Ser Ser Ala Ser Leu Ser Ser
    370                 375                 380
Asp Ser Tyr Ile Pro Leu Thr Leu Glu Met Leu Thr Leu Arg His Cys
385                 390                 395                 400
Asp Ile Asn Glu Phe Pro Asn Ile Leu Lys Thr Leu Lys Glu Leu Val
                405                 410                 415
Tyr Ile Asp Ile Ser Asn Asn Arg Met Lys Gly Lys Ile Pro Glu Trp
            420                 425                 430
Leu Trp Ser Leu Pro Leu Leu Gln Ser Val Thr Leu Gly Asn Asn Tyr
        435                 440                 445
Phe Thr Gly Phe Gln Gly Ser Ala Glu Ile Leu Val Asn Ser Ser Val
    450                 455                 460
Leu Leu Leu Tyr Leu Asp Ser Asn Asn Phe Glu Gly Ala Leu Pro Asp
465                 470                 475                 480
Leu Pro Leu Ser Ile Lys Gly Phe Gly Val Ala Ser Asn Ser Phe Thr
                485                 490                 495
Ser Glu Ile Pro Leu Ser Ile Cys Asn Arg Ser Ser Leu Ala Ala Ile
            500                 505                 510
Asp Leu Ser Tyr Asn Asn Phe Thr Gly Pro Ile Pro Pro Cys Leu Arg
        515                 520                 525
Asn Leu Glu Leu Val Tyr Leu Arg Asn Asn Leu Glu Gly Ser Ile
    530                 535                 540
Pro Asp Ala Leu Cys Asp Gly Ala Ser Leu Arg Thr Leu Asp Val Ser
545                 550                 555                 560
His Asn Arg Leu Thr Gly Lys Leu Pro Arg Ser Phe Val Asn Cys Ser
                565                 570                 575
Ser Leu Lys Phe Leu Ser Val Ile Asn Asn Arg Ile Glu Asp Thr Phe
```

-continued

```
                580                 585                 590
Pro Phe Trp Leu Lys Ala Leu Pro Asn Leu Gln Val Leu Thr Leu Arg
            595                 600                 605

Ser Asn Arg Phe Tyr Gly Pro Ile Ser Pro His Gln Gly Pro Leu
610                 615                 620

Gly Phe Pro Glu Leu Arg Ile Phe Glu Ile Ser Asp Asn Lys Phe Thr
625                 630                 635                 640

Gly Ser Leu Pro Pro Asn Tyr Phe Val Asn Trp Lys Ala Ser Ser Arg
            645                 650                 655

Thr Met Asn Gln Asp Gly Gly Leu Tyr Met Val Tyr Glu Glu Lys Leu
            660                 665                 670

Phe Asp Glu Gly Gly Tyr Gly Tyr Thr Asp Ala Leu Asp Leu Gln Tyr
            675                 680                 685

Lys Gly Leu His Met Glu Gln Ala Lys Ala Leu Thr Ser Tyr Ala Ala
            690                 695                 700

Ile Asp Phe Ser Gly Asn Arg Leu Glu Gly Gln Ile Pro Glu Ser Ile
705                 710                 715                 720

Gly Leu Leu Lys Ala Leu Ile Ala Val Asn Ile Ser Asn Asn Ala Phe
            725                 730                 735

Thr Gly His Ile Pro Leu Ser Met Ala Asn Leu Glu Asn Leu Glu Ser
            740                 745                 750

Leu Asp Met Ser Arg Asn Gln Leu Ser Gly Thr Ile Pro Asn Gly Leu
            755                 760                 765

Gly Ser Ile Ser Phe Leu Ala Tyr Ile Asn Val Ser His Asn Gln Leu
            770                 775                 780

Thr Gly Glu Ile Pro Gln Gly Thr Gln Ile Thr Gly Gln Ser Lys Ser
785                 790                 795                 800

Ser Phe Glu Gly Asn Ala Gly Leu Cys Gly Leu Pro Leu Lys Glu Ser
            805                 810                 815

Cys Phe Gly Thr Gly Ala Pro Pro Met Tyr His Gln Lys Gln Glu Asp
            820                 825                 830

Lys Glu Glu Glu Glu Glu Glu Glu Glu Glu Glu Val Leu Asn
            835                 840                 845

Gly Arg Ala Val Ala Ile Gly Tyr Gly Ser Gly Leu Leu Gly Leu
850                 855                 860

Ala Ile Ala Gln Val Ile Ala Ser Tyr Lys Pro Glu Trp Leu Lys
865                 870                 875                 880

Ile Ile Gly Leu Asn Lys Arg Lys Arg
            885                 890
```

<210> SEQ ID NO 30
<211> LENGTH: 2655
<212> TYPE: DNA
<213> ORGANISM: Arabidopsis thaliana
<220> FEATURE:
<221> NAME/KEY: CDS
<222> LOCATION: (1)..(2655)

<400> SEQUENCE: 30

```
atg tct gaa ttg ctt ttc cgt ttg aat ttt ctc ttg cta ctc tta ctc    48
Met Ser Glu Leu Leu Phe Arg Leu Asn Phe Leu Leu Leu Leu Leu Leu
1               5                   10                  15 tct tgt gtc tcc ttg gct tca agc ttc ttc tct ttt aat gac ccg gtt    96
Ser Cys Val Ser Leu Ala Ser Ser Phe Phe Ser Phe Asn Asp Pro Val
            20                  25                  30 gtt ggt ctt ggt gct tgt ggt ccc cac cag att caa gcc ttt acg cag    144
```

| | | | | | | | | | | | | | | |
|---|---|---|---|---|---|---|---|---|---|---|---|---|---|---|
| Val | Gly | Leu | Gly | Ala | Cys | Gly | Pro | His | Gln | Ile | Gln | Ala | Phe | Thr | Gln |
| | | 35 | | | | 40 | | | | 45 | | | | |

```
ttc aaa aac gag ttt gat act cat gct tgc aac cat agt gac tcc ttg      192
Phe Lys Asn Glu Phe Asp Thr His Ala Cys Asn His Ser Asp Ser Leu
 50                  55                  60 aat ggg gtg tgg tgc gat aac tcc acg ggc gcg gtc atg aag cta cga      240
Asn Gly Val Trp Cys Asp Asn Ser Thr Gly Ala Val Met Lys Leu Arg
 65                  70                  75                  80 ctc agg gcc tgt ctc agt gga act cta aaa tct aac agt agc ctc ttc      288
Leu Arg Ala Cys Leu Ser Gly Thr Leu Lys Ser Asn Ser Ser Leu Phe
                 85                  90                  95 cag ttt cat cag ctt cgt cac ctt tat ctc tct tac aac aac ttc acc      336
Gln Phe His Gln Leu Arg His Leu Tyr Leu Ser Tyr Asn Asn Phe Thr
             100                 105                 110 ccc tct tca atc cct tcc gag ttt gga atg ctc aac aaa tta gag gtt      384
Pro Ser Ser Ile Pro Ser Glu Phe Gly Met Leu Asn Lys Leu Glu Val
             115                 120                 125 ttg ttt atg tct act ggt ggc ttc cta ggc caa gtt cct tcc tct ttt      432
Leu Phe Met Ser Thr Gly Gly Phe Leu Gly Gln Val Pro Ser Ser Phe
130                 135                 140 agt aac cta agc atg ctt tcc gct tta ctc ctc cac cat aac gag ctc      480
Ser Asn Leu Ser Met Leu Ser Ala Leu Leu Leu His His Asn Glu Leu
145                 150                 155                 160 act ggt agt tta tcg ttt gtg cgg aat tta cgc aag ctc aca att tta      528
Thr Gly Ser Leu Ser Phe Val Arg Asn Leu Arg Lys Leu Thr Ile Leu
                165                 170                 175 gat gtt tct cat aat cac ttt tct gga act ctt aat ccc aac agt agc      576
Asp Val Ser His Asn His Phe Ser Gly Thr Leu Asn Pro Asn Ser Ser
             180                 185                 190 ctc ttt gag ttg cac aac ctc gct tac ctt gat ctc ggt tct aac aac      624
Leu Phe Glu Leu His Asn Leu Ala Tyr Leu Asp Leu Gly Ser Asn Asn
             195                 200                 205 ttc acc tcc tct tca ctc cct tat gaa ttt ggt aat ctc aac aaa cta      672
Phe Thr Ser Ser Ser Leu Pro Tyr Glu Phe Gly Asn Leu Asn Lys Leu
             210                 215                 220 gag tta ttg gat gtt agc tct aat agc ttc ttc ggt caa gtt ccc ccc      720
Glu Leu Leu Asp Val Ser Ser Asn Ser Phe Phe Gly Gln Val Pro Pro
225                 230                 235                 240 aca att agt aac ctc acc cag tta acc gag ttg tac ctt ccc ttg aac      768
Thr Ile Ser Asn Leu Thr Gln Leu Thr Glu Leu Tyr Leu Pro Leu Asn
                245                 250                 255 gac ttc act ggt agt ctt ccg ctt gta caa aat cta acc aag ctc tcc      816
Asp Phe Thr Gly Ser Leu Pro Leu Val Gln Asn Leu Thr Lys Leu Ser
             260                 265                 270 att cta cat ctt tct gat aat cac ttc tct gga acc atc cct tct tct      864
Ile Leu His Leu Ser Asp Asn His Phe Ser Gly Thr Ile Pro Ser Ser
             275                 280                 285 ctc ttc act atg cct ttc tta tcc tat ctt gat tta ggt gga aac aat      912
Leu Phe Thr Met Pro Phe Leu Ser Tyr Leu Asp Leu Gly Gly Asn Asn
             290                 295                 300 ctc agt ggt tct att gaa gtt cct aac tcc tct ttg tcg tca agg cta      960
Leu Ser Gly Ser Ile Glu Val Pro Asn Ser Ser Leu Ser Ser Arg Leu
305                 310                 315                 320 gag aat ttg aac cta ggt gaa aac cat ttt gaa gga aaa atc ata gag     1008
Glu Asn Leu Asn Leu Gly Glu Asn His Phe Glu Gly Lys Ile Ile Glu
                325                 330                 335 cct atc tca aag ctt atc aac ctc aaa gag ctc cac ctt tct ttc cta     1056
Pro Ile Ser Lys Leu Ile Asn Leu Lys Glu Leu His Leu Ser Phe Leu
             340                 345                 350
```

```
aac aca agc tac cca att aat ttg aaa ctc ttc tcc tct ctc aaa tat    1104
Asn Thr Ser Tyr Pro Ile Asn Leu Lys Leu Phe Ser Ser Leu Lys Tyr
        355                 360                 365 ttg ttg ctc ctc gat ctt tcc ggt ggt tgg ata tct cag gct agt tta    1152
Leu Leu Leu Leu Asp Leu Ser Gly Gly Trp Ile Ser Gln Ala Ser Leu
    370                 375                 380 agt ttg gat tca tac att cca tcg acc ttg gaa gca tta ctc ttg aaa    1200
Ser Leu Asp Ser Tyr Ile Pro Ser Thr Leu Glu Ala Leu Leu Leu Lys
385                 390                 395                 400 cac tgc aac atc agt gtt ttc cca aac atc tta aag acc ctt ccg aat    1248
His Cys Asn Ile Ser Val Phe Pro Asn Ile Leu Lys Thr Leu Pro Asn
                405                 410                 415 ttg gag ttt att gcc tta tca acc aat aaa atc agt ggg aaa atc cca    1296
Leu Glu Phe Ile Ala Leu Ser Thr Asn Lys Ile Ser Gly Lys Ile Pro
            420                 425                 430 gag tgg tta tgg agc ctt cct cgt ctg agc tca gtt ttc att gaa gaa    1344
Glu Trp Leu Trp Ser Leu Pro Arg Leu Ser Ser Val Phe Ile Glu Glu
        435                 440                 445 aat ttg ttt act ggc ttc gaa ggt tca tca gaa att tta gta aat tca    1392
Asn Leu Phe Thr Gly Phe Glu Gly Ser Ser Glu Ile Leu Val Asn Ser
    450                 455                 460 tct gta cgg atc tta aat ttg ctg tca aac aat tta gaa gga gca ctt    1440
Ser Val Arg Ile Leu Asn Leu Leu Ser Asn Asn Leu Glu Gly Ala Leu
465                 470                 475                 480 cca cat cta ccg ctc tct gtc aac tac ttc tct gca aga aac aat aga    1488
Pro His Leu Pro Leu Ser Val Asn Tyr Phe Ser Ala Arg Asn Asn Arg
                485                 490                 495 tac gga ggc gac ata cct ctt tca atc tgc agt aga agg tca ctt gtt    1536
Tyr Gly Gly Asp Ile Pro Leu Ser Ile Cys Ser Arg Arg Ser Leu Val
            500                 505                 510 ttc ctt gat cta agc tac aac aac ttc acc ggt cca att cct cca tgt    1584
Phe Leu Asp Leu Ser Tyr Asn Asn Phe Thr Gly Pro Ile Pro Pro Cys
        515                 520                 525 cca agt aac ttc ttg att ttg aat ctc cgg aag aac aac ttg gaa gga    1632
Pro Ser Asn Phe Leu Ile Leu Asn Leu Arg Lys Asn Asn Leu Glu Gly
    530                 535                 540 agt att cca gac act tat tat gcc gat gca cct cta cgg tca ctc gac    1680
Ser Ile Pro Asp Thr Tyr Tyr Ala Asp Ala Pro Leu Arg Ser Leu Asp
545                 550                 555                 560 gtt ggc tac aat cga tta aca gga aag ctt cca agg tct ctt cta aat    1728
Val Gly Tyr Asn Arg Leu Thr Gly Lys Leu Pro Arg Ser Leu Leu Asn
                565                 570                 575 tgc tca gct cta cag ttt cta agt gtg gac cac aac gga atc aaa gat    1776
Cys Ser Ala Leu Gln Phe Leu Ser Val Asp His Asn Gly Ile Lys Asp
            580                 585                 590 aca ttt cct ttc tcc ctt aag gct tta ccg aaa ttg caa gtc ctt att    1824
Thr Phe Pro Phe Ser Leu Lys Ala Leu Pro Lys Leu Gln Val Leu Ile
        595                 600                 605 ctc cat tca aac aac ttc tat ggt cct cta tct cct cct aat caa ggc    1872
Leu His Ser Asn Asn Phe Tyr Gly Pro Leu Ser Pro Pro Asn Gln Gly
    610                 615                 620 tct ctg ggt ttt cct gag ctg cgg ata ctt gag ata gct ggt aat aaa    1920
Ser Leu Gly Phe Pro Glu Leu Arg Ile Leu Glu Ile Ala Gly Asn Lys
625                 630                 635                 640 ttc act ggt agc ttg ccc cca gat ttt ttt gag aat tgg aaa gca tca    1968
Phe Thr Gly Ser Leu Pro Pro Asp Phe Phe Glu Asn Trp Lys Ala Ser
                645                 650                 655 tca ctc acg atg aat gaa gat caa ggt cta tat atg gta tat aac aag    2016
Ser Leu Thr Met Asn Glu Asp Gln Gly Leu Tyr Met Val Tyr Asn Lys
            660                 665                 670
```

```
gtt gtt tac ggg acc tat tac ttc acc tct ctg gaa gct ata gat tta      2064
Val Val Tyr Gly Thr Tyr Tyr Phe Thr Ser Leu Glu Ala Ile Asp Leu
            675                 680                 685 caa tat aaa ggt ctg tct atg gag caa aat agg gtc ctt agt tcc tca      2112
Gln Tyr Lys Gly Leu Ser Met Glu Gln Asn Arg Val Leu Ser Ser Ser
    690                 695                 700 gcg acc att gat ttt tct gga aat aga ctt gaa gga gaa att cct gaa      2160
Ala Thr Ile Asp Phe Ser Gly Asn Arg Leu Glu Gly Glu Ile Pro Glu
705                 710                 715                 720 tct att ggt ctc tta aag gca ctg atc gca ctc aac tta tcg aac aac      2208
Ser Ile Gly Leu Leu Lys Ala Leu Ile Ala Leu Asn Leu Ser Asn Asn
                725                 730                 735 gcc ttc aca ggc cat att cct ctg tct ttg gcc aat ctt aag aag atc      2256
Ala Phe Thr Gly His Ile Pro Leu Ser Leu Ala Asn Leu Lys Lys Ile
            740                 745                 750 gag tca cta gac cta tca agt aac caa ctc tca ggg aca att cct aat      2304
Glu Ser Leu Asp Leu Ser Ser Asn Gln Leu Ser Gly Thr Ile Pro Asn
        755                 760                 765 gga ata ggg act ctc tcg ttt ttg gca tac atg aac gtg tct cac aac      2352
Gly Ile Gly Thr Leu Ser Phe Leu Ala Tyr Met Asn Val Ser His Asn
    770                 775                 780 caa ctc aac ggt gaa ata cca caa gga aca cag ata act ggg caa cct      2400
Gln Leu Asn Gly Glu Ile Pro Gln Gly Thr Gln Ile Thr Gly Gln Pro
785                 790                 795                 800 aaa tcg tca ttt gaa gga aat gca ggg ctt tgt ggt ttg cct ctt caa      2448
Lys Ser Ser Phe Glu Gly Asn Ala Gly Leu Cys Gly Leu Pro Leu Gln
                805                 810                 815 gaa agt tgc ttt ggg act aac gca cca cca gca caa cat cct aaa gaa      2496
Glu Ser Cys Phe Gly Thr Asn Ala Pro Pro Ala Gln His Pro Lys Glu
            820                 825                 830 gaa gaa gaa gag gaa gaa gaa gag gaa caa gtg ttg aat tgg aaa ggc      2544
Glu Glu Glu Glu Glu Glu Glu Glu Glu Gln Val Leu Asn Trp Lys Gly
        835                 840                 845 gtg gga ata ggg tat ggg gtt ggt gtg tta ctt gga ttg gca ata gca      2592
Val Gly Ile Gly Tyr Gly Val Gly Val Leu Leu Gly Leu Ala Ile Ala
    850                 855                 860 caa ctc att gct tca tac aaa ccg gag tgg cta gtt ttt ctg ttt cag      2640
Gln Leu Ile Ala Ser Tyr Lys Pro Glu Trp Leu Val Phe Leu Phe Gln
865                 870                 875                 880 agc aga aac cat taa                                                   2655
Ser Arg Asn His <210> SEQ ID NO 31
<211> LENGTH: 884
<212> TYPE: PRT
<213> ORGANISM: Arabidopsis thaliana

<400> SEQUENCE: 31

Met Ser Glu Leu Leu Phe Arg Leu Asn Phe Leu Leu Leu Leu Leu
1               5                   10                  15

Ser Cys Val Ser Leu Ala Ser Ser Phe Phe Ser Phe Asn Asp Pro Val
                20                  25                  30

Val Gly Leu Gly Ala Cys Gly Pro His Gln Ile Gln Ala Phe Thr Gln
            35                  40                  45

Phe Lys Asn Glu Phe Asp Thr His Ala Cys Asn His Ser Asp Ser Leu
    50                  55                  60

Asn Gly Val Trp Cys Asp Asn Ser Thr Gly Ala Val Met Lys Leu Arg
65                  70                  75                  80
```

```
Leu Arg Ala Cys Leu Ser Gly Thr Leu Lys Ser Asn Ser Ser Leu Phe
                85                  90                  95

Gln Phe His Gln Leu Arg His Leu Tyr Leu Ser Tyr Asn Asn Phe Thr
            100                 105                 110

Pro Ser Ser Ile Pro Ser Glu Phe Gly Met Leu Asn Lys Leu Glu Val
        115                 120                 125

Leu Phe Met Ser Thr Gly Gly Phe Leu Gly Gln Val Pro Ser Ser Phe
    130                 135                 140

Ser Asn Leu Ser Met Leu Ser Ala Leu Leu His His Asn Glu Leu
145                 150                 155                 160

Thr Gly Ser Leu Ser Phe Val Arg Asn Leu Arg Lys Leu Thr Ile Leu
                165                 170                 175

Asp Val Ser His Asn His Phe Ser Gly Thr Leu Asn Pro Asn Ser Ser
            180                 185                 190

Leu Phe Glu Leu His Asn Leu Ala Tyr Leu Asp Leu Gly Ser Asn Asn
        195                 200                 205

Phe Thr Ser Ser Ser Leu Pro Tyr Glu Phe Gly Asn Leu Asn Lys Leu
    210                 215                 220

Glu Leu Leu Asp Val Ser Ser Asn Ser Phe Phe Gly Gln Val Pro Pro
225                 230                 235                 240

Thr Ile Ser Asn Leu Thr Gln Leu Thr Glu Leu Tyr Leu Pro Leu Asn
                245                 250                 255

Asp Phe Thr Gly Ser Leu Pro Leu Val Gln Asn Leu Thr Lys Leu Ser
            260                 265                 270

Ile Leu His Leu Ser Asp Asn His Phe Ser Gly Thr Ile Pro Ser Ser
        275                 280                 285

Leu Phe Thr Met Pro Phe Leu Ser Tyr Leu Asp Leu Gly Gly Asn Asn
    290                 295                 300

Leu Ser Gly Ser Ile Glu Val Pro Asn Ser Ser Leu Ser Ser Arg Leu
305                 310                 315                 320

Glu Asn Leu Asn Leu Gly Glu Asn His Phe Glu Gly Lys Ile Ile Glu
                325                 330                 335

Pro Ile Ser Lys Leu Ile Asn Leu Lys Glu Leu His Leu Ser Phe Leu
            340                 345                 350

Asn Thr Ser Tyr Pro Ile Asn Leu Lys Leu Phe Ser Ser Leu Lys Tyr
        355                 360                 365

Leu Leu Leu Leu Asp Leu Ser Gly Gly Trp Ile Ser Gln Ala Ser Leu
    370                 375                 380

Ser Leu Asp Ser Tyr Ile Pro Ser Thr Leu Glu Ala Leu Leu Leu Lys
385                 390                 395                 400

His Cys Asn Ile Ser Val Phe Pro Asn Ile Leu Lys Thr Leu Pro Asn
                405                 410                 415

Leu Glu Phe Ile Ala Leu Ser Thr Asn Lys Ile Ser Gly Lys Ile Pro
            420                 425                 430

Glu Trp Leu Trp Ser Leu Pro Arg Leu Ser Ser Val Phe Ile Glu Glu
        435                 440                 445

Asn Leu Phe Thr Gly Phe Glu Gly Ser Ser Glu Ile Leu Val Asn Ser
    450                 455                 460

Ser Val Arg Ile Leu Asn Leu Leu Ser Asn Asn Leu Glu Gly Ala Leu
465                 470                 475                 480

Pro His Leu Pro Leu Ser Val Asn Tyr Phe Ser Ala Arg Asn Asn Arg
                485                 490                 495

Tyr Gly Gly Asp Ile Pro Leu Ser Ile Cys Ser Arg Arg Ser Leu Val
```

```
                500             505             510
    Phe Leu Asp Leu Ser Tyr Asn Asn Phe Thr Gly Pro Ile Pro Pro Cys
                    515             520             525
    Pro Ser Asn Phe Leu Ile Leu Asn Leu Arg Lys Asn Leu Glu Gly
            530             535             540
    Ser Ile Pro Asp Thr Tyr Tyr Ala Asp Ala Pro Leu Arg Ser Leu Asp
    545             550             555             560
    Val Gly Tyr Asn Arg Leu Thr Gly Lys Leu Pro Arg Ser Leu Leu Asn
                    565             570             575
    Cys Ser Ala Leu Gln Phe Leu Ser Val Asp His Asn Gly Ile Lys Asp
            580             585             590
    Thr Phe Pro Phe Ser Leu Lys Ala Leu Pro Lys Leu Gln Val Leu Ile
            595             600             605
    Leu His Ser Asn Asn Phe Tyr Gly Pro Leu Ser Pro Asn Gln Gly
            610             615             620
    Ser Leu Gly Phe Pro Glu Leu Arg Ile Leu Glu Ile Ala Gly Asn Lys
    625             630             635             640
    Phe Thr Gly Ser Leu Pro Pro Asp Phe Phe Glu Asn Trp Lys Ala Ser
                    645             650             655
    Ser Leu Thr Met Asn Glu Asp Gln Gly Leu Tyr Met Val Tyr Asn Lys
                    660             665             670
    Val Val Tyr Gly Thr Tyr Tyr Phe Thr Ser Leu Glu Ala Ile Asp Leu
            675             680             685
    Gln Tyr Lys Gly Leu Ser Met Glu Gln Asn Arg Val Leu Ser Ser Ser
            690             695             700
    Ala Thr Ile Asp Phe Ser Gly Asn Arg Leu Glu Gly Glu Ile Pro Glu
    705             710             715             720
    Ser Ile Gly Leu Leu Lys Ala Leu Ile Ala Leu Asn Leu Ser Asn Asn
                    725             730             735
    Ala Phe Thr Gly His Ile Pro Leu Ser Leu Ala Asn Leu Lys Lys Ile
                    740             745             750
    Glu Ser Leu Asp Leu Ser Ser Asn Gln Leu Ser Gly Thr Ile Pro Asn
            755             760             765
    Gly Ile Gly Thr Leu Ser Phe Leu Ala Tyr Met Asn Val Ser His Asn
            770             775             780
    Gln Leu Asn Gly Glu Ile Pro Gln Gly Thr Gln Ile Thr Gly Gln Pro
    785             790             795             800
    Lys Ser Ser Phe Glu Gly Asn Ala Gly Leu Cys Gly Leu Pro Leu Gln
                    805             810             815
    Glu Ser Cys Phe Gly Thr Asn Ala Pro Pro Ala Gln His Pro Lys Glu
                    820             825             830
    Glu Glu Glu Glu Glu Glu Glu Gln Val Leu Asn Trp Lys Gly
            835             840             845
    Val Gly Ile Gly Tyr Gly Val Gly Val Leu Gly Leu Ala Ile Ala
            850             855             860
    Gln Leu Ile Ala Ser Tyr Lys Pro Glu Trp Leu Val Phe Leu Phe Gln
    865             870             875             880
    Ser Arg Asn His

<210> SEQ ID NO 32
<211> LENGTH: 2673
<212> TYPE: DNA
<213> ORGANISM: Arabidopsis thaliana
<220> FEATURE:
```

<221> NAME/KEY: CDS
<222> LOCATION: (1)..(2673)

<400> SEQUENCE: 32

```
atg tct aaa tcg ctt ttg cgt ttg acg ttt ctc ttg cta ctc tta ctc      48
Met Ser Lys Ser Leu Leu Arg Leu Thr Phe Leu Leu Leu Leu Leu Leu
1               5                   10                  15 tct tgt gtc tcc cct tca agc ttc ttc act ttt aat aac cct gct gaa      96
Ser Cys Val Ser Pro Ser Ser Phe Phe Thr Phe Asn Asn Pro Ala Glu
            20                  25                  30 ggt cct ggt gct tgt ggt ccc cac cag att caa gcc ttt acg cag ttc     144
Gly Pro Gly Ala Cys Gly Pro His Gln Ile Gln Ala Phe Thr Gln Phe
        35                  40                  45 aag aac gag ttt gat act cgt gct tgc aac cat agt gac cct tgg aat     192
Lys Asn Glu Phe Asp Thr Arg Ala Cys Asn His Ser Asp Pro Trp Asn
50                  55                  60 gga gtg tgg tgc gat aac tcc acg ggt gcg gtc acg atg cta caa ctc     240
Gly Val Trp Cys Asp Asn Ser Thr Gly Ala Val Thr Met Leu Gln Leu
65                  70                  75                  80 agg gca tgt ctt agc gga act ctg aaa cct aac agt agc ctt ttc cag     288
Arg Ala Cys Leu Ser Gly Thr Leu Lys Pro Asn Ser Ser Leu Phe Gln
                85                  90                  95 ttt cat cat ctc cgt tcc ctt ctt ctc cct cat aac aac ttc acc tcc     336
Phe His His Leu Arg Ser Leu Leu Leu Pro His Asn Asn Phe Thr Ser
            100                 105                 110 tct tca att tct tcc aag ttt gga atg ctc aac aac tta gag gta ttg     384
Ser Ser Ile Ser Ser Lys Phe Gly Met Leu Asn Asn Leu Glu Val Leu
        115                 120                 125 tct ctt tca agt agt ggc ttc ctc gcc caa gtt cct ttt tca ttt agt     432
Ser Leu Ser Ser Ser Gly Phe Leu Ala Gln Val Pro Phe Ser Phe Ser
    130                 135                 140 aac cta agc atg ctt tcc gct tta gac ctt tcc aaa aac gag ctc act     480
Asn Leu Ser Met Leu Ser Ala Leu Asp Leu Ser Lys Asn Glu Leu Thr
145                 150                 155                 160 ggt agt tta tca ttt gtg cgg aat cta cgc aag ctc aga gtt tta gat     528
Gly Ser Leu Ser Phe Val Arg Asn Leu Arg Lys Leu Arg Val Leu Asp
                165                 170                 175 gtt tct tat aat cac ttc tct gga att ttg aat ccc aat agt agc ctc     576
Val Ser Tyr Asn His Phe Ser Gly Ile Leu Asn Pro Asn Ser Ser Leu
            180                 185                 190 ttt gag ttg cac cac ctc att tac ctt aat ctc cgt tac aac aac ttc     624
Phe Glu Leu His His Leu Ile Tyr Leu Asn Leu Arg Tyr Asn Asn Phe
        195                 200                 205 acc tcc tct tca ctc cct tat gaa ttt ggc aat ctc aac aaa cta gag     672
Thr Ser Ser Ser Leu Pro Tyr Glu Phe Gly Asn Leu Asn Lys Leu Glu
    210                 215                 220 gtc ttg gat gtt tcc tct aat agc ttc ttc ggt caa gtt cct ccc act     720
Val Leu Asp Val Ser Ser Asn Ser Phe Phe Gly Gln Val Pro Pro Thr
225                 230                 235                 240 att agt aac cta acc cag tta acc gag ttg tac ctt ccc ttg aac gac     768
Ile Ser Asn Leu Thr Gln Leu Thr Glu Leu Tyr Leu Pro Leu Asn Asp
                245                 250                 255 ttc act ggt agt ctt ccg ctt gta caa aat cta acc aag ctc tcc att     816
Phe Thr Gly Ser Leu Pro Leu Val Gln Asn Leu Thr Lys Leu Ser Ile
            260                 265                 270 cta cat ctt ttt ggt aat cac ttc tct gga aca atc cct tct tct ctc     864
Leu His Leu Phe Gly Asn His Phe Ser Gly Thr Ile Pro Ser Ser Leu
        275                 280                 285 ttc act atg cct ttc tta tca tca att tat tta aat aaa aac aat ctc     912
Phe Thr Met Pro Phe Leu Ser Ser Ile Tyr Leu Asn Lys Asn Asn Leu
```

```
            290                 295                 300
agt ggt tct att gaa gtt cct aac tcc tct tcc tca tca agg cta gag      960
Ser Gly Ser Ile Glu Val Pro Asn Ser Ser Ser Ser Ser Arg Leu Glu
305                 310                 315                 320 cat ttg tac cta ggg aaa aac cat tta gga aaa atc cta gag cct atc     1008
His Leu Tyr Leu Gly Lys Asn His Leu Gly Lys Ile Leu Glu Pro Ile
                325                 330                 335 gca aag ctt gtt aac ctt aaa gag ctc gac ctt tct ttc cta aac aca     1056
Ala Lys Leu Val Asn Leu Lys Glu Leu Asp Leu Ser Phe Leu Asn Thr
            340                 345                 350 agc cac cca att gac tta agt ctc ttc tcc tct ctc aaa tct ttg ttg     1104
Ser His Pro Ile Asp Leu Ser Leu Phe Ser Ser Leu Lys Ser Leu Leu
        355                 360                 365 ctc ctc gat ctt tcc ggt gat tgg ata tca aag gct agt tta act ttg     1152
Leu Leu Asp Leu Ser Gly Asp Trp Ile Ser Lys Ala Ser Leu Thr Leu
370                 375                 380 gat tca tac att cca tct acc ctg gaa gtg ttg cgt ttg gag cat tgc     1200
Asp Ser Tyr Ile Pro Ser Thr Leu Glu Val Leu Arg Leu Glu His Cys
385                 390                 395                 400 gac atc agt gag ttc cca aac gtc ttc aag acc ctt cat aat ttg gag     1248
Asp Ile Ser Glu Phe Pro Asn Val Phe Lys Thr Leu His Asn Leu Glu
                405                 410                 415 tat att gcc tta tcc aac aat aga atc agt gga aaa ttt cca gag tgg     1296
Tyr Ile Ala Leu Ser Asn Asn Arg Ile Ser Gly Lys Phe Pro Glu Trp
            420                 425                 430 tta tgg agc ctt cct cga ctg agc tca gtg ttc att aca gat aat ttg     1344
Leu Trp Ser Leu Pro Arg Leu Ser Ser Val Phe Ile Thr Asp Asn Leu
        435                 440                 445 tta act ggc ttt gaa ggg tca tca gaa gtt tta gta aat tca tca gtg     1392
Leu Thr Gly Phe Glu Gly Ser Ser Glu Val Leu Val Asn Ser Ser Val
450                 455                 460 cag atc tta agt ttg gat aca aac agt tta gaa ggg gca ctc ccg cat     1440
Gln Ile Leu Ser Leu Asp Thr Asn Ser Leu Glu Gly Ala Leu Pro His
465                 470                 475                 480 cta ccg ctc tct atc aac tat ttc tct gca ata gac aat aga ttc gga     1488
Leu Pro Leu Ser Ile Asn Tyr Phe Ser Ala Ile Asp Asn Arg Phe Gly
                485                 490                 495 ggc gac ata cct ctt tca atc tgt aat aga agc tcg ctt gat gtc ctt     1536
Gly Asp Ile Pro Leu Ser Ile Cys Asn Arg Ser Ser Leu Asp Val Leu
            500                 505                 510 gat cta agc tac aac aac ttc agc gga caa att cct cca tgt ctg agt     1584
Asp Leu Ser Tyr Asn Asn Phe Ser Gly Gln Ile Pro Pro Cys Leu Ser
        515                 520                 525 aac tta ttg tat ttg aaa ctc cga aag aac aac ttg gaa gga agt att     1632
Asn Leu Leu Tyr Leu Lys Leu Arg Lys Asn Asn Leu Glu Gly Ser Ile
530                 535                 540 cct gac aag tat tat gtg gat acg cct cta cga tca ttc gac gtt ggt     1680
Pro Asp Lys Tyr Tyr Val Asp Thr Pro Leu Arg Ser Phe Asp Val Gly
545                 550                 555                 560 tac aat cga tta aca ggg aag ctc cca agg tct ctt ata aat tgc tca     1728
Tyr Asn Arg Leu Thr Gly Lys Leu Pro Arg Ser Leu Ile Asn Cys Ser
                565                 570                 575 gct cta cag ttt cta agt gtg gac cac aac gga atc aaa gat aca ttt     1776
Ala Leu Gln Phe Leu Ser Val Asp His Asn Gly Ile Lys Asp Thr Phe
            580                 585                 590 cct ttt tac ctt aag gct tta ccg aaa ttg caa gtc ctt ctc ctc agt     1824
Pro Phe Tyr Leu Lys Ala Leu Pro Lys Leu Gln Val Leu Leu Leu Ser
        595                 600                 605 tca aac gaa ttc tat ggt cct cta tct cct cct aat caa ggt cct ctg     1872
```

-continued

| | | |
|---|---|---|
| Ser Asn Glu Phe Tyr Gly Pro Leu Ser Pro Pro Asn Gln Gly Pro Leu<br>610 615 620 | | |
| ggt ttt cct gag ctg cgg ata ctg gag ata gct ggt aat aaa cta acc<br>Gly Phe Pro Glu Leu Arg Ile Leu Glu Ile Ala Gly Asn Lys Leu Thr<br>625 630 635 640 | 1920 | |
| gga agc ttg ccc cca gat ttt ttt gtg aat tgg aaa gca tca tca cac<br>Gly Ser Leu Pro Pro Asp Phe Phe Val Asn Trp Lys Ala Ser Ser His<br>645 650 655 | 1968 | |
| aca atg aat gaa gat ctg ggt cta tat atg gta tat agc aag gtt att<br>Thr Met Asn Glu Asp Leu Gly Leu Tyr Met Val Tyr Ser Lys Val Ile<br>660 665 670 | 2016 | |
| ttc ggg aac tat cac ctc acc tat tat gaa act ata gat tta cga tat<br>Phe Gly Asn Tyr His Leu Thr Tyr Tyr Glu Thr Ile Asp Leu Arg Tyr<br>675 680 685 | 2064 | |
| aaa ggt cta tct atg gag cag gag aac gtc ctt act tcc tca gcc acc<br>Lys Gly Leu Ser Met Glu Gln Glu Asn Val Leu Thr Ser Ser Ala Thr<br>690 695 700 | 2112 | |
| att gat ctt tct gga aac aga ctt gaa gga gaa att cct gaa tct ctc<br>Ile Asp Leu Ser Gly Asn Arg Leu Glu Gly Glu Ile Pro Glu Ser Leu<br>705 710 715 720 | 2160 | |
| ggt ctc tta aag gca ttg atc gca ctc aac tta tcg aac aac gcc ttc<br>Gly Leu Leu Lys Ala Leu Ile Ala Leu Asn Leu Ser Asn Asn Ala Phe<br>725 730 735 | 2208 | |
| aca ggc cat att cct ctg tct ttg gct aat ctt aag aag atc gag tca<br>Thr Gly His Ile Pro Leu Ser Leu Ala Asn Leu Lys Lys Ile Glu Ser<br>740 745 750 | 2256 | |
| cta gac cta tca agt aac caa ctc tca ggg aca att cct aat gga cta<br>Leu Asp Leu Ser Ser Asn Gln Leu Ser Gly Thr Ile Pro Asn Gly Leu<br>755 760 765 | 2304 | |
| ggg act ctc tcg ttt ttg gcg tac atg aac gtg tct cac aac caa ctc<br>Gly Thr Leu Ser Phe Leu Ala Tyr Met Asn Val Ser His Asn Gln Leu<br>770 775 780 | 2352 | |
| aac ggt gaa ata cca caa gga aca caa ata act ggg caa cct aaa tcg<br>Asn Gly Glu Ile Pro Gln Gly Thr Gln Ile Thr Gly Gln Pro Lys Ser<br>785 790 795 800 | 2400 | |
| tcc ttc gaa gga aat gca ggg ctt tgt ggt ttt cct ctt caa gaa agt<br>Ser Phe Glu Gly Asn Ala Gly Leu Cys Gly Phe Pro Leu Gln Glu Ser<br>805 810 815 | 2448 | |
| tgc ttt ggg act aac gcg cca cca gca cag aag cct aaa gaa gaa gaa<br>Cys Phe Gly Thr Asn Ala Pro Pro Ala Gln Lys Pro Lys Glu Glu Glu<br>820 825 830 | 2496 | |
| gaa gcg gaa gaa gat gag caa gag tta aac tgg aaa gca gtg gca ata<br>Glu Ala Glu Glu Asp Glu Gln Glu Leu Asn Trp Lys Ala Val Ala Ile<br>835 840 845 | 2544 | |
| ggg tat ggg gtt gga gtg tta ctt gga ttg gcg ata gca caa ctc att<br>Gly Tyr Gly Val Gly Val Leu Leu Gly Leu Ala Ile Ala Gln Leu Ile<br>850 855 860 | 2592 | |
| gct tca tac aaa cca gag tgg cta gtt tgt ctg gtt aaa agc aga aac<br>Ala Ser Tyr Lys Pro Glu Trp Leu Val Cys Leu Val Lys Ser Arg Asn<br>865 870 875 880 | 2640 | |
| ccg tta cga tct ttt ttt ggt ttt gag tat taa<br>Pro Leu Arg Ser Phe Phe Gly Phe Glu Tyr<br>885 890 | 2673 | |

<210> SEQ ID NO 33
<211> LENGTH: 890
<212> TYPE: PRT
<213> ORGANISM: Arabidopsis thaliana

<400> SEQUENCE: 33

```
Met Ser Lys Ser Leu Arg Leu Thr Phe Leu Leu Leu Leu Leu
1               5                   10                  15
Ser Cys Val Ser Pro Ser Ser Phe Phe Thr Phe Asn Asn Pro Ala Glu
            20              25                  30
Gly Pro Gly Ala Cys Gly Pro His Gln Ile Gln Ala Phe Thr Gln Phe
            35              40                  45
Lys Asn Glu Phe Asp Thr Arg Ala Cys Asn His Ser Asp Pro Trp Asn
50                      55                  60
Gly Val Trp Cys Asp Asn Ser Thr Gly Ala Val Thr Met Leu Gln Leu
65                      70                  75                  80
Arg Ala Cys Leu Ser Gly Thr Leu Lys Pro Asn Ser Ser Leu Phe Gln
            85                  90                  95
Phe His His Leu Arg Ser Leu Leu Pro His Asn Asn Phe Thr Ser
                100                 105                 110
Ser Ser Ile Ser Ser Lys Phe Gly Met Leu Asn Asn Leu Glu Val Leu
            115                 120                 125
Ser Leu Ser Ser Ser Gly Phe Leu Ala Gln Val Pro Phe Ser Phe Ser
        130                 135                 140
Asn Leu Ser Met Leu Ser Ala Leu Asp Leu Ser Lys Asn Glu Leu Thr
145                 150                 155                 160
Gly Ser Leu Ser Phe Val Arg Asn Leu Arg Lys Leu Arg Val Leu Asp
                165                 170                 175
Val Ser Tyr Asn His Phe Ser Gly Ile Leu Asn Pro Asn Ser Ser Leu
            180                 185                 190
Phe Glu Leu His His Leu Ile Tyr Leu Asn Leu Arg Tyr Asn Asn Phe
        195                 200                 205
Thr Ser Ser Ser Leu Pro Tyr Glu Phe Gly Asn Leu Asn Lys Leu Glu
    210                 215                 220
Val Leu Asp Val Ser Ser Asn Ser Phe Phe Gly Gln Val Pro Pro Thr
225                 230                 235                 240
Ile Ser Asn Leu Thr Gln Leu Thr Glu Leu Tyr Leu Pro Leu Asn Asp
                245                 250                 255
Phe Thr Gly Ser Leu Pro Leu Val Gln Asn Leu Thr Lys Leu Ser Ile
            260                 265                 270
Leu His Leu Phe Gly Asn His Phe Ser Gly Thr Ile Pro Ser Ser Leu
        275                 280                 285
Phe Thr Met Pro Phe Leu Ser Ser Ile Tyr Leu Asn Lys Asn Asn Leu
    290                 295                 300
Ser Gly Ser Ile Glu Val Pro Asn Ser Ser Ser Ser Arg Leu Glu
305                 310                 315                 320
His Leu Tyr Leu Gly Lys Asn His Leu Gly Lys Ile Leu Glu Pro Ile
                325                 330                 335
Ala Lys Leu Val Asn Leu Lys Glu Leu Asp Leu Ser Phe Leu Asn Thr
            340                 345                 350
Ser His Pro Ile Asp Leu Ser Leu Phe Ser Ser Leu Lys Ser Leu Leu
        355                 360                 365
Leu Leu Asp Leu Ser Gly Asp Trp Ile Ser Lys Ala Ser Leu Thr Leu
    370                 375                 380
Asp Ser Tyr Ile Pro Ser Thr Leu Glu Val Leu Arg Leu Glu His Cys
385                 390                 395                 400
Asp Ile Ser Glu Phe Pro Asn Val Phe Lys Thr Leu His Asn Leu Glu
                405                 410                 415
Tyr Ile Ala Leu Ser Asn Asn Arg Ile Ser Gly Lys Phe Pro Glu Trp
```

```
                420             425             430
Leu Trp Ser Leu Pro Arg Leu Ser Ser Val Phe Ile Thr Asp Asn Leu
            435             440             445

Leu Thr Gly Phe Glu Gly Ser Ser Glu Val Leu Val Asn Ser Ser Val
450             455             460

Gln Ile Leu Ser Leu Asp Thr Asn Ser Leu Glu Gly Ala Leu Pro His
465             470             475             480

Leu Pro Leu Ser Ile Asn Tyr Phe Ser Ala Ile Asp Asn Arg Phe Gly
            485             490             495

Gly Asp Ile Pro Leu Ser Ile Cys Asn Arg Ser Ser Leu Asp Val Leu
            500             505             510

Asp Leu Ser Tyr Asn Asn Phe Ser Gly Gln Ile Pro Pro Cys Leu Ser
            515             520             525

Asn Leu Leu Tyr Leu Lys Leu Arg Lys Asn Asn Leu Glu Gly Ser Ile
            530             535             540

Pro Asp Lys Tyr Tyr Val Asp Thr Pro Leu Arg Ser Phe Asp Val Gly
545             550             555             560

Tyr Asn Arg Leu Thr Gly Lys Leu Pro Arg Ser Leu Ile Asn Cys Ser
                565             570             575

Ala Leu Gln Phe Leu Ser Val Asp His Asn Gly Ile Lys Asp Thr Phe
            580             585             590

Pro Phe Tyr Leu Lys Ala Leu Pro Lys Leu Gln Val Leu Leu Leu Ser
            595             600             605

Ser Asn Glu Phe Tyr Gly Pro Leu Ser Pro Asn Gln Gly Pro Leu
610             615             620

Gly Phe Pro Glu Leu Arg Ile Leu Glu Ile Ala Gly Asn Lys Leu Thr
625             630             635             640

Gly Ser Leu Pro Pro Asp Phe Phe Val Asn Trp Lys Ala Ser Ser His
                645             650             655

Thr Met Asn Glu Asp Leu Gly Leu Tyr Met Val Tyr Ser Lys Val Ile
            660             665             670

Phe Gly Asn Tyr His Leu Thr Tyr Tyr Glu Thr Ile Asp Leu Arg Tyr
            675             680             685

Lys Gly Leu Ser Met Glu Gln Glu Asn Val Leu Thr Ser Ser Ala Thr
            690             695             700

Ile Asp Leu Ser Gly Asn Arg Leu Glu Gly Glu Ile Pro Glu Ser Leu
705             710             715             720

Gly Leu Leu Lys Ala Leu Ile Ala Leu Asn Leu Ser Asn Asn Ala Phe
                725             730             735

Thr Gly His Ile Pro Leu Ser Leu Ala Asn Leu Lys Lys Ile Glu Ser
            740             745             750

Leu Asp Leu Ser Ser Asn Gln Leu Ser Gly Thr Ile Pro Asn Gly Leu
            755             760             765

Gly Thr Leu Ser Phe Leu Ala Tyr Met Asn Val Ser His Asn Gln Leu
            770             775             780

Asn Gly Glu Ile Pro Gln Gly Thr Gln Ile Thr Gly Gln Pro Lys Ser
785             790             795             800

Ser Phe Glu Gly Asn Ala Gly Leu Cys Gly Phe Pro Leu Gln Glu Ser
                805             810             815

Cys Phe Gly Thr Asn Ala Pro Pro Ala Gln Lys Pro Lys Glu Glu Glu
            820             825             830

Glu Ala Glu Glu Asp Glu Gln Glu Leu Asn Trp Lys Ala Val Ala Ile
            835             840             845
```

-continued

| | | | | | | | | | | | | |
|---|---|---|---|---|---|---|---|---|---|---|---|---|
|Gly|Tyr|Gly|Val|Gly|Val|Leu|Leu|Gly|Leu|Ala|Ile|Ala|Gln|Leu|Ile|
| |850| | | |855| | | |860| | | | | | |

| | | | | | | | | | | | | | | | |
|---|---|---|---|---|---|---|---|---|---|---|---|---|---|---|---|
|Ala|Ser|Tyr|Lys|Pro|Glu|Trp|Leu|Val|Cys|Leu|Val|Lys|Ser|Arg|Asn|
|865| | | | |870| | | |875| | | | |880| |

| | | | | | | | | |
|---|---|---|---|---|---|---|---|---|
|Pro|Leu|Arg|Ser|Phe|Phe|Gly|Phe|Glu|Tyr|
| | | | |885| | | | |890|

<210> SEQ ID NO 34
<211> LENGTH: 2646
<212> TYPE: DNA
<213> ORGANISM: Arabidopsis thaliana
<220> FEATURE:
<221> NAME/KEY: CDS
<222> LOCATION: (1)..(2646)

<400> SEQUENCE: 34

| | | | | | | | | | | | | | | | | |
|---|---|---|---|---|---|---|---|---|---|---|---|---|---|---|---|---|
|atg|tct|gaa|ttg|ctt|ctc|cgt|ttg|aat|ttt|ctc|ttg|ctc|ctc|tta|ctc|48|
|Met|Ser|Glu|Leu|Leu|Leu|Arg|Leu|Asn|Phe|Leu|Leu|Leu|Leu|Leu|Leu| |
|1| | | |5| | | | |10| | | | |15| | |

| | | | | | | | | | | | | | | | | |
|---|---|---|---|---|---|---|---|---|---|---|---|---|---|---|---|---|
|tct|tgt|gtc|tcc|cct|tca|agc|ttc|gtc|act|ttt|aat|aac|cct|gtt|gtt|96|
|Ser|Cys|Val|Ser|Pro|Ser|Ser|Phe|Val|Thr|Phe|Asn|Asn|Pro|Val|Val| |
| | | | |20| | | | |25| | | | |30| | |

| | | | | | | | | | | | | | | | | |
|---|---|---|---|---|---|---|---|---|---|---|---|---|---|---|---|---|
|ggt|ctt|ggt|gct|tgt|ggt|ccc|cac|cag|att|caa|gcg|ttt|acg|cag|ttc|144|
|Gly|Leu|Gly|Ala|Cys|Gly|Pro|His|Gln|Ile|Gln|Ala|Phe|Thr|Gln|Phe| |
| | |35| | | | |40| | | | |45| | | | |

| | | | | | | | | | | | | | | | | |
|---|---|---|---|---|---|---|---|---|---|---|---|---|---|---|---|---|
|aag|aac|gag|ttt|aat|act|cgt|gct|tgc|aac|cat|agt|tcc|cct|tgg|aat|192|
|Lys|Asn|Glu|Phe|Asn|Thr|Arg|Ala|Cys|Asn|His|Ser|Ser|Pro|Trp|Asn| |
|50| | | | |55| | | | |60| | | | | | |

| | | | | | | | | | | | | | | | | |
|---|---|---|---|---|---|---|---|---|---|---|---|---|---|---|---|---|
|gga|gtg|tgg|tgc|gat|aac|tct|acg|ggc|gca|gtc|acg|aag|ata|caa|ttc|240|
|Gly|Val|Trp|Cys|Asp|Asn|Ser|Thr|Gly|Ala|Val|Thr|Lys|Ile|Gln|Phe| |
|65| | | | |70| | | | |75| | | | |80| |

| | | | | | | | | | | | | | | | | |
|---|---|---|---|---|---|---|---|---|---|---|---|---|---|---|---|---|
|atg|gcc|tgt|ctc|agt|gga|act|ctg|aaa|tcc|aac|agt|agt|ctt|ttc|cag|288|
|Met|Ala|Cys|Leu|Ser|Gly|Thr|Leu|Lys|Ser|Asn|Ser|Ser|Leu|Phe|Gln| |
| | | | |85| | | | |90| | | | |95| | |

| | | | | | | | | | | | | | | | | |
|---|---|---|---|---|---|---|---|---|---|---|---|---|---|---|---|---|
|ttt|cat|gag|ctt|cgt|tcc|ctt|ctc|atc|cat|aac|aac|ttc|acc|tcc| |336|
|Phe|His|Glu|Leu|Arg|Ser|Leu|Leu|Ile|His|Asn|Asn|Phe|Thr|Ser| | |
| | | |100| | | | |105| | | | |110| | | |

| | | | | | | | | | | | | | | | | |
|---|---|---|---|---|---|---|---|---|---|---|---|---|---|---|---|---|
|tct|tca|att|tct|tcc|aag|ttt|gga|atg|ctc|aac|aaa|tta|gag|gta|ttg|384|
|Ser|Ser|Ile|Ser|Ser|Lys|Phe|Gly|Met|Leu|Asn|Lys|Leu|Glu|Val|Leu| |
| | |115| | | | |120| | | | |125| | | | |

| | | | | | | | | | | | | | | | | |
|---|---|---|---|---|---|---|---|---|---|---|---|---|---|---|---|---|
|ttt|ctt|tca|agt|agt|ggc|ttc|ctc|ggc|caa|gtt|cct|ttt|tca|ttc|agt|432|
|Phe|Leu|Ser|Ser|Ser|Gly|Phe|Leu|Gly|Gln|Val|Pro|Phe|Ser|Phe|Ser| |
| |130| | | | |135| | | | |140| | | | | |

| | | | | | | | | | | | | | | | | |
|---|---|---|---|---|---|---|---|---|---|---|---|---|---|---|---|---|
|aac|cta|agc|atg|ctt|tcc|gct|tta|gac|ctt|tcc|gat|aac|gag|ctc|act|480|
|Asn|Leu|Ser|Met|Leu|Ser|Ala|Leu|Asp|Leu|Ser|Asp|Asn|Glu|Leu|Thr| |
|145| | | | |150| | | | |155| | | | |160| |

| | | | | | | | | | | | | | | | | |
|---|---|---|---|---|---|---|---|---|---|---|---|---|---|---|---|---|
|ggt|agt|tta|tca|ttt|gtg|cgg|aat|cta|cgc|aag|ctc|aga|gtt|tta|gat|528|
|Gly|Ser|Leu|Ser|Phe|Val|Arg|Asn|Leu|Arg|Lys|Leu|Arg|Val|Leu|Asp| |
| | | | |165| | | | |170| | | | |175| | |

| | | | | | | | | | | | | | | | | |
|---|---|---|---|---|---|---|---|---|---|---|---|---|---|---|---|---|
|gtt|tct|tat|aat|cat|ttc|tct|gga|att|ttg|aat|ccc|aat|agt|agc|ctc|576|
|Val|Ser|Tyr|Asn|His|Phe|Ser|Gly|Ile|Leu|Asn|Pro|Asn|Ser|Ser|Leu| |
| | | |180| | | | |185| | | | |190| | | |

| | | | | | | | | | | | | | | | | |
|---|---|---|---|---|---|---|---|---|---|---|---|---|---|---|---|---|
|ttt|gag|ttg|cac|cac|ctc|act|tac|ctt|agt|ctc|ggt|tct|aac|agc|ttc|624|
|Phe|Glu|Leu|His|His|Leu|Thr|Tyr|Leu|Ser|Leu|Gly|Ser|Asn|Ser|Phe| |
| | |195| | | | |200| | | | |205| | | | |

| | | | | | | | | | | | | | | | | |
|---|---|---|---|---|---|---|---|---|---|---|---|---|---|---|---|---|
|acc|tcc|tct|aca|ctc|ccg|tat|gaa|ttt|ggc|aat|ctc|aac|aaa|cta|gag|672|
|Thr|Ser|Ser|Thr|Leu|Pro|Tyr|Glu|Phe|Gly|Asn|Leu|Asn|Lys|Leu|Glu| |
|210| | | | |215| | | | |220| | | | | | |

| | | | | | | | | | | | | | | | | |
|---|---|---|---|---|---|---|---|---|---|---|---|---|---|---|---|---|
|tta|ttg|gat|gtt|agc|tct|aat|agc|ttc|ttc|ggt|caa|gtt|ccc|ccc|aca|720|
|Leu|Leu|Asp|Val|Ser|Ser|Asn|Ser|Phe|Phe|Gly|Gln|Val|Pro|Pro|Thr| |

```
              225                 230                 235                 240
att agt aac ctc acc cag tta acc gag ttg tac ctt ccc ttg aac gac        768
Ile Ser Asn Leu Thr Gln Leu Thr Glu Leu Tyr Leu Pro Leu Asn Asp
                    245                 250                 255 ttc act ggt agt ctt cca ctt gta caa aat cta acc aag ctc tcc att        816
Phe Thr Gly Ser Leu Pro Leu Val Gln Asn Leu Thr Lys Leu Ser Ile
            260                 265                 270 cta gca ctt ttt ggt aat cac ttc tct gga aca atc cct tct tct ctc        864
Leu Ala Leu Phe Gly Asn His Phe Ser Gly Thr Ile Pro Ser Ser Leu
        275                 280                 285 ttc act atg cct ttc tta tcc tat ctt tca tta aaa gga aac aat ctc        912
Phe Thr Met Pro Phe Leu Ser Tyr Leu Ser Leu Lys Gly Asn Asn Leu
    290                 295                 300 aac ggt tca att gaa gtt cct aac tcc tct tcg tca tca agg cta gag        960
Asn Gly Ser Ile Glu Val Pro Asn Ser Ser Ser Ser Ser Arg Leu Glu
305                 310                 315                 320 agt ttg tac cta ggt aaa aac cat ttt gaa gga aaa atc cta aag cct       1008
Ser Leu Tyr Leu Gly Lys Asn His Phe Glu Gly Lys Ile Leu Lys Pro
                325                 330                 335 atc tca aag ctc atc aac ctc aaa gag ctc gac ctt tct ttc cta agc       1056
Ile Ser Lys Leu Ile Asn Leu Lys Glu Leu Asp Leu Ser Phe Leu Ser
            340                 345                 350 aca agc tac cca att gac tta agt ctc ttt tcc tct ttc aaa tcc ttg       1104
Thr Ser Tyr Pro Ile Asp Leu Ser Leu Phe Ser Ser Phe Lys Ser Leu
        355                 360                 365 ttg gtc ctc gat ctt acc ggt gat tgg ata tct cag gca ggt tta agt       1152
Leu Val Leu Asp Leu Thr Gly Asp Trp Ile Ser Gln Ala Gly Leu Ser
    370                 375                 380 tcg gat tca tac atc tca ttg acc ttg gaa gca ttg tat atg aag cag       1200
Ser Asp Ser Tyr Ile Ser Leu Thr Leu Glu Ala Leu Tyr Met Lys Gln
385                 390                 395                 400 tgc aac atc agt gat ttc cca aac atc tta aag agc ctt ccg aat ttg       1248
Cys Asn Ile Ser Asp Phe Pro Asn Ile Leu Lys Ser Leu Pro Asn Leu
                405                 410                 415 gag tgt att gac gta tcc aac aat aga gtc agt ggg aaa atc cca gag       1296
Glu Cys Ile Asp Val Ser Asn Asn Arg Val Ser Gly Lys Ile Pro Glu
            420                 425                 430 tgg tta tgg agc ctt cct cgt ctg agc tca gtg ttc att gga gat aat       1344
Trp Leu Trp Ser Leu Pro Arg Leu Ser Ser Val Phe Ile Gly Asp Asn
        435                 440                 445 ttg tta act ggc ttc gaa ggt tca tca gaa att tta gta aat tca tcg       1392
Leu Leu Thr Gly Phe Glu Gly Ser Ser Glu Ile Leu Val Asn Ser Ser
    450                 455                 460 gtg cag atc tta gtt ttg gat tca aac agt tta gaa ggg gca ctt ccg       1440
Val Gln Ile Leu Val Leu Asp Ser Asn Ser Leu Glu Gly Ala Leu Pro
465                 470                 475                 480 cat cta cca ctc tct atc atc tac ttc tct gca aga tac aat aga ttc       1488
His Leu Pro Leu Ser Ile Ile Tyr Phe Ser Ala Arg Tyr Asn Arg Phe
                485                 490                 495 aaa ggc gac ata cct ctt tca atc tgc aat aga agc tcg ctt gat gtc       1536
Lys Gly Asp Ile Pro Leu Ser Ile Cys Asn Arg Ser Ser Leu Asp Val
            500                 505                 510 ctt gat tta aga tac aac aac ttc acc ggt cca att ccg cca tgt ctc       1584
Leu Asp Leu Arg Tyr Asn Asn Phe Thr Gly Pro Ile Pro Pro Cys Leu
        515                 520                 525 agt aac tta cta ttt ttg aat ctc cgg aag aac aac ttg gaa gga agt       1632
Ser Asn Leu Leu Phe Leu Asn Leu Arg Lys Asn Asn Leu Glu Gly Ser
    530                 535                 540 att cca gac act tat ttt gcc gat gca cct cta cgg tca ctc gac gtt       1680
```

```
Ile Pro Asp Thr Tyr Phe Ala Asp Ala Pro Leu Arg Ser Leu Asp Val
545                 550                 555                 560 ggc tac aat cga tta acg gga aag ctt cca agg tct ctt cta aat tgc         1728
Gly Tyr Asn Arg Leu Thr Gly Lys Leu Pro Arg Ser Leu Leu Asn Cys
                565                 570                 575 tca gct cta cag ttt ctt agt gtg gac cac aac gga atc gaa gat aca         1776
Ser Ala Leu Gln Phe Leu Ser Val Asp His Asn Gly Ile Glu Asp Thr
            580                 585                 590 ttt cct ttt tac ctt aag gtt tta ccg aaa ttg caa gtc ctt ctc ctc         1824
Phe Pro Phe Tyr Leu Lys Val Leu Pro Lys Leu Gln Val Leu Leu Leu
        595                 600                 605 agt tca aac aaa ttc tat ggt cct cta tct cct cca aat caa ggc tct         1872
Ser Ser Asn Lys Phe Tyr Gly Pro Leu Ser Pro Pro Asn Gln Gly Ser
    610                 615                 620 ctg ggt ttt cct gag ctg cgg ata ctt gag ata gct ggt aat aaa cta         1920
Leu Gly Phe Pro Glu Leu Arg Ile Leu Glu Ile Ala Gly Asn Lys Leu
625                 630                 635                 640 acc gga agc ttg ccc caa gat ttt ttt gtg aac tgg aaa gca tca tca         1968
Thr Gly Ser Leu Pro Gln Asp Phe Phe Val Asn Trp Lys Ala Ser Ser
                645                 650                 655 ctc acg atg aat gaa gat caa ggt cta tat atg gta tat agc aag gtt         2016
Leu Thr Met Asn Glu Asp Gln Gly Leu Tyr Met Val Tyr Ser Lys Val
            660                 665                 670 gtt tac ggg att tat tac ctc agc tat ctg gca act ata gat tta caa         2064
Val Tyr Gly Ile Tyr Tyr Leu Ser Tyr Leu Ala Thr Ile Asp Leu Gln
        675                 680                 685 tat aaa ggt cta tct atg gag caa aag tgg gtt ctt act tcc tca gcc         2112
Tyr Lys Gly Leu Ser Met Glu Gln Lys Trp Val Leu Thr Ser Ser Ala
    690                 695                 700 acc att gat ctt tct gga aac aga ctt gaa gga gaa att cct gaa tct         2160
Thr Ile Asp Leu Ser Gly Asn Arg Leu Glu Gly Glu Ile Pro Glu Ser
705                 710                 715                 720 atc ggt ctc tta aag gca cta atc gca ctc aac tta tcg aac aac gcc         2208
Ile Gly Leu Leu Lys Ala Leu Ile Ala Leu Asn Leu Ser Asn Asn Ala
                725                 730                 735 ttc aca ggc cat att cct ctg tct ttg gcc aat ctt gtg aag atc gag         2256
Phe Thr Gly His Ile Pro Leu Ser Leu Ala Asn Leu Val Lys Ile Glu
            740                 745                 750 tca cta gac cta tca agt aac caa ctc tca ggg acc att cct aat gga         2304
Ser Leu Asp Leu Ser Ser Asn Gln Leu Ser Gly Thr Ile Pro Asn Gly
        755                 760                 765 cta ggg act ctc tcg ttt ttg gcg tac gtg aac gtg tct cac aac caa         2352
Leu Gly Thr Leu Ser Phe Leu Ala Tyr Val Asn Val Ser His Asn Gln
    770                 775                 780 ctc aac ggt gaa ata cca caa gga aca cag ata act ggg caa cct aaa         2400
Leu Asn Gly Glu Ile Pro Gln Gly Thr Gln Ile Thr Gly Gln Pro Lys
785                 790                 795                 800 tcg tca ttt gaa gga aat gca ggg ctt tgt ggt ttg cct ctt caa caa         2448
Ser Ser Phe Glu Gly Asn Ala Gly Leu Cys Gly Leu Pro Leu Gln Gln
                805                 810                 815 aga tgc ttt ggg act aat gca cca cca gca cat cag ttt aaa gaa gaa         2496
Arg Cys Phe Gly Thr Asn Ala Pro Pro Ala His Gln Phe Lys Glu Glu
            820                 825                 830 gaa gat gaa gaa cag gaa caa gtg ttg aac tgg gaa ggc gtg gca ata         2544
Glu Asp Glu Glu Gln Glu Gln Val Leu Asn Trp Glu Gly Val Ala Ile
        835                 840                 845 ggg tat ggg gtt gga gtg tta ctt gga ttg gca ata gca caa ctc att         2592
Gly Tyr Gly Val Gly Val Leu Leu Gly Leu Ala Ile Ala Gln Leu Ile
    850                 855                 860
```

| | | | | | | | | | | | | | | | |
|---|---|---|---|---|---|---|---|---|---|---|---|---|---|---|---|
| gct | tca | tac | aaa | cca | gag | tgg | cta | gct | tgt | ctg | att | aag | agc | aga | aac | 2640 |
| Ala | Ser | Tyr | Lys | Pro | Glu | Trp | Leu | Ala | Cys | Leu | Ile | Lys | Ser | Arg | Asn | |
| 865 | | | | 870 | | | | | 875 | | | | | 880 | | | cgt taa  2646
Arg

<210> SEQ ID NO 35
<211> LENGTH: 881
<212> TYPE: PRT
<213> ORGANISM: Arabidopsis thaliana

<400> SEQUENCE: 35

Met Ser Glu Leu Leu Leu Arg Leu Asn Phe Leu Leu Leu Leu Leu
1               5                   10                  15

Ser Cys Val Ser Pro Ser Ser Phe Val Thr Phe Asn Asn Pro Val Val
            20                  25                  30

Gly Leu Gly Ala Cys Gly Pro His Gln Ile Gln Ala Phe Thr Gln Phe
        35                  40                  45

Lys Asn Glu Phe Asn Thr Arg Ala Cys Asn His Ser Pro Trp Asn
50                  55                  60

Gly Val Trp Cys Asp Asn Ser Thr Gly Ala Val Thr Lys Ile Gln Phe
65                  70                  75                  80

Met Ala Cys Leu Ser Gly Thr Leu Lys Ser Asn Ser Ser Leu Phe Gln
                85                  90                  95

Phe His Glu Leu Arg Ser Leu Leu Ile His Asn Asn Phe Thr Ser
            100                 105                 110

Ser Ser Ile Ser Ser Lys Phe Gly Met Leu Asn Lys Leu Glu Val Leu
        115                 120                 125

Phe Leu Ser Ser Ser Gly Phe Leu Gly Gln Val Pro Phe Ser Phe Ser
130                 135                 140

Asn Leu Ser Met Leu Ser Ala Leu Asp Leu Ser Asp Asn Glu Leu Thr
145                 150                 155                 160

Gly Ser Leu Ser Phe Val Arg Asn Leu Arg Lys Leu Arg Val Leu Asp
                165                 170                 175

Val Ser Tyr Asn His Phe Ser Gly Ile Leu Asn Pro Asn Ser Ser Leu
            180                 185                 190

Phe Glu Leu His His Leu Thr Tyr Leu Ser Leu Gly Ser Asn Ser Phe
        195                 200                 205

Thr Ser Ser Thr Leu Pro Tyr Glu Phe Gly Asn Leu Asn Lys Leu Glu
210                 215                 220

Leu Leu Asp Val Ser Ser Asn Ser Phe Phe Gly Gln Val Pro Pro Thr
225                 230                 235                 240

Ile Ser Asn Leu Thr Gln Leu Thr Glu Leu Tyr Leu Pro Leu Asn Asp
                245                 250                 255

Phe Thr Gly Ser Leu Pro Leu Val Gln Asn Leu Thr Lys Leu Ser Ile
            260                 265                 270

Leu Ala Leu Phe Gly Asn His Phe Ser Gly Thr Ile Pro Ser Ser Leu
        275                 280                 285

Phe Thr Met Pro Phe Leu Ser Tyr Leu Ser Leu Lys Gly Asn Asn Leu
290                 295                 300

Asn Gly Ser Ile Glu Val Pro Asn Ser Ser Ser Ser Arg Leu Glu
305                 310                 315                 320

Ser Leu Tyr Leu Gly Lys Asn His Phe Glu Gly Lys Ile Leu Lys Pro
                325                 330                 335

Ile Ser Lys Leu Ile Asn Leu Lys Glu Leu Asp Leu Ser Phe Leu Ser

-continued

```
               340             345              350
Thr Ser Tyr Pro Ile Asp Leu Ser Leu Phe Ser Phe Lys Ser Leu
        355             360             365
Leu Val Leu Asp Leu Thr Gly Asp Trp Ile Ser Gln Ala Gly Leu Ser
        370             375         380
Ser Asp Ser Tyr Ile Ser Leu Thr Leu Glu Ala Leu Tyr Met Lys Gln
385             390             395             400
Cys Asn Ile Ser Asp Phe Pro Asn Ile Leu Lys Ser Leu Pro Asn Leu
            405             410             415
Glu Cys Ile Asp Val Ser Asn Asn Arg Val Ser Gly Lys Ile Pro Glu
            420             425             430
Trp Leu Trp Ser Leu Pro Arg Leu Ser Ser Val Phe Ile Gly Asp Asn
            435             440             445
Leu Leu Thr Gly Phe Glu Gly Ser Ser Glu Ile Leu Val Asn Ser Ser
        450             455             460
Val Gln Ile Leu Val Leu Asp Ser Asn Ser Leu Glu Gly Ala Leu Pro
465             470             475             480
His Leu Pro Leu Ser Ile Ile Tyr Phe Ser Ala Arg Tyr Asn Arg Phe
            485             490             495
Lys Gly Asp Ile Pro Leu Ser Ile Cys Asn Arg Ser Ser Leu Asp Val
            500             505             510
Leu Asp Leu Arg Tyr Asn Asn Phe Thr Gly Pro Ile Pro Pro Cys Leu
        515             520             525
Ser Asn Leu Leu Phe Leu Asn Leu Arg Lys Asn Asn Leu Glu Gly Ser
        530             535             540
Ile Pro Asp Thr Tyr Phe Ala Asp Ala Pro Leu Arg Ser Leu Asp Val
545             550             555             560
Gly Tyr Asn Arg Leu Thr Gly Lys Leu Pro Arg Ser Leu Leu Asn Cys
            565             570             575
Ser Ala Leu Gln Phe Leu Ser Val Asp His Asn Gly Ile Glu Asp Thr
            580             585             590
Phe Pro Phe Tyr Leu Lys Val Leu Pro Lys Leu Gln Val Leu Leu Leu
            595             600             605
Ser Ser Asn Lys Phe Tyr Gly Pro Leu Ser Pro Asn Gln Gly Ser
        610             615             620
Leu Gly Phe Pro Glu Leu Arg Ile Leu Glu Ile Ala Gly Asn Lys Leu
625             630             635             640
Thr Gly Ser Leu Pro Gln Asp Phe Phe Val Asn Trp Lys Ala Ser Ser
            645             650             655
Leu Thr Met Asn Glu Asp Gln Gly Leu Tyr Met Val Tyr Ser Lys Val
            660             665             670
Val Tyr Gly Ile Tyr Tyr Leu Ser Tyr Leu Ala Thr Ile Asp Leu Gln
            675             680             685
Tyr Lys Gly Leu Ser Met Glu Gln Lys Trp Val Leu Thr Ser Ser Ala
            690             695             700
Thr Ile Asp Leu Ser Gly Asn Arg Leu Glu Gly Glu Ile Pro Glu Ser
705             710             715             720
Ile Gly Leu Leu Lys Ala Leu Ile Ala Leu Asn Leu Ser Asn Asn Ala
            725             730             735
Phe Thr Gly His Ile Pro Leu Ser Leu Ala Asn Leu Val Lys Ile Glu
            740             745             750
Ser Leu Asp Leu Ser Ser Asn Gln Leu Ser Gly Thr Ile Pro Asn Gly
        755             760             765
```

```
Leu Gly Thr Leu Ser Phe Leu Ala Tyr Val Asn Val Ser His Asn Gln
    770                 775                 780

Leu Asn Gly Glu Ile Pro Gln Gly Thr Gln Ile Thr Gly Gln Pro Lys
785                 790                 795                 800

Ser Ser Phe Glu Gly Asn Ala Gly Leu Cys Gly Leu Pro Leu Gln Gln
                805                 810                 815

Arg Cys Phe Gly Thr Asn Ala Pro Pro Ala His Gln Phe Lys Glu Glu
                820                 825                 830

Glu Asp Glu Glu Gln Glu Gln Val Leu Asn Trp Glu Gly Val Ala Ile
                835                 840                 845

Gly Tyr Gly Val Gly Val Leu Leu Gly Leu Ala Ile Ala Gln Leu Ile
            850                 855                 860

Ala Ser Tyr Lys Pro Glu Trp Leu Ala Cys Leu Ile Lys Ser Arg Asn
865                 870                 875                 880

Arg
```

<210> SEQ ID NO 36
<211> LENGTH: 2595
<212> TYPE: DNA
<213> ORGANISM: Arabidopsis thaliana
<220> FEATURE:
<221> NAME/KEY: CDS
<222> LOCATION: (1)..(2595)

<400> SEQUENCE: 36

```
atg aag acc gtg ttt aaa tcg ctt ctg ctt ttg cat ttt ctc ttg cta      48
Met Lys Thr Val Phe Lys Ser Leu Leu Leu Leu His Phe Leu Leu Leu
1               5                   10                  15 ctc tta ctc tgt ttt gtc tcc cct tcg agc ttt ttc ctt cta aaa gtt      96
Leu Leu Leu Cys Phe Val Ser Pro Ser Ser Phe Phe Leu Leu Lys Val
            20                  25                  30 ccg gtt ggt ggt ctt gtt gct tgt cgt ctc cgc cag agt caa gcc ttt     144
Pro Val Gly Gly Leu Val Ala Cys Arg Leu Arg Gln Ser Gln Ala Phe
        35                  40                  45 atg cag ttc aag gac gag ttt gat acc cgc cat tgc aac cac agt gac     192
Met Gln Phe Lys Asp Glu Phe Asp Thr Arg His Cys Asn His Ser Asp
    50                  55                  60 gac ttc aat gga gtc tgg tgc gat aac tcc acg ggt gcg gtc aca gtg     240
Asp Phe Asn Gly Val Trp Cys Asp Asn Ser Thr Gly Ala Val Thr Val
65                  70                  75                  80 cta caa ctc agg gac tgt ctc agt gga act ctg aag tca aac agt agc     288
Leu Gln Leu Arg Asp Cys Leu Ser Gly Thr Leu Lys Ser Asn Ser Ser
                85                  90                  95 ctc ttc ggg ttt cat cag ctc cgt tat ctt gct ctc aat cga aac aac     336
Leu Phe Gly Phe His Gln Leu Arg Tyr Leu Ala Leu Asn Arg Asn Asn
            100                 105                 110 ttc acc tct gct tcg ctc cct tca gag ttc tgc aat ctc aac aaa tta     384
Phe Thr Ser Ala Ser Leu Pro Ser Glu Phe Cys Asn Leu Asn Lys Leu
        115                 120                 125 aag ctc ttg tct ctt ttc tct aat ggc ttt ata gat ctt tcc cat aat     432
Lys Leu Leu Ser Leu Phe Ser Asn Gly Phe Ile Asp Leu Ser His Asn
    130                 135                 140 gat ctc atg ggt agt ttc ccg ctg gtg cga aat cta ggc aag ctc gca     480
Asp Leu Met Gly Ser Phe Pro Leu Val Arg Asn Leu Gly Lys Leu Ala
145                 150                 155                 160 gtt tta gac ctt tcg gat aat cac ttc tct gga act ctg aat ccc aac     528
Val Leu Asp Leu Ser Asp Asn His Phe Ser Gly Thr Leu Asn Pro Asn
                165                 170                 175
```

```
aat agc ctc ttt gag ttg cac tcc ctc cgt tac ctg aat ctg gct ttc    576
Asn Ser Leu Phe Glu Leu His Ser Leu Arg Tyr Leu Asn Leu Ala Phe
        180                 185                 190 aat aac att agt tcc tca ctt cct tcc aaa ttt ggc aat ctc aac aaa    624
Asn Asn Ile Ser Ser Ser Leu Pro Ser Lys Phe Gly Asn Leu Asn Lys
            195                 200                 205 tta gag gtc tta tct ctt tct ttt aat ggc ttt tct ggt caa tgt ttt    672
Leu Glu Val Leu Ser Leu Ser Phe Asn Gly Phe Ser Gly Gln Cys Phe
    210                 215                 220 ccc aca att agt aac ctt acc cgg ata acg cag ctg tac ctc cac aat    720
Pro Thr Ile Ser Asn Leu Thr Arg Ile Thr Gln Leu Tyr Leu His Asn
225                 230                 235                 240 aat gag ctc acc ggt agt ttc cca ctt gta caa aac cta act aag ctc    768
Asn Glu Leu Thr Gly Ser Phe Pro Leu Val Gln Asn Leu Thr Lys Leu
                245                 250                 255 tct ttt cta gga ctt tcg gat aat ctc ttt tct gga acc att cct tct    816
Ser Phe Leu Gly Leu Ser Asp Asn Leu Phe Ser Gly Thr Ile Pro Ser
            260                 265                 270 tac ctc ttc act ttc cct tcc tta tca act ctt gat ctg cgt gaa aat    864
Tyr Leu Phe Thr Phe Pro Ser Leu Ser Thr Leu Asp Leu Arg Glu Asn
        275                 280                 285 gat ctc tcc ggt tct att gaa gtt cct aac tca tct acc tca tct aag    912
Asp Leu Ser Gly Ser Ile Glu Val Pro Asn Ser Ser Thr Ser Ser Lys
    290                 295                 300 ctc gag atc atg tac ctt ggg ttt aac cat ctt gaa gga aaa atc cta    960
Leu Glu Ile Met Tyr Leu Gly Phe Asn His Leu Glu Gly Lys Ile Leu
305                 310                 315                 320 gag ccg atc tca aag ctt atc aac ctc aag cgt ctc gac ctt tct ttc   1008
Glu Pro Ile Ser Lys Leu Ile Asn Leu Lys Arg Leu Asp Leu Ser Phe
                325                 330                 335 cta aat aca agc tac cca att gac tta aac ctc ttg tct cct ctc aaa   1056
Leu Asn Thr Ser Tyr Pro Ile Asp Leu Asn Leu Leu Ser Pro Leu Lys
            340                 345                 350 tct ttg tct tac ctt gat ttt tcg ggt aat agt tta tct cca gcc agt   1104
Ser Leu Ser Tyr Leu Asp Phe Ser Gly Asn Ser Leu Ser Pro Ala Ser
        355                 360                 365 tta agt tca agt tcg tac atc ccg ctg agc atg gaa agc ata gtc ttg   1152
Leu Ser Ser Ser Ser Tyr Ile Pro Leu Ser Met Glu Ser Ile Val Leu
    370                 375                 380 tcg ctc tgc ggc atc cgc gag ttc cca aac atc tta aaa cat ctt caa   1200
Ser Leu Cys Gly Ile Arg Glu Phe Pro Asn Ile Leu Lys His Leu Gln
385                 390                 395                 400 aac ttg att cat ata gac ata acc agt aat caa att aaa gga aaa ata   1248
Asn Leu Ile His Ile Asp Ile Thr Ser Asn Gln Ile Lys Gly Lys Ile
                405                 410                 415 cct gag tgg tta tgg acc ctt cct cag cta agc ttc gtg gat att tcc   1296
Pro Glu Trp Leu Trp Thr Leu Pro Gln Leu Ser Phe Val Asp Ile Ser
            420                 425                 430 aat aat tcg ttc aac ggt ttc caa ggt tcg gca gaa gtt ttt gta aac   1344
Asn Asn Ser Phe Asn Gly Phe Gln Gly Ser Ala Glu Val Phe Val Asn
        435                 440                 445 tta tca gtg cgg att tta atg ttg gat gca aac aat ttt gaa gga gca   1392
Leu Ser Val Arg Ile Leu Met Leu Asp Ala Asn Asn Phe Glu Gly Ala
    450                 455                 460 ctt cct act cta cca ctc tct atc atc ggc ttc tct gcg att cat aat   1440
Leu Pro Thr Leu Pro Leu Ser Ile Ile Gly Phe Ser Ala Ile His Asn
465                 470                 475                 480 agt ttc aca gga gag ata cct ctt tca atc tgc aac cga aca tct ctt   1488
Ser Phe Thr Gly Glu Ile Pro Leu Ser Ile Cys Asn Arg Thr Ser Leu
                485                 490                 495
```

```
aca atg gtt gat cta tcc tac aac aac ttc acc ggt cca att cct caa     1536
Thr Met Val Asp Leu Ser Tyr Asn Asn Phe Thr Gly Pro Ile Pro Gln
        500                 505                 510 tgt ctt agt aac ttc atg ttt gtc aat ctc cgg aag aac gac ctg gaa     1584
Cys Leu Ser Asn Phe Met Phe Val Asn Leu Arg Lys Asn Asp Leu Glu
        515                 520                 525 gga agt atc cct gac act ttc tat act gat tct tct cta aaa tca ctt    1632
Gly Ser Ile Pro Asp Thr Phe Tyr Thr Asp Ser Ser Leu Lys Ser Leu
530                 535                 540 gac gtt ggc tac aat cga cta acc gga aag ctt cca agg tct ctt cta    1680
Asp Val Gly Tyr Asn Arg Leu Thr Gly Lys Leu Pro Arg Ser Leu Leu
545                 550                 555                 560 aat tgc tcc tct ctg aga ttt cta agc gtt gac aac aac aga gtc aaa    1728
Asn Cys Ser Ser Leu Arg Phe Leu Ser Val Asp Asn Asn Arg Val Lys
                565                 570                 575 gac aca ttt cct ttc tgg ctc aag gct tta cca aat ttg cgt gtc ctt    1776
Asp Thr Phe Pro Phe Trp Leu Lys Ala Leu Pro Asn Leu Arg Val Leu
                580                 585                 590 acc ctt cgt tca aac aaa ttc tac ggt cct ata tct cct cct cat caa    1824
Thr Leu Arg Ser Asn Lys Phe Tyr Gly Pro Ile Ser Pro Pro His Gln
                595                 600                 605 ggt cct ctc ggg ttt cca gag ttg cgg ata ttt gag ata gct gat aat    1872
Gly Pro Leu Gly Phe Pro Glu Leu Arg Ile Phe Glu Ile Ala Asp Asn
610                 615                 620 atg ttt act gga agc ttg cca cca agt ttc ttt gtg aat tgg aaa gca    1920
Met Phe Thr Gly Ser Leu Pro Pro Ser Phe Phe Val Asn Trp Lys Ala
625                 630                 635                 640 tca gcc ctc acg aag aat gaa gat ggc gga tta tat atg gtg tat gaa    1968
Ser Ala Leu Thr Lys Asn Glu Asp Gly Gly Leu Tyr Met Val Tyr Glu
                645                 650                 655 tac gat aag gct gct aac agt cca gtt cgc tac act tat aca gat acc    2016
Tyr Asp Lys Ala Ala Asn Ser Pro Val Arg Tyr Thr Tyr Thr Asp Thr
                660                 665                 670 ata gat ttg caa tac aaa ggt cta cac atg gag caa gag agg gtc ctt    2064
Ile Asp Leu Gln Tyr Lys Gly Leu His Met Glu Gln Glu Arg Val Leu
                675                 680                 685 act tct tat gcc gcc att gat ttt tct gga aac aga cta caa gga cag    2112
Thr Ser Tyr Ala Ala Ile Asp Phe Ser Gly Asn Arg Leu Gln Gly Gln
        690                 695                 700 att cct gaa tcc att ggt ctc ttg aag gca ttg att gcg ctc aac tta    2160
Ile Pro Glu Ser Ile Gly Leu Leu Lys Ala Leu Ile Ala Leu Asn Leu
705                 710                 715                 720 tcg aac aac gca ttc aca ggc cat att cct ctg tct ttc gcc aat ctt    2208
Ser Asn Asn Ala Phe Thr Gly His Ile Pro Leu Ser Phe Ala Asn Leu
                725                 730                 735 atg aat ctc gag tca cta gac atg tca gga aac caa ctc tct ggg act    2256
Met Asn Leu Glu Ser Leu Asp Met Ser Gly Asn Gln Leu Ser Gly Thr
                740                 745                 750 att cct aat gga ctt ggg agc ctc tcg ttt ttg gtg tac ata agt gtg    2304
Ile Pro Asn Gly Leu Gly Ser Leu Ser Phe Leu Val Tyr Ile Ser Val
        755                 760                 765 gct cat aac aaa ctc aaa ggt gaa ata cca caa gga aca caa att acc    2352
Ala His Asn Lys Leu Lys Gly Glu Ile Pro Gln Gly Thr Gln Ile Thr
770                 775                 780 ggg caa att aaa tca tct ttc gaa ggg aat gca ggg ctt tgt ggt ctt    2400
Gly Gln Ile Lys Ser Ser Phe Glu Gly Asn Ala Gly Leu Cys Gly Leu
785                 790                 795                 800 cct ctc cag gaa act tgc ttt gac tct agt gtg cca ccg ata caa cca    2448
Pro Leu Gln Glu Thr Cys Phe Asp Ser Ser Val Pro Pro Ile Gln Pro
```

|  |  |  |  |  |  |  |  |  |  |  |  |  |  |  |  |  |
|---|---|---|---|---|---|---|---|---|---|---|---|---|---|---|---|---|
|  |  |  | 805 |  |  |  |  | 810 |  |  |  |  | 815 |  |  |  |
| aag | caa | gaa | gac | gaa | gaa | aaa | gga | gag | gtg | att | aac | tgg | aaa | gca | gta | 2496 |
| Lys | Gln | Glu | Asp | Glu | Glu | Lys | Gly | Glu | Val | Ile | Asn | Trp | Lys | Ala | Val |  |
|  |  |  | 820 |  |  |  |  | 825 |  |  |  |  | 830 |  |  |  |
| gct | ata | gga | tat | gct | cct | gga | ttg | ttg | ttt | gga | ttg | gca | ata | gca | cat | 2544 |
| Ala | Ile | Gly | Tyr | Ala | Pro | Gly | Leu | Leu | Phe | Gly | Leu | Ala | Ile | Ala | His |  |
|  |  | 835 |  |  |  |  | 840 |  |  |  |  | 845 |  |  |  |  |
| ctc | att | gct | tca | tac | aag | cca | gag | tgg | ctc | gtc | aaa | att | att | ggc | ttc | 2592 |
| Leu | Ile | Ala | Ser | Tyr | Lys | Pro | Glu | Trp | Leu | Val | Lys | Ile | Ile | Gly | Phe |  |
|  | 850 |  |  |  |  | 855 |  |  |  |  | 860 |  |  |  |  |  |
| tga |  |  |  |  |  |  |  |  |  |  |  |  |  |  |  | 2595 |

<210> SEQ ID NO 37
<211> LENGTH: 864
<212> TYPE: PRT
<213> ORGANISM: Arabidopsis thaliana

<400> SEQUENCE: 37

Met Lys Thr Val Phe Lys Ser Leu Leu Leu His Phe Leu Leu
1               5                   10                  15

Leu Leu Leu Cys Phe Val Ser Pro Ser Ser Phe Phe Leu Leu Lys Val
            20                  25                  30

Pro Val Gly Gly Leu Val Ala Cys Arg Leu Arg Gln Ser Gln Ala Phe
        35                  40                  45

Met Gln Phe Lys Asp Glu Phe Asp Thr Arg His Cys Asn His Ser Asp
    50                  55                  60

Asp Phe Asn Gly Val Trp Cys Asp Asn Ser Thr Gly Ala Val Thr Val
65                  70                  75                  80

Leu Gln Leu Arg Asp Cys Leu Ser Gly Thr Leu Lys Ser Asn Ser Ser
                85                  90                  95

Leu Phe Gly Phe His Gln Leu Arg Tyr Leu Ala Leu Asn Arg Asn Asn
            100                 105                 110

Phe Thr Ser Ala Ser Leu Pro Ser Glu Phe Cys Asn Leu Asn Lys Leu
        115                 120                 125

Lys Leu Leu Ser Leu Phe Ser Asn Gly Phe Ile Asp Leu Ser His Asn
    130                 135                 140

Asp Leu Met Gly Ser Phe Pro Leu Val Arg Asn Leu Gly Lys Leu Ala
145                 150                 155                 160

Val Leu Asp Leu Ser Asp Asn His Phe Ser Gly Thr Leu Asn Pro Asn
                165                 170                 175

Asn Ser Leu Phe Glu Leu His Ser Leu Arg Tyr Leu Asn Leu Ala Phe
            180                 185                 190

Asn Asn Ile Ser Ser Ser Leu Pro Ser Lys Phe Gly Asn Leu Asn Lys
        195                 200                 205

Leu Glu Val Leu Ser Leu Ser Phe Asn Gly Phe Ser Gly Gln Cys Phe
    210                 215                 220

Pro Thr Ile Ser Asn Leu Thr Arg Ile Thr Gln Leu Tyr Leu His Asn
225                 230                 235                 240

Asn Glu Leu Thr Gly Ser Phe Pro Leu Val Gln Asn Leu Thr Lys Leu
                245                 250                 255

Ser Phe Leu Gly Leu Ser Asp Asn Leu Phe Ser Gly Thr Ile Pro Ser
            260                 265                 270

Tyr Leu Phe Thr Phe Pro Ser Leu Ser Thr Leu Asp Leu Arg Glu Asn
        275                 280                 285

Asp Leu Ser Gly Ser Ile Glu Val Pro Asn Ser Ser Thr Ser Ser Lys

```
            290                 295                 300
Leu Glu Ile Met Tyr Leu Gly Phe Asn His Leu Glu Gly Lys Ile Leu
305                 310                 315                 320

Glu Pro Ile Ser Lys Leu Ile Asn Leu Lys Arg Leu Asp Leu Ser Phe
                325                 330                 335

Leu Asn Thr Ser Tyr Pro Ile Asp Leu Asn Leu Leu Ser Pro Leu Lys
                340                 345                 350

Ser Leu Ser Tyr Leu Asp Phe Ser Gly Asn Ser Leu Ser Pro Ala Ser
            355                 360                 365

Leu Ser Ser Ser Tyr Ile Pro Leu Ser Met Glu Ser Ile Val Leu
370                 375                 380

Ser Leu Cys Gly Ile Arg Glu Phe Pro Asn Ile Leu Lys His Leu Gln
385                 390                 395                 400

Asn Leu Ile His Ile Asp Ile Thr Ser Asn Gln Ile Lys Gly Lys Ile
                405                 410                 415

Pro Glu Trp Leu Trp Thr Leu Pro Gln Leu Ser Phe Val Asp Ile Ser
                420                 425                 430

Asn Asn Ser Phe Asn Gly Phe Gln Gly Ser Ala Glu Val Phe Val Asn
            435                 440                 445

Leu Ser Val Arg Ile Leu Met Leu Asp Ala Asn Asn Phe Glu Gly Ala
450                 455                 460

Leu Pro Thr Leu Pro Leu Ser Ile Ile Gly Phe Ser Ala Ile His Asn
465                 470                 475                 480

Ser Phe Thr Gly Glu Ile Pro Leu Ser Ile Cys Asn Arg Thr Ser Leu
                485                 490                 495

Thr Met Val Asp Leu Ser Tyr Asn Asn Phe Thr Gly Pro Ile Pro Gln
                500                 505                 510

Cys Leu Ser Asn Phe Met Phe Val Asn Leu Arg Lys Asn Asp Leu Glu
            515                 520                 525

Gly Ser Ile Pro Asp Thr Phe Tyr Thr Asp Ser Ser Leu Lys Ser Leu
530                 535                 540

Asp Val Gly Tyr Asn Arg Leu Thr Gly Lys Leu Pro Arg Ser Leu Leu
545                 550                 555                 560

Asn Cys Ser Ser Leu Arg Phe Leu Ser Val Asp Asn Asn Arg Val Lys
                565                 570                 575

Asp Thr Phe Pro Phe Trp Leu Lys Ala Leu Pro Asn Leu Arg Val Leu
                580                 585                 590

Thr Leu Arg Ser Asn Lys Phe Tyr Gly Pro Ile Ser Pro His Gln
            595                 600                 605

Gly Pro Leu Gly Phe Pro Glu Leu Arg Ile Phe Glu Ile Ala Asp Asn
610                 615                 620

Met Phe Thr Gly Ser Leu Pro Pro Ser Phe Val Asn Trp Lys Ala
625                 630                 635                 640

Ser Ala Leu Thr Lys Asn Glu Asp Gly Gly Leu Tyr Met Val Tyr Glu
                645                 650                 655

Tyr Asp Lys Ala Ala Asn Ser Pro Val Arg Tyr Thr Tyr Thr Asp Thr
                660                 665                 670

Ile Asp Leu Gln Tyr Lys Gly Leu His Met Glu Gln Glu Arg Val Leu
            675                 680                 685

Thr Ser Tyr Ala Ala Ile Asp Phe Ser Gly Asn Arg Leu Gln Gly Gln
            690                 695                 700

Ile Pro Glu Ser Ile Gly Leu Leu Lys Ala Leu Ile Ala Leu Asn Leu
705                 710                 715                 720
```

```
Ser Asn Asn Ala Phe Thr Gly His Ile Pro Leu Ser Phe Ala Asn Leu
                725                 730                 735

Met Asn Leu Glu Ser Leu Asp Met Ser Gly Asn Gln Leu Ser Gly Thr
            740                 745                 750

Ile Pro Asn Gly Leu Gly Ser Leu Ser Phe Leu Val Tyr Ile Ser Val
        755                 760                 765

Ala His Asn Lys Leu Lys Gly Glu Ile Pro Gln Gly Thr Gln Ile Thr
    770                 775                 780

Gly Gln Ile Lys Ser Ser Phe Glu Gly Asn Ala Gly Leu Cys Gly Leu
785                 790                 795                 800

Pro Leu Gln Glu Thr Cys Phe Asp Ser Ser Val Pro Pro Ile Gln Pro
                805                 810                 815

Lys Gln Glu Asp Glu Glu Lys Gly Glu Val Ile Asn Trp Lys Ala Val
            820                 825                 830

Ala Ile Gly Tyr Ala Pro Gly Leu Leu Phe Gly Leu Ala Ile Ala His
        835                 840                 845

Leu Ile Ala Ser Tyr Lys Pro Glu Trp Leu Val Lys Ile Ile Gly Phe
    850                 855                 860

<210> SEQ ID NO 38
<211> LENGTH: 1770
<212> TYPE: DNA
<213> ORGANISM: Arabidopsis thaliana
<220> FEATURE:
<221> NAME/KEY: CDS
<222> LOCATION: (1)..(1770)

<400> SEQUENCE: 38 atg cct ttc ttg tct tat ctt gat tta agt gag aat cat ctc act ggc      48
Met Pro Phe Leu Ser Tyr Leu Asp Leu Ser Glu Asn His Leu Thr Gly
1               5                   10                  15 tca ttt gaa atc tct aat tct tcg tct aaa ctt gag aac tta aat ctt      96
Ser Phe Glu Ile Ser Asn Ser Ser Ser Lys Leu Glu Asn Leu Asn Leu
            20                  25                  30 ggg aat aac cat ttt gaa aca gag atc ata gat cct gtt ttg agg tta     144
Gly Asn Asn His Phe Glu Thr Glu Ile Ile Asp Pro Val Leu Arg Leu
        35                  40                  45 gtt aat ctc agg tat cta agc ctc tct ttc cta aac aca agc cac cca     192
Val Asn Leu Arg Tyr Leu Ser Leu Ser Phe Leu Asn Thr Ser His Pro
    50                  55                  60 att gac tta tca att ttc tct cct ctc cag tct ttg aca cac ctt gat     240
Ile Asp Leu Ser Ile Phe Ser Pro Leu Gln Ser Leu Thr His Leu Asp
65                  70                  75                  80 ctt cac ggc aac agt tta aca cta acg agt gtg tat tca gac att gac     288
Leu His Gly Asn Ser Leu Thr Leu Thr Ser Val Tyr Ser Asp Ile Asp
                85                  90                  95 ttt cca aag aac atg gag atc ttg ctc ttg tct gga tgc aac atc agt     336
Phe Pro Lys Asn Met Glu Ile Leu Leu Leu Ser Gly Cys Asn Ile Ser
            100                 105                 110 gaa ttc ccc aga ttc tta aag tcc tta aag aag tta tgg tat tta gat     384
Glu Phe Pro Arg Phe Leu Lys Ser Leu Lys Lys Leu Trp Tyr Leu Asp
        115                 120                 125 ctt tcc agc aac aga atc aaa gga aac gtt cct gat tgg ata tgg agt     432
Leu Ser Ser Asn Arg Ile Lys Gly Asn Val Pro Asp Trp Ile Trp Ser
    130                 135                 140 ctt cct ctt tta gtc tct ctg gat ctt agt aac aat tca ttc acc ggt     480
Leu Pro Leu Leu Val Ser Leu Asp Leu Ser Asn Asn Ser Phe Thr Gly
145                 150                 155                 160
```

-continued

| | | |
|---|---|---|
| ttc aac ggt tca ttg gat cat gtt tta gcc aac tca tcg gtc caa gta<br>Phe Asn Gly Ser Leu Asp His Val Leu Ala Asn Ser Ser Val Gln Val<br>165                           170                   175 | 528 |
| cta gat att gct tta aac tct ttc aaa gga tca ttc cct aat cca ccg<br>Leu Asp Ile Ala Leu Asn Ser Phe Lys Gly Ser Phe Pro Asn Pro Pro<br>          180                     185                      190 | 576 |
| gtc tct atc atc aac ttg tct gct tgg aac aat agt ttc aca gga gac<br>Val Ser Ile Ile Asn Leu Ser Ala Trp Asn Asn Ser Phe Thr Gly Asp<br>    195                       200                 205 | 624 |
| att cct ctc tcg gtc tgt aac aga acc tct ctt gat gtt ctt gat ctg<br>Ile Pro Leu Ser Val Cys Asn Arg Thr Ser Leu Asp Val Leu Asp Leu<br>210                       215                 220 | 672 |
| tcc tac aac aac ttc act ggc tca att cct cca tgt atg ggt aat ttc<br>Ser Tyr Asn Asn Phe Thr Gly Ser Ile Pro Pro Cys Met Gly Asn Phe<br>225                      230                 235                 240 | 720 |
| acc ata gtg aat ctc cgg aag aac aag ttg gaa gga aac att cca gac<br>Thr Ile Val Asn Leu Arg Lys Asn Lys Leu Glu Gly Asn Ile Pro Asp<br>                   245                 250                 255 | 768 |
| gag ttt tat agc ggt gct ttg acg cag aca ctt gat gtt gga tac aat<br>Glu Phe Tyr Ser Gly Ala Leu Thr Gln Thr Leu Asp Val Gly Tyr Asn<br>          260                     265                     270 | 816 |
| caa cta acc gga gaa ctt cca aga tct ctc ctg aat tgc tca ttc ata<br>Gln Leu Thr Gly Glu Leu Pro Arg Ser Leu Leu Asn Cys Ser Phe Ile<br>    275                       280                 285 | 864 |
| agg ttt ctt agt gtg gat cac aac aga atc aat gat tca ttt ccc ttg<br>Arg Phe Leu Ser Val Asp His Asn Arg Ile Asn Asp Ser Phe Pro Leu<br>290                       295                 300 | 912 |
| tgg ctc aag gca ttg ccc aat ttg aaa gtc ctt act ctc cgt tca aac<br>Trp Leu Lys Ala Leu Pro Asn Leu Lys Val Leu Thr Leu Arg Ser Asn<br>305                       310                 315                 320 | 960 |
| agt ttc cat ggt cct atg tct cca cca gat gat caa agt tct ctt gca<br>Ser Phe His Gly Pro Met Ser Pro Pro Asp Asp Gln Ser Ser Leu Ala<br>                   325                 330                 335 | 1008 |
| ttt ccc aag ctc cag ata ctt gaa ata tcg cat aac aga ttt acg gga<br>Phe Pro Lys Leu Gln Ile Leu Glu Ile Ser His Asn Arg Phe Thr Gly<br>          340                     345                     350 | 1056 |
| agc tta cca acg aat tac ttt gcg aat tgg agt gta aaa tct ctc aag<br>Ser Leu Pro Thr Asn Tyr Phe Ala Asn Trp Ser Val Lys Ser Leu Lys<br>    355                       360                 365 | 1104 |
| atg tat gat gaa gag agg cta tat atg gga gac tat tcg agt gat cgg<br>Met Tyr Asp Glu Glu Arg Leu Tyr Met Gly Asp Tyr Ser Ser Asp Arg<br>370                       375                 380 | 1152 |
| ttt gtt tat gaa gat act ttg gat ttg caa tac aaa ggt cta tac atg<br>Phe Val Tyr Glu Asp Thr Leu Asp Leu Gln Tyr Lys Gly Leu Tyr Met<br>385                       390                 395                 400 | 1200 |
| gag caa ggc aag gtt ctt act ttc tac tcc gcc att gat ttc tct ggc<br>Glu Gln Gly Lys Val Leu Thr Phe Tyr Ser Ala Ile Asp Phe Ser Gly<br>                   405                 410                 415 | 1248 |
| aac aag ctt gaa gga gag att cca gaa tct att ggt ctt ttg aaa aca<br>Asn Lys Leu Glu Gly Glu Ile Pro Glu Ser Ile Gly Leu Leu Lys Thr<br>          420                     425                     430 | 1296 |
| ttg att gct ctc aac tta tca aac aac tca ttc act gga cat att ccg<br>Leu Ile Ala Leu Asn Leu Ser Asn Asn Ser Phe Thr Gly His Ile Pro<br>    435                       440                 445 | 1344 |
| atg tct ttc gct aat gtg aca gag ctc gag tca ttg gac ttg tca ggg<br>Met Ser Phe Ala Asn Val Thr Glu Leu Glu Ser Leu Asp Leu Ser Gly<br>450                       455                 460 | 1392 |
| aac aaa ctc tcg ggg gaa att cca caa gaa ctc gga aga cta tcg tat<br>Asn Lys Leu Ser Gly Glu Ile Pro Gln Glu Leu Gly Arg Leu Ser Tyr<br>465                       470                 475                 480 | 1440 |

```
tta gcg tac ata gat gtc tct gat aat caa ctc act ggt aaa ata cca   1488
Leu Ala Tyr Ile Asp Val Ser Asp Asn Gln Leu Thr Gly Lys Ile Pro
            485                 490                 495 caa gga aca caa atc ata ggg cag cct aaa tcc tca ttt gaa gga aat   1536
Gln Gly Thr Gln Ile Ile Gly Gln Pro Lys Ser Ser Phe Glu Gly Asn
        500                 505                 510 tca ggg tta tgt ggt ctt cct ctt gaa gaa agc tgt tta aga gaa gac   1584
Ser Gly Leu Cys Gly Leu Pro Leu Glu Glu Ser Cys Leu Arg Glu Asp
    515                 520                 525 gca cca tcg aca caa gag ccc gaa gaa gaa gaa gaa ata ttg gag       1632
Ala Pro Ser Thr Gln Glu Pro Glu Glu Glu Glu Glu Ile Leu Glu
530                 535                 540 tgg aga gca gcg gca ata ggg tat gga cca ggg gtg ttg ttt gga ttg   1680
Trp Arg Ala Ala Ala Ile Gly Tyr Gly Pro Gly Val Leu Phe Gly Leu
545                 550                 555                 560 gca att gga cat gtt gtt gct ttg tac aag cca ggg tgg ttc atc aag   1728
Ala Ile Gly His Val Val Ala Leu Tyr Lys Pro Gly Trp Phe Ile Lys
                565                 570                 575 aat aat ggt cag aat agg ctt aga ggc atc aga cac cct tag           1770
Asn Asn Gly Gln Asn Arg Leu Arg Gly Ile Arg His Pro
            580                 585
```

<210> SEQ ID NO 39
<211> LENGTH: 589
<212> TYPE: PRT
<213> ORGANISM: Arabidopsis thaliana

<400> SEQUENCE: 39

```
Met Pro Phe Leu Ser Tyr Leu Asp Leu Ser Glu Asn His Leu Thr Gly
1               5                   10                  15

Ser Phe Glu Ile Ser Asn Ser Ser Lys Leu Glu Asn Leu Asn Leu
            20                  25                  30

Gly Asn Asn His Phe Glu Thr Glu Ile Ile Asp Pro Val Leu Arg Leu
            35                  40                  45

Val Asn Leu Arg Tyr Leu Ser Leu Ser Phe Leu Asn Thr Ser His Pro
    50                  55                  60

Ile Asp Leu Ser Ile Phe Ser Pro Leu Gln Ser Leu Thr His Leu Asp
65                  70                  75                  80

Leu His Gly Asn Ser Leu Thr Leu Thr Ser Val Tyr Ser Asp Ile Asp
                85                  90                  95

Phe Pro Lys Asn Met Glu Ile Leu Leu Leu Ser Gly Cys Asn Ile Ser
            100                 105                 110

Glu Phe Pro Arg Phe Leu Lys Ser Leu Lys Lys Leu Trp Tyr Leu Asp
        115                 120                 125

Leu Ser Ser Asn Arg Ile Lys Gly Asn Val Pro Asp Trp Ile Trp Ser
    130                 135                 140

Leu Pro Leu Leu Val Ser Leu Asp Leu Ser Asn Asn Ser Phe Thr Gly
145                 150                 155                 160

Phe Asn Gly Ser Leu Asp His Val Leu Ala Asn Ser Ser Val Gln Val
                165                 170                 175

Leu Asp Ile Ala Leu Asn Ser Phe Lys Gly Ser Phe Pro Asn Pro Pro
            180                 185                 190

Val Ser Ile Ile Asn Leu Ser Ala Trp Asn Asn Ser Phe Thr Gly Asp
        195                 200                 205

Ile Pro Leu Ser Val Cys Asn Arg Thr Ser Leu Asp Val Leu Asp Leu
    210                 215                 220
```

```
Ser Tyr Asn Asn Phe Thr Gly Ser Ile Pro Pro Cys Met Gly Asn Phe
225                 230                 235                 240

Thr Ile Val Asn Leu Arg Lys Asn Lys Leu Glu Gly Asn Ile Pro Asp
            245                 250                 255

Glu Phe Tyr Ser Gly Ala Leu Thr Gln Thr Leu Asp Val Gly Tyr Asn
            260                 265                 270

Gln Leu Thr Gly Glu Leu Pro Arg Ser Leu Leu Asn Cys Ser Phe Ile
        275                 280                 285

Arg Phe Leu Ser Val Asp His Asn Arg Ile Asn Asp Ser Phe Pro Leu
        290                 295                 300

Trp Leu Lys Ala Leu Pro Asn Leu Lys Val Leu Thr Leu Arg Ser Asn
305                 310                 315                 320

Ser Phe His Gly Pro Met Ser Pro Pro Asp Asp Gln Ser Ser Leu Ala
                325                 330                 335

Phe Pro Lys Leu Gln Ile Leu Glu Ile Ser His Asn Arg Phe Thr Gly
                340                 345                 350

Ser Leu Pro Thr Asn Tyr Phe Ala Asn Trp Ser Val Lys Ser Leu Lys
        355                 360                 365

Met Tyr Asp Glu Glu Arg Leu Tyr Met Gly Asp Tyr Ser Ser Asp Arg
370                 375                 380

Phe Val Tyr Glu Asp Thr Leu Asp Leu Gln Tyr Lys Gly Leu Tyr Met
385                 390                 395                 400

Glu Gln Gly Lys Val Leu Thr Phe Tyr Ser Ala Ile Asp Phe Ser Gly
                405                 410                 415

Asn Lys Leu Glu Gly Glu Ile Pro Glu Ser Ile Gly Leu Leu Lys Thr
            420                 425                 430

Leu Ile Ala Leu Asn Leu Ser Asn Asn Ser Phe Thr Gly His Ile Pro
        435                 440                 445

Met Ser Phe Ala Asn Val Thr Glu Leu Glu Ser Leu Asp Leu Ser Gly
    450                 455                 460

Asn Lys Leu Ser Gly Glu Ile Pro Gln Glu Leu Gly Arg Leu Ser Tyr
465                 470                 475                 480

Leu Ala Tyr Ile Asp Val Ser Asp Asn Gln Leu Thr Gly Lys Ile Pro
                485                 490                 495

Gln Gly Thr Gln Ile Ile Gly Gln Pro Lys Ser Ser Phe Glu Gly Asn
            500                 505                 510

Ser Gly Leu Cys Gly Leu Pro Leu Glu Glu Ser Cys Leu Arg Glu Asp
        515                 520                 525

Ala Pro Ser Thr Gln Glu Pro Glu Glu Glu Glu Ile Leu Glu
        530                 535                 540

Trp Arg Ala Ala Ala Ile Gly Tyr Gly Pro Gly Val Leu Phe Gly Leu
545                 550                 555                 560

Ala Ile Gly His Val Val Ala Leu Tyr Lys Pro Gly Trp Phe Ile Lys
                565                 570                 575

Asn Asn Gly Gln Asn Arg Leu Arg Gly Ile Arg His Pro
            580                 585

<210> SEQ ID NO 40
<211> LENGTH: 2403
<212> TYPE: DNA
<213> ORGANISM: Arabidopsis thaliana
<220> FEATURE:
<221> NAME/KEY: CDS
<222> LOCATION: (1)..(2403)

<400> SEQUENCE: 40
```

```
atg cgt ttg cat ttt tgc tcg cta ctc tta ctc tac tgt atc gtc ttc      48
Met Arg Leu His Phe Cys Ser Leu Leu Leu Leu Tyr Cys Ile Val Phe
1               5                   10                  15 gtt tca agc ttc ttg acg acc gac gct ctt gct tgt ctt cct gac cag      96
Val Ser Ser Phe Leu Thr Thr Asp Ala Leu Ala Cys Leu Pro Asp Gln
            20                  25                  30 atc caa gct cta atc caa ttc aag aat gag ttt gaa tct gac ggc tgc     144
Ile Gln Ala Leu Ile Gln Phe Lys Asn Glu Phe Glu Ser Asp Gly Cys
        35                  40                  45 aac cgc agt gac tac tta aac gga gtc cag tgt gat aac acg act ggt     192
Asn Arg Ser Asp Tyr Leu Asn Gly Val Gln Cys Asp Asn Thr Thr Gly
    50                  55                  60 gcg gtc acg aag ctt cag ctc cca agt ggt tgc ttc act gga act ctc     240
Ala Val Thr Lys Leu Gln Leu Pro Ser Gly Cys Phe Thr Gly Thr Leu
65                  70                  75                  80 aaa cca aac agt agt ctc ttt gag ttg cat cag ctt cgt tac ctt aat     288
Lys Pro Asn Ser Ser Leu Phe Glu Leu His Gln Leu Arg Tyr Leu Asn
                85                  90                  95 ctc tct cac aac aac ttc act tcc tct tca ctc cct tct gaa ttc agc     336
Leu Ser His Asn Asn Phe Thr Ser Ser Ser Leu Pro Ser Glu Phe Ser
            100                 105                 110 aat ctc acc aga tta gag gtt ttg tct ctt gcc tct agt agc ttt act     384
Asn Leu Thr Arg Leu Glu Val Leu Ser Leu Ala Ser Ser Ser Phe Thr
        115                 120                 125 ggt caa gtt cct tcc tca att agt aac ctt atc ttg ctt acc cat tta     432
Gly Gln Val Pro Ser Ser Ile Ser Asn Leu Ile Leu Leu Thr His Leu
    130                 135                 140 aac ctt tcc cat aat gag ctc act ggt agt ttc cca cct gta aga aac     480
Asn Leu Ser His Asn Glu Leu Thr Gly Ser Phe Pro Pro Val Arg Asn
145                 150                 155                 160 cta aca aag ctt tcc ttt tta gac ctt tct tac aat caa ttc tca gga     528
Leu Thr Lys Leu Ser Phe Leu Asp Leu Ser Tyr Asn Gln Phe Ser Gly
                165                 170                 175 gcc ata cct ttt gat tta cta ccc act ttg cct ttc ttg tct tat ctt     576
Ala Ile Pro Phe Asp Leu Leu Pro Thr Leu Pro Phe Leu Ser Tyr Leu
            180                 185                 190 gat ctg aaa aag aat cat ctc act ggt tct att gat gtc cca aac tct     624
Asp Leu Lys Lys Asn His Leu Thr Gly Ser Ile Asp Val Pro Asn Ser
        195                 200                 205 tct tct tca tct aag cta gtt cgt ttg tcc ctt ggg ttt aac caa ttt     672
Ser Ser Ser Ser Lys Leu Val Arg Leu Ser Leu Gly Phe Asn Gln Phe
    210                 215                 220 gaa gga aaa atc ata gag cct atc tca aag ctc ata aac ctc aac cat     720
Glu Gly Lys Ile Ile Glu Pro Ile Ser Lys Leu Ile Asn Leu Asn His
225                 230                 235                 240 ctt gaa ctt gct tcc cta aac ata agt cac cca att gac tta cgc gtc     768
Leu Glu Leu Ala Ser Leu Asn Ile Ser His Pro Ile Asp Leu Arg Val
                245                 250                 255 ttc gct cct ctc aaa tct ttg ttg gtc ttt gat att cgt caa aat agg     816
Phe Ala Pro Leu Lys Ser Leu Leu Val Phe Asp Ile Arg Gln Asn Arg
            260                 265                 270 tta tta cca gcc agt tta agt tca gat tca gag ttt cca ttg agc tta     864
Leu Leu Pro Ala Ser Leu Ser Ser Asp Ser Glu Phe Pro Leu Ser Leu
        275                 280                 285 ata agc ttg att ttg atc cag tgc gac att atc gag ttt cca aac atc     912
Ile Ser Leu Ile Leu Ile Gln Cys Asp Ile Ile Glu Phe Pro Asn Ile
    290                 295                 300 ttt aag acc ctt caa aac ttg gag cat ata gac att tcc aac aat cta     960
Phe Lys Thr Leu Gln Asn Leu Glu His Ile Asp Ile Ser Asn Asn Leu
```

```
                    305                 310                 315                 320
atc aaa ggg aaa gta cct gag tgg ttt tgg aag ctt cct cgt ctt agc         1008
Ile Lys Gly Lys Val Pro Glu Trp Phe Trp Lys Leu Pro Arg Leu Ser
                        325                 330                 335 ata gca aat ctt gtt aac aat tct ttg act ggt ttc gaa ggt tct tca         1056
Ile Ala Asn Leu Val Asn Asn Ser Leu Thr Gly Phe Glu Gly Ser Ser
                340                 345                 350 gaa gtt tta ctt aac tca tca gtg cag tta cta gat ttt gcc tat aac         1104
Glu Val Leu Leu Asn Ser Ser Val Gln Leu Leu Asp Phe Ala Tyr Asn
            355                 360                 365 tcc atg aca gga gcg ttt cct act cca cca ctc ggt tcg atc tac ttg         1152
Ser Met Thr Gly Ala Phe Pro Thr Pro Pro Leu Gly Ser Ile Tyr Leu
        370                 375                 380 tct gcg tgg aac aat agt ttc aca ggg aac ata cct ctc tca atc tgc         1200
Ser Ala Trp Asn Asn Ser Phe Thr Gly Asn Ile Pro Leu Ser Ile Cys
385                 390                 395                 400 aac cga agc tct ctc atc gtc ctt gat cta tcc tac aac aaa ttc acc         1248
Asn Arg Ser Ser Leu Ile Val Leu Asp Leu Ser Tyr Asn Lys Phe Thr
                        405                 410                 415 ggt cca att cct caa tgt ctg agt aac tta aaa gta gta aac ctc agg         1296
Gly Pro Ile Pro Gln Cys Leu Ser Asn Leu Lys Val Val Asn Leu Arg
                420                 425                 430 aag aac agc ttg gaa gga agt ata cct gac gag ttc cat agc ggt gct         1344
Lys Asn Ser Leu Glu Gly Ser Ile Pro Asp Glu Phe His Ser Gly Ala
            435                 440                 445 aag aca cag acg ctt gac gtt ggc tat aat cga cta acc ggg aag ctt         1392
Lys Thr Gln Thr Leu Asp Val Gly Tyr Asn Arg Leu Thr Gly Lys Leu
        450                 455                 460 cca aaa tca ctt ttg aat tgc tcc tct ctg agg ttt ctg agt gtt gac         1440
Pro Lys Ser Leu Leu Asn Cys Ser Ser Leu Arg Phe Leu Ser Val Asp
465                 470                 475                 480 aac aac aga att gaa gac acg ttt cct ttc tgg ctg aag gcg cta ccc         1488
Asn Asn Arg Ile Glu Asp Thr Phe Pro Phe Trp Leu Lys Ala Leu Pro
                        485                 490                 495 aat ttg cat gtc ttg act ctc cgt tca aac aga ttc ttc ggc cat ctc         1536
Asn Leu His Val Leu Thr Leu Arg Ser Asn Arg Phe Phe Gly His Leu
                500                 505                 510 tct cct cct gat cga ggt cct ctc gcg ttt ccc gag ctg cgg ata ctt         1584
Ser Pro Pro Asp Arg Gly Pro Leu Ala Phe Pro Glu Leu Arg Ile Leu
            515                 520                 525 gaa ttg tca gat aac agc ttt act gga agc ttg cca cca aat ttc ttt         1632
Glu Leu Ser Asp Asn Ser Phe Thr Gly Ser Leu Pro Pro Asn Phe Phe
        530                 535                 540 gtt aac tgg aaa gca tca tca ccc aag ata aat gaa gat ggg cgt att         1680
Val Asn Trp Lys Ala Ser Ser Pro Lys Ile Asn Glu Asp Gly Arg Ile
545                 550                 555                 560 tat atg gga gac tac aag aat gct tat tat atc tat gaa gat aca atg         1728
Tyr Met Gly Asp Tyr Lys Asn Ala Tyr Tyr Ile Tyr Glu Asp Thr Met
                        565                 570                 575 gat ttg caa tac aaa ggt cta ttc atg gag cag ggg aaa gtc ctt act         1776
Asp Leu Gln Tyr Lys Gly Leu Phe Met Glu Gln Gly Lys Val Leu Thr
                580                 585                 590 ttc tac agc acc att gat ttc tct gga aac aaa ctt gaa gga cag att         1824
Phe Tyr Ser Thr Ile Asp Phe Ser Gly Asn Lys Leu Glu Gly Gln Ile
            595                 600                 605 cct gag tct att ggt ctg ttg aag gaa ttg ata gcg ctc aac tta tcg         1872
Pro Glu Ser Ile Gly Leu Leu Lys Glu Leu Ile Ala Leu Asn Leu Ser
        610                 615                 620 aac aac gcc ttc act ggc cat att cct atg tct ttg gca aat gtt acg         1920
Asn Asn Ala Phe Thr Gly His Ile Pro Met Ser Leu Ala Asn Val Thr
```

```
Asn Asn Ala Phe Thr Gly His Ile Pro Met Ser Leu Ala Asn Val Thr
625                 630                 635                 640 gag ctc gag tca cta gac ctg tca aga aat caa cta tca ggg aat att     1968
Glu Leu Glu Ser Leu Asp Leu Ser Arg Asn Gln Leu Ser Gly Asn Ile
            645                 650                 655 cca aga gaa ctc ggg agc ctc tca ttt ctg gcg tac ata agt gta gct     2016
Pro Arg Glu Leu Gly Ser Leu Ser Phe Leu Ala Tyr Ile Ser Val Ala
        660                 665                 670 cat aac caa ctc aaa ggt gaa ata cca cag gga cca cag ttt agt ggg     2064
His Asn Gln Leu Lys Gly Glu Ile Pro Gln Gly Pro Gln Phe Ser Gly
            675                 680                 685 caa gct gaa tca tca ttt gaa ggg aat gta ggt ctc tgt ggt ctt cct     2112
Gln Ala Glu Ser Ser Phe Glu Gly Asn Val Gly Leu Cys Gly Leu Pro
        690                 695                 700 ctc caa gga agt tgc gtt gcg cca cca aca aaa tat ccc aag gaa gaa     2160
Leu Gln Gly Ser Cys Val Ala Pro Pro Thr Lys Tyr Pro Lys Glu Glu
705                 710                 715                 720 gac gaa gaa gaa gaa gag gac gaa gtg att gag tgg aaa gca gtg ttt     2208
Asp Glu Glu Glu Glu Asp Glu Val Ile Glu Trp Lys Ala Val Phe
                725                 730                 735 ttc ggg tat tgg cct gga ctg tta ctt gga ttg gta atg gca cac gtt     2256
Phe Gly Tyr Trp Pro Gly Leu Leu Leu Gly Leu Val Met Ala His Val
            740                 745                 750 att gct tca ttc aag ccg aag tgg ttt gtc aag ata ctt ggt cca gct     2304
Ile Ala Ser Phe Lys Pro Lys Trp Phe Val Lys Ile Leu Gly Pro Ala
        755                 760                 765 aag ggc aag caa gta gat cca gtt aga ttg ttt atg aat ctg gat tca     2352
Lys Gly Lys Gln Val Asp Pro Val Arg Leu Phe Met Asn Leu Asp Ser
770                 775                 780 aga tgg gac agt ttt aat aat aag gat act gta gaa gaa gtg ata     2400
Arg Trp Asp Ser Phe Asn Asn Lys Asp Thr Val Glu Glu Val Ile
785                 790                 795                 800 tga                                                                 2403

<210> SEQ ID NO 41
<211> LENGTH: 800
<212> TYPE: PRT
<213> ORGANISM: Arabidopsis thaliana

<400> SEQUENCE: 41

Met Arg Leu His Phe Cys Ser Leu Leu Leu Tyr Cys Ile Val Phe
1               5                   10                  15

Val Ser Ser Phe Leu Thr Thr Asp Ala Leu Ala Cys Leu Pro Asp Gln
                20                  25                  30

Ile Gln Ala Leu Ile Gln Phe Lys Asn Glu Phe Glu Ser Asp Gly Cys
            35                  40                  45

Asn Arg Ser Asp Tyr Leu Asn Gly Val Gln Cys Asp Asn Thr Thr Gly
        50                  55                  60

Ala Val Thr Lys Leu Gln Leu Pro Ser Gly Cys Phe Thr Gly Thr Leu
65                  70                  75                  80

Lys Pro Asn Ser Ser Leu Phe Glu Leu His Gln Leu Arg Tyr Leu Asn
                85                  90                  95

Leu Ser His Asn Asn Phe Thr Ser Ser Ser Leu Pro Ser Glu Phe Ser
            100                 105                 110

Asn Leu Thr Arg Leu Glu Val Leu Ser Leu Ala Ser Ser Ser Phe Thr
        115                 120                 125

Gly Gln Val Pro Ser Ser Ile Ser Asn Leu Ile Leu Leu Thr His Leu
    130                 135                 140
```

```
Asn Leu Ser His Asn Glu Leu Thr Gly Ser Phe Pro Pro Val Arg Asn
145                 150                 155                 160

Leu Thr Lys Leu Ser Phe Leu Asp Leu Ser Tyr Asn Gln Phe Ser Gly
            165                 170                 175

Ala Ile Pro Phe Asp Leu Leu Pro Thr Leu Pro Phe Leu Ser Tyr Leu
            180                 185                 190

Asp Leu Lys Lys Asn His Leu Thr Gly Ser Ile Asp Val Pro Asn Ser
            195                 200                 205

Ser Ser Ser Ser Lys Leu Val Arg Leu Ser Leu Gly Phe Asn Gln Phe
            210                 215                 220

Glu Gly Lys Ile Ile Glu Pro Ile Ser Lys Leu Ile Asn Leu Asn His
225                 230                 235                 240

Leu Glu Leu Ala Ser Leu Asn Ile Ser His Pro Ile Asp Leu Arg Val
            245                 250                 255

Phe Ala Pro Leu Lys Ser Leu Leu Val Phe Asp Ile Arg Gln Asn Arg
            260                 265                 270

Leu Leu Pro Ala Ser Leu Ser Ser Asp Ser Glu Phe Pro Leu Ser Leu
            275                 280                 285

Ile Ser Leu Ile Leu Ile Gln Cys Asp Ile Ile Glu Phe Pro Asn Ile
            290                 295                 300

Phe Lys Thr Leu Gln Asn Leu Glu His Ile Asp Ile Ser Asn Asn Leu
305                 310                 315                 320

Ile Lys Gly Lys Val Pro Glu Trp Phe Trp Lys Leu Pro Arg Leu Ser
            325                 330                 335

Ile Ala Asn Leu Val Asn Asn Ser Leu Thr Gly Phe Glu Gly Ser Ser
            340                 345                 350

Glu Val Leu Leu Asn Ser Ser Val Gln Leu Leu Asp Phe Ala Tyr Asn
            355                 360                 365

Ser Met Thr Gly Ala Phe Pro Thr Pro Leu Gly Ser Ile Tyr Leu
            370                 375                 380

Ser Ala Trp Asn Asn Ser Phe Thr Gly Asn Ile Pro Leu Ser Ile Cys
385                 390                 395                 400

Asn Arg Ser Ser Leu Ile Val Leu Asp Leu Ser Tyr Asn Lys Phe Thr
            405                 410                 415

Gly Pro Ile Pro Gln Cys Leu Ser Asn Leu Lys Val Val Asn Leu Arg
            420                 425                 430

Lys Asn Ser Leu Glu Gly Ser Ile Pro Asp Glu Phe His Ser Gly Ala
            435                 440                 445

Lys Thr Gln Thr Leu Asp Val Gly Tyr Asn Arg Leu Thr Gly Lys Leu
            450                 455                 460

Pro Lys Ser Leu Leu Asn Cys Ser Ser Leu Arg Phe Leu Ser Val Asp
465                 470                 475                 480

Asn Asn Arg Ile Glu Asp Thr Phe Pro Phe Trp Leu Lys Ala Leu Pro
            485                 490                 495

Asn Leu His Val Leu Thr Leu Arg Ser Asn Arg Phe Gly His Leu
            500                 505                 510

Ser Pro Pro Asp Arg Gly Pro Leu Ala Phe Pro Glu Leu Arg Ile Leu
            515                 520                 525

Glu Leu Ser Asp Asn Ser Phe Thr Gly Ser Leu Pro Pro Asn Phe Phe
            530                 535                 540

Val Asn Trp Lys Ala Ser Ser Pro Lys Ile Asn Glu Asp Gly Arg Ile
545                 550                 555                 560
```

```
Tyr Met Gly Asp Tyr Lys Asn Ala Tyr Tyr Ile Tyr Glu Asp Thr Met
            565                 570                 575
Asp Leu Gln Tyr Lys Gly Leu Phe Met Glu Gln Gly Lys Val Leu Thr
        580                 585                 590
Phe Tyr Ser Thr Ile Asp Phe Ser Gly Asn Lys Leu Glu Gly Gln Ile
            595                 600                 605
Pro Glu Ser Ile Gly Leu Leu Lys Glu Leu Ile Ala Leu Asn Leu Ser
    610                 615                 620
Asn Asn Ala Phe Thr Gly His Ile Pro Met Ser Leu Ala Asn Val Thr
625                 630                 635                 640
Glu Leu Glu Ser Leu Asp Leu Ser Arg Asn Gln Leu Ser Gly Asn Ile
            645                 650                 655
Pro Arg Glu Leu Gly Ser Leu Ser Phe Leu Ala Tyr Ile Ser Val Ala
                660                 665                 670
His Asn Gln Leu Lys Gly Glu Ile Pro Gln Gly Pro Gln Phe Ser Gly
            675                 680                 685
Gln Ala Glu Ser Ser Phe Glu Gly Asn Val Gly Leu Cys Gly Leu Pro
    690                 695                 700
Leu Gln Gly Ser Cys Val Ala Pro Pro Thr Lys Tyr Pro Lys Glu Glu
705                 710                 715                 720
Asp Glu Glu Glu Glu Asp Glu Val Ile Glu Trp Lys Ala Val Phe
                725                 730                 735
Phe Gly Tyr Trp Pro Gly Leu Leu Leu Gly Leu Val Met Ala His Val
            740                 745                 750
Ile Ala Ser Phe Lys Pro Lys Trp Phe Val Lys Ile Leu Gly Pro Ala
            755                 760                 765
Lys Gly Lys Gln Val Asp Pro Val Arg Leu Phe Met Asn Leu Asp Ser
    770                 775                 780
Arg Trp Asp Ser Phe Asn Asn Lys Asp Thr Val Glu Glu Val Ile
785                 790                 795                 800

<210> SEQ ID NO 42
<211> LENGTH: 2427
<212> TYPE: DNA
<213> ORGANISM: Arabidopsis thaliana
<220> FEATURE:
<221> NAME/KEY: CDS
<222> LOCATION: (1)..(2427)

<400> SEQUENCE: 42 atg tta ttc ttc ata aaa gtt ttc atg aag acc ata ctg tcg gtg ctc      48
Met Leu Phe Phe Ile Lys Val Phe Met Lys Thr Ile Leu Ser Val Leu
1               5                   10                  15 tta ctg ttt ttt atc ttt gct tca agc ttc act ctt gtt gtt gga ctt      96
Leu Leu Phe Phe Ile Phe Ala Ser Ser Phe Thr Leu Val Val Gly Leu
            20                  25                  30 gct ggt tgt cgt ccc gat cag att caa gca ctg aca cag ttc aaa aac     144
Ala Gly Cys Arg Pro Asp Gln Ile Gln Ala Leu Thr Gln Phe Lys Asn
        35                  40                  45 gag ttt gat tcc agc gat tgc aac caa act gac tac ttc aat gga gtc     192
Glu Phe Asp Ser Ser Asp Cys Asn Gln Thr Asp Tyr Phe Asn Gly Val
    50                  55                  60 cag tgc gat aac aag acc ggt gtg gtc aca aag cta caa ctc cca agt     240
Gln Cys Asp Asn Lys Thr Gly Val Val Thr Lys Leu Gln Leu Pro Ser
65                  70                  75                  80 ggc tgc ctt cat gga tct atg aag cct aac agt agc ctc ttc gga ttg     288
Gly Cys Leu His Gly Ser Met Lys Pro Asn Ser Ser Leu Phe Gly Leu
                85                  90                  95
```

```
cag cat ctt cgt tac ctt aat ctc tca aat aac aac ttc acc tct gct      336
Gln His Leu Arg Tyr Leu Asn Leu Ser Asn Asn Asn Phe Thr Ser Ala
        100                 105                 110 tcg ctc cct tct gga ttt gga aat ctc aac aga tta gag gtc ttg tat      384
Ser Leu Pro Ser Gly Phe Gly Asn Leu Asn Arg Leu Glu Val Leu Tyr
        115                 120                 125 ctt tcc tct aat ggc ttt cta ggt caa gtt cct tcc tca ttt agt aac      432
Leu Ser Ser Asn Gly Phe Leu Gly Gln Val Pro Ser Ser Phe Ser Asn
130                 135                 140 ctt agc cag ctt aac att tta gac ctt tcc cat aat gag ctc acg ggt      480
Leu Ser Gln Leu Asn Ile Leu Asp Leu Ser His Asn Glu Leu Thr Gly
145                 150                 155                 160 agt ttc cca ttt gta caa aat cta acc aaa ctc tcg att tta gtg ctt      528
Ser Phe Pro Phe Val Gln Asn Leu Thr Lys Leu Ser Ile Leu Val Leu
                165                 170                 175 tcc tat aat cac ttc tct gga acc atc cct tct tct ctc ctc act ttg      576
Ser Tyr Asn His Phe Ser Gly Thr Ile Pro Ser Ser Leu Leu Thr Leu
            180                 185                 190 cct ttc tta tca tct ctt gat ctg cgt gaa aac tat ctc act ggt tct      624
Pro Phe Leu Ser Ser Leu Asp Leu Arg Glu Asn Tyr Leu Thr Gly Ser
        195                 200                 205 att gaa gct cct aac tcc tct acg tca tct agg ctt gag ttc atg tac      672
Ile Glu Ala Pro Asn Ser Ser Thr Ser Ser Arg Leu Glu Phe Met Tyr
210                 215                 220 ctt ggg aat aac cat ttt gaa gga caa atc cta gag cct atc tca aag      720
Leu Gly Asn Asn His Phe Glu Gly Gln Ile Leu Glu Pro Ile Ser Lys
225                 230                 235                 240 ctc atc aac ctc aag cat ctc gac ctc tct ttc cta aaa aca agc tac      768
Leu Ile Asn Leu Lys His Leu Asp Leu Ser Phe Leu Lys Thr Ser Tyr
                245                 250                 255 cca att gac tta aac ctt ttc tcc tct ttc aaa tct ttg gtg agg ctt      816
Pro Ile Asp Leu Asn Leu Phe Ser Ser Phe Lys Ser Leu Val Arg Leu
            260                 265                 270 gtt ctt tcc ggt aat agt tta ttg gct act agt ata act tca gat tcc      864
Val Leu Ser Gly Asn Ser Leu Leu Ala Thr Ser Ile Thr Ser Asp Ser
        275                 280                 285 aag atc cca ctg aac ttg gag aat ttg gtc ttg tta agt tgc ggc ctc      912
Lys Ile Pro Leu Asn Leu Glu Asn Leu Val Leu Leu Ser Cys Gly Leu
290                 295                 300 att gag ttc cca acc atc tta aag aac ctt acg aaa ttg gag cat ata      960
Ile Glu Phe Pro Thr Ile Leu Lys Asn Leu Thr Lys Leu Glu His Ile
305                 310                 315                 320 gac ctt tcc aac aat aaa ata aaa ggg aaa gtc cct gag tgg ttt tgg     1008
Asp Leu Ser Asn Asn Lys Ile Lys Gly Lys Val Pro Glu Trp Phe Trp
                325                 330                 335 aac ctt cct cgt ctc cgc aga gtg aat ctt ttt aac aat ttg ttc acc     1056
Asn Leu Pro Arg Leu Arg Arg Val Asn Leu Phe Asn Asn Leu Phe Thr
            340                 345                 350 gat tta gaa ggt tcg gag gaa gtt tta gtg aat tca tcg gtg agg ctt     1104
Asp Leu Glu Gly Ser Glu Glu Val Leu Val Asn Ser Ser Val Arg Leu
        355                 360                 365 tta gat ttg gct tat aac cat ttt aga gga cca ttt cct aaa cca cca     1152
Leu Asp Leu Ala Tyr Asn His Phe Arg Gly Pro Phe Pro Lys Pro Pro
370                 375                 380 ctc tct atc aac ctc tta tct gca tgg aac aat agt ttc aca gga aac     1200
Leu Ser Ile Asn Leu Leu Ser Ala Trp Asn Asn Ser Phe Thr Gly Asn
385                 390                 395                 400 ata cct ctt gaa acc tgc aac cga agc tct ctt gct att ctt gac cta     1248
Ile Pro Leu Glu Thr Cys Asn Arg Ser Ser Leu Ala Ile Leu Asp Leu
```

-continued

```
                405                 410                 415
tcc tac aac aac tta acc ggt cca att cct cga tgt ttg agt gat ttc    1296
Ser Tyr Asn Asn Leu Thr Gly Pro Ile Pro Arg Cys Leu Ser Asp Phe
        420                 425                 430 caa gag tct ctc att gta gtg aac ctc cgg aag aac aac ttg gaa ggc    1344
Gln Glu Ser Leu Ile Val Val Asn Leu Arg Lys Asn Asn Leu Glu Gly
            435                 440                 445 agt ctt cca gat ata ttt tct gat ggt gcc ttg ctt cgg aca ctt gac    1392
Ser Leu Pro Asp Ile Phe Ser Asp Gly Ala Leu Leu Arg Thr Leu Asp
450                 455                 460 gtt ggc tac aat caa cta acc ggg aag ctt cca agg tct ctt ctg aat    1440
Val Gly Tyr Asn Gln Leu Thr Gly Lys Leu Pro Arg Ser Leu Leu Asn
465                 470                 475                 480 tgc tcc atg cta agg ttt gta agt gta gac cac aac aaa atc aaa gac    1488
Cys Ser Met Leu Arg Phe Val Ser Val Asp His Asn Lys Ile Lys Asp
                485                 490                 495 aca ttt cct ttc tgg ctt aag gct ttg cct gat tta caa gca ctt acc    1536
Thr Phe Pro Phe Trp Leu Lys Ala Leu Pro Asp Leu Gln Ala Leu Thr
            500                 505                 510 ctc cgt tca aac aaa ttc cat ggc cct ata tct cct cct gat cga ggt    1584
Leu Arg Ser Asn Lys Phe His Gly Pro Ile Ser Pro Pro Asp Arg Gly
        515                 520                 525 cct ctt gcg ttt ccc aag ctg cgc ata ctt gaa ata tca gat aac aac    1632
Pro Leu Ala Phe Pro Lys Leu Arg Ile Leu Glu Ile Ser Asp Asn Asn
530                 535                 540 ttt aca gga agc ttg cca cca aat tac ttt gtg aat tgg gaa gca tca    1680
Phe Thr Gly Ser Leu Pro Pro Asn Tyr Phe Val Asn Trp Glu Ala Ser
545                 550                 555                 560 tca ctc cag atg aat gaa gat ggg aga atc tat atg gga gac tac aac    1728
Ser Leu Gln Met Asn Glu Asp Gly Arg Ile Tyr Met Gly Asp Tyr Asn
                565                 570                 575 aat cct tac tat atc tac gaa gat aca gtg gat ttg caa tac aaa ggt    1776
Asn Pro Tyr Tyr Ile Tyr Glu Asp Thr Val Asp Leu Gln Tyr Lys Gly
            580                 585                 590 cta ttc atg gag caa gga aag gtc ctt act tcc tat gcc acc att gat    1824
Leu Phe Met Glu Gln Gly Lys Val Leu Thr Ser Tyr Ala Thr Ile Asp
        595                 600                 605 ttt tct ggg aac aaa ctt gaa gga cag att ccc gaa tcc att ggt ctt    1872
Phe Ser Gly Asn Lys Leu Glu Gly Gln Ile Pro Glu Ser Ile Gly Leu
610                 615                 620 ttg aag gca ttg att gca ctc aac tta tca aac aac gca ttc aca ggc    1920
Leu Lys Ala Leu Ile Ala Leu Asn Leu Ser Asn Asn Ala Phe Thr Gly
625                 630                 635                 640 cat att cct ctg tct ttg gca aac gtg aca gag ctg gag tca cta gac    1968
His Ile Pro Leu Ser Leu Ala Asn Val Thr Glu Leu Glu Ser Leu Asp
                645                 650                 655 ctc tca aga aac caa ctc tca ggg act att cct aat gga ctg aag acc    2016
Leu Ser Arg Asn Gln Leu Ser Gly Thr Ile Pro Asn Gly Leu Lys Thr
            660                 665                 670 ctc tcg ttt ttg gcg tac ata agt gtg gcc cat aac caa ctc ata ggt    2064
Leu Ser Phe Leu Ala Tyr Ile Ser Val Ala His Asn Gln Leu Ile Gly
        675                 680                 685 gaa att cca caa ggg aca caa atc act ggg caa tct aaa tcc tcc ttt    2112
Glu Ile Pro Gln Gly Thr Gln Ile Thr Gly Gln Ser Lys Ser Ser Phe
690                 695                 700 gaa ggg aat gca ggt ctt tgt ggt ctt cct ctc caa gga agt tgc ttt    2160
Glu Gly Asn Ala Gly Leu Cys Gly Leu Pro Leu Gln Gly Ser Cys Phe
705                 710                 715                 720 gcg cca cca aca cca cag cca aag gaa gaa gac gaa gat gaa gaa gtg    2208
```

| | | | | | | | | | | | | |
|---|---|---|---|---|---|---|---|---|---|---|---|---|
| Ala | Pro | Pro | Thr | Pro | Gln | Pro | Lys | Glu | Glu | Asp | Glu | Val |
| | | | 725 | | | | 730 | | | | 735 | |

```
tta aac tgg aaa gca gtg gtt ata ggg tat tgg cct gga ctg tta ctt    2256
Leu Asn Trp Lys Ala Val Val Ile Gly Tyr Trp Pro Gly Leu Leu Leu
        740                 745                 750 gga ttg ata atg gca cac gtt att gct tca ttc aag ccg aag tgg tta    2304
Gly Leu Ile Met Ala His Val Ile Ala Ser Phe Lys Pro Lys Trp Leu
            755                 760                 765 gtc aag ata gtt ggt ccg gag aag cgc aag gaa gac aat cca gtt aga    2352
Val Lys Ile Val Gly Pro Glu Lys Arg Lys Glu Asp Asn Pro Val Arg
    770                 775                 780 ttg ttt atg act ctg gat tca aga tgg gat agt ttt aat aat aag aag    2400
Leu Phe Met Thr Leu Asp Ser Arg Trp Asp Ser Phe Asn Asn Lys Lys
785                 790                 795                 800 aac gta gaa caa aaa agt gat atg taa                                2427
Asn Val Glu Gln Lys Ser Asp Met
                805
```

<210> SEQ ID NO 43
<211> LENGTH: 808
<212> TYPE: PRT
<213> ORGANISM: Arabidopsis thaliana

<400> SEQUENCE: 43

```
Met Leu Phe Phe Ile Lys Val Phe Met Lys Thr Ile Leu Ser Val Leu
1               5                   10                  15

Leu Leu Phe Phe Ile Phe Ala Ser Ser Phe Thr Leu Val Val Gly Leu
            20                  25                  30

Ala Gly Cys Arg Pro Asp Gln Ile Gln Ala Leu Thr Gln Phe Lys Asn
        35                  40                  45

Glu Phe Asp Ser Ser Asp Cys Asn Gln Thr Asp Tyr Phe Asn Gly Val
    50                  55                  60

Gln Cys Asp Asn Lys Thr Gly Val Val Thr Lys Leu Gln Leu Pro Ser
65                  70                  75                  80

Gly Cys Leu His Gly Ser Met Lys Pro Asn Ser Ser Leu Phe Gly Leu
                85                  90                  95

Gln His Leu Arg Tyr Leu Asn Leu Ser Asn Asn Phe Thr Ser Ala
            100                 105                 110

Ser Leu Pro Ser Gly Phe Gly Asn Leu Asn Arg Leu Glu Val Leu Tyr
        115                 120                 125

Leu Ser Ser Asn Gly Phe Leu Gly Gln Val Pro Ser Ser Phe Ser Asn
    130                 135                 140

Leu Ser Gln Leu Asn Ile Leu Asp Leu Ser His Asn Glu Leu Thr Gly
145                 150                 155                 160

Ser Phe Pro Phe Val Gln Asn Leu Thr Lys Leu Ser Ile Leu Val Leu
                165                 170                 175

Ser Tyr Asn His Phe Ser Gly Thr Ile Pro Ser Ser Leu Leu Thr Leu
            180                 185                 190

Pro Phe Leu Ser Ser Leu Asp Leu Arg Glu Asn Tyr Leu Thr Gly Ser
        195                 200                 205

Ile Glu Ala Pro Asn Ser Ser Thr Ser Ser Arg Leu Glu Phe Met Tyr
    210                 215                 220

Leu Gly Asn Asn His Phe Glu Gly Gln Ile Leu Glu Pro Ile Ser Lys
225                 230                 235                 240

Leu Ile Asn Leu Lys His Leu Asp Leu Ser Phe Leu Lys Thr Ser Tyr
                245                 250                 255
```

-continued

```
Pro Ile Asp Leu Asn Leu Phe Ser Ser Phe Lys Ser Leu Val Arg Leu
            260                 265                 270

Val Leu Ser Gly Asn Ser Leu Leu Ala Thr Ser Ile Thr Ser Asp Ser
        275                 280                 285

Lys Ile Pro Leu Asn Leu Glu Asn Leu Val Leu Leu Ser Cys Gly Leu
        290                 295                 300

Ile Glu Phe Pro Thr Ile Leu Lys Asn Leu Thr Lys Leu Glu His Ile
305                 310                 315                 320

Asp Leu Ser Asn Asn Lys Ile Lys Gly Lys Val Pro Glu Trp Phe Trp
                325                 330                 335

Asn Leu Pro Arg Leu Arg Arg Val Asn Leu Phe Asn Asn Leu Phe Thr
            340                 345                 350

Asp Leu Glu Gly Ser Glu Val Leu Val Asn Ser Ser Val Arg Leu
            355                 360                 365

Leu Asp Leu Ala Tyr Asn His Phe Arg Gly Pro Phe Pro Lys Pro Pro
    370                 375                 380

Leu Ser Ile Asn Leu Leu Ser Ala Trp Asn Asn Ser Phe Thr Gly Asn
385                 390                 395                 400

Ile Pro Leu Glu Thr Cys Asn Arg Ser Ser Leu Ala Ile Leu Asp Leu
            405                 410                 415

Ser Tyr Asn Asn Leu Thr Gly Pro Ile Pro Arg Cys Leu Ser Asp Phe
            420                 425                 430

Gln Glu Ser Leu Ile Val Val Asn Leu Arg Lys Asn Asn Leu Glu Gly
            435                 440                 445

Ser Leu Pro Asp Ile Phe Ser Asp Gly Ala Leu Leu Arg Thr Leu Asp
    450                 455                 460

Val Gly Tyr Asn Gln Leu Thr Gly Lys Leu Pro Arg Ser Leu Leu Asn
465                 470                 475                 480

Cys Ser Met Leu Arg Phe Val Ser Val Asp His Asn Lys Ile Lys Asp
            485                 490                 495

Thr Phe Pro Phe Trp Leu Lys Ala Leu Pro Asp Leu Gln Ala Leu Thr
            500                 505                 510

Leu Arg Ser Asn Lys Phe His Gly Pro Ile Ser Pro Asp Arg Gly
    515                 520                 525

Pro Leu Ala Phe Pro Lys Leu Arg Ile Leu Glu Ile Ser Asp Asn Asn
    530                 535                 540

Phe Thr Gly Ser Leu Pro Pro Asn Tyr Phe Val Asn Trp Glu Ala Ser
545                 550                 555                 560

Ser Leu Gln Met Asn Glu Asp Gly Arg Ile Tyr Met Gly Asp Tyr Asn
            565                 570                 575

Asn Pro Tyr Tyr Ile Tyr Glu Asp Thr Val Asp Leu Gln Tyr Lys Gly
            580                 585                 590

Leu Phe Met Glu Gln Gly Lys Val Leu Thr Ser Tyr Ala Thr Ile Asp
        595                 600                 605

Phe Ser Gly Asn Lys Leu Glu Gly Gln Ile Pro Glu Ser Ile Gly Leu
    610                 615                 620

Leu Lys Ala Leu Ile Ala Leu Asn Leu Ser Asn Asn Ala Phe Thr Gly
625                 630                 635                 640

His Ile Pro Leu Ser Leu Ala Asn Val Thr Glu Leu Glu Ser Leu Asp
                645                 650                 655

Leu Ser Arg Asn Gln Leu Ser Gly Thr Ile Pro Asn Gly Leu Lys Thr
            660                 665                 670

Leu Ser Phe Leu Ala Tyr Ile Ser Val Ala His Asn Gln Leu Ile Gly
```

```
              675                 680                 685
Glu Ile Pro Gln Gly Thr Gln Ile Thr Gly Gln Ser Lys Ser Ser Phe
        690                 695                 700

Glu Gly Asn Ala Gly Leu Cys Gly Leu Pro Leu Gln Gly Ser Cys Phe
705                 710                 715                 720

Ala Pro Pro Thr Pro Gln Pro Lys Glu Glu Asp Glu Asp Glu Glu Val
                725                 730                 735

Leu Asn Trp Lys Ala Val Val Ile Gly Tyr Trp Pro Gly Leu Leu Leu
            740                 745                 750

Gly Leu Ile Met Ala His Val Ile Ala Ser Phe Lys Pro Lys Trp Leu
        755                 760                 765

Val Lys Ile Val Gly Pro Glu Lys Arg Lys Glu Asp Asn Pro Val Arg
    770                 775                 780

Leu Phe Met Thr Leu Asp Ser Arg Trp Asp Ser Phe Asn Asn Lys Lys
785                 790                 795                 800

Asn Val Glu Gln Lys Ser Asp Met
                805
```

<210> SEQ ID NO 44
<211> LENGTH: 25
<212> TYPE: DNA
<213> ORGANISM: Artificial Sequence
<220> FEATURE:
<223> OTHER INFORMATION: Synthetic DNA

<400> SEQUENCE: 44
tgctttcgcc attaaatagc gacgg                                    25

<210> SEQ ID NO 45
<211> LENGTH: 23
<212> TYPE: DNA
<213> ORGANISM: Artificial Sequence
<220> FEATURE:
<223> OTHER INFORMATION: Synthetic DNA

<400> SEQUENCE: 45
cgctgcggac atctacattt ttg                                      23

<210> SEQ ID NO 46
<211> LENGTH: 22
<212> TYPE: DNA
<213> ORGANISM: Artificial Sequence
<220> FEATURE:
<223> OTHER INFORMATION: Synthetic DNA

<400> SEQUENCE: 46
tcccggacat gaagccattt ac                                       22

<210> SEQ ID NO 47
<211> LENGTH: 16
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 47

```
ngtcgaswga nawgaa                                                   16

<210> SEQ ID NO 48
<211> LENGTH: 538
<212> TYPE: DNA
<213> ORGANISM: Arabidopsis thaliana

<400> SEQUENCE: 48
cgatgcttgt ccatatccaa acatttcagc catttagtgc tctcactaaa catctttaa    60 caaaatatga ataacattc ccaaaattgc gatcaaaagg ctagaaacat cttcaacaat   120
tatgacagtc ctaaaccaac agttcaaaca cgttttatat ctgtttggcc aaattaaacg   180
aatataacat aaaaatacga ttgatcttag acaattacta aagtttctaa ataataatct   240
atactttcac aaaacaagaa atacaaattg attcttgcgc agaaagtgct ttggtaccta   300 cttttttac caccttcct tttcaattga gacatcaaca cattcactaa aacaaactct     360
caaactgctc taaacgacac cgtttagtta cagataactt tacttgtatt taaagtcacc   420
aaaagtttga attttttattt gtgccttcca caaagcttta agcttaaaca cagtcaatgg   480
ccgtccttcc gccataaaag gacaaaaaaa aagcttccct cttttcacaa aaccctaa     538

<210> SEQ ID NO 49
<211> LENGTH: 311
<212> TYPE: DNA
<213> ORGANISM: Arabidopsis thaliana
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t

<400> SEQUENCE: 49
gaatcctgtc cgtctgttaa ccacatttta taatagttcc attatcgacg aaaaaacntg    60
tcttgattnc tactttgaca aacctgtgag agtaagtcac aaaacaaata ttcttcagac   120 aatgttttg ataagatttt gataagcata tgattcttgg acaggttagt ggtgacatac    180
gcatcacatt ctaccagaaa atgattggaa gccgcctttt ttatacttgc ttcaacacag   240
cttttataac caatggctta cttcaggtaa agaattctcc agatgcctca aactcattct   300
tctcactcga c                                                         311

<210> SEQ ID NO 50
<211> LENGTH: 498
<212> TYPE: DNA
<213> ORGANISM: Arabidopsis thaliana
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 50
taaccttacg ctttgctcgg tcccagacgc aagattacat ctctttctat ggnttgagat    60
cgnacggacg gctgtttgag gacggtccaa ttgccactag ccagatttac gtgcatagca   120
agttaatgat tgttgatgac cggatcgcag tgatcggatc ttctaatata aacgatagga   180
```

-continued

| | |
|---|---|
| gcttactagg ttcacgagac tctgaggtac tttcaaaaat ccaattcatt ctttattgca | 240 |
| gcaaaacaga gttatgtatt catttgaatc aatcatgttt cagatcggtg ttgtgattga | 300 |
| agacaaagaa ttcgtggaat cttcgatgaa cggaatgaag tggatggccg ggaagttctc | 360 |
| ttacagtctt agatgttcct tgtggtcaga gcatctcggc cttcacgccg agaggtaat | 420 |
| tttaaaaaat ttctagaaac gcctactact atacatttt gacttcagaa acctttattt | 480 |
| tcatctcact cgaccaaa | 498 |

```
<210> SEQ ID NO 51
<211> LENGTH: 633
<212> TYPE: DNA
<213> ORGANISM: Arabidopsis thaliana
<220> FEATURE:
<221> NAME/KEY: misc_feature
<222> LOCATION: (56)..(57)
<223> OTHER INFORMATION: n is a, c, g, or t

<400> SEQUENCE: 51
```

| | |
|---|---|
| tctttggtct gttgatgaga ctctagttgc ggattgcagt gaggtataag catagnncca | 60 |
| cagccggtta atattaaatg gagatgaata tgtaattaac acggtttcgt ctgaccgatt | 120 |
| caccagagtc tccggttagt tcattaaggg tttgctcaaa cgctttctcc tctgcttccc | 180 |
| taatttcgga acattcgcc tgattttctg agattttgga atttcttcga attgattgcc | 240 |
| atgctgagct caagatttcg actgctgaaa tcgaggcgac ttgcggagcc acctccggct | 300 |
| gatgtcgcgg ttatgtgtat ttgcaggaaa tgaaagtgat ctccttattg cggcaaatca | 360 |
| gccacttcct gtcgactaaa actgtggtgc agcatgtaag aacaaatgca agttcggaca | 420 |
| aacgtgttgt cttggtcagt ggttttactt ggcttagtct tcgattctct acgcgtttca | 480 |
| gcgtcaagtt ttctagatct ctaaagcttt cgtgctcgcc gatataaatc tctaatatcg | 540 |
| gtcccgtaag atcgaattag attcgcgtcg tttttaagg aaccaaaata atggcgcaac | 600 |
| aatcgttgtt ctacagtttc atcctcactc gac | 633 |

```
<210> SEQ ID NO 52
<211> LENGTH: 244
<212> TYPE: DNA
<213> ORGANISM: Arabidopsis thaliana
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (147)..(148)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
```

```
<220> FEATURE:
<221> NAME/KEY: misc_feature
<222> LOCATION: (244)..(244)
<223> OTHER INFORMATION: n is a, c, g, or t

<400> SEQUENCE: 52
tcctgagtcc tagttacatt tatanaaata taatccattt acaattgaat tcnttgtagc      60
aaanggataa tagttaggca ttagagtcac taggtagtct aggttcacaa catggnacat    120
accatgcgac gtaggtaatg gccatannag cacgaagcaa gagctaccat aaggacgccc    180
gataccacgc cgatgtattc tgtcaaatga tacatgtcca tcttcttgtt catctcncnc    240 gacn                                                                  244

<210> SEQ ID NO 53
<211> LENGTH: 42
<212> TYPE: DNA
<213> ORGANISM: Artificial Sequence
<220> FEATURE:
<223> OTHER INFORMATION: Synthetic DNA

<400> SEQUENCE: 53
acgcgtcgac ccatcatgaa aacgatctca atcttcttcg tc                        42

<210> SEQ ID NO 54
<211> LENGTH: 38
<212> TYPE: DNA
<213> ORGANISM: Artificial Sequence
<220> FEATURE:
<223> OTHER INFORMATION: Synthetic DNA

<400> SEQUENCE: 54
tgtacatgta caagtgagaa cggtagataa gtaagtgg                             38

<210> SEQ ID NO 55
<211> LENGTH: 38
<212> TYPE: DNA
<213> ORGANISM: Artificial Sequence
<220> FEATURE:
<223> OTHER INFORMATION: Synthetic DNA

<400> SEQUENCE: 55
acgcgtcgac caaacgacgt atctcataag tcgacgca                             38

<210> SEQ ID NO 56
<211> LENGTH: 38
<212> TYPE: DNA
<213> ORGANISM: Artificial Sequence
<220> FEATURE:
<223> OTHER INFORMATION: Synthetic DNA

<400> SEQUENCE: 56
tgtacatgta caggagaact ttgaagatca tcgagagg                             38

<210> SEQ ID NO 57
<211> LENGTH: 33
<212> TYPE: DNA
<213> ORGANISM: Artificial Sequence
<220> FEATURE:
<223> OTHER INFORMATION: Synthetic DNA

<400> SEQUENCE: 57
acgcgtcgac ccatcacaca cacatacaca cac                                  33

<210> SEQ ID NO 58
```

```
<211> LENGTH: 43
<212> TYPE: DNA
<213> ORGANISM: Artificial Sequence
<220> FEATURE:
<223> OTHER INFORMATION: Synthetic DNA

<400> SEQUENCE: 58
tgtacatgta cacagcgtaa atgaagaaca ccccaaactg aac          43

<210> SEQ ID NO 59
<211> LENGTH: 35
<212> TYPE: DNA
<213> ORGANISM: Artificial Sequence
<220> FEATURE:
<223> OTHER INFORMATION: Synthetic DNA

<400> SEQUENCE: 59
acgcgtcgac atgtcaggat cacatctgcg tttgc                    35

<210> SEQ ID NO 60
<211> LENGTH: 35
<212> TYPE: DNA
<213> ORGANISM: Artificial Sequence
<220> FEATURE:
<223> OTHER INFORMATION: Synthetic DNA

<400> SEQUENCE: 60
tgtacatgta catcagcact tgctcctgtt cttcg                    35

<210> SEQ ID NO 61
<211> LENGTH: 31
<212> TYPE: DNA
<213> ORGANISM: Artificial Sequence
<220> FEATURE:
<223> OTHER INFORMATION: Synthetic DNA

<400> SEQUENCE: 61
acgcgtcgac atggagtcga gttatgtggt g                        31

<210> SEQ ID NO 62
<211> LENGTH: 23
<212> TYPE: DNA
<213> ORGANISM: Artificial Sequence
<220> FEATURE:
<223> OTHER INFORMATION: Synthetic DNA

<400> SEQUENCE: 62
ccggaatagg accggagaag ctg                                 23

<210> SEQ ID NO 63
<211> LENGTH: 23
<212> TYPE: DNA
<213> ORGANISM: Artificial Sequence
<220> FEATURE:
<223> OTHER INFORMATION: Synthetic DNA

<400> SEQUENCE: 63
cagcttctcc ggtcctattc cgg                                 23

<210> SEQ ID NO 64
<211> LENGTH: 26
<212> TYPE: DNA
<213> ORGANISM: Artificial Sequence
<220> FEATURE:
<223> OTHER INFORMATION: Synthetic DNA

<400> SEQUENCE: 64
```

```
catcactcgc cacttgtagc tcccgc                                          26

<210> SEQ ID NO 65
<211> LENGTH: 26
<212> TYPE: DNA
<213> ORGANISM: Artificial Sequence
<220> FEATURE:
<223> OTHER INFORMATION: Synthetic DNA

<400> SEQUENCE: 65
gcgggagcta caagtggcga gtgatg                                          26

<210> SEQ ID NO 66
<211> LENGTH: 30
<212> TYPE: DNA
<213> ORGANISM: Artificial Sequence
<220> FEATURE:
<223> OTHER INFORMATION: Synthetic DNA

<400> SEQUENCE: 66
tgtacatgta cagtagcaaa acagcggagt                                      30
```

GENE CAPABLE OF IMPARTING ENVIRONMENTAL STRESS RESISTANCE TO PLANTS AND METHOD FOR UTILIZING THE SAME

CROSS REFERENCE TO RELATED APPLICATIONS

This application is a National Stage of International Application No. PCT/JP2010/006254 filed on Oct. 22, 2010, which claims priority from Japanese Patent Application No. 2009-250524, filed on Oct. 30, 2009, the contents of all of which are incorporated herein by reference in their entirety.

TECHNICAL FIELD

The present invention relates to a plant into which a given gene has been introduced or in which an expression control region of an endogenous gene has been altered, a method for imparting environmental stress resistance to a plant by introducing a given gene thereinto or altering an expression control region of an endogenous gene therein and a method for producing a plant to which environmental stress resistance has been imparted.

BACKGROUND ART

The possibility of plant growth depends on different environmental factors such as temperature, humidity, and concentrations of salts in soil. In some cases, an environment characterized by such factors is suitable for a certain plant but not for other plants. In general, the above factors that would influence plant growth are referred to as environmental stresses. Cases in which a given plant cannot grow or is fatally damaged in an environment characterized by certain environmental stresses are explained by noting that the plant lacks environmental stress resistance. On the other hand, cases in which a plant that can grow in an environment characterized by certain environmental stresses are explained by noting that such plant has environmental stress resistance.

Plants are cultivated for the purpose of using some tissues thereof (e.g., seeds, roots, leaves, or stems) or for the purpose of producing various materials, such as fats and oils. Examples of fats and oils produced from plants that have been heretofore known include soybean oil, sesame oil, olive oil, coconut oil, rice oil, cottonseed oil, sunflower oil, corn oil, safflower oil, palm oil, and rapeseed oil. Such fats and oils are extensively used for household and industrial applications. Also, fats and oils produced from plants are used as raw materials for biodiesel fuel or bioplastic, and the applicability thereof is increasing for alternative energy to petroleum.

If environmental stress resistance can be imparted to a plant, it becomes possible to expand the area in which the plant can grow, allowing the effective use of limited ground space. In particular, an energy crop such as sugarcane is used as a material for biofuel. Therefore, it desirable for such energy crop to gain resistance to a variety of environmental stresses. That is to say, if environmental stress resistance can be imparted to the above energy crop, the energy crop can be cultivated in an area in which the crop cannot be cultivated due to the above described environmental factors. Techniques for imparting environmental stress resistance to plants are described in Patent Documents 1 and 2 and Non-Patent Document 1. Patent Document 1 discloses a method for imparting salt stress resistance to a plant by introducing a gene involved in the synthesis of glycine betaine serving as an osmolyte to the plant. Both Patent Document 2 and Non-Patent Document 1 disclose a method for imparting environmental stress resistance to a plant by introducing a gene encoding a tobacco-derived receptor-like protein into the plant.

In addition, in Patent Document 2 and Non-Patent Document 1, a gene encoding a receptor-like protein is introduced. However, these documents do not disclose examples of gene introduction with the use of a gene encoding a receptor-like protein having a leucine-rich repeat structure or a gene encoding a receptor-like protein kinase having a leucine-rich repeat structure. Further, Non-Patent Documents 2 and 3 report that a receptor-like protein kinase having a leucine-rich repeat structure plays an important role in the reaction to stress.

CITATION LIST

Patent Literature

PTL 1: JP Patent Publication (Kokai) No. 8-266179 A (1996)
PTL 2: JP Patent Publication (Kokai) No. 2001-252084 A
PTL 3: JP Patent Publication (Kohyo) No. 2007-530063 A Non Patent Literature NPL 1: Plant Physiology, February 2003, Vol. 131, pp. 454-462
NPL 2: Plant Physiology, April 2007, Vol. 113, pp. 1203-1212
NPL 3: Plant Cell, April 2005, Vol. 17(4), pp. 1105-1119

SUMMARY OF INVENTION

Technical Problem

It is currently impossible to impart environmental stress resistance to a plant by introducing a gene encoding a receptor-like protein having a leucine-rich repeat structure or a gene encoding a receptor-like protein kinase having a leucine-rich repeat structure into the plant.

Therefore, in view of the above circumstances, it is an object of the present invention to provide a technique for searching for a gene having a novel function of imparting environmental stress resistance to a plant or improving the environmental stress resistance of a plant, thereby allowing environmental stress resistance to be imparted to a plant or allowing the environmental stress resistance of a plant to be improved.

Solution to Problem

In order to attain the above object, the present inventors newly discovered that environmental stress resistance can be imparted to a plant by analyzing many proteins having leucine-rich repeat structures and introducing a specific gene encoding a receptor-like protein having a leucine-rich repeat structure or a specific gene encoding a receptor-like protein kinase having a leucine-rich repeat structure into a plant or altering an expression control region of an endogenous gene. This has led to the completion of the present invention.

Specifically, the plant of the present invention is a plant into which at least one gene has been introduced, such gene being selected from the group consisting of a gene encoding a receptor-like protein having a leucine-rich repeat structure that is selected from a 1st group (including At5g40170, At2g25440, At2g32680, At3g24900, At3g25020, At3g25010, At2g33020, At2g33080, At2g32660, At2g33050, and At2g33060), a gene encoding a receptor-like kinase having a leucine-rich repeat structure that is selected from a 2nd group (including At3g28450, At1g27190, and At1g69990), and a gene encoding a receptor-like kinase having a leucine-rich repeat structure that is selected from a 3rd group (including At3g47570, At3g47580, At3g47090, At3g47110, At5g20480, and At5g39390), or it is a plant in which an expression control region of an endogenous gene has been altered.

In addition, the method for imparting environmental stress resistance to a plant of the present invention comprises introducing at least one gene selected from the group consisting of a gene encoding a receptor-like protein having a leucine-rich repeat structure that is selected from a 1st group (including At5g40170, At2g25440, At2g32680, At3g24900, At3g25020, At3g25010, At2g33020, At2g33080, At2g32660, At2g33050, and At2g33060), a gene encoding a receptor-like kinase having a leucine-rich repeat structure that is selected from a 2nd group (including At3g28450, At1g27190, and At1g69990), and a gene encoding a receptor-like kinase having a leucine-rich repeat structure that is selected from a 3rd group (including At3g47570, At3g47580, At3g47090, At3g47110, At5g20480, and At5g39390), or altering an expression control region of an endogenous gene.

Further, the method for producing a plant of the present invention comprises the steps of: preparing a transformed plant into which at least one gene has been introduced, such gene being selected from the group consisting of a gene encoding a receptor-like protein having a leucine-rich repeat structure that is selected from the 1st group (including At5g40170, At2g25440, At2g32680, At3g24900, At3g25020, At3g25010, At2g33020, At2g33080, At2g32660, At2g33050, and At2g33060), a gene encoding a receptor-like kinase having a leucine-rich repeat structure that is selected from the 2nd group (including At3g28450, At1g27190, and At1g69990), and a gene encoding a receptor-like kinase having a leucine-rich repeat structure that is selected from the 3rd group (including At3g47570, At3g47580, At3g47090, At3g47110, At5g20480, and At5g39390), or a transformed plant in which an expression control region of an endogenous gene has been altered; and evaluating environmental stress resistance of progeny plants of the transformed plant and selecting a line with significantly improved environmental stress resistance.

Here, examples of a gene encoding a receptor-like protein having a leucine-rich repeat structure that is selected from the 1st group include genes specified by At5g40170, At2g25440, At2g32680, At3g24900, At3g25020, At3g25010, At2g33020, At2g33080, At2g32660, At2g33050, and At2g33060 and genes functionally equivalent thereto. Particularly preferably, a gene selected from the 1st group is a gene selected from the group consisting of genes specified by At2g25440, At2g32680, At3g24900, At3g25020, At3g25010, At2g33020, and At2g33080 and genes functionally equivalent thereto. Further preferably, a gene selected from the 1st group is a gene selected from the group consisting of genes specified by At2g33020 and At2g33080 and genes functionally equivalent thereto.

Particularly preferably, a gene encoding a receptor-like protein having a leucine-rich repeat structure that is selected from the 1st group encodes any one of the following proteins (a) to (c):
(a) a protein comprising the amino acid sequence shown in SEQ ID NO: 2;
(b) a protein comprising an amino acid sequence that has a deletion, a substitution, an addition, or an insertion of one or a plurality of amino acids with respect to the amino acid sequence shown in SEQ ID NO: 2 and has a leucine-rich repeat structure and receptor-like activity; and
(c) a protein that is encoded by a polynucleotide hybridizing under stringent conditions to a polynucleotide comprising a nucleotide sequence complementary to the nucleotide sequence shown in SEQ ID NO: 1 and has a leucine-rich repeat structure and receptor-like activity.

In addition, examples of a gene encoding a receptor-like kinase having a leucine-rich repeat structure selected from the 2nd group include genes specified by At3g28450, At1g27190, and At1g69990 and genes functionally equivalent thereto. Particularly preferably, examples of a gene selected from the 2nd group include genes selected from the group consisting of genes specified by At1g27190 and At1g69990 and genes functionally equivalent thereto.

Particularly preferably, a gene encoding a receptor-like kinase having a leucine-rich repeat structure that is selected from the 2nd group is a gene encoding any one of the following proteins (a) to (c):
(a) a protein comprising the amino acid sequence shown in SEQ ID NO: 4;
(b) a protein comprising an amino acid sequence that has a deletion, a substitution, an addition, or an insertion of one or a plurality of amino acids with respect to the amino acid sequence shown in SEQ ID NO: 4 and has a leucine-rich repeat structure and receptor-like kinase activity; and
(c) a protein that is encoded by a polynucleotide hybridizing under stringent conditions to a polynucleotide comprising a nucleotide sequence complementary to the nucleotide sequence shown in SEQ ID NO: 3 and has a leucine-rich repeat structure and receptor-like kinase activity.

Further, examples of a gene encoding a receptor-like kinase having a leucine-rich repeat structure that is selected from the 3rd group include genes specified by At3g47570, At3g47580, At3g47090, At3g47110, At5g20480, and At5g39390 and genes functionally equivalent thereto. Particularly preferable examples of a gene that is selected from the 3rd group include genes specified by At3g47110, At5g20480, and At5g39390 and genes functionally equivalent thereto. Further preferable examples of a gene selected from the 3rd group include genes specified by At5g20480 and At5g39390 and genes functionally equivalent thereto.

Particularly preferably, a gene encoding a receptor-like kinase having a leucine-rich repeat structure that is selected from the 3rd group is a gene encoding any one of the following proteins (a) to (c):
(a) a protein comprising the amino acid sequence shown in SEQ ID NO: 6;
(b) a protein comprising an amino acid sequence that has a deletion, a substitution, an addition, or an insertion of one or a plurality of amino acids with respect to the amino acid sequence shown in SEQ ID NO: 6 and has a leucine-rich repeat structure and receptor-like kinase activity; and
(c) a protein that is encoded by a polynucleotide hybridizing under stringent conditions to a polynucleotide comprising a nucleotide sequence complementary to the nucleotide sequence shown in SEQ ID NO: 5 and has a leucine-rich repeat structure and receptor-like kinase activity.

Examples of plants to be subjected to the present invention include dicotyledons such as plants of the family Brassicaceae. Examples of plants of the family Brassicaceae include *Arabidopsis thaliana* and rapeseed. Other examples of plants to be subjected to the present invention include monocotyledons such as plants of the family Gramineae. Examples of plants of the family Gramineae include rice and sugarcane.

Advantageous Effects of Invention

The plant of the present invention is a plant that exhibits significant improvement over the wild-type plant in terms of resistance to environmental stresses such as salt stress. In addition, according to the method for imparting environmental stress of the present invention, a target plant can exhibit significant improvement over the wild-type plant in terms of environmental stress resistance. Further, according to the method for producing a plant of the present invention, a plant that exhibits significant improvement over the wild-type plant in terms of environmental stress resistance can be produced. Therefore, for example, with the use of the present invention, the plant cultivation conditions can be significantly extended, the production volume can be increased when a plant itself is produced, and the costs of plant production can be reduced.

DESCRIPTION OF EMBODIMENTS

Figure 1:
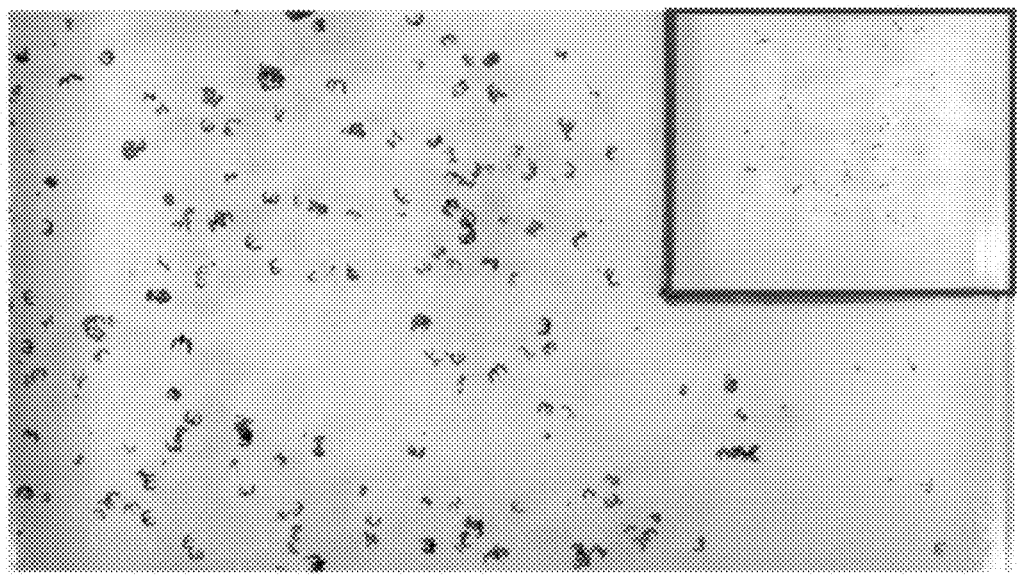
FIG. 1 is a photograph showing the state of germination or growth (in a medium with a high salt concentration) of transformed plants into which a fragment containing ORF of At1g69990 has been introduced and that of wild-type plants.

Hereinafter, the present invention is described in detail.

The plant of the present invention is a plant into which a gene encoding a receptor-like protein (hereinafter abbreviated as LRR-RLP) having a leucine-rich repeat structure, a gene encoding a receptor-like kinase (hereinafter abbreviated as LRR-RLK) having leucine-rich repeat structure, or a gene functionally equivalent to the LRR-RLP gene or the LRR-RLK gene has been introduced or a plant in which an expression control region of an endogenous gene has been altered. This plant exhibits improvement over the wild-type plant in terms of environmental stress resistance. The term "environmental stress" used herein refers to salt stress, high temperature stress, dry stress, and the like. Particularly preferably, the type of environmental stress resistance imparted to the plant of the present invention is salt stress resistance. That is, preferably, the plant of the present invention exhibits improvement over the wild-type plant in terms of salt stress resistance. The improvement of resistance to environmental stresses such as salt stress indicates that a plant can grow under conditions in which there exist environmental stresses that make it impossible or difficult for the wild-type plant to grow.

The expression level of a target gene can be significantly increased to a greater level than that of the wild-type plant with the introduction of an exogenous target gene into the plant or the alteration of an expression control region of an endogenous gene in the target plant. In addition, the LRR-RLP gene, the LRR-RLK gene, or the like described above may be expressed in all plant tissues of the plant of the present invention. It may also be expressed in at least some of the plant tissues. Here, the term "plant tissue(s)" refers to plant organ(s) such as leaves, stems, seeds, roots, and flowers.

In addition, the term "expression control region" includes in its meaning a promoter region for the binding of RNA polymerase and a region for the binding of a different transcription factor. For the alteration of the transcriptional control region, it is preferable to substitute, for example, a promoter region in the endogenous transcriptional control region with a promoter region that can be more highly expressed than the endogenous promoter region.

LRR-RLP Gene

According to the present invention, the LRR-RLP gene comprises a gene encoding a receptor-like protein having a leucine-rich repeat structure, which is selected from the 1st group including a gene specified by At5g40170 (referred as the At5g40170 gene (with the same applying to the following genes)), the At2g25440 gene, the At2g32680 gene, the At3g24900 gene, the At3g25020 gene, the At3g25010 gene, the At2g33020 gene, the At2g33080 gene, the At2g32660 gene, the At2g33050 gene, and the At2g33060 gene. Herein, the term "1st group" refers to a group composed of the group of genes that can be evaluated as being functionally equivalent or identical to the At2g33080 gene introduced into a plant in a manner such that salt stress resistance is improved in the plant as described in the Examples below. The group of genes that can be evaluated as being functionally equivalent or identical to the At2g33080 gene can be searched for or identified using, for example, the SALAD Database.

More specifically, for *Arabidopsis*, examples of LRR-RLP genes included in the 1st group are the At5g40170 gene, the At2g25440 gene, the At2g32680 gene, the At3g24900 gene, the At3g25020 gene, the At3g25010 gene, the At2g33020 gene, the At2g33080 gene, the At2g32660 gene, the At2g33050 gene, and the At2g33060 gene. According to the present invention, at least one gene selected from the above group of genes is introduced or an expression control region of an endogenous gene is altered. In particular, a target gene for gene introduction or alteration of an expression control region of the present invention is preferably the At2g25440 gene, the At2g32680 gene, the At3g24900 gene, the At3g25020 gene, the At3g25010 gene, the At2g33020 gene, or the At2g33080 gene, and more preferably the At2g33020 gene or the At2g33080 gene. According to the present invention, it is particularly preferable to introduce the At2g33080 gene or alter an expression control region of the endogenous At2g33080 gene.

As examples, the nucleotide sequence of the coding region of the At2g33080 gene is shown in SEQ ID NO: 1 and the amino acid sequence of a protein encoded by the At2g33080 gene is shown in SEQ ID NO: 2. In addition, the nucleotide sequences of the coding regions of the following genes are shown in SEQ ID NOS: 24, 26, 28, 30, 32, 34, 36, 38, 40, and 42, respectively: the At5g40170 gene, the At2g25440 gene, the At2g32680 gene, the At3g24900 gene, the At3g25020 gene, the At3g25010 gene, the At2g33020 gene, the At2g32660 gene, the At2g33050 gene, and the At2g33060 gene. The amino acid sequences of encoded proteins are shown in SEQ ID NOS: 25, 27, 29, 31, 33, 35, 37, 39, 41, and 43.

In addition, according to the present invention, a gene functionally equivalent to an above described *Arabidopsis*-derived LRR-RLP gene such as the At2g33080 gene may be introduced or an expression control region of an endogenous gene may be altered. Here, the term "functionally equivalent gene" refers to a gene encoding LRR-RLP that is included in the 1st group and is obtained from a non-*Arabidopsis* organism.

The above described functionally equivalent gene is not particularly limited. Such gene can be identified by searching a database containing gene sequences of a variety of organisms. Specifically, for example, the DDBJ/EMBL/GenBank international nucleotide sequence database or the SWISS-PROT database is searched with the use of the nucleotide sequence shown in SEQ ID NO: 1 or the amino acid sequence shown in SEQ ID NO: 2 as a query sequence. Thus, a target gene can be readily searched for or identified in the database.

Here, the non-*Arabidopsis* organism is not limited. However, an example thereof is rice. Specifically, an example of a functionally equivalent gene is the Os01g0132100 gene from rice. In addition, an example of a functionally equivalent gene from a non-*Arabidopsis* or non-rice plant is a cabbage (*Brassica oleracea*)-derived gene (UniProt database accession no. ACB59218). The nucleotide sequence of the coding region of the Os01g0132100 gene is shown in SEQ ID NO: 7. The amino acid sequence of a protein encoded by the gene is shown in SEQ ID NO: 8. The nucleotide sequence of the coding region of the ACB59218 gene is shown in SEQ ID NO: 9. The amino acid sequence of a protein encoded by the gene is shown in SEQ ID NO: 10.

In addition, according to the present invention, an LRR-RLP gene is not limited to the above described LRR-RLP genes comprising the nucleotide sequences shown in SEQ ID NOS: 1, 7, 9, 24, 26, 28, 30, 32, 34, 36, 38, 40, and 42 and encoding the amino acid sequences shown in SEQ ID NOS: 2, 8, 10, 25, 27, 29, 31, 33, 35, 37, 39, 41, and 43. Hence, the LRR-RLP gene may be a gene that contains an amino acid sequence having a deletion, a substitution, an addition, or an insertion of one or a plurality of amino acids with respect to the amino acid sequences shown in SEQ ID NOS: 2, 8, 10, 25, 27, 29, 31, 33, 35, 37, 39, 41, and 43, and functions as an LRR-RLP gene. Here the term "a plurality of amino acids" refers to 1 to 20, preferably 1 to 10, more preferably 1 to 7, further preferably 1 to 5, and particularly preferably 1 to 3 amino acids, for example. In addition, amino acid deletion, substitution, or addition can be performed by altering a nucleotide sequence encoding the above LRR-RLP gene by a technique known in the art. Mutation can be introduced into a nucleotide sequence by a known technique such as the Kunkel method or the Gapped duplex method or a method based thereof. For example, mutation is introduced with a mutagenesis kit using site-directed mutagenesis (e.g., Mutant-K or Mutant-G (both are trade names of TAKARA Bio)) or the like, or a LA PCR in vitro Mutagenesis series kit (trade name, TAKARA Bio). Also, a mutagenesis method may be: a method using a chemical mutation agent represented by EMS (ethyl methanesulfonate), 5-bromouracil, 2-aminopurine, hydroxylamine, N-methyl-N'-nitro-N nitrosoguanidine, or other carcinogenic compounds; or a method that involves radiation treatment or ultraviolet [UV] treatment typically using X-rays, alpha rays, beta rays, gamma rays, an ion beam, or the like.

Also, LRR-RLP genes may be genes homologous to LRR-RLP genes comprising the nucleotide sequences shown in SEQ ID NOS: 1, 7, and 9 and encoding the amino acid sequences shown in SEQ ID NOS: 2, 8, 10, 25, 27, 29, 31, 33, 35, 37, 39, 41, and 43. Here, the term "homologous gene" generally refers to a gene that has evolutionarily branched off from a common ancestor gene, including a homologous gene (ortholog) of 2 types of species and a homologous gene (paralog) generated by overlapping branching that takes place within the same species. In other words, the above term "functionally equivalent gene" refers to a homologous gene such as an ortholog or a paralog. Furthermore, the above term "functionally equivalent gene" may also refer to a gene that does not evolve from a common gene, but simply has analogous functions.

Examples of genes having functions similar to those of the LRR-RLP genes comprising the nucleotide sequences shown in SEQ ID NOS: 1, 7, 9, 24, 26, 28, 30, 32, 34, 36, 38, 40, and 42 and encoding the amino acid sequences shown in SEQ ID NOS: 2, 8, 10, 25, 27, 29, 31, 33, 35, 37, 39, 41, and 43 include genes encoding proteins having amino acid sequences that have 70% or more, preferably 80% or more, more preferably 90% or more, and most preferably 95% or more similarity to these amino acid sequences and having LRR-RLP activity. Here, the value of similarity refers to a value that can be found based on default setting using a computer mounted with a BLAST (Basic Local Alignment Search Tool) program and a database containing gene sequence information.

Also, genes having functions similar to those of the LRR-RLP genes comprising the nucleotide sequences shown in SEQ ID NOS: 1, 7, 9, 24, 26, 28, 30, 32, 34, 36, 38, 40, and 42 and encoding the amino acid sequences shown in SEQ ID NOS: 2, 8, 10, 25, 27, 29, 31, 33, 35, 37, 39, 41, and 43 can be identified by, when the plant genome information remains unclarified, extracting the genome from a target plant or constructing a cDNA library for a target plant and then isolating a genomic region or cDNA hybridizing under stringent conditions to at least some portions of the LRR-RLP genes comprising the nucleotide sequences shown in SEQ ID NOS: 1, 7, 9, 24, 26, 28, 30, 32, 34, 36, 38, 40, and 42. Here, the term "stringent conditions" refers to conditions under which namely a specific hybrid is formed, but a non-specific hybrid is never formed. For example, such conditions comprise hybridization at 45 degrees C. with 6×SSC (sodium chloride/sodium citrate), followed by washing at 50 degrees C. to 65 degrees C. with 0.2-1×SSC and 0.1% SDS. Alternatively, such conditions comprise hybridization at 65 degrees C. to 70 degrees C. with 1×SSC, followed by washing at 65 degrees C. to 70 degrees C. with 0.3×SSC. Hybridization can be performed by a conventionally known method such as a method described in J. Sambrook et al. Molecular Cloning, A Laboratory Manual, 2nd Ed., Cold Spring Harbor Laboratory (1989).

LRR-RLK Gene

According to the present invention, an LRR-RLK gene comprises a gene encoding a receptor-like kinase having a leucine-rich repeat structure and is selected from the 2nd group including the At3g28450 gene, the At1g27190 gene, and the At1g69990 gene or the 3rd group including the At3g47570 gene, the At3g47580 gene, the At3g47090 gene, the At3g47110 gene, the At5g20480 gene, and the At5g39390 gene.

Here, the term "2nd group" refers to a group composed of the group of genes that can be evaluated as being functionally equivalent or identical to the At1g69990 gene introduced into a plant in a manner such that salt stress resistance can be improved in the plant as described in the Examples below. In addition, the term "3rd group" refers to a group composed of the group of genes that can be evaluated as being functionally equivalent or identical to the Ag5g39390 gene introduced into a plant in a manner such that salt stress resistance is improved in the plant as described in the Examples below. The group of genes that can be evaluated as being functionally equivalent or identical to the At1g69990 gene or the Ag5g39390 gene can be searched for or identified using, for example, the SALAD Database.

More specifically, examples of LRR-RLK genes that are included in the 2nd group for *Arabidopsis* are the At3g28450 gene, the At1g27190 gene, and the At1g69990 gene. According to the present invention, at least one gene selected from the above group of genes is introduced or an expression control region of an endogenous gene is altered. In particular, a target gene for gene introduction or alteration of an expression control region is preferably the At1g27190 gene or the At1g69990 gene. According to the present invention, it is particularly preferable to introduce the At1g69990 gene or alter an expression control region of the endogenous At1g69990 gene.

As examples, the nucleotide sequence of the coding region of the At1g69990 gene is shown in SEQ ID NO: 3 and the amino acid sequence of a protein encoded by the At1g69990 gene is shown in SEQ ID NO: 4.

More specifically, examples of LRR-RLP genes that are included in the 3rd group for *Arabidopsis* are the At3g47570 gene, the At3g47580 gene, the At3g47090 gene, the At3g47110 gene, the At5g20480 gene, and the At5g39390 gene. According to the present invention, at least one gene selected from the above group of genes is introduced or the expression control region of an endogenous gene is modified. In particular, a target gene for gene introduction or alteration of an expression control region is preferably the At3g47110 gene, the At5g20480 gene, or the At5g39390 gene, and more preferably the At5g20480 gene or the At5g39390 gene. According to the present invention, it is particularly preferable to introduce the At5g39390 gene or alter an expression control region of the endogenous At5g39390 gene.

As examples, the nucleotide sequence of the coding region of the At5g39390 gene is shown in SEQ ID NO: 5 and the amino acid sequence of a protein encoded by the At5g39390 gene is shown in SEQ ID NO: 6.

In addition, according to the present invention, a gene functionally equivalent to an above described *Arabidopsis*-derived LRR-RLK gene such as the At1g69990 gene or the At5g39390 gene may be introduced or an expression control region of an endogenous gene may be altered. Here, the term "functionally equivalent gene" refers to a gene encoding LRR-RLK that is included in the 2nd or 3rd group and is obtained from a non-*Arabidopsis* organism.

The above described functionally equivalent gene is not particularly limited. Such gene can be identified by searching a database containing gene sequences of a variety of organisms. Specifically, for example, the DDBJ/EMBL/GenBank international nucleotide sequence database or the SWISS-PROT database is searched with the use of the nucleotide sequence shown in SEQ ID NO: 3 or 5 or the amino acid sequence shown in SEQ ID NO: 4 or 6 as a query sequence. Thus, a target gene can be readily searched for or identified in the database.

Here, the non-*Arabidopsis* organism is not limited. However, an example thereof is rice. Specifically, an example of a functionally equivalent gene of the At1g69990 gene is the Os04g0487200 gene from rice. In addition, examples of functionally equivalent genes of the At1g69990 gene from non-*Arabidopsis* or non-rice plant include a Sitka Spruce (*Picea sitchensis*)-derived gene (UniProt database accession no. ABR16721) and a European grape vine (*Vitis vinifera*)-derived gene (UniProt database accession no. CAO14859).

The nucleotide sequence of the coding region of the Os04g0487200 gene is shown in SEQ ID NO: 11. The amino acid sequence of a protein encoded by the gene is shown in SEQ ID NO: 12. The nucleotide sequence of the coding region of the ABR16721 gene is shown in SEQ ID NO: 13. The amino acid sequence of a protein encoded by the gene is shown in SEQ ID NO: 14. The amino acid sequence of a protein encoded by the coding region of the CAO14859 gene is shown in SEQ ID NO: 15.

In addition, examples of the above described functionally equivalent genes of the At5g39390 gene include the Os02g0215700 gene and the 02g0215500 gene from rice. Also, examples of functionally equivalent genes of the At5g39390 gene from a non-*Arabidopsis* or non-rice plant include European grape vine (*Vitis vinifera*)-derived genes (UniProt database accession nos. CAN83822 and CAO41339).

The nucleotide sequence of the coding region of the Os02g0215700 gene is shown in SEQ ID NO: 16. The amino acid sequence of a protein encoded by the gene is shown in SEQ ID NO: 17. The nucleotide sequence of the coding region of the Os02g0215500 gene is shown in SEQ ID NO: 18. The amino acid sequence of a protein encoded by the gene is shown in SEQ ID NO: 19. The nucleotide sequence of the coding region of the CAN83822 gene is shown in SEQ ID NO: 20. The amino acid sequence of a protein encoded by the gene is shown in SEQ ID NO: 21. The nucleotide sequence of the coding region of the CAO41339 gene is shown in SEQ ID NO: 22. The amino acid sequence of a protein encoded by the gene is shown in SEQ ID NO: 23.

In addition, according to the present invention, an LRR-RLK gene is not limited to the above described LRR-RLK genes comprising the nucleotide sequences shown in SEQ ID NOS: 3, 5, 11, 13, 16, 18, 20, and 22 and encoding the amino acid sequences shown in SEQ ID NOS: 4, 6, 12, 14, 15, 17, 19, 21, and 23. Hence, the LRR-RLK gene may be a gene that contains an amino acid sequence having a deletion, a substitution, an addition, or an insertion of one or a plurality of amino acids with respect to the amino acid sequences shown in SEQ ID NOS: 4, 6, 12, 14, 15, 17, 19, 21, and 23, and functions as an LRR-RLK gene. Here the term "a plurality of amino acids" refers to 1 to 20, preferably 1 to 10, more preferably 1 to 7, further preferably 1 to 5, and particularly preferably 1 to 3 amino acids, for example. In addition, amino acid deletion, substitution, or addition can be performed by altering a nucleotide sequence encoding the above LRR-RLK gene by a technique known in the art. That is to say, the method described in the paragraph regarding the "LRR-RLP gene" described above can be used.

In addition, an LRR-RLK gene may be a homologous gene described in the above paragraph regarding the "LRR-RLP gene." Examples of an LRR-RLK gene include genes encoding proteins having amino acid sequences that have 70% or more, preferably 80% or more, more preferably 90% or more, and most preferably 95% or more similarity to the amino acid sequences shown in SEQ ID NOS: 4, 6, 12, 14, 15, 17, 19, 21, and 23 and having LRR-RLK activity.

Herein, the word "similarity" has the same meaning described in the above paragraph regarding the "LRR-RLP gene." Further, as described in the above paragraph regarding the "LRR-RLP gene," an LRR-RLK gene can be identified by extracting the genome from a target plant or constructing a cDNA library for a target plant and isolating a genomic region or cDNA that hybridizes under stringent conditions to at least some portions of the LRR-RLK genes comprising the nucleotide sequences shown in SEQ ID NOS: 3, 5, 11, 13, 16, 18, 20, and 22. Here, the term "stringent conditions" has the same meaning described in the above paragraph regarding the "LRR-RLP gene."

The plant of the present invention is a plant that exhibits significant improvement over the wild-type plant in terms of resistance to environmental stresses such as salt stress with the introduction of an LRR-RLP gene included in the 1st group, an LRR-RLK gene included in the 2nd group, or an LRR-RLK gene included in the 3rd group or the alteration of an expression control region of an endogenous gene. An example of a technique for introducing such gene into a plant is a technique for introducing an expression vector in which an above described exogenous gene is arranged under control of a promoter that enables expression in the plant. An example of a technique for altering an expression control region of an endogenous gene is a technique for altering a promoter for an endogenous gene in a target plant.

A preferred example is a technique for introducing an expression vector in which the above gene is arranged under control of a promoter that enables expression into a target plant.

Expression Vector

An expression vector is constructed to contain a promoter that enables expression within a plant and the above described LRR-RLP gene or LRR-RLK gene. As a vector serving as a mother body for an expression vector, various conventionally known vectors can be used. For example, plasmids, phages, cosmids, or the like can be used and such vector can be appropriately selected depending on plant cells into which it is introduced and introduction methods. Specific examples of such vector include pBR322, pBR325, pUC19, pUC119, pBluescript, pBluescriptSK, and pBI vectors. Particularly, when a method for introduction of a vector into a plant uses *Agrobacterium*, a pBI binary vector is preferably used. Specific examples of such pBI binary vector include pBIG, pBIN19, pBI101, pBI121, and pBI221.

A promoter to be used herein is not particularly limited, as long as it enables expression of the above described gene within a plant. Any known promoter can be appropriately used. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose 1,5-bisphosphate carboxylase-oxidase small subunit gene promoter, and a napin gene promoter. Of these, a cauliflower mosaic virus 35S promoter, an actin gene promoter, or a ubiquitin gene promoter can be more preferably used. The use of each of the above promoters enables strong expression of any gene when it is introduced into plant cells.

Also, a promoter having functions of causing site-specific expression in a plant can also be used herein. As such promoter, any conventionally known promoter can be used. When the above described gene is site-specifically expressed using such promoter, a plant in which the above gene is expressed in its organ exhibits improvement over the wild-type plant in terms of environmental stress resistance.

In addition, an expression vector may further contain other DNA segments in addition to a promoter and the above gene. Such other DNA segments are not particularly limited and examples thereof include a terminator, a selection marker, an enhancer, and a nucleotide sequence for enhancing translation efficiency. Also, the above recombinant expression vector may further have a T-DNA region. A T-DNA region can enhance efficiency for gene introduction particularly when the above recombinant expression vector is introduced into a plant using *Agrobacterium*.

A transcription terminator is not particularly limited, as long as it has functions as a transcription termination site and may be any known transcription terminator. For example, specifically, a transcription termination region (Nos terminator) of a nopaline synthase gene, a transcription termination region (CaMV35S terminator) of cauliflower mosaic virus 35S, or the like can be preferably used. Of them, the Nos terminator can be more preferably used. In the case of the above recombinant vector, a phenomenon such that an unnecessarily long transcript is synthesized and that a strong promoter decreases the number of copies of a plasmid after introduction into plant cells can be prevented by arranging a transcription terminator at an appropriate position.

As a transformant selection marker, a drug resistance gene can be used, for example. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics.

An example of a nucleotide sequence for increasing translation efficiency is an omega sequence from tobacco mosaic virus. This omega sequence is arranged in an untranslated region (5'UTR) of a promoter, so that the translation efficiency of the fusion gene can be increased. As such, the recombinant expression vector may contain various DNA segments depending on purposes.

A method for constructing a recombinant expression vector is not particularly limited. To an appropriately selected vector serving as a mother body, the above promoter and the above gene, and if necessary, the above other DNA segments may be introduced in an predetermined order. For example, the above gene and a promoter (and, if necessary, a transcription terminator or the like) are linked to construct an expression cassette and then the cassette may be introduced into a vector. In construction of an expression cassette, for example, cleavage sites of DNA segments are prepared to have protruding ends complementary to each other and then performing a reaction with a ligation enzyme, making it possible to specify the order of the DNA segments. In addition, when an expression cassette contains a terminator, DNA segments may be arranged in the following order from upstream: a promoter, the above gene, and a terminator. Also, reagents for construction of an expression vector (that is, types of restriction enzymes, ligation enzymes, and the like) are also not particularly limited. Hence, commercially available reagents can be appropriately selected and used.

Also, a method for replicating (a method for producing) the above expression vector is not particularly limited and conventionally known replication methods can be used herein. In general, such expression vector may be replicated within *Escherichia coli* as a host. At this time, preferred types of *Escherichia coli* may be selected depending on the types of vector.

Transformation

The above-described expression vector is introduced into a target plant by a general transformation method. A method for introducing an expression vector into plant cells (transformation method) is not particularly limited. Conventionally known appropriate introduction methods can be used depending on plant cells. Specifically, a method using *Agrobacterium* or a method that involves direct introduction into plant cells can be used, for example. As a method using *Agrobacterium*, a method described in Bechtold, E., Ellis, J. and Pelletier, G. (1993) In Planta *Agrobacterium*-mediated gene transfer by infiltration of adult *Arabidopsis* plants. C. R. Acad. Sci. Paris Sci. Vie, 316, 1194-1199, or a method described in Zyprian E, Kado Cl, *Agrobacterium*-mediated plant transformation by novel mini-T vectors in conjunction with a high-copy vir region helper plasmid, Plant Molecular Biology, 1990, 15 (2), 245-256 can be employed, for example.

As a method for directly introducing an expression vector into plant cells, microinjection, electroporation, a polyethylene glycol method, a particle gun method, protoplast fusion, a calcium phosphate method, or the like can be employed.

Also, when a method for directly introducing DNA into plant cells is employed, DNA that can be used herein contains transcriptional units required for the expression of a target gene, such as a promoter and a transcription terminator, and a target gene. Vector functions are not essential in such case. Moreover, a DNA that contains a protein coding region alone of a target gene having no transcriptional unit may be used herein, as long as it is integrated into a host's transcriptional unit and then the target gene can be expressed.

Examples of plant cells into which the above expression vector or an expression cassette containing no expression vector, but a target gene is introduced include cells of each tissue of plant organs such as flowers, leaves, and roots, calluses, and suspension-cultured cells. At this time, an appropriate expression vector may be constructed according to the types of plant to be produced or a versatile expression vector may be constructed in advance and then introduced into plant cells.

Plants into which an expression vector is introduced or in other words, plants which are improved to have environmental stress resistance are not particularly limited. Specifically, any plant can be expected to have effects of improving environmental stress resistance by inducing the expression of the above genes. Examples of target plants include, but are not limited to, dicotyledons and monocotyledons, such as plants (see below) belonging to the families Brassicaceae, Gramineae, Solanaceae, Leguminosae, Salicaceae, and the like.

Family Brassicaceae: *Arabidopsis thaliana*, rapeseed (*Brassica rapa, Brassica napus, Brassica campestris*), cabbage (*Brassica oleracea* var. *capitata*), napa (*Brassica rapa* var. *pekinensis*), ging-geng-cai (*Brassica rapa* var. *chinensis*), turnip (*Brassica rapa* var. *rapa*), turnip greens (*Brassica rapa* var. *hakabura*), potherb mustard (*Brassica rapa* var. *lancinifolia*), Komatsuna (*Brassica rapa* var. *peruviridis*), pak choi (*Brassica rapa* var. *chinensis*), daikon (*Raphanus sativus*), Japanese horseradish (*Wasabia japonica*), and the like.

Family Solanaceae: tobacco (*Nicotiana tabacum*), eggplant (*Solanum melongena*), potato (*Solaneum tuberosum*), tomato (*Lycopersicon lycopersicum*), chile pepper (*Capsicum annuum*), petunia, and the like.

Family Leguminosae: soy (*Glycine max*), pea (*Pisum sativum*), broad bean (*Vicia faba*), Wisteria (*Wisteria floribunda*), peanuts (*Arachis hypogaea*), bird's foot trefoil (*Lotus corniculatus* var. *japonicus*), common bean (*Phaseolus vulgaris*), azuki bean (*Vigna angularis*), Acacia, and the like.

Family Asteraceae: florists' daisy (*Chrysanthemum morifolium*), sunflower (*Helianthus annuus*), and the like.

Family Arecaceae: oil palm (*Elaeis guineensis, Elaeis oleifera*), coconut (*Cocos nucifera*), date palm (*Phoenix dactylifera*), copernicia, and the like.

Family Anacardiaceae: wax tree (*Rhus succedanea*), cashew nut (*Anacardium occidentale*), lacquer tree (*Toxicodendron vernicifluum*), mango (*Mangifera indica*), pistachio (*Pistacia vera*), and the like.

Family Cucurbitaceae: pumpkin (*Cucurbita maxima, Cucurbita moschata, Cucurbita pepo*), cucumber (*Cucumis sativus*), snake gourd (*Trichosanthes cucumeroides*), gourd (*Lagenaria siceraria* var. *gourda*), and the like.

Family Rosaceae: almond (*Amygdalus communis*), rose (*Rosa*), strawberry (*Fragaria*), cherry (*Prunus*), apple (*Malus pumila* var. *domestica*), and the like.

Family Caryophyllaceae: carnation (*Dianthus caryophyllus*) and the like.

Family Salicaceae: poplar (*Populus trichocarpa, Populus nigra*, or *Populus tremula*) and the like.

Family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), erianthus (*Erianthus ravenae*), miscanthus (Japanese silver grass) (*Miscanthus virgatum*), sorghum (*Sorghum*) and switchgrass (*Panicum*), and the like.

Family Liliaceae: tulip (*Tulipa*), lily (*Lilium*), and the like.

Of these examples, energy crops such as sugarcane, corn, rapeseed, and sunflower, which can serve as raw materials for biofuel, may be preferable targets. It is possible to significantly extend cultivation areas and cultivation conditions for a relevant energy crop by improving the environmental stress resistance of the energy crop. Specifically, it becomes possible to cultivate energy crops even in areas in which wild-type plants cannot grow under the influence of environmental factors (e.g., average temperature, concentration of salt in soil, etc.). Accordingly, the costs of biofuels such as bioethanol, biodiesel, biomethanol, bioDME, bioGTL (BTL), and biobutanol can be reduced Also, as described above, LRR-RLP genes and LRR-RLK genes that can be used in the present invention can be isolated from various plants and used. Such LRR-RLP genes and LRR-RLK genes can be appropriately selected and used, depending on the types of target plants to be improved in terms of environmental stress resistance. Specifically, when a target plant is a monocotyledon, an LRR-RLP gene or an LRR-RLK gene that has been isolated from a monocotyledon is preferably introduced. In particular, when a target plant is rice, the rice-derived LRR-RLP gene (SEQ ID NO: 7) or LRR-RLK gene (SEQ ID NO: 11, 16 or 18) is preferably introduced.

In addition, in the present invention, even when a target plant is a monocotyledon, a dicotyledon-derived LRR-RLP gene or LRR-RLK gene may be introduced. Specifically, for example, the *Arabidopsis thaliana*-derived LRR-RLP gene or LRR-RLK gene may be introduced into not only dicotyledons, but also a variety of plants that are classified as monocotyledons.

Other Steps and Methods

After the above transformation, a step of selecting proper transformants from plants can be performed by a conventionally known method. Such selection method is not particularly limited. For example, selection can be made based on drug resistance such as hygromycin resistance. Alternatively, after the growth of transformants, a transformant having significantly improved environmental stress resistance in its entirety or in its arbitrary organ or tissue may be selected.

Also, progeny plants can be obtained from transformed plants obtained by transformation according to a conventional method. Progeny plants retaining a trait into which the LRR-RLP gene or LRR-RLK gene has been introduced are selected based on the environmental stress resistance. Therefore, a stable plant line capable of exhibiting improved environmental stress resistance because of having the above trait can be produced. Also, plant cells or reproductive materials, such as seeds, fruits, stocks, calluses, tubers, cut ears, or lumps, may be obtained from a transformed plant or an offspring plant thereof. A stable plant line capable of exhibiting improved environmental stress resistance because of having the above trait can be mass-produced therefrom based on such materials.

In addition, the plant of the present invention may include a matter comprising at least any one of an adult plant, plant cells, plant tissue, callus, and seeds. That is, according to the present invention, any matter in a state that allows it to eventually grow to become a plant can be regarded as a plant. In addition, plant cells include plant cells in various forms. Examples of such plant cells include suspension-cultured cells, protoplasts, and leaf sections. As a result of proliferation/differentiation of such plant cells, a plant can be obtained. In addition, a plant can be reproduced from plant cells by a conventionally known method depending on the types of plant cells.

As described above, according to the present invention, it is possible to provide a plant that exhibits improvement over the wild-type plant in terms of resistance to environmental stresses such as salt stress with the introduction of an LRR-RLP gene or an LRR-RLK gene thereinto or the alteration of an expression control region of an endogenous gene therein.

EXAMPLES

The present invention is hereafter described in greater detail with reference to the following examples, although the technical scope of the present invention is not limited thereto.

Example 1

1. Materials and Methods 1-1. Experimental Materials

As experimental materials, seeds of *Arabidopsis thaliana* mutants (Activation-tag T-DNA lines: Weigel T-DNS lines, Total of 20072 lines) were used. In addition, the seeds were purchased from the Nottingham *Arabidopsis* Stock Centre (NASC). Regarding the seeds used as experimental materials, Weigel, D., et al., Plant Physiol., 122, 1003-1013 (2000) can be referred to.

1-2. Methods 1-2-1. Selection of Salt-Resistant Mutants

Seeds of Weigel T-DNA lines were aseptically sowed on 125 mM or 150 mM NaCl-containing modified MS agar (1%) medium [vitamins in B5 medium, 10 g/l sucrose, and 8 g/L agar (for bacterial medium; Wako Pure Chemical Industries, Ltd.)] and then cultured at 22 degrees C. under 30-100 micromol/m$^2$/sec illumination (a cycle of 16 hours in the light/8 hours in the dark). Two to 4 weeks after sowing, salt-resistant mutant candidates were selected. In addition, regarding MS medium, see Murashige, T. et al. (1962) Physiol. Plant., 15, 473-497. Also, regarding the B5 medium, see Gamborg, O. L. et al. (1968) Experimental Cell Research, 50, 151-158.

1-2-2. DNA Preparation

A site for insertion of T-DNA into the genome of the thus selected salt-resistant *Arabidopsis thaliana* line was determined by a TAIL-PCR method. First, young leaves were harvested from the cultivated *Arabidopsis thaliana* plants and then crushed under liquid nitrogen freezing. DNA was prepared using a DNA preparation kit (DNeasy Plant Mini Kit, QIAGEN) according to the standard protocols included with the kit.

1-2-3. TAIL-PCR Method and Presumption of T-DNA Insertion Site

Three (3) types of specific primers, TL1, TL2, and TL3, were determined to be located near the left T-DNA sequence (T-DNA left border) of an activation-tagging vector (pSKI015: GenBank accession No. AF187951) used in Weigel T-DNA lines. With the use of an arbitrary primer P1 and the following PCR reaction solutions and reaction conditions, TAIL-PCR (supervisors, Isao Shimamoto and Takuji Sasaki, New Edition, Plant PCR Experimental Protocols, 2000, pp. 83-89, Shujunsha, Tokyo, Japan; Genomics 25, 674-681, 1995; Plant J., 8, 457-463, 1995) was performed, so that genomic DNA adjacent to T-DNA was amplified.

The specific sequences of the primers TL1, TL2, TL3, and P1 are as follows.

```
                                         (SEQ ID NO: 44)
TL1: 5'-TGC TTT CGC CAT TAA ATA GCG ACG G-3'

(SEQ ID NO: 45)
TL2: 5'-CGC TGC GGA CAT CTA CAT TTT TG-3'

(SEQ ID NO: 46)
TL3: 5'-TCC CGG ACA TGA AGC CAT TTA C-3'

(SEQ ID NO: 47)
P1: 5'-NGT CGA SWG ANA WGA A-3'
```

In addition, in SEQ ID NO: 47, "n" represents "a," "g," "c," or "t" (location: 1 and 11), "s" represents "g" or "c" (location: 7), and "w" represents "a" or "t" (location: 8 and 13).

The 1$^{st}$ PCR reaction solution composition and reaction conditions are shown in Table 1 and Table 2, respectively.

TABLE 1

| | |
|---|---|
| Template (genomic DNA) | 10 ng |
| 10 × PCR buffer (Takara Bio) | 2 microliters |
| 2.5 mM dNTPs (Takara Bio) | 1.6 microliters |

TABLE 1-continued

| | |
|---|---|
| 1st specific primer (TL1: SEQ ID NO: 44) | 0.5 pmol |
| Arbitrary primer P1 (SEQ ID NO: 47) | 100 pmol |
| TaKaRa Ex Taq (Takara Bio) | 1.0 unit |
| Total | 20 microliters |

TABLE 2

| | |
|---|---|
| #1: | 94 degrees C. (30 seconds)/95 degrees C. (30 seconds) |
| #2: | 5 cycles of 94 degrees C. (30 seconds)/65 degrees C. (30 seconds)/72 degrees C. (1 minute) |
| #3: | 1 cycle of 94 degrees C. (30 seconds)/25 degrees C. (1 minute)→raised to 72 degrees C. within 3 minutes/72 degrees C. (3 minutes) |
| #4: | 94 degrees C. (15 seconds)/65 degrees C. (30 seconds)/72 degrees C. (1 minute), 94 degrees C. (15 seconds)/68 degrees C. (30 seconds)/72 degrees C. (1 minute), and 15 cycles of 94 degrees C. (15 seconds)/44 degrees C. (30 seconds)/72 degrees C. (1 minute) |
| #5: | 72 degrees C. (3 minutes) |

The $2^{nd}$ PCR reaction solution composition and reaction conditions are shown in Table 3 and Table 4, respectively.

TABLE 3

| | |
|---|---|
| Template (50-fold dilution of the $1^{st}$ PCR product) | 1 microliter |
| 10 × PCR buffer (Takara Bio) | 2 microliters |
| 2.5 mM dNTPs (Takara Bio) | 1.5 microliters |
| $2^{nd}$ specific primer (TL2: SEQ ID NO: 45) | 5 pmol |
| Arbitrary primer P1 (SEQ ID NO: 47) | 100 pmol |
| TaKaRa Ex Taq (Takara Bio) | 0.8 unit |
| Total | 20 microliters |

TABLE 4

| | |
|---|---|
| #6: | 94 degrees C. (15 seconds)/64 degrees C. (30 seconds)/72 degrees C. (1 minute), 94 degrees C. (15 seconds)/64 degrees C. (30 seconds)/72 degrees C. (1 minute), and 12 cycles of 94 degrees C. (15 seconds)/44 degrees C. (30 seconds)/72 degrees C. (1 minute) |
| #5: | 72 degrees C. (5 minutes) |

The $3^{rd}$ PCR reaction solution composition and reaction conditions are shown in Table 5 and Table 6, respectively.

TABLE 5

| | |
|---|---|
| Template (50-fold dilution of the $2^{nd}$ PCR product) | 1 microliter |
| 10 × PCR buffer (Takara Bio) | 5 microliters |
| 2.5 mM dNTPs (Takara Bio) | 0.5 microliter |
| $3^{rd}$ specific primer (TL3: SEQ ID NO: 46) | 10 pmol |
| Arbitrary primer P1 (SEQ ID NO: 47) | 100 pmol |
| TaKaRa Ex Taq (Takara Bio) | 1.5 unit |
| Total | 50 microliters |

TABLE 6

| | |
|---|---|
| #7: | 20 cycles of 94 degrees C. (30 seconds)/44 degrees C. (30 seconds)/72 degrees C. (1 minute) |
| #5: | 72 degrees C. (3 minutes) |

Subsequently, the $2^{nd}$ and the $3^{rd}$ reaction products were subjected to agarose gel electrophoresis and then the presence or the absence of amplification and the specificity of reaction products were confirmed. Also, the 3rd amplification products were subjected to a sequencing reaction directly using a BigDye Terminator Cycle Sequencing Kit Ver. 3. 1 (Applied Biosystems) and the specific primer TL3. Thus, a nucleotide sequence was determined using an ABI PRISM 3100 Genetic Analyzer (Applied Biosystems).

As a result, 5 different nucleotide sequences were determined. Specifically, the 538-bp sequence information, the 311-bp sequence information, the 498-bp sequence information, the 633-bp sequence information, and the 245-bp sequence information were obtained. The obtained sequences are shown in SEQ ID NOS: 48 to 52.

The *Arabidopsis* Information Resource (TAIR: http://www.*arabidopsis*.org/) was subjected to a BLAST search with the use of the obtained sequence information. Thus, the T-DNA insertion sites were found to exist in the following order: a site between the *Arabidopsis* chromosome 1 gene [AGI (The *Arabidopsis* Genome Initiative gene code) code: At1g69990] and the gene [AGI (The *Arabidopsis* Genome Initiative gene code) code: At1g70000]; a site of the *Arabidopsis* chromosome 5 gene [AGI (The *Arabidopsis* Genome Initiative gene code) code: At5g39400]; a site of the *Arabidopsis* chromosome 3 gene [AGI (The *Arabidopsis* Genome Initiative gene code) code: At3g05630]; a site of the *Arabidopsis* chromosome 2 gene [AGI (The *Arabidopsis* Genome Initiative gene code) code: At2g33110]; and a site between the *Arabidopsis* chromosome 1 gene [AGI (The *Arabidopsis* Genome Initiative gene code) code: At1g71810] and the gene [AGI (The *Arabidopsis* Genome Initiative gene code) code: At1g71820].

1-2-4. Prediction of Activated Genes

Activated genes were predicted based on the sequences of presumed open reading frame (ORF) genes existing within 10-Kb ranges near the respective T-DNA insertion sites (the site between At1g69990 and At1g70000, the site of At5g39400, the site of At3g05630, the site of At2g33110, and the site between At1g71810 and At1g71820) revealed in 1-2-3. above.

1-2-5. Obtainment of Predicted Genes

For amplification of fragments containing the ORF regions of the LRR-RLK (leucine-rich repeat receptor-like protein kinase) gene (At1g69990), the LRR-RLK (leucine-rich repeat receptor-like protein kinase) gene (At5g39390), the LRR (leucine-rich repeat) protein gene (At3g05650), and the LRR (leucine-rich repeat) protein gene (At2g33080) that had been predicted to be activated in 1-2-4, a pair of PCR primers were designed and synthesized for each fragment based on the sequence information disclosed at the TAIR (http://www.*arabidopsis*.org/home.html) (table 7). In addition, these primers were designed, so that a restriction enzyme site required for introduction into expression vectors was added to each primer (table 7).

TABLE 7

| Gene | Forward | Reverse | Restriction enzyme site | |
|---|---|---|---|---|
| At1g69990 | 5'-ACG CGT CGA CCC ATC ATG AAA ACG ATC TCA ATC TTC TTC GTC-3' (SEQ ID NO: 53) | 5'-TGT ACA TGT ACA AGT GAG AAC GGT AGA TAA GTA AGT GG-3' (SEQ ID NO: 54) | Sal I | BsrG I |
| At5g39390 | 5'-ACG CGT CGA CCA AAC GAC GTA TCT CAT AAG TCG ACG CA-3' (SEQ ID NO: 55) | 5'-TGT ACA TGT ACA GGA GAA CTT TGA AGA TCA TCG AGA GG-3' (SEQ ID NO: 56) | Sal I | BsrG I |
| At3g05650 | 5'-ACG CGT CGA CCC ATC ACA CAC ACA TAC ACA CAC-3' (SEQ ID NO: 57) | 5'-TGT ACA TGT ACA CAG CGT AAA TGA AGA ACA CCC AAA ACT GAA C-3' (SEQ ID NO: 58) | Sal I | BsrG I |
| At2g33080 | 5'-ACG CGT CGA CAT GTC AGG ATC ACA TCT GCG TTT GC-3' (SEQ ID NO: 59) | 5'-TGT ACA TGT ACA TCA GCA CTT GCT CCT GTT CTT CG-3' (SEQ ID NO: 60) | Sal I | BsrG I |

In order to amplify a fragment containing the ORF region of the LRR-RLK (leucine-rich repeat receptor-like protein kinase) gene (At1g71830), three pairs of primers were designed and synthesized based on the sequence information disclosed in TAIR (http://www.*arabidopsis*.org/home.html) (table 8). Here, the set of primers (Forward 1 and Reverse 3) were designed so that a restriction enzyme site required for introduction into expression vectors was added to each primer (table 8).

TABLE 8

| Gene | Forward | Reverse | Restriction enzyme site |
|---|---|---|---|
| At1g71830 | Forward 1 5'-ACG CGT CGA CAT GGA GTC GAG TTA TGT GGT G-3' (SEQ ID NO: 61) | Reverse 1 5'-CCG GAA TAG GAC CGG AGA AGC TG-3' (SEQ ID NO: 62) | Sal I |
| | Forward 2 5'-CAG CTT CTC CGG TCC TAT TCC GG-3' (SEQ ID NO: 63) | Reverse 2 5'-CAT CAC TCG CCA CTT GTA GCT CCC GC-3' (SEQ ID NO: 64) | |
| | Forward 3 5'-GCG GGA GCT ACA AGT GGC GAG TGA TG-3' (SEQ ID NO: 65) | Reverse 3 5'-TGT ACA TGT ACA GTA GCA AAA CAG CGG AGT-3' (SEQ ID NO: 66) | BsrG I |

According to the method described in 1-2-2, a template DNA was prepared from wild-type *Arabidopsis thaliana* (eco-type Col-0). Takara Ex Taq (Takara Bio Inc.) and Platinum Pfx DNA Polymerase (Invitrogen) or Phusion High-Fidelity DNA Polymerase (New England BioLabs: NEB) were used as enzymes and a pair of primers listed in table 7 were used as primers. For the PCR reaction solution composition and reaction conditions, the protocols attached to each enzyme were referred to. In addition, for the LRR-RLK gene (At1g71830), PCR was performed using the three pairs of primers listed in table 8 and Platinum Pfx DNA Polymerase (Invitrogen) as an enzyme such that the three pairs of PCR amplification products were obtained. PCR amplification products were subjected to electrophoresis with 2% agarose gel (TAE buffer) and then fragments were stained with ethidium bromide. A gel containing target fragments was excised using a scalpel. Target DNA fragments were eluted and purified using GFX PCR DNA and a GEL Band Purification Kit (Amersham). Overlapping PCR was conducted with the use of the three DNA fragments as templates and Forward 1 and Reverse 3 as primers.

As in the above case, each PCR amplification product was subjected to agarose gel electrophoresis, followed by excision and purification. Adenin was added to the thus obtained DNA fragment using an A-Addition Kit (QIAGEN). The amplified DNA to which adenine had been added was ligated to a TA-Cloning pCR2.1 vector using a TOPO TA Cloning Kit (Invitrogen) and then transformed into competent cells (*E. coli* TOP 10) included with the kit. After transformation, cells were cultured in LB medium supplemented with 50 microliter/ml kanamycin and then transformants were selected. Colonies that had appeared were subjected to liquid culture in LB medium supplemented with 50 microliter/ml kanamycin. Plasmid DNA was prepared from the thus obtained microorganisms using a Plasmid Mini Kit (QIAGEN).

A fragment containing the ORF of the LRR-RLK gene (At1g69990), a fragment containing the ORF of the LRR-RLK gene (At5g39390), a fragment containing the ORF of the LRR protein gene (At3g05650), a fragment containing the ORF of the LRR protein gene (At2g33080), and a fragment containing the ORF of the LRR-RLK gene (At1g71830) were separately cloned into vectors, followed by determination of the nucleotide sequence and sequence analysis.

1-2-6. Construction of Plant Expression Vectors

Fragments containing ORFs of the LRR-RLK gene (At1g69990), the LRR-RLK gene (At5g39390), the LRR protein gene (At3g05650), the LRR protein gene (At2g33080), and the LRR-RLK gene (At1g71830) were inserted into a plant expression vector pBI121 containing an omega sequence from tobacco mosaic virus. Thus, constructs were prepared.

First, the pCR2.1 vector, in which a fragment containing ORF of the LRR-RLK gene (At1g69990) had been cloned in 1-2-5, was treated with restriction enzymes Sal I and BsrG I.

Next, similarly pBI121 containing an omega sequence was treated with restriction enzymes Sal I and BsrG I. The products digested with these restriction enzymes were subjected to 0.8% agarose gel electrophoresis. A fragment of about 1850 bp containing ORF of the LRR-RLK gene (At1g69990) and pBI121 containing the omega sequence were each fractioned and purified from the gel using GFX PCR DNA and a GEL Band Purification Kit (Amersham).

For introduction of a fragment containing ORF of the LRR-RLK gene (At1g69990) using a pBI121 fragment containing the omega sequence as a vector, the vector and the insert were mixed at a ratio of 1:10, followed by an overnight ligation reaction at 16 degrees C. using an equivalent amount of a TaKaRa Ligation Kit ver. 2 (Takara Bio Inc.).

The total amount of the reaction solution was added to 100 microliters of competent cells (E. coli strain DH5 alpha, TOYOBO), so that transformation was performed according to protocols included with the kit. Cells were applied to LB agar medium containing 50 microgram/ml kanamycin and then cultured overnight. Colonies that had appeared were subjected to liquid culture in LB medium supplemented with 50 microgram/ml kanamycin. Plasmid DNA was prepared from the thus obtained microorganisms using a Plasmid Mini Kit (QIAGEN).

The thus obtained fragment containing ORF of the LRR-RLK gene (At1g69990) was subcloned into an expression vector, followed by determination of the nucleotide sequence and sequence analysis.

The LRR-RLK gene (At5g39390), the LRR protein gene (At2g33080), and the LRR-RLK gene (At1g71830) were incorporated into expression vectors in the manner described above, followed by nucleotide sequence determination and sequence analysis. The LRR protein gene (At3g05650) was cloned into a TA-Cloning pCR2.1 vector, treated with a SalI restriction enzyme, and blunt-ended with a DNA Blunting Kit (Takara Bio Inc.), followed by treatment with phenol chloroform and then with a BsrG I restriction enzyme. Similarly, pBI121 containing the omega sequence was treated with a SalI restriction enzyme and blunt-ended with a DNA Blunting Kit (Takara Bio Inc.), followed by treatment with phenol chloroform and then with a BsrG I restriction enzyme. Each gene was incorporated into an expression vector in the manner described above, followed by nucleotide sequence determination and sequence analysis.

1-2-7. Gene Introduction into *Arabidopsis thaliana* Using *Agrobacterium* Method The plant expression vector constructed in 1-2-6 was introduced into *Agrobacterium tumefaciens* C58C1 strain by electroporation (Plant Molecular Biology Manual, Second Edition, B. G. Stanton, A. S. Robbert, Kluwer Acdemic Publishers, 1994). Subsequently, *Agrobacterium tumefaciens* in which the plant expression vector had been introduced was introduced into wild-type *Arabidopsis thaliana* (eco-type Col-0) by an infiltration method described by Clough et al. (Plant J., 16, 735-743, 1998).

Transformants were selected using kanamycin-containing medium. T2 generation plants were produced by self-pollination from the transformants.

1-2-8. Confirmation of the Phenotype of Transformant

Salt Resistance Test:

Seeds prepared in 1-2-7. and seeds of a non-recombinant wild-type *Arabidopsis* plant used as a control were aseptically sowed on a modified MS agar medium containing 150 mM NaCl. They were cultivated under conditions of 22 degrees C. and 16 hours in the light/8 hours in the dark, and with a light intensity ranging from about 30 to 45 micro E/cm$^2$.

2. Results

Figure 2:
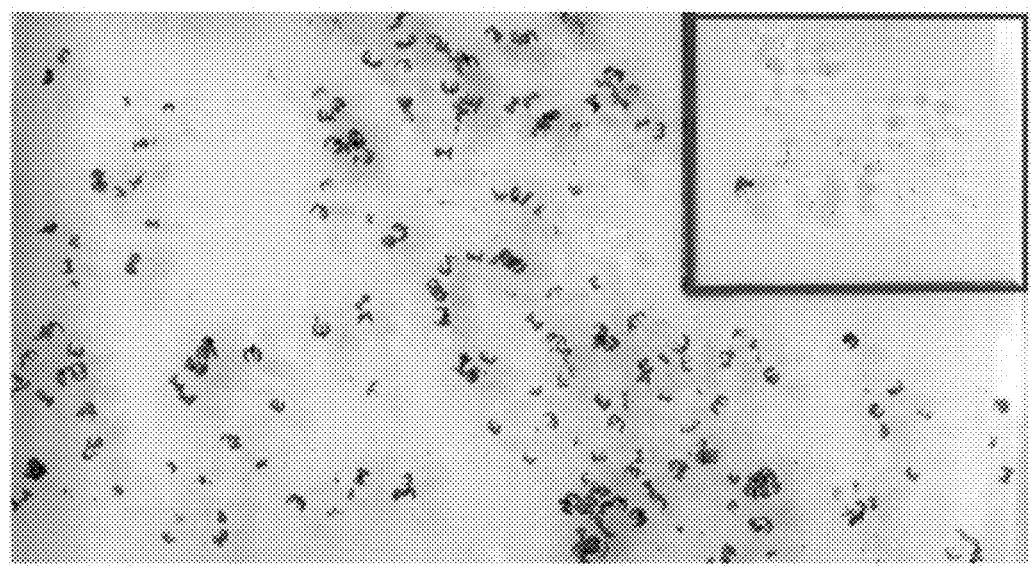
FIG. 2 is a photograph showing the state of germination or growth (in a medium with a high salt concentration) of transformed plants into which a fragment containing ORF of At5g39390 has been introduced and that of wild-type plants.
Figure 3:
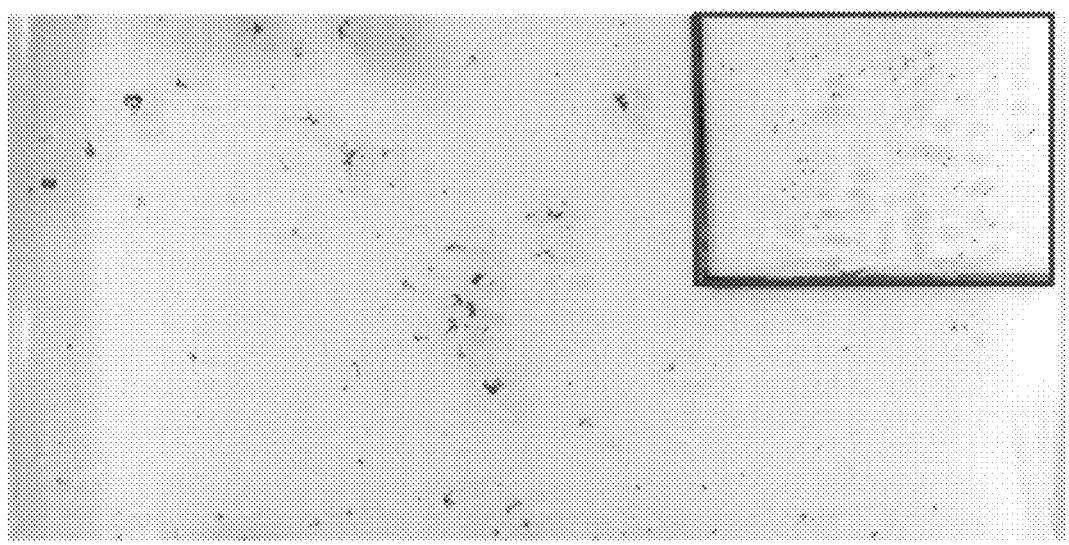
FIG. 3 is a photograph showing the state of germination or growth (in a medium with a high salt concentration) of transformed plants into which a fragment containing ORF of At3g05650 has been introduced and that of wild-type plants.
Figure 4:
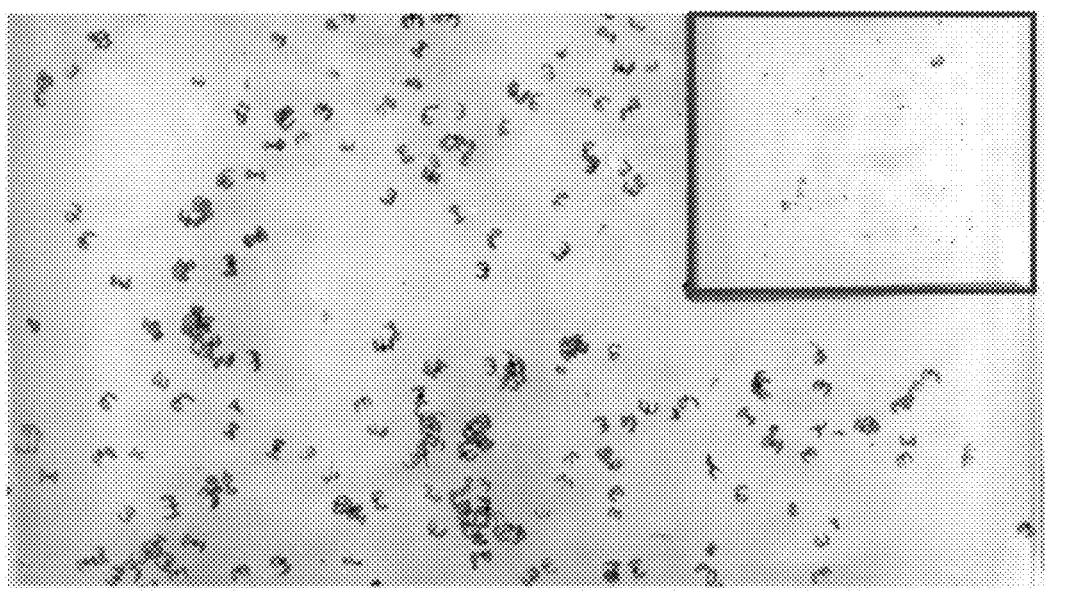
FIG. 4 is a photograph showing the state of germination or growth (in a medium with a high salt concentration) of transformed plants into which a fragment containing ORF of At2g33080 has been introduced and that of wild-type plants.

FIGS. 1 to 5 show photographs of plates containing transformed plants into which fragments containing the ORFs of the wild-type gene, the LRR-RLK gene (At1g69990), the LRR-RLK gene (At5g39390), the LRR-RLP gene (At3g05650), the LRR-RLP gene (At2g33080), and the LRR-RLK gene (At1g71830) were separately introduced, each photograph indicating the salt resistance test results described in 1-2-8. above. FIGS. 1, 2, and 4 show that the transformed plants into which fragments containing the ORFs of the LRR-RLK gene (At1g69990), the LRR-RLK gene (At5g39390), and the LRR-RLP gene (At2g33080) had been introduced germinated and grew in a medium with a high salt concentration. The results revealed that the transformed plants exhibited improvement over the wild-type plant in terms of salt resistance.

Figure 5:
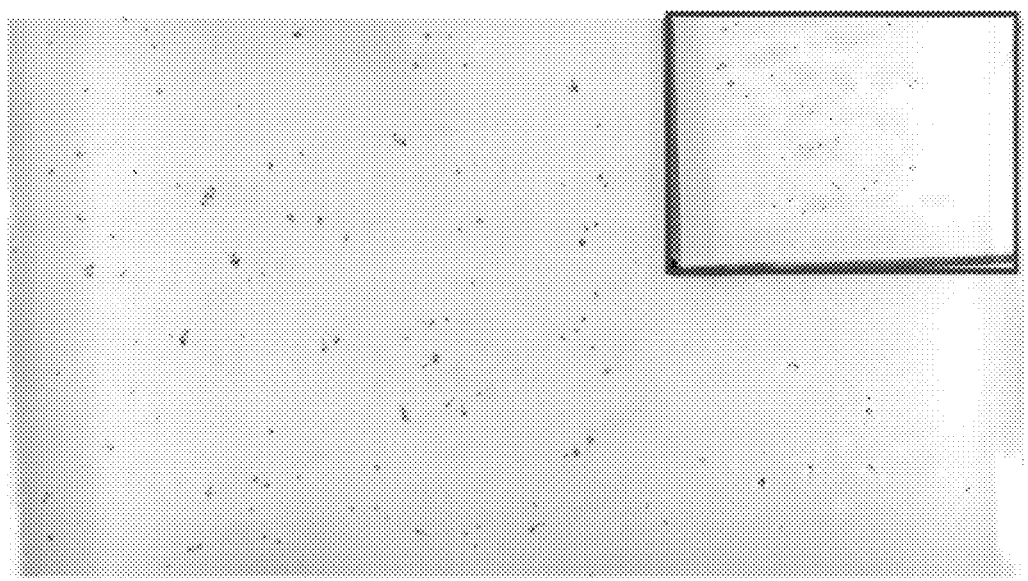
FIG. 5 is a photograph showing the state of germination or growth (in a medium with a high salt concentration) of transformed plants into which a fragment containing ORF of At1g71830 has been introduced and that of wild-type plants.

However, as shown in FIGS. 3 and 5, the transformed plants into which fragments containing the ORFs of the LRR-RLP gene (At3g05650) and the LRR-RLK gene (At1g71830) had been introduced did not exhibit clearly improved salt resistance.

The invention claimed is:

1. A transgenic plant into which at least one gene has been introduced, wherein the introduced gene encodes a protein comprising the amino acid sequence shown in SEQ ID NO: 2, wherein the introduced gene is expressed in said transgenic plant, and wherein said transgenic plant has improved salt resistance as compared to a plant without said gene introduced.

2. A method for producing the transgenic plant of claim 1, said method comprising introducing, into a plant, a gene encoding a protein comprising the amino acid sequence shown in SEQ ID NO: 2, and allowing the introduced gene to be expressed in said plant, wherein said transgenic plant has improved salt resistance as compared to a plant without said gene introduced.

3. A method for selecting a plant with improved salt resistance, said method comprising:
   (a) producing a transgenic plant by introducing, into a plant, a gene encoding a protein comprising the amino acid sequence shown in SEQ ID NO:2, and allowing the introduced gene to be expressed in said plant;
   (b) generating progeny plants of the transgenic plant;
   (c) evaluating salt resistance of the progeny plants; and
   (d) selecting a plant with improved salt resistance as compared to a plant without said gene introduced.

* * * * *